US011365416B2

United States Patent
Jo et al.

(10) Patent No.: US 11,365,416 B2
(45) Date of Patent: Jun. 21, 2022

(54) MODULATORS OF EZH2 EXPRESSION

(71) Applicant: Ionis Pharmaceuticals, Inc., Carlsbad, CA (US)

(72) Inventors: Minji Jo, Vista, CA (US); Youngsoo Kim, San Diego, CA (US); Robert MacLeod, San Diego, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 67 days.

(21) Appl. No.: 17/045,426

(22) PCT Filed: Apr. 11, 2019

(86) PCT No.: PCT/US2019/027090
§ 371 (c)(1),
(2) Date: Oct. 5, 2020

(87) PCT Pub. No.: WO2019/200172
PCT Pub. Date: Oct. 17, 2019

(65) Prior Publication Data
US 2021/0155935 A1    May 27, 2021

Related U.S. Application Data

(60) Provisional application No. 62/656,244, filed on Apr. 11, 2018.

(51) Int. Cl.
*C12N 15/113* (2010.01)
*A61P 35/00* (2006.01)

(52) U.S. Cl.
CPC .......... *C12N 15/1137* (2013.01); *A61P 35/00* (2018.01); *C12Y 201/01043* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01)

(58) Field of Classification Search
CPC ............ C12N 15/1137; C12N 2310/11; C12N 2310/315; C12N 2310/321; C12N 2310/3231; C12N 2310/3341; C12N 2310/341; A61P 35/00; C12Y 201/01043
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |

(Continued)

FOREIGN PATENT DOCUMENTS

| | | |
|---|---|---|
| WO | WO 2003/070887 | 8/2003 |
| WO | WO 2008/109534 | 9/2008 |

(Continued)

OTHER PUBLICATIONS

Alimova et al., "Targeting the enhancer of zeste homologue 2 in medulloblastoma" Int J Cancer (2012) 131: 1800-1809.
Branch et al., "A good antisense molecule is hard to find," TIBS (1998) 23:45-50.
Cardoso et al., "The human EZH2 gene: genomic organisation and revised mapping in 7q35 within the critical region for malignant myeloid disorders" Eur J Hum Genet (2000) 8: 174-180.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

(Continued)

*Primary Examiner* — J. E. Angell
(74) *Attorney, Agent, or Firm* — Knobbe, Martens, Olson & Bear, LLP

(57) ABSTRACT

The present embodiments provide methods, compounds, and compositions useful for inhibiting EZH2 expression, which may be useful for treating, preventing, or ameliorating a cancer associated with EZH2.

18 Claims, No Drawings
Specification includes a Sequence Listing.

(56) References Cited

U.S. PATENT DOCUMENTS

| | | | |
|---|---|---|---|
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,300,319 | B1 | 10/2001 | Manoharan |
| 6,426,220 | B1 | 7/2002 | Bennett et al. |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,660,720 | B2 | 12/2003 | Manoharan |
| 6,770,748 | B2 | 8/2004 | Imanishi et al. |
| 7,015,315 | B1 | 3/2006 | Cook et al. |
| 7,053,207 | B2 | 5/2006 | Wengel et al. |
| 7,101,993 | B1 | 9/2006 | Cook et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,666,854 | B2 | 2/2010 | Seth et al. |
| 7,687,616 | B1 | 3/2010 | Bentwich et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,875,733 | B2 | 1/2011 | Bhat et al. |
| 7,928,218 | B2 | 4/2011 | McSwiggen et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,090,542 | B2 | 1/2012 | Khvorova et al. |
| 8,106,022 | B2 | 1/2012 | Manoharan et al. |
| 8,124,745 | B2 | 2/2012 | Allerson et al. |
| 8,153,365 | B2 | 4/2012 | Wengel et al. |
| 8,178,503 | B2 | 5/2012 | Rigoutsos et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,440,803 | B2 | 5/2013 | Swayze et al. |
| 8,501,805 | B2 | 8/2013 | Seth et al. |
| 8,524,682 | B2 | 9/2013 | Chirmaiyan et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,728,736 | B2 | 5/2014 | Leamon et al. |
| 8,828,956 | B2 | 9/2014 | Manoharan et al. |
| 9,005,906 | B2 | 4/2015 | Swayze et al. |
| 9,012,421 | B2 | 4/2015 | Migawa et al. |
| 9,127,276 | B2 | 8/2015 | Prakash et al. |
| 9,290,760 | B2 | 3/2016 | Rajeev et al. |
| 2001/0053519 | A1 | 12/2001 | Fodor et al. |
| 2003/0158403 | A1 | 8/2003 | Manoharan et al. |
| 2003/0175906 | A1 | 9/2003 | Manoharan et al. |
| 2003/0228597 | A1 | 12/2003 | Cowsert et al. |
| 2004/0171570 | A1 | 9/2004 | Allerson et al. |
| 2004/0241651 | A1 | 12/2004 | Olek et al. |
| 2005/0130923 | A1 | 6/2005 | Bhat et al. |
| 2005/0159382 | A1 | 7/2005 | McSwiggen et al. |
| 2005/0244851 | A1 | 11/2005 | Blume et al. |
| 2006/0148740 | A1 | 7/2006 | Platenburg |
| 2007/0031844 | A1 | 2/2007 | Khvorova et al. |
| 2008/0039618 | A1 | 2/2008 | Allerson et al. |
| 2010/0190837 | A1 | 7/2010 | Migawa et al. |

(56) References Cited

U.S. PATENT DOCUMENTS

| | | |
|---|---|---|
| 2010/0197762 A1 | 8/2010 | Swayze et al. |
| 2011/0054005 A1 | 3/2011 | Naito et al. |
| 2011/0064664 A1 | 3/2011 | Lopez-Berestein et al. |
| 2012/0052487 A9 | 3/2012 | Khvorova et al. |
| 2013/0011922 A1 | 1/2013 | Quay et al. |
| 2013/0130378 A1 | 5/2013 | Manoharan et al. |
| 2014/0107330 A1 | 4/2014 | Freier et al. |
| 2015/0018540 A1 | 1/2015 | Prakash et al. |
| 2015/0141320 A1 | 5/2015 | Krieg et al. |
| 2015/0184153 A1 | 7/2015 | Freier et al. |
| 2015/0191727 A1 | 7/2015 | Migawa et al. |
| 2015/0232836 A1 | 8/2015 | Krieg et al. |
| 2015/0267195 A1 | 9/2015 | Seth et al. |
| 2015/0275212 A1 | 10/2015 | Albaek et al. |

FOREIGN PATENT DOCUMENTS

| | | |
|---|---|---|
| WO | WO 2016/138353 | 9/2016 |
| WO | WO 2019/200172 | 10/2019 |

OTHER PUBLICATIONS

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bcl-2/bcl-xLbispecific antisense oligonucleotide against tumors of diverse histologic origins" J. Natl. Cancer Inst. (2001) 93:463-471.

International Search Report for PCT/US2019/027090 dated Aug. 27, 2019.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Woolf et al., "Specificity of antisense oligonucleotides in vivo" PNAS (1992) 89: 7305-7309.

Xia et al., "EZH2 silencing with RNAi enhances irradiation-induced inhibition of human lung cancer growth in vitro and in vivo" Oncol Lett (2012) 4: 135-140.

SEQUENCE LISTING

```
<160> NUMBER OF SEQ ID NOS: 1592

<210> SEQ ID NO 1
<211> LENGTH: 2681
<212> TYPE: DNA
<213> ORGANISM: Homo sapiens

<400> SEQUENCE: 1
ggcggcgctt gattgggctg gggggggccaa ataaaagcga tggcgattgg gctgccgcgt      60
ttggcgctcg gtccggtcgc gtccgacacc cggtgggact cagaaggcag tggagccccg     120
gcggcggcgg cggcggcgcg cggggcgac gcgcgggaac aacgcgagtc ggcgcgcggg     180
acgaagaata atcatgggcc agactgggaa gaaatctgag aagggaccag tttgttggcg     240
gaagcgtgta aaatcagagt acatgcgact gagacagctc aagaggttca gacgagctga     300
tgaagtaaag agtatgttta gttccaatcg tcagaaaatt ttggaaagaa cggaaatctt     360
aaaccaagaa tggaaacagc gaaggataca gcctgtgcac atcctgactt cttgttcggt     420
gaccagtgac ttggattttc aacacaagt catcccatta aagactctga atgcagttgc     480
ttcagtaccc ataatgtatt cttggtctcc cctacagcag aattttatgg tggaagatga     540
aactgtttta cataacattc cttatatggg agatgaagtt ttagatcagg atggtacttt     600
```

| | | | |
|---|---|---|---|
| cattgaagaa | ctaataaaaa | attatgatgg | gaaagtacac | ggggatagag | aatgtgggtt | 660 |
| tataaatgat | gaaatttttg | tggagttggt | gaatgcccct | ggtcaatata | atgatgatga | 720 |
| cgatgatgat | gatggagacg | atcctgaaga | aagagaagaa | aagcagaaag | atctggagga | 780 |
| tcaccgagat | gataaagaaa | gccgccacc | tcggaaattt | ccttctgata | aaattttga | 840 |
| agccatttcc | tcaatgtttc | cagataaggg | cacagcagaa | gaactaaagg | aaaaatataa | 900 |
| agaactcacc | gaacagcagc | tcccaggcgc | acttcctcct | gaatgtaccc | ccaacataga | 960 |
| tggaccaaat | gctaaatctg | ttcagagaga | gcaaagctta | cactcctttc | atacgctttt | 1020 |
| ctgtaggcga | tgttttaaat | atgactgctt | cctacatcct | tttcatgcaa | cacccaacac | 1080 |
| ttataagcgg | aagaacacag | aaacagctct | agacaacaaa | ccttgtggac | cacagtgtta | 1140 |
| ccagcatttg | gagggagcaa | aggagtttgc | tgctgctctc | accgctgagc | ggataaagac | 1200 |
| cccaccaaaa | cgtccaggag | gccgcagaag | aggacggctt | cccaataaca | gtagcaggcc | 1260 |
| cagcacccc | accattaatg | tgctggaatc | aaaggataca | gacagtgata | gggaagcagg | 1320 |
| gactgaaacg | gggggagaga | acaatgataa | agaagaagaa | gagaagaaag | atgaaacttc | 1380 |
| gagctcctct | gaagcaaatt | ctcggtgtca | acaccaata | aagatgaagc | caaatattga | 1440 |
| acctcctgag | aatgtggagt | ggagtggtgc | tgaagcctca | atgtttagag | tcctcattgg | 1500 |
| cacttactat | gacaatttct | gtgccattgc | taggttaatt | gggaccaaaa | catgtagaca | 1560 |
| ggtgtatgag | tttagagtca | aagaatctag | catcatagct | ccagctcccg | ctgaggatgt | 1620 |
| ggatactcct | ccaaggaaaa | agaagaggaa | acaccggttg | tgggctgcac | actgcagaaa | 1680 |
| gatacagctg | aaaaaggacg | gctcctctaa | ccatgtttac | aactatcaac | cctgtgatca | 1740 |
| tccacggcag | ccttgtgaca | gttcgtgccc | ttgtgtgata | gcacaaaatt | tttgtgaaaa | 1800 |
| gttttgtcaa | tgtagttcag | agtgtcaaaa | ccgctttccg | ggatgccgct | gcaaagcaca | 1860 |
| gtgcaacacc | aagcagtgcc | cgtgctacct | ggctgtccga | gagtgtgacc | ctgacctctg | 1920 |
| tcttacttgt | ggagccgctg | accattggga | cagtaaaaat | gtgtcctgca | agaactgcag | 1980 |
| tattcagcgg | ggctccaaaa | agcatctatt | gctggcacca | tctgacgtgg | caggctgggg | 2040 |
| gattttatc | aaagatcctg | tgcagaaaaa | tgaattcatc | tcagaatact | gtggagagat | 2100 |
| tatttctcaa | gatgaagctg | acagaagagg | gaaagtgtat | gataaataca | tgtgcagctt | 2160 |
| tctgttcaac | ttgaacaatg | attttgtggt | ggatgcaacc | cgcaagggta | acaaaattcg | 2220 |
| ttttgcaaat | cattcggtaa | atccaaactg | ctatgcaaaa | gttatgatgg | ttaacggtga | 2280 |
| tcacaggata | ggtatttttg | ccaagagagc | catccagact | ggcgaagagc | tgtttttga | 2340 |
| ttacagatac | agccaggctg | atgccctgaa | gtatgtcggc | atcgaaagag | aaatggaaat | 2400 |
| cccttgacat | ctgctacctc | ctccccctc | tctgaaaca | gctgccttag | cttcaggaac | 2460 |
| ctcgagtact | gtgggcaatt | tagaaaaga | acatgcagtt | tgaaattctg | aatttgcaaa | 2520 |
| gtactgtaag | aataatttat | agtaatgagt | ttaaaaatca | acttttatt | gccttctcac | 2580 |
| cagctgcaaa | gtgttttgta | ccagtgaatt | tttgcaataa | tgcagtatgg | tacattttc | 2640 |
| aactttgaat | aaagaatact | tgaacttgtc | cttgttgaat | c | | 2681 |

<210> SEQ ID NO 2
<211> LENGTH: 84000
<212> TYPE: DNA
<213> ORGANISM: Homo sapiens

<400> SEQUENCE: 2
ctaggccctg gggttacaac tttggggctt aactgttttt cgtttcatct tttaacttta     60

```
ataccaaatc tttgttgttc acacagaaca atctttacag aaatgaaaaa gcttggtgac       120
cctcaacctc catatccacc tttgtgttta gcctggcttt ctgcttcatc taggcccctt       180
gagtaactgg cattcacaca cacacttgct tatatgttta ctattcatta cacacattaa       240
aaattttttt tcccattgaa atagtcatag aggtctgtta aataggcctg tatattttct       300
tgctttcctg ggttagacat cttcagacag ttttctttt ggtagcaaaa gcaaatact         360 tcttccccct cctaactttg ctgtatttgt catatacgga aaggagtcgc gagacatcat       420
gaaccccaca tacaatgaag tccttctgga atattttcaa attatcccct ttttctgcca       480
ttactgtggc ctaaactacc ttgcttaaat ggacaatgtc atcattgaat caagaaaata       540
ctgtgatcca ctggcatccc ttttcacctt agccttcata tcatatttat attaaatgtc       600
tgttatatat atttagtatc atcccaccta gctctttaat ggttagagtc caacctacac       660
actcttccca gtgggaatgg ctgctctata aagttctttg tacgtgtttt ttttttttcc       720
taacattcac ttggtgccaa taattatatt ttgtccaatc acttttttttt tttttttaaag    780 agatagggtc tcactctgtt gctcaggctg agcacagtg atgtgatcat agctcacggt        840
aaccttggga tcctgagctc aagcagaccc ctcacctcag cctcagggc aggtgggacc        900 ataggtactt ctgtgccacc acactcagtt attttttaaa tttcttgtag agatagggtc      960
ttgctatgtt gcccaggctg gtctcggagc ttcccacctc gacttctgaa agtactgggg      1020
ttacaggtgt gaaccactaa gtctggcctg gaatatcttg atccatccat tccttgattc      1080
taaacgtcta gcaatttaca tgacatttca caccatgttg cagagttata tactgctttg      1140
atttgcttta tggtagtctc taatttcgtt gatcttcctc ttaaaaatgc cttgttttaa      1200
tatttagtat tacaggactg ataagttcag taatttgata agcaacttag ggataagtag      1260
ttaatttctg aggtttaaat tgctggtttt aaaaaattgt aaattggtgg cctagacaga      1320
tgcattttat cttggagaat gaatgtattc gtgactggaa gtaatggcag ctataattcg      1380
ttacgttatt ttacagtcac atctcagctg cataacctat ttacttttg cagtgttatc       1440 actgattcac aagacaattt tgcttttatc tgggcacatg attgcttgtt tctccttatc      1500
ttttagcttc cctttatata tactttccaa cattggagtg attcagaata tatgtgagga      1560
atgggatggt gatttaggaa aggcgggaaa attatgggct aaatcatctg atgaaaaatt      1620
ctggcccagc gcagtggctc acgcctgtaa tcccagcact tgggaggcc gagacgggcg        1680 gatcacaaag tcaggagatc gagaccatcc tggctaacac ggtgaaaccc cgtctctact      1740
aaaaacacaa aaaattagtc gggtgtggtg gcaggcacct gtggtcccca gctactcggg      1800
aggctgaggc aggagaatgg tgtgaacccg ggaggcgggg cttgcagtga gctgagatgg      1860
tgccactgca ctccagcctg ggcgacagtg tgagactccg tttcttaaaa aaaaaaaaaa      1920
aaaaaaaatt ctggctagtt attaaattca ttaaaaatat ttcttcagat ttttaccca       1980 acagttcata ggtgacctt tttcagtttc cagtatgaac tctcaatatg aatctcagt        2040 ttacatgaca atggtatttt accccataga tacatcctag taaaaataaa ttcggaatac      2100
tcttaactgc attgccacat gaagcaatag gagagactgt atcctaagca gaatccctct      2160
aattcctctg ggttgaggta gcttgacccc ccataaccaa gatcaatttt ttttttttt      2220 ttgagatgga gtctcgctct gtcgcccagg ctggagtgca gtggcgtgat ctcggctcac      2280
tgcaagctcc gcctcccggg ttcacgccat tctcctgcct cagcctcccg agtagctggg      2340
actacaggcg cccgccacca cgcccggcta attttttgta ttttagtag agacggggtt       2400
```

```
tcaccgttat tagccaggat ggtctcgatc tcctgacctt atgatccgcc cgcctcggcc    2460
tcccaaagtg ctgggattac aggcgtgagc caccgcgcct tgcaaatatc ctcacacttt    2520
gcagaggcgg caagtgaaca gtgctcatct tgataaagga tttttaacac tgacacgtgc    2580
ttagaactac gaacagtgga agggtctgaa atggcagcaa tgtcgccctt tcacaggttt    2640
ctagggcgat aagcactgca agctcggcca gccaaagtcc agcggtgggg gaaaaaacgg    2700
ccaaggcagc agcagacata atcaaacagg gcccgggtcg gcggcggtgg ctcacgcctg    2760
taatcccagc actttgggag gccgaggcgg gcggatcacc agaagtcggg agttcgagac    2820
cagcctgacc aagacccgtc tctactaaaa atagaaaatt agccgggcgt ggtggcgcat    2880
gcctgtaatc cagctactcg ggaggctgag gcatgagaat cgcttgaacc cggaaggcgg    2940
aggttgcggt gagtcgagat cgcgccattg cactccagcc tggacaacca gagcgaaact    3000
ccgtctcagg agaaaaaaaa aaaagtagta acgggtccgg cggcagcgcg cgggccgggc    3060
gagcgtctcc cggcaaacgc ggcgccacag ctgagccgac ctccggggcc cgcgccctcc    3120
cctccccggg caccactagg agcggccagc ccggcctcg gctccgcgcg cggggaaacg    3180
agcgcggcgg ttaaaaccgt taccaccccc gagttttgaa ctggttcaaa cttggcttcc    3240
agcacccgcc ccgcccctcc cccgcccggg aactctgcgg cgccggttcc cgccaagagc    3300
cgccggcgct tcgtcccgcc cttcggccgg ttcccgccac ctatcctccc cgcctcccgt    3360
ccgcggcggg ctccgggccc ccgcgatgtc tccggtcccc cgcgtgcctg cacaccgcct    3420
tcctgagagg cgccgtgtgt tcagcgaaag aacaaagaga cggcggcggc gcttccacac    3480
ggccagtggc gtcccttaca gcgaaccccg ccgccgcccg cgcgcgcacg cgctgccagt    3540
gcccgcccgc ccacgagccc tgagcgcact ctgcgtgggg ctggctcggc gcctccgagc    3600
ccggcggggc ctgtgattgg acgggcgccc gcctcgcgtc ccgccaatcg gggcggcgct    3660
tgattgggct gggggggcca aataaaagcg atggcgattg gctgccgcg tttggcgctc    3720 ggtccggtcg cgtccgacac ccggtgggac tcagaaggca gtggagcccc ggcggcggcg    3780
gcggcggcgc gcggggggcga cgcgcgggaa caacgcgagt cggcgcgcgg gacgaaggta    3840
acgccccgct gcgggcggcc cggccggcgg ggctccggga gtgcgaaccg ggcggcggcg    3900
gcggcgccag gacctccccg ccactgctgt gccggtcccg ggtatcgccg agcggggctc    3960
accggggcgc cgcgtttgta ggcgtgcggg gggtggaggg tgagggagga gccccctcc    4020 ccggaaggag ctgtgagctt cgggctggcc cgcgggaccc tgcgagtgag gcagcgcaca    4080
cccctggagc tgcggggcgg ggggcgtgtg ggggctcct ttcccggtgc ttgtcctggc    4140
cggggcgccg gggccggggt cggggcgttc cggtgcccgg tccagggtgg cagctcgagc    4200
ctcaagtctc ctttgtgtgg cgcggccgcg gcgggagcgc ccgggtggga cgggacagac    4260
acaagttggt gggacccagc cgccgagtcc gcactcagac aaaggacgga ctgtgtctcc    4320
ggagggctcg gcgcgagggg aaggggcatg acacccgggc ccgccggcgg gcgggagagg    4380
ggcgtgggga ggcgcgggcc gctgccgggg tgggcagggc tcggccctcg cctcgcgcac    4440 gccccccggtc ccgggcgcgc cgaccccggg ctgggccgc ggcgctcgcg gacgacgtt    4500 cgcggcgggg aactcggagt agcttcgcct ctgacgtttc cccacgacgc accccgaaat    4560
ccccctgagc tccggcggtc gcgggctgcc ctcgccgcct ggtctggctt tatgctaagt    4620
ttgagggaag agtcgagctg ctctgctctc tattgattgt gtttctggag ggcgtcctgt    4680
tgaattccca cttcattgtg tacatcccct tccgttcccc ccaaaaatct gtgccacagg    4740
gttacttttt gaaagcggga ggaatcgaga agcacgatct tttggaaaac ttggtgaacg    4800
```

```
cctagtgagt tgccactttc taaagaatcg taatccttaa acattacaag ctgttttggc    4860
caacttgtgt gatacatctg agaatggcga caggtgctaa cgaaatcaac tgtcattcag    4920
ccagattatt ccccaaatcc cgacgggttg aatgaggatg aggtggtaga agtaggtgat    4980
caaaatagaa tggctatgac aaatgtgtgt ttagattata cggttagcag tttcttatta    5040
attggtctcg ttttctgtga acaatagctt tggtgattca gaaaagactg catggagaaa    5100
tgtttgttgc ctaagaaatt taacgtgtgc tgtccacagt taaacttcct ttatcacaca    5160
ggatctgtaa catttaaatt catttggaaa taaaaatgtg tctttgctat ttacttaaag    5220
gcttgctttt tagggttcaa gcaagttatt attagtttaa ttttgtggcg ttttgatgtc    5280
atcataaaac agcatttaat aaaccttttga aaaacacgaa tgctgtcaca attgaatgta    5340
gtttatactt ttaggggttt tggagtttat tttctattac tcttcataag cattagcaac    5400
taattcatgt ttaggaatac tgtacaagtg tgtaatccta acttgtttat ttgtaatttt    5460
atttgcagga aaacaagtat ttaagatata ttttaatttt ctattcatgg tctctaaagt    5520
taggaatagg taggattcta gtcatagata taaagcgtct tgttctctct tttcggaggt    5580
gtgtggggtg atgtaatatt taaggttttcc cggaaacagg aacactgcat cttaaattct    5640 cgttttttgtg gaaagtgaat atattccaag aaaacaagtt agaaaaacat aggcgttctt    5700
ctggttgcac tgtcctatat gataaagatc taatgtgcat ctgctaactt aaggtttcat    5760
aaaaatggag acaaataaat gcaatataaa tttattacat atattttgga gagtgttgac    5820
accactgtac gggcattcca ggtgctggtc taagtgttga gacattataa caaaaaagta    5880
acgtttatat tagttactat taattctgta tttaaaaaat cctattaata atcttgtcca    5940
ttatgagata aggtagttat gcagattttt ggcagaaatt cggatatttt aggatacata    6000
tgtgtgtgtg tgtgtgtgtg tgtgtgtgcg cgcgcgtgtg tgtgtgtgta tatgtttttt    6060 ttttttttgag acagagcctt gctctgtcgt ccaggctgga gtgcagtggc tggatctggg    6120
ctcactacaa tctctgcctc ccgggtttaa ggaattcccc tgcctcagcc tcccgagtag    6180
ctggaactac aggcacgcac cacgacaccc ggctaatttt tgtatttta gcagagacag    6240 ggtttcacca tgttggccag gctggtctcg aactcctgac ctgaagtgat gtacccgcct    6300
ccgcctccca aaatgctgat ccagacgtga gccaccacgc ccagcctagg ataaaaattt    6360
ctaactttgc ccttgagtgt tctctgtatt tgataattac tattctttgt acttgccatg    6420
agatattttg aaaaacatct ctttggggaa ttggtttaaa aattcatatt aaattatttt    6480
ctggtacaat tgagaatgta tttagtcagt ttaagtagca gtgacttaaa acacacttgt    6540
tgatctagtg tagttagaaa aagttctgat actttgatac ctagctttgc cttgcacaaa    6600
tacatttaag tgaatatctt tatgttggcc atttaaaaat tttaggcaaa tttctccaag    6660
tcatactgga attttcccag gataccttcc ttcttttgag gtagtgtgct caaggattct    6720
gaatttattt cagtattacc ctttacatga gcagtgattg agaagttga tctgcttttt    6780 aaaaaccaac aaggacaaat cctccaatat aatgtattct gtggttaatt agcaatgatt    6840
tatggattag ccttgaagtc tttatatcag tatagatgac aaattttctg taaatcatga    6900
tagattctat atgagtaggt gaaatcttcg ggggagagca taagtgaaca gcagcaattc    6960
attaaattca gagaaaggtt catggtcaga tgatacatac tttaccttct ggaggtcttc    7020
cctgaattcc cactcttgtg ttcccacagg gttttatcat atttttattgt agcatgactc    7080 aattgtattg taatcacttg tttatgcatc cctctcttcc ctacagtcaa agtgcctcct    7140
```

```
ggtagaggct ctgtcttatt tttttctttg tatacctagt acctacgttg gtatttgcta    7200
gagaataggg gttttaaata tagttgaatg aattaaggaa atatgaaaaa tgtagggaaa    7260
taatttgaca aaggaacttg caaagtgaac aggatatgtt agtattcatg tgaggaactt    7320
tgaaatgtgt ttttctccct ctttaatagg gaatgattac aaagaaaaat agttgtcaag    7380
gtgaacaagt tccaagtttt tcctagttat aatctgtagt actaaacatt agatatcctt    7440
tagatgcaac tattcactc ggacaactgg agagaacttg atgaatcatc tggatattta    7500
gtaatagtat ttgcttaatt tgatttaatg ttgatattga tgatctcttt gcaaaaatat    7560
aaggaaggga aagggcgaga gagggtagta gatctttaa ctgaaaagct gttttgttat    7620
aattcatgag ttctttattg gagtaaattg aggtaggttt tggagctaaa actgaaggat    7680
gtagcgacag tgtaattgga tcatttattg ggatgctttt catcattctt ttaaaatgat    7740
ttaaatacag attagcaaat ttagtgatac ctcaaaagtt acagctggta aatttctaag    7800
atagttgcac cattccatat cttgccactg ttccactact tggtataaaa atatgacaaa    7860
tttgtgttta gattatgtgg ttagcagttt cttaataatt ggtcttgttt tccattaaca    7920
atagcaagac agaacaagat catagctcac tgcatcctta aactcctggg ctcaagggat    7980
cctcctgtct cagcctcctg agtaactggt attaccagtg caccattg tggtgactta    8040 tttaatttt taattttttg tagagatggg atcctgcttt gttgcccacg ttgatctcaa    8100
actcctggct ccaggcaatc ctcctgcctt ggcctcttaa agtacaggga tgacaggctg    8160
agccattgtg tttgacccag atacttttt tttttgagac ggagtctcga agtgattct    8220 tgtgcctcag cctcctgagt agctgggact acaagcgtgc gccaccacgc tcggctaatt    8280
tatttattta ttatttatta tttatttttt tgagatgcag tgtcactctg tcacctagac    8340
tggagtgcag tggcaccatc ttggctcact gcaacctcca cctcctgggt tcaaatgatt    8400
ctcctgcctc acctctcaag tagttgggat tacaggcatg caccaccagg cctggctaat    8460
ttttgtattt ttagtagtga tgggatttca ccatgttggc caggctggtc tcgaactccc    8520
gacctcaggt gatccacctg ccctggcctc ccaaagtact aggattacag gcgtcagtca    8580
ctgtgcccag cctccgataa ttttttatatt ttagtagaaa ctgggttca ctgtgttggc    8640 caggctggtc tggaactcct gacctcaagt gattgacctg cctcgtcctc ccaaagtggt    8700
gggattatag gtgtgagcca ccacacccctg ctgtgttgtt tttgttttg tttttgtttt    8760 ttgttttttgt ttttgatat ggagtctcac acttgttgcc caggctggag tgcagtggcg    8820
tgatctcggc tcactgcaac ctctgcctcc tgggttcaag cgattctcct acctcagcct    8880
cccgagtagc tgggattacg ggaacgcacc accacacctg gctaattttt gtatttttag    8940
ttgagatggg gtttcaccac gttggccaag ctagtctcga actgctgacc tcagatgatc    9000
cgcctgcctc ggcctcccaa agtgctggga ttacaggcgt gagctactgc gcacgcctgg    9060
cctggatact ttttaaacat ttttaaatta aaattttttt tttggagaca gggtcttgtt    9120
gtcacccagg ctggagtgca gatgcgtgat ctcagttcac tgcaacctct gcctcctggg    9180
ctcaagcgat ccttccatct cagcctccca agtagctggg actacaagtg catgccacca    9240
cgcctggcta atttttgtat ttttttgtaga cagggtttt tgccatgttg cccaggctgg    9300
tcttgaactc ctgaactcaa gagatccacc tacctcagcc tcccaaagtg ctgggattat    9360
aggtgtgacc cactgcaccc agcttttgtt tttaatattt gtaagaacca ccttgtgtct    9420
gccaacaggc gaattaacaa aatgtggtat ataaccaat gaaaacataa aaggagtgaa    9480
ataaagacgt aaaaggagtg aaatttcaaa ataaaagtaa aaagatttca aaataattca    9540
```

```
gacataaaag gagtgaaatt ctgatacatg gatggagctg gagaatatta tgcttagtga    9600
aataagccag atacaacctt ttgtacaaaa atacaaaatt gtatgatctc atttatatga    9660
ggtagttaga agaggcaact ctatggagac agaaagtaga atagaggtta ccagggctgt    9720
gaggggagag gtgaatgggg agtttaatga atacagagtt tctgtttgga atggtgaaaa    9780
aattctggag atggataata gtgatggttg aacaatattt tgaatatatt taatgccaca    9840
gaattgtaca cttaaaaatg gttaaaatgg taaattttac acgatatgta tctgtatcta    9900
tatatatctc tctctatatc tatatatctt accagaatac aaaatttaat aacacactcc    9960 gaaaacctt  acagatgagg aaactgaaga aaactgtcta caggggagga gttaagaatt    10020
tgcccaggat tattcagctg ggaatttgca ttcgggatcc aaacttagtt ctgtttcact    10080
acatattatc tactccatat tatctgttct gtgttatctg ctggctttct gggtgattaa    10140
agatatgtca gctccgagaa gaatgagttt atttgaatca ttcagaaagt tacatttaaa    10200
agtaggtaat tgtagtttga tggaaggtac agtgtgaaac cctagacaga ctaaaggtta    10260
actttgagga tttctttctc agccagagtg gtaatagtat gcatttgaga ggggaggaga    10320
gtagagttct aaggatgtgg tcttgggaga cagtttcttg ggttccagtc cctgagctac    10380
caatttgtgt ctggggtgtt atcctcttga tgtcttagca tccctatctg taaattggtg    10440
aggataatga taacatctga taaggtggtt gtgaggatta aaggaattga tacatgtgaa    10500
atccttagaa ctgtacctgg caaaaagtgt ttgataaatg attttcagtt attgtgccaa    10560
tattatttta gagttgatgt actttctcat taatggaacc aaaacacttct caagttaaaa    10620 ttacgtgctt aggactggta agttacaaaa atggtaccac acgttttatc tatttcaatt    10680
tagaaatgtc tgttgattaa atgtgttcgc tttaaactac tgaaacaatg tagacattta    10740
taaaatgaaa gcgtattgat ccctgttatc tcattcgcta cctttaacgg tttggtgtat    10800
attcttcccc aaattttcaa atatattcat atatgaatat gtattttac  atacatttta    10860 taaaaatggg accaagttat ttggttctaa catggctttt ttttaaggtc aatacaaaga    10920
tctgttttat taaaaaataa ttgatattcc tttagggctc actatatgct tggtactctt    10980
ctaagtcatt atttatata  gatactataa tatcgagaga tggagagatt aagtaacaac    11040
tagttagtgg tagaggaagg attttaattt gggtacgtta gcttcaaagt cctgatctcc    11100
cagccaggga tcatttttgg taaggcctgt gagctgaaaa cgttaacact tttaaaagag    11160
ttgtaaaaca ataccacccc acttccctga agaacatata agggagacta gataccgcct    11220
gccaagccta aaatacttac catgtggccc tttacagaga aagtttgctg ccccttgctc    11280
taagccatcc agctgtacct ctttggtgta aggggggtgc atagtattcc agtttatgaa    11340
tgtgcattac gcagcaaacc aatctgttgt gattgacatt gttttctctc ctgaaaagaa    11400
gtgaacatcc ttatgtatct ttgaacattt gtgtgacaat tttctataga gttggctctt    11460
tcaagattat gaacatttct agttttaata ggtgttgtca agttatatta atttttagtt    11520
aaaacaacaa ctgtattgaa gtataattta catacaataa aaagcacaca tttgaagggt    11580
atgatttgag gagttttgac aaatgtatgc acctgcaccg ctgcctggat caagatctat    11640
aatggttgcc atcatctcag agtcctttca tcctcttta  cagtcattct ctcaacttt    11700 tttttttcc  ctccaagatg gagtcttgct ctgtcaccca ggctggagtg caatggcatg    11760
atctcggctc actgcaacct ccgcctcctg gttcaagca  attctcctgc ctcagtctcc    11820
cgagtagctg ggattacagg cgtctgccac cacacccagc taatttttgt agttttaggc    11880
```

```
gagatctcag ctcactgcaa ccttgacctc ctgggctcaa tcgaacctct cacctcagcc   11940
tcccaagtag ctaggaccac aggcatgtac caccatgccc agctaacatt tattattaat   12000 attttttgt agagatgggg ttttcctgtg tcgcccagga tggtttccaa ctcctgggct    12060
caaatgattc tgccttggcc tcccaaagtg ttgggattac aggcatgagc cgcggcacct   12120
gacttgtagt aaactctctg aattaatatt ccattgtagg catgtgctac agttttaaa   12180 ttcatttacc catggatgga cataggac tgttgtcagc tgttgataaa gctgctatca    12240
ccatttgtat gtcttttcctg gacatgtttt agtggtaaat attgattta ctttgtaaga   12300 aaccgttaaa ctcttttcca aaatagttgt accattttaa attgaaagtt acagttgtaa   12360
ctgtgcagga gttacagttt cttcacattt tcattgacac ttcgtgttgc cagtctttta   12420
aattttggcc atcaaatgag tattaagtat ctcattgtgg gtttgtgttt ctcagatgat   12480
caatgatgtt ggaacatctt ttcatatgct tattggccat ttgtgtactt tttttggttc   12540
aagccttttg tcccttaaaa aaattggatt gtttgtctgg ttgagtggca agaggtcttt   12600
atatgttctg ggtacatagt cacattatct gtcagattgt gttgcaaata ttttattgtt   12660 cattttgtt tgattttgtg tattttaat actataaga tcaagttaaa actttaatat    12720
gggaagcata atcagataaa ttatgtgaaa caaattgtcc ttaattcacg agtcatttaa   12780
ttagtgtaac aaaatgttat gcatttgcag aaacttgtaa actaaaagga tattattcat   12840
atgctgttag gtgtatggat gataattttt tttaattaaa ctagttttga aaattattgt   12900
atttagtaat tctcttcatt ttgcataatt caaacctttt catttattag tgagttaagc   12960
cttaaatttt ttcttcaaag gataaatgag aatattaaaa gtaaaagtg accttgatct    13020 tagaatgggg tatgtagaaa tgatgattgc caaacttagt ttccctactt tgacaatcaa   13080
gtaaaatttt ttttttttt ttttgagacg gagtcttgct ctgtccccca ggctggagtg    13140
cggtggcgcg atctcggctc actgcaagct ctgcctcctg ggttcacgct gttctcctgc   13200
ctaagcctcc cgtaaatttt tttattatag aaatggatgg cttttcagat tatatatact   13260
tggtttctat acactatttt attttgtaa agtagcagtt cttttgctca acacctgaat    13320
tgcccccaca ataaatttt agttttctt caatattcaa gtaatacata acttttcctt     13380
ttcctgttta acaaagaaaa aaatatataa agcaagctgt tggacctcca ttgggtgttg   13440
tttaccacca ctgtaggtga tcgtggcatt gtccacctca gtcttctcat ggctgtggat   13500
tcaagttaag aaattcctga aggtagcatt ccaggtagtc tgtagaacag cccaaactct   13560
ctgaattagt attatctctg ataggtgttt tttttttctt tgcttttta tttgagacgg    13620 ggttttgctc tgtcacccag cctggatttc agtggcacaa tcttggctta ctgcaacctc   13680
cacctcctgg gctgaaacaa tcctcccaca tcagtctcct gagtagctgg gaccacaggc   13740
acatgccacc atgcccagct aattttttat attttgtta gagacagagt ttcactatgt    13800
tgcccaggtt ggtctcaaga ttcctgagct caagcgatgt tcccatcttg gcctcccaaa   13860
gtgctgggat tacaggcatg agccgctgtg cctggccctg gtagttttct tcttatatct   13920
ttctcctgtt gatctcactt gattttctta ctagtctaca ggaaatttca cgtggagatt   13980
ctgtgcctgt cctctttctg gaatatcttc cttattttag catctcaaca tgctgttcag   14040
cttctggctt gaaaccaccc ctctcccatc ccaaccaagt taagcagctt ctttcctgct   14100
tagaagtacc ataacatgtg tattaatctt ttttttttc tctctccttc ccttcatttt   14160
aagctccttt ttattaatct gtagggcaga gcttagaaaa aggttttgt atattgtaag   14220 tactaataaa atatttgtga agttgatttg ggacttggga gacctctctt ctgtaagcaa   14280
```

```
ctcaataaat aattatttaa gtaccatcct cacccagtgt actgttagct gctgttatga  14340
tattgattac tgtaaaattt taaagtatat ccttggtaga ctgttgatca aagtcagaaa  14400
gcttgagaaa ctctgaggca aaaaaaaaaa aaaaaaaaaa aaatgaagag catgaaatga  14460
ttctgcaaac tgatcttaca atgatctttc tttttttttt ttttttttttg agacagagtc  14520
tcactctgtc acccaggctg gcgtgcagtg gcaggatctt ggctcactgc agtctctgcc  14580
tcccaggttc cagtgattct cctgcttcag cctcccaggt agctgggatt acaggcacac  14640
gccactacgc ccggctagtt tttgtatttt tagtagagat ggggtttcac tatgttggcc  14700
agactggtct tgaactcctg acctcaggtg atctgcctgc cttggccttg caaagtgcta  14760
ggattacagg catgagccac catgcccggc ctctttttttt cttttttctt ttcttttttg  14820
tacacagttt cactctgttg cccaggctgg agtatagtgg cgtgatcata gctcactaca  14880
tcctcagact cctgggttca ggggatcttc ccatctcagc ctcccaagta gctaggacta  14940
tagacgtgag acacgatgtc tggctaattt tttacatttt ttatttttg tagagttggg  15000
gtcttatatg ttgcccaggg tggcctgcca ccttgtcctc ccaaagctgg gattataggc  15060
ttgaatcaga tcccagtgat ctttatccct cagctgcatt tatatgggct aaattcatac  15120
atagtatatc aagatgtctt caggaagttt aaaaaaaaaa aggtatcaaa aagacagtat  15180
gtcatgactg ctttatctat tttagtctct tagttttga tactaaagac tagaccggag  15240
aaatgcttta acaaatcaca aaaatctaag aaaatagaca gttaattatt tttaaacagt  15300
ggaagaattt caatcataat taaagcagct tttgtatttt ttgatgtcat agcctatagt  15360
gaaatttcat atattctgtt tgtagataca tgagttccta cgatatgctt gcacataata  15420
gaactaatta ctatttgttg agaacctaac ctgtacctaa tatacatgta gtttctaaat  15480
caaacatttt acttttttta aaaattgtaa aaagcccata gtaaattaat catgtttacc  15540
atttaaaaat gtacagttca gtagtgttaa atacattcac attgttgcac aacagatctc  15600
tagaactttt ttgtcttgca gaactgaaat tctgtaccca ttgagcacta attcccactt  15660
cccccctcccc ccaaattctt ggcagccacc tttctacttt ctgtttccat gattttgac  15720
tgttttagat acttacatgc atgggattaa acagtatttg cccctttgtg attagcttat  15780
tttgcttagc ataatgtcat tgaggttctt ccatgttgta gcatgtgaca gaatttttt  15840
cttttctgta aaggctgtat actatttcgt tgtatgtata gactgcattt taaaatccat  15900
ttatctattg gtggacattt gggttgcttg gtgatttggt gattcactat tcatggttag  15960
ccaggagtaa tatgcagtaa atgttggtat acaaatatct ctttgagatc ctgctttgaa  16020
ttcttttgga tatatggttg cccattgaac aacacagctt tgaactatgt ggatccatct  16080
ataagtggat ttttttcaac cagccataga tagaaaatat actattcggc tgggcgtggt  16140
ggctgatgcc tgtaatccca gcacttggga ggctggggtg ggaggatcag ttgaggccag  16200
gagttcgaga ccagcctgga caacatagtg agacctcatc tctacaaaaa ataaaaaagt  16260
tagctaggtg tggtggcatg cgcctgtagt ttcagctact taggaggctg agacaggagg  16320
attgcttgag cctgggaggt cgaggctgca gtgagctgtt attcatgcca ttgcactcca  16380
gccagggcaa cagaacaaga ccctgctcaa aaaaaaaaaa aaagaaaata cactatttgt  16440
gggatgtgaa acttgtgtat agggtgggtg ggcttttttgt atatgcaggt tccataggtc  16500
agatttgggg gtttgagtat gagtgaattt ggatgtatac aggtggtcct ggaaccagtc  16560
ttattcttcc tcttcttttt tttttttttt tttttttaat tattcgtctt ttattttttg  16620
```

```
gaaccactct tctgcatatg ctgtgggatg actgtatatc cagaattgtg attgctggat    16680
catatggtag ttctatttta atgttttgag taacctcagt actgttttcc ataatggctg    16740 cacgatttt  acagtcctac ccacagtgca caaaggtttc gatgtctctg catccttgcc    16800
aacacttgtt attttctgtt tcttttggta gtggccaaca taatgggtgt gaggtgctat    16860
ctcattgtgg ttttgatttg cattaacaat gttgagtatc cttcatgttt attcacccca    16920
aatattttac ttttgaattt attgaaaatc atgcatttta attatgtaaa actcaatacc    16980
atgcatcatt tgttaaatgg gaaaaggaga atttgtcctt atgactatta taaaatattc    17040
taataaggtg aaccttttt  tttttttct  ttgagacaag gtctcgctgt gtcatccagg    17100
ctggaatgca gtggcgcagt cttggcttac tgcagcctct gcctcctggg ttcaagtgat    17160
tctcctgcct cagcctcctg agtagttggt attacaggta tgcaccacca cacctggcta    17220
atttttgcat ttttatagag tcggggtttc accatgttgg cctggctggt aataagatga    17280 acttttatact ttttttttt  tttttgagac agagtcccac tctgtcacct aggtgcagtg    17340
gcacgatgat ggctcactgc agccttgacc tcctgggctc aagtgatcct ccacctcagc    17400
ctctcaggta tctgggatta caggtatgca ccaccacccc tagctaattt ttgtattttt    17460
ttgtagagat ggggtttcgc catgttgccc ggctggtct  agaactccta ggatcaagtg    17520
atctcccacc ttggagtccc caggtgctgg gattacaggc atgagccact gcattgggcc    17580
agaactttat acttattaaa cagtatgctg atgataggaa aaaactgtgc aatccttatt    17640
cataaaattc tgatctaaaa cgtgttatat taaaattaat taataatgca agcaaaattg    17700
gcaaatttat ttgtaaaccc cattttgggc tacttcgaaa attatttatg gatcagaaaa    17760
ggttgggaaa tactttttcta gagtaattga gcaggccctg tagatggcag aagtgttgct    17820
tgaactggcg tagaggaaga aagtgttgaa ttgccccact taattcctta agtaattttg    17880 cctcttttgga gaatatttgc ctgaaataga gaactcaagt tatgctatga agattctttt    17940
tgaaaaatag agacagggtc tcacattgcc caggctggtc tcaaactcgt gggctcaagt    18000
gaccctttca ccttggcctc ccagagtgca gggattacag gcatgagcca tcatgccaga    18060
ccaagaagat atttttggagg gctacatccc accagtagct tgatgttgta caaagagtgg    18120
taggctctgg gcgaggctct gccattatac tagttgtatt tccttggcac gtagcttttg    18180
tggatctctc ctcttcatgg tgacatgaat gagatgaata aataatgaa  caacttgtgt    18240 ttactgagta tctaccatgt atgtgcctgc agagaggatg tcttcatttt gcagatgaag    18300
taattagtaa ataacttgcc taggttccct caggtagtgg gcccttgaag aatgggcttt    18360
tatggccaag tgcattggct cacgccagta atcccagcac tttgagcggc tgaggtggga    18420
ggattgcttg agcccaggag ttcaagacca gcctggacaa caaagtgagg ccccatttct    18480
acaaaaaatt agccacatgt ggtggcattt gcctgtagtc ccagctgcat gggagagtga    18540
ggtgagaggg tcgcttgagc ccagaaggta gagactgcag tgagccgtgt ttgcacccct    18600
gcactccagc ctgtgtgaca gagtgagact gtgtctccaa aaaaaaaaaa aaaaaaaaa    18660 aaggctattg ctgcctatag ggtccttttt agtgcaaata ctaggattct aagcacttgg    18720
tttctgttac ccaggtcaaa ctatttcttt ggagagtttg attaccatca caggtgatgg    18780
taagattctc cctagctggc atttaatcca gtggttatat gcatctttcc caaattcttt    18840
atcaagttgg tcaattcata gaacatctaa tgctgattat aagcctatta tcttgcttgt    18900
gtctctgcac tatgggcata atagcaccta aaagcttttg ctataatgga ctatgatgta    18960
tctgaataaa ttacctttat aaacaatcaa atctaaattg gcaagttcaa atttacccaa    19020
```

```
tttttcttat agaatttacc tttgcagtta aagaaataat tgttttttac catttgtcta   19080
gtatgacttg ttatttacaa atagcatgta actggccagc tgtactatac acattttcta   19140
gaaaagaaaa tttcttcaaa tttcttattg ggtgccttag tcttttaccc attagggcta   19200
ttcaaataaa gaatgagata ttctcttatt ctctagaaag agacattcta tactaatgga   19260
aataccaact tttaaatcta gactaccaaa aaaaaagtca tgttttcta ccctagaggc   19320 tatagattct taatgtcagc cactcatcct ggccctctca tttcttctt ttcccatatg   19380 gaagttctag ggtgatatag tttggctctg tggccccacc caaatcacgc gtcaaattgt   19440
aatccccaaa gttggaggag gggtctggtg ggaagtgatt gaatcatggg ggcagacttt   19500
tcccttgctg ttctcctgac agtgagttct cgtgacagtg agttctcgtg agatctggtt   19560
gtttaaaatt atgtagcacc tgccactttg ctctctcttc ccctgcatc agccacgtat   19620 aatgtgctgg cttccccttt gctttccact gtgatgataa gtttcctgag gcttccccag   19680
ccatgcttcc tgtatagcct gctgaactgt aagcaaatta aacctctttt ctttataaat   19740
tacccaccct cagctctttta tagcaatgtg agaatggact aatacagaaa atatgtacca   19800
cagaagtggg gcatcacaat aaagatacct gaaaatgtgg atgcagcttt tggactgagt   19860
aatgggcaca ggttggtaca gtttggaggg ctcagaacaa gacaggaaga taagggaatg   19920
tttggaactt cctagagact tgttgaatgg ttttgaccaa aatgctgata gtgatatgga   19980
cagagatggc taggctgatg aagtctcaga tgaagatgag gaacttattg gggaactgga   20040
gtaaaagtca ctcttgctat gtgttagcaa agagactggc agcattgtgc tcctgctcta   20100
gggatctgtt gaactttaaa cttgagatgt ttagggtatc tggcggaaga aatttctaaa   20160
agcagcaacg tgttcaagaa gtggcctggc tgcttctaaa agcctgtgct catttgcata   20220
agcaaataaa tgacctgaaa ctggaactta aatttaaaag ggaagcagaa cataaaagtt   20280
tagaaaattt gcagcctgcc atgtggtaga aaagaaaatc tcactttctg gggagaaatt   20340
caagctggct gcagaaattt acataagagg acgatacatg gggtaaaatg cttttttcctc   20400 ccctaaaagc cttggtatta atctggaaat agcaggaagg taactgtagg aattatataa   20460
tgggtttccc tgtgcttggt catgtctttg tatcattttcc ataggtcagt ggagactcag   20520
aaaaccagtt tctctgggct tttgataagt aatgttatag taatcaacag atggtaactt   20580
tcggtaaaac aaattgtctt catctgtttt gtgctggtat aacggaatat ctgagactgg   20640
gtaattttta aaattatttta tttatttatt tttgagatgg gagttttgct cttttgccc   20700 aggctggact acaatggtgc gatctcggcc cactgcaacc tccgcctcct gggttcaagt   20760
gattctcctg cctcagcctc ccgagtagct gggattacag ttgcctacca ccatgcctag   20820
ctaattttgt attttttagta gagacagggt ttcaccatgt tggccaggct ggtgttgaac   20880
tcctgccctc aggttatctg cctgcctcgg cttcccaaag tgctgggatt acaggcgtga   20940
gccaccacgc ctggccaaga ctgggtaatt tataaagaat agaagttggc caggcacagt   21000
ggctcacgtc tgtaatccca gcactttggg aggctgaggc gggtggatca cttgaggtta   21060
ggagttcgag accagcctgg ccaacatggt gaaaccccat ctctaccaaa aaataaaaat   21120
tagccgggtg cgttgatgtg cacctgtagt ctcagctact tggaaggctg aggtgggaga   21180
atcacttgaa cccaggaggt ggaggttgca gtgagacaga attcgccac tgccctctag   21240 cccaggcaac agagtgagac cctgtctcac aaaaggaata aatatatata tatatgcata   21300
tatgtatata tatatgcata tacgtacata tatatgcata tacgtatata cgtatatgta   21360
```

```
tatgtatata tacatatatg catatatatt atatataata tatagtgtat acaatatatg    21420
tatatacgta tatatatgta tatatgtata tatatgtata tacgtatata tatgtatata    21480
cacatatata tgtatatacg tatatatatt tttcacagtt ttgggggctg ggaagtttaa    21540
gatcaaggta cctgcatctc atgaaggctt tcttactgtg tcctcttata gcagaagata    21600 gaagggcaa gctgggaata actccctcag tcagactctt gtataagggc attcacaagg     21660
caggaaccgt cgtggtctaa tcacctctga aggccccat ctcttaatac tgttacatgg     21720
acaacacctg agttttttgag ggacaccttc agaccatagc acagatactg acaagtctca   21780
tcaattatta agtaaatagt acttgaaggg tttgaaattt tgtagtaccc cggcagtgtg    21840
tttatatttg tgataaattt taagtatagg aaaatcatgg aaagacttac tgctcataac    21900
tgccgtacct cgtttacctc tatctttccc taaactacta ctgttcttag caagatcatg    21960
aactgtgggg ccgacataag ccagaggagt ttctgaagag tctgcttcag tgagggttc     22020 tgttgatagc catagaataa agaaatggca ctttgcagac attggtactt ccttgaaaga    22080
actggctgtg gcatatacag aactcaaaaa ttgaaattac tagataatgg ttacttggtt    22140
tagattgcct ggaaattatg agaggttctg taaatgcttt gggattagta gtttgaacca    22200
cctagtccat tttatgattc tgtcttcaga atatagaagg aattgcatct tatttgggga   22260
ttaggatata aagttagtgt acaaggcaaa atagcatgta ggcaaagtta cccatgcaga    22320
gtttgtggga agatgcctta ccacaaacca gtaccttctt tttaggttca agaccagccc    22380 attttttcctc tagaatgaga acagatcatt gctcttctgt tgagcacaga gttgttggtt   22440
tgtacttaag ggcaatcctg ttagaatcac tcctgagtgg ctaaatatct tcagtctgag    22500
agacttgtcc agcaggttat gggaacagca gattcatgtc acctgtctct tgctcactta    22560
ggcaaacgct tagtgtctgg aatggtgggt agaaccttg tatttactac caaaattgag     22620 cttctctga cattttttgct caatgtatgt tagatttgtg taagttaaat tagatgttgg    22680
cttatgcgtg gtataagatt taaaatagac ttccttagcaa aaagaacacc tggtatcaga   22740
ttgacttacc ccttcatttt gtttgctttt attcagtgaa gtgttgaaat aacaggtatc    22800
tcatgtctca tctttgaatt ataatgaatt ttgtatcata gctttagttt ctggtacttt    22860
tttttttttt tttttgagac aagtctcgct ctgtcaccca ggctgaagag cagtggcgcg    22920
atctcagctt aacgcatcct ctgcctccta ggttcaagcg attctcctgc ctcagactcc    22980
caaatagctg agatcacagg cacctgccac catacccggc taatttttgt attttttagta   23040 gagatggggt tttaccgtgt tggccaggct gatctccaac tcctgacctc aggtgattcg    23100
cccgccttgg cctcccaaag tgctaggatt acaggcgtga gccacttggc cccagcctct    23160
gatacctatt ttttttccgtt tttcctccaa cagtgtttct gtaaactgag tatatactcg   23220
atgaaatgag aagatttaac ttataaaatc gatttagtat agttttcaag aaaaacttaa    23280
actttttttt tcttttttttc ctttttttttt tttttttgag acagtctcac tgtgattgcc   23340
caggctggag tgcagtggca caatcttggc tcactgcagc cttggcctcc tgggctcagg    23400
tgattggttc tcccacctca gcctccagag tatcttggac tataggcaca tgccatcacg    23460
cctggctaat ttgtattttt agtagagaca gggtttcacc atattgtcca ggctggtctc    23520
aaactcctgg actcaggcaa tctgcctgcc ttagcctccc aaagtgctgg gattacaggt    23580
gtgagccatg gccccagct gaaaacttta acctttagat gtcaattcag ttagtgagtc     23640
tgttttatct gttgttcaag caaattcttt aaaacactta aaatagttca gttcttcagt    23700
tggttgaaat ttatatggcc atttcttttc taagcagtac tctcagataa acaccagaat    23760
```

```
gctggtctat ggacttcagt ttgaaatcaa tagtttactg tcttgctgga aggaggaaag   23820
tgatcttact gttgtggaaa atatatcact gcagaatcta ctcactttg ctgcaacggt    23880 caagttaatg ttttctatca ttcagctaag attgctaaat tagtataact ttccttttgcc  23940 tttgaacttt ttagcactac agaaaccagg actacaaata tgttctttac tttttttctgt  24000 tattttcccc tatcatgaga cttcttgaag gcgaatgctg ttcattatgc tttctcatct   24060
gtactttcat gtacatgtaa tccactgtag tgaaggcact aaaacctgtt gtattttcca   24120
catttcgata gatctctcac aggatttaac acttttggaa tgctcagtaa attattattg   24180
actgcttgat aatacctctt tgttcctgcc tttccccaag tccttcaaca gaagtttctt   24240
ctagcacttt gcaggtcagt tgagtggact atttgagtcc ctcacagtaa tgagcttgtg   24300 tgttttttgtc attctttttt cttttttga aaaaacaata gagtcattta aggaagcaaa   24360
aaggtccctg ggtcaagatt tttattttat cttttatggt ggtagggtga ggtgtgagta   24420
tttagggaga tggttggtag gatggcgttg tcttagggtt gcaggaggat cagaagggtg   24480
actgtaacta ctgatgatat cttacagtgg tgaaggagaa gataagtgaa aacagaggca   24540
atttgtttaa acgaattta gtagatatta gtctcttaat ttggcactga catatgacag   24600
attatttcat ttaaattctg tagtttgaca ggtataataa agtacccttc attaaatatt   24660
cttcacatat actcttgttt gcctttttct agttgcaaga gtggtgattt ctatgtttca   24720
ttataaattt tagaaatata taatttgaat atattgtctg ttctaggttc tctgtgagtc   24780
aagaaaaggc agggtattat gacttcggat tcgtatgatg tctggatata tttaagggga   24840
gcagttctca aagtgtggcc tgggattatg ggatcaaaac tattttttct ttctttcttt   24900
cttttttttt ttttttttgag acagggtctc actctgtcat ccaggctgga gtgcagtggc   24960
gacatcttgg cccactgcaa cctctgcctc ccaggttcaa gtgattcttg tgtctcaacc   25020
tcccagaaac tattttcata ataatactga gttgttcctt gcttttttt aaaaaaacaa    25080 aacaaaacaa aaacaaacaa aaaaaccatg ttggacattt gtacccacgg tgcaaaagca   25140
atgaataaac actgttggca ccttagcact tgcagttaaa aaagccagtt ttgtttgaga   25200
atgtccttga tgaagtacta aaaatgatta atttattaa atcttgatcc ttgcgtgcat    25260
gcagttgtaa cattctgtgc aacaagatgg gaatgtgtgt aaagtgcttc tgctgcatat   25320
tgaggtatgt tgggttttga gcaaaagcac ttacgtgatt aagttgtgag ctccactagc   25380
cacttttttc atggaaattt cattttact taaaagagg tctgacaaac catgattatt    25440
cagacttagg tatttggcag acttttttta aatcaatgaa gtgagactgt cacttcaagg   25500
aaaacaactg accatatttg ttggcagaga gaacatttgg gctttcaagc aaaaattaaa   25560 attttggaa aactttgtc tgttactgtg agcatgacag cttcccagta cttaaagact    25620
ttctgatgag attaatgggt ttaacaacat gattttttga aatatgccaa cttctggaaa   25680
atctgcgtaa ctcagtggac cagtactttt tagatgagga atgatgattt ataacattgt   25740
gcctgagtta aagattcatt taaagtgaat agactaatga atgttaatgt ggcagagtag   25800
gaaaagttca ctgatacaat ttcggattcc atgttgcatc taatcttgta agaaagaaat   25860
taccactgct aactgaagta tggtggttat tttgaggaaa agcacctgtg agattgagtt   25920
gtgaactgaa ctagccactt tttaatagaa ctgttttggt gtaatatcaa agcacgagat   25980
ccacaatgac ctcagaaggc tattcaaaca ctctcccttt tctaagctaa gtatgtttga   26040
gactggattt tcttcatata cttgaaccaa aacaacatat tggaacagat tgaatgcaga   26100
```

```
aacagttacg agaatccgtt tcctattaga cagatattaa agaaattggc aaaaatgtaa  26160
agcaccactt actaattaat ttttttttt tttttttaaa taaaagaagg ctatgttgct   26220
caggctggtc tgaaactcct gggctcaagt ggtcctcctg cctcagcccc gcaaagtgct   26280
aggattatag gcatgagcaa ccacgcttgc cctcactcac taattttttt taaaggaaaa   26340
taagtttctt tttaaaaatg tgttatttat attaggtaca gttggccctc catattttca   26400
ggttcagctt ctgtgcattc aacaactgca gatcaaaaat acttgtggaa aaagccaat    26460 aaaataatag aacagggcgg gcgctgtggc tcatgcctgt aatcccagca ctttgggagg   26520
ccaatccggg tggatcacct gaggtcagga gttcgagacc agcctggcca catggtgaa    26580 accctgtctc tactaaaaat acaaaaatta gctgggcatg gtagtgtgtg cctgtaatcc   26640
cagctactca ggaggctgag acaggagaat cgcttgaacc ctggaggcgg aggttgcagt   26700
gagccaagat tgcgccactg cactccagcc tgggtgacag agtgagactc tgtctccaaa   26760
aaaaaaaaaa aagatacaaa taatacagta taacaaggat ttatataaca ttttacattg   26820
tattagatga tcataagtaa tctagagcca gatgatttaa agtataaagg agaatgtgca   26880
taggttatat gcaaatactg tgccatttta tataagagat gagcatctgt ggattttggt   26940
atccatgaag ttcctggaac caatacccc tagaccccca tggatactga gggcttgcta    27000
taacagtttt taataaaaat aaaaaacagg ccaggtgtag tggctcacac ctgtaatccc   27060
agcactttgg gaggccaagg tgaggtgatt gtttgagccc aggaattcaa gaccagcctg   27120
ggcaacatgg cgaaaccctg tctctgctaa aaatagaaaa caatagccag acatggtagt   27180
gtgcacatgt ggtcccagct acctgggaag ttgagatgag aggatcacct aagcccagga   27240
gggcgaggct gtagtgagcc gtgattgcgc cagtgcactt cagccagggc cagagtgaga   27300
ccttgtctca aaaaataaa ataaaataaa agtaaattgt aaaaaactct ttagtttttc    27360
atttctatta tgttaaatgt taatagctat aacacatata aactaaacag gtcatgagac   27420
caaaatgctg aagaatggtg ttaatggtgt tcttacttac tttgaattac cgttttatt    27480 tttctatgct agctaattac tatgtgaata attaacctca atgaagttct gtattctctg   27540
ttgtagcagt ggctgattta gggctcagtt gtcttttgac ctgttcttcc ttctcatatg   27600
attgcatctc gattttaat tttagactta gttttaatt ctaaattaa aaatcttttt     27660 tttttttct tctatgccca ctgctgtcaa cccagtcagg gcccttatca ctttattctt    27720
gaattacttc agttctccat tttttttctc atgtggtgtt tttcaaactt gagtgttgat   27780
tggaatccca gggttaattc aactttaatt ttatgaatat gatttcatat aagttcctta   27840
tgataaaacc agagcagatt tacaaattaa atatagacca tcaaattagc tgtacatatt   27900
taaggatgag attttgttaa aaccaaatag tcaatgttag agcttataga atggcatagc   27960
ctcaggatca gctttataat cagttttttt aaatttggct tgataatact aacagagaat   28020 ggctattgc ataaatatgt tttataaaat ggtgttaact tttagtcttt gttcaggata    28080
atgagaccta ctagttaacc agaacggggc cagcaagcaa ctcttgaatg ctagttttaa   28140
tgcctgatca aaattctgta aagctgtgtt gatcactgag gcgttgcgga tatactgagc   28200
ctgcattaag tggatatta atctaattat ttctggaatc tttaccagaa aacatgctct    28260
tacatagttt gctcctgggt tgctgttgg tgaactgccg ttggttggtg ggatctctgt    28320
gtcccatggg ctttgccaca cagctggggc tctgagtact tcagctcaca ttcctttgtt   28380 tgccacccctt gccttaactc acttacctgt attgtttttt ctcccatagc actcaacatc   28440
atcttacatg taaacatttt actttgttgt tgttgttgtt gttgttgttg ttgttttga    28500
```

```
gacagagtct tgctctgttg cccaggctgg tgcagtggca catcttggct cactgaaatc   28560
cctgcttcct gggctcaagt gattctcatg cctcagcctc cttagtagcc gggactacag   28620
gtgtgtgcca ccactcctgg ctaattttg tattttagt agagacgggg tttcaccgtc    28680
ttggccaggc tggtcttgaa ctcctggcct caggtcatcc acctgcttca gcctcccaaa   28740
gtgctgggat cacaggcatg agctactgca cctgacactt tgtttttaac tgtttctgtc   28800
caactagatt ttaagctgta taagggcaca gattttaat tgttaattgc taagtcttca    28860
gtttctattg tagtctctgg cttgtattag atgctcaata aatatttgtt gacttaatga   28920
atgcatatta acccttcttt tctttattca actgcaaact caaatactct tttctgagtt   28980
gtgtgctctc actgtgggta agaccagtt tttctcttca ttttaaacac aactaaactg    29040
gccctgaatt gtatagaatc cttttgattt gttgtttgat cagtacaagt tcagtcagtg   29100
gcacagttac ttcccttgat tcagattctg tagaagccta aaagtgcatt atctcttcaa   29160
gtagacatgt catcatatag gctgctatgg agatctttt ttttccttt aaattgtttg    29220 tgtaacagtt tctgttttaa aacagtggaa ttaccagcct ggacactata gtgagacact   29280
ttctctacaa aaataaatt aaaaaaaatt agctgggtgt ggtggagtac acctgtagtc     29340
cccagctact cgagaggctg aggcagaaag attgcctgag cccaggaatt tgaggcttca   29400
gtgagttggg attgcatcac tgcactccag cctggacgac agagtgagac cttgtccctt   29460
ccaaaaaaat tgaaaagta gaattatatt tgggagtttt tttcctcaaa ttcctttgaa    29520
gttaagattt ataaagtat gggaggccaa gctgggatta tcatttgggc ccagatgttc     29580
caggctgcag tgagctacgg tcgggccacg gaactccagc ctggggaaca gagtgagccc   29640
tgcctcaaaa taataataaa aataataata atagtacaag ctctcttaat tactacctgt   29700
tttttttttg agacagagtc ttgctctgtc acccaggctg gagtgcagtg gcgctatcta   29760
ggctcattgc aagctctgcc tcccgggttc acgccattct cctgcctcag cctcccgagt   29820
agctgggact acaggtgccc gccaccacgc ctggctaatt ttttgtattt ttagtagaga   29880
tggggtttca ccttgttagc aagaatggtc tcgatctcct gacctcgtga tctgcctgcc   29940
ttggcctccc aaagtgctgg gattataggc gtgagccact gcgcctggcc actacctgtt   30000
ttttttttta atcctatgtt tttaaataat tctaatcatc tattcatatt ttttgtttct   30060
cctatttaac attttatgta acatttttag attttaaaat ttgtttctgt tatcacttct   30120
aaaagtgaat gttatttta aaaatgaatg cctttacatt gggttgttat gtaacctaat    30180
ttgctttaac aaataacttt attttggagt aattttattt ttaattattt atttatttat   30240
ttatttattt gggacggagt ctcgctctgt cgcccaggct ggaatgcaga ggtgcgatct   30300
ctgctcactg cagcctccac ctcctgggtt caagcaattc tcctgcctta gcctcccaag   30360
tagctgggat tacaggtgct cgccatcatg cccagctaat ttttgtattt ttagtagaga   30420
ctgggtttca ccatattggc caggctgctc ttgaactcct gacttacgtg atccgcctgc   30480
ctcagcctcc caaagtgctg ggattaacaa gcatgagcca ctgcacctgg cctatttttgg  30540 aatactttg gatttatata gccatggtat atttgttaaa actaagaaat cagtatcagt    30600
atgttgtcat taactaaact caagacttta tttggatttt gccagttatt ccactaatgt   30660
ctttctttgg ttggttggtt ggttggtttc aggatccaat ccaagatacc acagttcatt   30720
tagttatcat gtctcctaag tttttctgat ctgtggttgt tctcagcatt tccttatttt   30780
tcatgacctc ttaatcgttt taaagtgtat tggtcagatg ttttgtaaga atgtcctttg   30840
```

```
atttcggctt atcggatgtt ttcttatgat taggctgaag ttatgggttg aggtctgggg   30900
gaaggatacc acagaggtga aatccccatc tcatttcatc acatcgggga gtacataatg   30960
acagcagtac ttaccattgc tcatgttaat ggttatggtt ttttttcaca gaaacattac   31020
tgtttccctt tccagactct tctttggaag tgaatcattg aatctagctc acgctcaggg   31080
ggaaggaaat tgaattctcc ctcccagaat ggggacatac actcatgtat cagttggaat   31140
tcttgtcagg agagttgttc cttctcctcc agttgtttat ttaatcactt atttatatca   31200
tagactcatg aataattatt ttattctgtt ataatactgt tatgatttac tctgctgctc   31260
aaattattcc agctttggcc actgagagtt tcttctgttt gcttccagtc tcggacctat   31320
ccgtctcctt tcatctttgg agcatttccc ttcttctact ggcttgcctt gtagtttccc   31380
tgtcccaacc ctagaatcag ctgtttctgc agaccctgct tccttgtatt tattggaagg   31440
tggtatttag aaacaaaagt cttgggtgca gggtatgctt attttattgc tcctggggtg   31500
tcactgcttc caggccctct gttggacaga ccctggaaat gcaggtattt cagctaacct   31560
gcatgtgcat acatacctac gtttctgtat ctatccgcat atattttaaa atacacgtga   31620
gttcatattg atatatctga ctaattcatc accacctctt gcttatttgt aacttctttc   31680
tgtgacattg agaaacttgg cacacattat ctacatttta tttacttatt tgtttaaccc   31740
tagtgtacat gtagagtatt ttcagaatta cagactggta cccttatgag aaacaaattt   31800
accagctaga gtacagagta gattgtccaa agttctgtag attagctccc cccgacctcc   31860
tgctccttcc atgagattat ctcataaaat tataatactg ttagacttgc tgtatagttt   31920
gcattctatc ctgagatccc ctgacatcct gttttgtttt tatttgcata cagtttacca   31980
tttaaaaaaa gtctttatat tgagttgtta acttttttaat ataaatgttg taattcctga   32040
tattactcat ctgccattta tgtagttgat agtcactact tttttttttt tttttttttt   32100
tttgagatgg agtcttgctc tgtcgcctag gctggagtgc agtgacgtgt tctcagctca   32160
ctgcaacctc cgcctcctag gttcaagcga ttctcctgcc tcagcctcct gagtagctgg   32220
gattacaggc gtgcatcacc acgcccggat aatttttgta ttttagtag agacggggtt   32280 tcaccatgtt gggcaggctg gtcttgaact cttgacctca tgatccacct gcctcggtct   32340
cccaaagtgc tgggattaca ggcgggagcc acagcgccca cctgatagcc actacttttt   32400
taatgctgat atagtgctta ccatctgtca ggcactgtct atgcaccgta ataaattta   32460 cttctcacaa tgactctgag gtggaggctc ttgaattagc cttttttcat gaggagagtg   32520
aggcacaaag atgtgcagta acttggccaa cttcacaccc agctgctaag tgggagaact   32580
tggatctgaa cccagggaat gagctttgga gtccaaactc ttgcttttttg tttaatgctg   32640 tgtataggac ttagaattaa tacaactaac tcttctctta ttagtttagt ttattacttg   32700
gaatttggtg tgaaatagag agtgctgcta ccccaattct ttgccccatg tgtgtaacag   32760
gcattattaa tcatgacagc actctctctg ctgagctaga acatggcctg gcctaaggcc   32820
aataatcctt atggacacaa ccctcaaagt ggttgtatga gatgaactct ccttgccatc   32880
tctgatcttg tctgttttga atcctgattc tagtgcccag tgcatggcac tgcgtgcctg   32940
cttctcctgg attcctctct catggtcttc ctttttacag ggacaggttt tctatattcc   33000
ccctcaggca taggatctgt ttctcttaag taattaattt ttatcactta ccaataattt   33060
aacatctata tgtctaagtt ctctttatat tgttttttctt atccttaccct acaaaatctc   33120 atttaccatt gatttaaatt tcagtatatt gaaacaatgg attgtaacat taaaaataaa   33180
tgaaattgcc aaatgatact aacagctgcc ttcaaagcat ttaaacatac aaacaggcac   33240
```

```
tattgaagac tggagagtta tcaaaattgg caatttttg gcagtcttgc tgtgaagtaa     33300 acattttaa aaggaaggac attgagaata ttgtaatcat attacttaca tcttgttggg     33360
tttggatttg accttacata gcctggtatt cagttaagag tcaaagttgc tgctattaat     33420
ttagttgaga aggataaata gtacatgtag tttattgttt tctttagaga aatagaaaca     33480
gaaacattta tttggccaga ccaaataggt ggtcattccc ttgatttagc aaatccttga     33540
ggtagaattt ttttttttt ttttttgagac ggagtctcac tgtgtcgccc aggctggaat     33600
gcagtggcac gatctcggct cactgcaagc tctgcctccc gggttcacgc cattctcctg     33660
cctcagcatc ccgagtagct gggactacag gtgcccgcca ccgcctggg ctaattttt      33720 gtatttttag tagagacggg gtttcactgt gttagtctcg atctcctgac ctcatgatct     33780
gcccatcttg gcctcccaaa gtgctgggat tattggcgtg agccaccgcg cctcccggta     33840
gaatttttaa agaagcaata agggctctga caatacctat gggactttt tcaaattatt     33900 cagttattgg cagctgggta aagagggaca ggaatgtctg atttaggtaa atacctctca     33960
caagtggagt aggggcgtat ctggtagaga acagtgctga ttccttggac ttgtgtggcc     34020
tggccacctg agaggtaggt aggaaggtgt gtcttggcca tgtcctgggg cctctgtaaa     34080
cctgagagga tggaggaagc tctacttttt ctgacgatgc tgttggtgat aatgaagtag     34140
gctatgagag cccatcttcc attaattcag atgttcctat acagtggcc ctctgtaaat      34200 gggattctac atttgtagat tcagccaact gtgggtaaaa atacttgaaa agaaacaaaa    34260
gtgtgtgtac tgaacatgta catacttttt tcttgccatt attccctaaa cataatagtt     34320
taacaactat ttatgtaata tttacattgt attaggtatt tagtaatcta gagatggttt     34380
taaagcaggg gtccctagtc cccaggccgt ggactggtac ccgtctgtgg cccgttagga    34440
actgggctgt acagcaggag gtgagctccg cctcctgtca gattggcagc agcattagat     34500
tctcacggaa gcgtgaaccc tattgtaagc tgcacacgtg agggatctag gttgcacact    34560
ccttaaaaga atcttttttt tttggagacg gagtctcgtc tcactgtgtt gcctaggctg    34620
gagtgcagtg gcatgatcct ggctcacctc aacctctgcc tcccaggttc aagtgattct    34680
cctgcctcag cttcctgagt agctgggatt acaggcacct gcctccacac ccagctaatt   34740
tttgtatttt tagtagaaac agggttttac catgttggcc agactggtct cgaattcctg    34800
acctcaagtg atctgcctgc cttggcctcc caaagtgctg ggatatgagc caccatgcct    34860
ggccatcctt atgagaatct aactaatgcc tgatgatctg aggtggaaca gtttcatcct    34920
gaaaccatgt accctctccc ctctttgtgg aaaaactgtc ttccacaaaa ccagtccctg    34980
gtgcaaaaaa gttggagact gctggtttaa agtatatggg agaatgtgta tacgttatgt    35040
aatagtgtac cattttatat cagggacttg agtcttcgtg gatttggta tctgttgggg      35100 gtcctggaac taatcctccg tggatatgga ggaacaactg tatatatggt ctcagtaata     35160
aatacgtatc tgagataccc tctgtattaa gaaaaaaag atgggaattt cttggctcat      35220
ataactgaat agttccgaaa tttgggaagg tctgcctgac ttagggctta ggtcatgaga    35280
ctacagttct ttcttggctt tgacttttgt tttttgtagt tgttgactct gttctttgag     35340
gctcttctcc aagatggctt ccaacaagtc cttgggcaaa cattttcca ggtttagacc      35400 taagggaga agagtgagca ttcttgtcct agcattgcag gaaacctgag attttcactg     35460
tgactgcact gattgtggcc gtgtatctaa ccctgtactg gtcactatgt ctagggagat    35520
gtaccttggt caggccaggg tcacaagcag cttgagtcag cttcctccag tgtacttggt     35580
```

```
agttctcaga gaagagttgg tgtgaagttc ccaagagaag ggtgaattga ccctgggtgg   35640
caaaaacaac atagcatcta ctctagtggg ataaagtaag atggtaaggc atggtgttca   35700
gggtatttct gagtttggtt tgattcacaa aatagattgt gaacactgta attgcccttta  35760 atttagtta acctatgtaa atgtaaatct gtgaggtgtc actacattct gctaaagctt    35820
tgatgggctc ctgccatatt ctggtttggc ttttgtatta aagagccatt gttgttttgg   35880
tttcactgta tacaggtaga cttttgtttt aatgaataga ggtataatct gttttgaaca   35940
ggaaaagctg cttttgtatt ctggataaag ttcatactag tgggatttca cctatgaaac   36000
taaacaaatc tttgaaaaat ttaaaaacca tatgtattta cacagtgtcc attcagtaga   36060
agtcgtttaa ataaaggctt ctgccaatat atgaatattt agagctgtat tttattattt   36120
tacttttttt gagacagggt ctcgctctgt cacctaggct ggagtgcagt ggtgtgaaga   36180
cagttcactg cagtctccac ctcacaggct caagagatcc tcccacctca gcttcctgag   36240
tagttgggac acaggtgtg cgccactaca cctggcttgc ttgcttgctt atttattgat    36300
ttgagatggg agtctcacta tattgcctag gctggtcttg aactcctggg ctcaatcctc   36360
caaccttggc ctcccaaaat gctgggttta caggcttgaa ccactgtacg tggccttgaa   36420
tctgtgtttt aatactatgc ttacttggct gtggtgttgt gaaagatca ctgaaaatgg    36480 agtcagaggc ctgatttgag ccagtcgttt gttgtggggg aaggaggtca ggggagctaa   36540
catctaaagg ctcactatat gccaggcaca gaaccaagtg tgtttgcatg tatatttcgt   36600
ttttgttgcc agactttgag gtaggtttta tggataaggt ctttaaggca atatcagctt   36660 cctttttaaaa aagaaattcc ggaaactgag ttttaggctg aagatctcta actggtagta   36720
gggacaactg aaccacaggg tcctaactga ccctgcgatt tatctccttt tgcgggggt    36780 ttcttgataa tagggtgcac tttacctcat tttttggctc aagcatggat aggccaccct   36840
tccttttcat acctatagct aagctttaca aatgatatgc tgataagata caagctactc   36900
gttattcatg tgggttaata gacctgtttg tttgcttgtt tttaagtcta tagccgcccc   36960
acccccaatc tacaatttca ccttctaagg ttttagttac tcattcaaac tgcagtctga   37020
aaatgttacg atattttgag agagagaaga ctctagctac gtaacttttg taacaatata   37080
ttgttataat tgttcatttt accattagtt attgctgtca gtctcttact gtgccttatt   37140
tataaattaa acttcatggg tatgtacgta taggaaaaaa catggtatat ttagagttta   37200
gtactatctg cagctttagg catccgctgt ggggttggcg ggggcggtc ttgggagata    37260 agtggggact actgtacaat tatcaggcac acacaggctc tgggattta caaatgagta    37320 aaagtggttc ttgctgttga agcacttaca gtgggaatag agtgaaatac atgaaaatgt   37380
gattttaata tgttataaat gctatgatgg tgggagtttg ttttgtgtaa aacatccttt   37440
taattggtac tttaaatttt aatattcttt cacaggtcta cctatttagt cttacacttt   37500
caaagaacta cctggatgct gtagatttc atgatatact ttattaggta tgttattaat   37560
ggtagaaaca gcatggaaag tcttccagaa tattagacaa ggacagttct agtactaaaa   37620
cataaaatgc taactaatgt cttcatcaag acataaaata tgtatcttaa aaaataaatt   37680
gtaagccagg cgcagtggct cacacctgta atcccagcac tttgggaggc tgaggcgggt   37740
ggatcacaag gtcaggagat tgagaccatc ctggctaaca cggtgaaacc ctgtctctac   37800
taaaaataca aaaaattagc ctggcgtggt ggcgggcacc ggtagtccca cctacttggg   37860
aggctgaggc aggagaatgg cgtgaacccg ggaggcagag cttgcagtga gcggagattg   37920
caccaccgca ctccagcttg ggggacagag tgagactcca tctcaaaaaa aagaaattg    37980
```

```
taataacacc cacattatac atcagtgaaa actaaacacg ttactaccct aggccttatt   38040 gcacagggt gctacctcca aggagaaatt tgtctaggca gcagatggac tagaggtgat    38100
tagcctatga gcgaatgagg ctacagatca ttccttttta tctgattcct tttctttcta   38160
gttcctaggc cttggaagca ctaagtggtc ttaagtaatt tgcatagaat tagttgagtt   38220
catctgttaa ctaactagca gataggaaga aaactattgt catgaaatta tttaaaaaat   38280
aataatgctc cagtttcttc tcatctttga tgtcctttgg tcctacctca ctgccttcct   38340
aacaccattt tctgctttac ctcaaagctg gggtcatctt gagtttagcc tgcttaatcc   38400
gagtgactgt cagcttttatt ccactttagc aactcgcagg caaggccaca cttggaaact   38460
tttcacttgg aatagttcta tcttggtgat tcatcagcc ttctttatgt caaatacact    38520
caaattcctg cccattctta tctcttcgtt cccttcaggt ccttagtcct tttaatttgt   38580
gactttcatt ctccaggtcc attcttatta aatgtctgcc agccagactt tagttgcccc   38640
ctgtccagct ttctcttgct cagacctaag atttctttag gttctttctt tgcctttga    38700 aatccagctc agcttttaag attgagttcc ttgttacctt tcctgccatc cttctgcagt   38760
tcctaatatt cttttctttc tcccaaagtg cttttgtata aacagtcagc cttccatatc   38820
cgtgagttcc aaatccatgg atcctgaatt catggattta accagctgca gataaaaat    38880 attcagaaaa aaaagatgg ttgcatctgt actgaacatg tctgtactgt tttgcttgtc    38940
attattttct aaacaataca gtataacaac tatttacatg gcatttacat tgtattaggg   39000
attataagta atctagaggt gatttaaagt atatgggagt ctcttatatc ccaggaagcc   39060
aggtaaaaaa aaaagtata tgggaggcta tgcataggtg atatgcaaat attacaccac   39120
tttatatcac ggacttttga gcatctgtgg attttggtat ccgaggggtg tcctggaacc   39180
agttccccag ggatactgaa gtatgtctgt ctatctcata ctatattttt cccttgtct    39240 taggtagact atcagctcca taggggcaag gatttaataa tatttgtata ttcatttat    39300 tcaagttcgt atacactgct tgggtcataa tatttattac atgcttgaga aaatgaattt   39360
cttcgcccct ttgttacagc tctgagtaaa cagccatctg ccttctctgt catctgttgg   39420
tggttgagta tttctgtaga aagttaccca ttggcctcag gactcttact ctaaatcttc   39480
ttcttaggca gttttctctg tgcatgaagt ttttatgtaa acaaatagat gaagcctgcc   39540
ctactcattt atttgctcaa gccagaaagt caccttcttc ttcactttcc atatttaaat   39600
catcatttgg tggaatttg gcctaagcaa ctcttgaatt cacgtacttt tccctgtcat    39660
cgccagtgtg gtgtagaagc ctctgtcacc ccttgtcggg atgctgtgct gcagcatcat   39720
ctaacctggt tgcagttatt ctttcactcc ctcaccgcac accctttac ttaaaacact    39780 aaaagtggct tctcattgtt cttaagataa agcacaaatt gttagtgtgg cctgtaaagc   39840
tttgcatagc ctgacagaga atgtcctgct aataatttga aggtacagga tgattttaat   39900
actttaggag aaaatgttct aggaaaagac gcttgtttag acttaaggtg aggactctgc   39960
agtatgaatt agacatctgg tgaactataa gctgtccccg catttaaaca taattggttc   40020
tgagagcctg caactaaaga taaggcagaa gaatttactt tgcatttcct gcattcctct   40080
tttcgcttga tagcagaaac ccctcatgtt aataaaggtg gcacaagagg caaaaataca   40140
gactttatca cagtgtttaa ggagaggtgc atgattaagt gtgtggggag agagtacctt   40200
tgtacatttt attatatggt gaactgtatg ttttctactt ttagtactgt ttgtaaattt   40260
tacttcttct tggatttacc tttttcagtt atattattcc attatgcctt gctactgtaa   40320
```

```
cagctaatga tgaaaaacag gatctgtctt tatattttct tccctccaca aatgtggatc    40380
tcatagagtt gaaaactagg ttgtgatata gtatagtata cctaattcct gtaatgggat    40440
catgttccta taatatggcc gcaatttagt gtagaatttt tgtaaataaa agtgtatttt    40500
aagtttaact taaactttca atgaagtgtt ttaaggattt aaccatgcag cacaaatgag    40560
cacctttctg taaatgccaa cagtgtaata tgtgtcattt cttcactgat tgttagtttg    40620
ctgcggatta aaacacaggt gatcatattc aggctggtta gattagtgat tttaatatga    40680
aaccattgct tttagaataa tcatgggcca gactgggaag aaatctgaga agggaccagt    40740
ttgttggcgg aagcgtgtaa aatcagagta catgcgactg agacagctca agaggttcag    40800
acgagctgat gaagtaaagg tataatttta tcttttgtga aaatgaatat acaattaagg    40860
ataggttttt tccccttccta agttcaataa gttttttattt aaaataattc tagccaagtt    40920
tgtatttaca ataagatgag tgaatacttg gaagcttagg ttcttgatct gtcttaacat    40980
tataccatgc acattaatca gtctttgttt agtatacttt tatttgcata tgcagctgca    41040
gaaatgcctc cctaaatata aagggatgca tttcatgatt ttatgtttct aaagtcattg    41100
tgattaaaaa aaaaaatata cacacacaca cacacacaca cacacacaca cacacacaca    41160
cagtcaacaa agaaaggatg gcaatcgttt cctgttctct aacccattgc aataaaataa    41220
cagatgtggt gttttttgtat tatttgaatg tgggaaacta tagtgtaaaa tctatatgca    41280
cctaagaaaa tgttcttgat attttttgagg atacactaga ttttttaacct gctttacagg    41340 tgttatacat tttctaacaa tgaacaattt ctccttttcct ctccttcatt ttttttttta    41400
agagtatgtt tagttccaat cgtcagaaaa ttttggaaag aacggaaatc ttaaaccaag    41460
aatggaaaca gcgaaggata cagcctgtgc acatcctgac ttctgtgagc tcattgcgcg    41520
ggactaggga ggttggttaa cataacatgt tgtagtaatt atcatcatct tttggtttat    41580
gctattggaa catttgtttg gttattggga ggaaatcatt gacctcaggg tgtccatctt    41640
tttattgcta tttctttttta atgtgcaact gttaatgact gctgtagatc acactattag    41700
ctattcctat aacagagttc taagtgtttg gaatatactt tgaactaggt agatgcctag    41760
attttataag aatgttgatt taaaaaaaaa agcttttaaa tcaaatactc tttaatgtcc    41820
tcatcagatc actatttaga gcaaggtttt ctgactcact gttgtaaccc caatttgaat    41880
tagccatgtg gtaagaaatg ttttaatatt catggacaag aaagcttttt attatatatt    41940
ttgttcaaag gctaagcctc tctataagaa ttttttaaatt tcttgttgag agattggaat    42000 ttcttttttct atagtacttt ctgaacgagc tagctcttaa ttactccaag agtttcctat    42060
tttcaaagaa aggcagtaaa tctatggtag aatctataat taaatatccc gttaaaacat    42120
gattgcagca agatgagaag aaaatggcaa agtctaaat agcttaggca tttctgtttt    42180
taagtgcctg tgttgtatag aaagacatgg cataggatat ttaaagggga gttgaagcaa    42240 aagggggaaag agcgagttgg aattaaaatt gcactatgta gtagattgtt tatctgaatg    42300
tctaaatatg ggaagcacct aaacaatgga atttgtttta agataatttt tcaacgagta    42360 gccatttta atataacatt attgtaacaa gcaacaattt gctattgtat gaggccttct    42420
ggagattgtg tgacatatga gcttcaaaga cttgtcagtg atatcccagt agcaacagac    42480
ataatcctaa tgcagatttt agtgatattc tggtggtctt gatggtgaca cttggaatga    42540
ttcttagtca tttatgcgtt ttgttaggtg acacctctgt aaagctctga cttataattg    42600
tataaatatt gattatacag tgacactttc ctcctcatct ggtacaggcc agagcctaga    42660
tgttagaggt cagtggcatg ggggaaaggg attcttttgg atgcccatca gaacgttctt    42720
```

```
aaagggaata aggatggggc ttttaagtaa ttgctttgaa agtttttatt tggtgacctt   42780
ttagaaatgt tgaattgaaa gaaaaacctc attttctctc tggaggaata aatcttagaa   42840
atttggagaa attaggtaga ttcacatgga aaacttattt ttgccaccca ttatgaatct   42900
cagaatgcta tcaaaagcct aacttaggtt tataataaaa gtcaacagca ataatgaatt   42960
gtgtcactgt gctaggtact ttgtacacat tacctctttt aatcttcatg ataaggaagg   43020
agtattacac tttttttttt ttaatccagg caaggaaact gagccttaga agcatttagt   43080
cagtttgcct gctctaatga tctgatgtgg gcccagaaga gcacactttg ctcagacaca   43140
tgaagtatta gtgaagtaca ttattgacat acaacttgaa ttgctcatag tatatttggc   43200
attaaattta agagtattgt ttgttcaagt ggatatttac taattgaaat tttcttttaa   43260
ttttgtcaaa tggagacaaa tcgttgaata taaagatacc taatgttcgt gagtttatgt   43320
gaaaaattgg gagaagaaat cagcatttta ataaaacaaa attgttttct aaagttagta   43380
cttccacagt accacacaca cacgcagatt gagaataaac attttcacag agtatggggg   43440
aaaaggagga aaataatccc cagccttagg aatccagttt ttgttgcata gaactctgac   43500
ctgattaagg tcagtcattt ttttttgttgc tggtgttggt agctgatcct gcttcagatg   43560
atccatctat tatttcccct ttccgccttt ttaaaccatc accactgact tttagaagcc   43620
agagtttata tcgtttgtga taagcttctt ggtgttatca caataaatcg taaagcttta   43680
gggctaaaaa ggactgtagt ggtctcatgg tccaacctcc tgacttttca gatgagaata   43740
tatccctgtt tattttttct ttcgtttaag catttccatc tacatattat ttcttttata   43800
tatttgaaag attctagtct gaagtaggtc aggtagggag gagaaaataa aagtgattct   43860
tgtttggcaa agactttcct agtggtaggc ttggcagaat ttcagactgc agtattgatt   43920
caaacacgta aagtctatag cattcaacat ttgaagtgcc attatagcat tgttttaatt   43980
aactgcttgc ttttataagc taattatatg taagtgctgg tgtcttcaat ttaaatcctc   44040
tgcagcatga caaatcaatg acaattttta gttcttttgt caggtcttaa acttatactc   44100
ccatttggcc gggcgcggtg gctcacgcct gtaatcccag cactttggga ggccgaggcg   44160
ggcggatcac gaggtcagga gatcgagacc atcctggcta acaaggtgaa accccgtctc   44220
tactaaaaat acaaaaaatt agccgggcgt ggtagcgggc gcctgtagtc ccagctactg   44280
gggaggctga ggcaggagaa tggcgtgaac ctgggaggcg gagcttgcag tgagccgaga   44340
tcgcgccact gcactccagc ctgggcgaca gagcgagacg ctgtctcaaa aaaaaaaaa   44400 aaaaaaaaaa aaaaaaactt atactcccat ttgtagttgt agaagtggat atactcagtt   44460
tgaaaatgac tgattttctc caagttattt tggtaaagaa tgtcggacaa agtttactg   44520 aagtgagtgc tttagatgct gacttcaggt cagggagctc tgcatttgaa cccaaagacc   44580
acatctccag tatgtggttt tcttactgtg tgtggttttg ttttgttttt gtgacagggt   44640
cttgctctgt tgcctaggct ggagtgcagt ggtacaatca cagcagcctt gacctcccag   44700
gctcaggcga tcctctcacc tcagcctcct gagtagctag gactacagtc acacgccacc   44760
acatcgggct aattttttt tttttttttt ttgagacgga gtttcgttct tgttgcccag   44820
gctggagtgc aatggtgcag tctcggctca ctgcaacctc tgcctccag gttcaagcga   44880 ttatcctgcc tcagcctcct gagtagctgg gattacaggc atatgccacc acgcccggct   44940 agttttgta tttttagtag agatggggtt tcatcatttt ggtcaggctg gtctcgaact   45000
cctgacctca ggtgatccac ccaccttggc ctcccaaagt gctgggatta caagtgtgag   45060
```

```
ccaccgagca catcgggcta attttttttgt attattttgt agagacaggg tcataccatg    45120
ttttccaggc tggtctcgaa ctcctgggct caagcaatcc atctgccttg gcctcccaaa    45180
gtactgggat tacaggtgtg agtcaccata cccgtcccct aatgtgtttt taagatactt    45240
tagggcaact cttttttttt tgttttgag attatagaac ctaagcatta ttgttcatag    45300
aattttaata cagaatgtgt ttacttttaa aaaacacttc tgacttttg aagacagtga    45360
ctatatctgt tttacgttta tttcttttat tcttaagtta atcttttaaa gaagcatcca    45420
gcttcacact gtcattaatc aatacatata ggtcaaggga tgtacatttt attcccataa    45480
tatgtcactg ttagtcaaga aattgttact aggtgacttt cataactttg tcttgtcaac    45540
cagtaataac tatgttctgt aggtcttcat attggtagtt atattcttca ttgtgtctct    45600
ttttccattt ttaatgaaga aactggttta agagttactc ttgaggttct cattaatgta    45660
tttctttttc gtacatctgc ccatttcttg ctgataatca aagacactt ctccttcact    45720
gacttcatat caaatgtttt tctactgtat gtgttatgac tgaaagagaa gtttgcttag    45780
atagtgcctg tcttctgggc aaatggtatg attagtttag taatttaatc catcttgcca    45840
atatacattt ctagattccc aggagaatat aatgttcttg taagagtttt gtatcttgtt    45900
tactaatgaa aagagagaat atggtgtata ttccttgggc ttcagaatgt ctaatagaag    45960
cagcatcaga aggggatcac ggtcctcgta tgaagaattt aaaaacttt ggacttttaa    46020
atatttacag atttgctctt catagtaata tttgaaatga ttttaagttc attgcttagc    46080
atttgatatt agcagatttt tttgggggga gaagcttcta tcaaaataat gtgtaaatta    46140
ttttgtatgt tggcagtttg gacttaacat ttttgttgaa ggagaagaaa aatacctgtt    46200
acatgtaaac actcgattgc atttttatt gatttagtaa tgaagttcct tcagttaatt    46260
gtaaatgaaa atttagtcac tgtttacaaa gaaaaataa tatcctagtg tatttcatgt    46320
ataatttagt gtacttact cagatacatt ctttgagtgt agtaacatgg tttctttata    46380
cattgcagga ttataggccc tataggttta gattctcatg aaccttttga gcaaatatgg    46440
cagaaagctg gtcactttc tcatgtcttt aaattaagtg gatggctctt caagtgtctg    46500
tcttactctt agtctgaaca tatacactca ttcttattgc ctcaaggaag tggtctctga    46560
gttgctttct gtagctcctt gcctctttta actattattg gtatttactt ggagagttga    46620
gtcttgttag gttaactgtc agtcattccc acctgtataa cttgtaaatc catgcagcct    46680
ttgctttctt tctggcttta tttaggctga aatagatgta acatttctta aatgatcata    46740
taaggatttt tttttcttg tgagcagaaa ctaatataag cattttatgc ttttccaaag    46800
ggttagctta aaaaaaaaag gtcatttgtg atatttgagt tcatatagca tcatatatta    46860
aatacatgtc atttattatg tttatatttt aaatttgatt atatatcttc agtttaaaag    46920
gtgaattta aaaagtcaaa tttaggcaac taataaaact agcagaagtt gcttttcatt    46980
tgtagttttt ctcctagaat attgtatata tagtttgtgt tttataaatt attgttataa    47040
agatcatgta tcttccccaa atgcaaaacc gagttctgac aactatttaa aaataaaaca    47100
acaaatccaa acaaacaaaa gtgcttggtt aatctggaat gttagaaatt gttttattct    47160
ctgaagaaac aagaaaattg cattagaccg aggacttttg ccataattta gctttataat    47220
agggattgac ttaaatttac tccttaggat tctgtcttac cttctcttag cagattttat    47280
aaaagaatat cacttgagta acatttttgga aaggctgggc agatttcata agctacccaa    47340
caaggcagtt ttatactagc taatgtgact acctgttggg ctaatgaaac tagtttaaaa    47400
gttttatctt tttctctcca ctgaacagat cattgtaaaa tgattattgt aaaaatttag    47460
```

```
ataacacaga aataggtaaa acagaaagca aaagtccctg tagtccaact gctctggctt   47520
ttattctttc agatttcatt ttctatatat actaggaggt taataatatt ttattttaa    47580 aaattattgg ccagatatac atcctttcca ttttgggcca tcactttaca acctctgtcc   47640
aaattttcat tcttttaaaa aatatgtagt gtttgacatt atggatatac cataattat    47700 tgccccattc ttgatggaca tttagatttt taattttac ttttgcaatc agtgctgtac    47760
tgaactttat atacatcctt gcatcttttg agtaattctg tagaagttcc tacaaataga   47820
attattagat caagatgata tgcatgttta aaaatttagc agatattacc aaatgcaccc   47880
tcaaaagttt tacattacac ccccaccagc tgtttatgga atgtctgttt acctatattc   47940
tcaacacaat attatcaatc ttaatcttca gtccaatagg taaaacattg ttagaattgg   48000
ttataccgtg tcttaattat tcagtgaagt taaatgtcag ttactgtttg tttatatttg   48060
tgaattggct gttacagtgt tggatcttgt gcaattaggt tgggcttttc ttatgattca   48120
taaggacttt ttgtatatta caaatactag ttttggctgg gtgcagtggc tcacgcctgt   48180
aatcccagca ctttgggagg ccaaggtggg cagaccttt gagatcagga attctagacc    48240
accctgacca acatggtgaa agcccatctt tactaaaaat acaaaaaaat tagctgggca   48300
tggtggtgtg cgcctgtagt cccagctact tgggaggctg aggcaggaga atgccttgaa   48360
cccaggaggc agaggtttca gtgagccgag atcacaagac tcaatctcaa aaaacaaaa   48420 aacaaaaaaa aatagttttt tttgtcatat gttttgcaga ttgcccccc cccattttga    48480 tgttatttct gatatatctt ggttatacag ttttttcttt taattttgt ctttcttaaa    48540 ggttccaaaa gtctttcttc acttcaagat tataaattat ctacctatct ttcctttagt   48600
tctctgtttt catttttata ttctaatatc atttaacca tcaggaattt cctttggtgt    48660
aaagaatggg taggggattt ggtttttaat tttgttcttt ttagtttcct ggttgtttca   48720
acactattta ctgagtaatt aatgaatagt gaggggcagt tgtaaacttg ttttgaaga    48780 tcagcagaat cagccttctt ggttggtggt ttcctgggca gttctaccac tcgagcaaga   48840
cctgaagtgt ttcccttcag aaaccacagc ctgtgccatc ttgctcactc actttccttc   48900
cttccttcct tccttccttc cttccttcct tccttcttc cttccttatt tgacagagtt    48960
ttgctctatt acccatgctg gagtgcagtg gcgtcatctt gtctcacctc aacctctgcc   49020
tcctgggttc aagctattct tgtgccttgg cctccagagc agctgggact acaggcatgc   49080
accaccacac ctggctaatt tttgtatttt agtaaagaca gggtttcacc atgttggcta   49140
ggctggtctt gaactcctga cctcaagtga tccgcccacc ttggcctccc aaagtgctgg   49200
gattacaggc ctgagccact gcgcctggtc ttgcccactc acttgaacct ctactacttt   49260
gtagtattaa acccagatcc actgatttaa gcaaggcttc aaaacaattt tactgccaca   49320
gcctatataa actatagatt tatataatac tctctgttcc attttagttg attttcccc    49380 caatgacaga aattgttctt ttttctactc acaggactgt tattgaatta gaaatttgaa   49440
tttacatgtg gtggatgaac atcactcttg ttacctgctt catgtacttt tttgagtgct   49500
tactacctgt gatgattatt ctgtttctga tctccagtac ttagcaaaac tggagttttt   49560
ccgcaaagct gcagatgagg gaatgattta ccttaacagc ccttcaggat tttaacctag   49620
gattaagtag gtttgcatgt ttgtgattcc tttcattcag ggcccggctt ctgaaggtag   49680
gatgcgggga agagctttaa ggatctaaat ttcctcccag cctgagcaac atagtgagat   49740
cccatctcaa taaaaaataa aaaaattagc cagatgtggt gacacgtact tgtagtccca   49800
```

```
gctactcggg aggctgaggt gagataatca tttgagccca ggagtttgag gctgcagtga   49860
gccatgattg caccactgca ctctaacctt ggcaacaaga gctagaccct gtctcaaaaa   49920
aaaaaaaaaa aaaaaaagga gtctaaactt cccgatactg tattccaaat gtcctatgtt   49980
aaatgctgtg ttatcattcc ccgcccettg gaatgtagaa accgttaatt acaggataaa   50040
agtgaactga gaagcaaata cccttgtgtt gtagggtaga ggttcttcac ccaatgtgga   50100
attggtctgt aacaaatact gaacaacaca aactgaaata atttacaatc tgatatgaat   50160
tactcttttt catttcttaa ctccaacact tgattagttg ctttcattaa atacatctgt   50220
gtcaatatct taatggggtt ttttcttccg tttttgtttc tgcctctctc ctgttggagc   50280
gactcatttc ttttcaagtg tcgtcttcaa tctcccttct cctattttgc cttctcaacc   50340
tgattatgaa ttcacttcca ttattgagct tctctttact ttatccaaat ttgctattta   50400
tctcattgca gttttctc agtacttact ttgcataaaa gtagcctgaa cttaaattat   50460
atacacggtc attttcacca gaagggctag ctaatttaaa acttgggcgt gttatctttt   50520 cttcctcaa gtcctgcaga atatagggta gtttcagaaa tcaccccag cttttctcta   50580 gacttggtga cagctgatgc tttcttctga ctcttccttt cctggagtgc cgaccttcct   50640
gcaccttcct cgctgttgtc acatggaaag gctacaggat gttagacaat gtcaacagtt   50700
tactatgtct ctggcatgaa ataaatggac caaccagtat ctgagaatat tttttacttg   50760
gctaattgat tgtatgtttt cccctactat atggaagttg gacttagcct ttctcatgtt   50820
aaagattatt cagaggcagg acggccatgg ctgttgtctt tgggatgtcc actgtaaaat   50880
ggggagtcat acctacctca cagggtagtt gtgaaattta aagaagctaa ctttggtaaa   50940
gtctctagca cagtgcttgg cacatagtag ggtgtgttaa tttctttccc ttccctgcag   51000
gccattcacc tgctcttccc tctacgattt tccataacac agttttact tggaaccagc   51060 cttctgccaa gagtctcagt ttggttgtgt actcctacaa ctactatttt tggcttgact   51120
tccctctcca gctcccagtg gtccagccac acagtcgcct attgtaccag ctggttgatg   51180
taagtctatc catcctcaga ggaacctggt tacttaccag taagctgtgt ttctctgaaa   51240
atgtagcatc cttggtaatg attcagtcc cccccatccc ctttttttt aaaccattga   51300 tgatgaatca tctctaactt ccttgtgtga tcctcaagtt ggaactggaa ttagagaatc   51360
taatttgttg ataaaggtct cctagtaagt tcctgagtcc aggacacatg gctctgacca   51420
ggtgaaatgt ggagacccat gaggtaaaaa ttcttttcac tactctgagt gacatgagac   51480
ttaattatgt aaactgtcaa ggatgataca ttttcaaaga aaataagtt gctggtaagt   51540 aactgggatt tttgagtaat ttttctgtaa gtcaataaat aagaatccca cgtttgtttt   51600
caccaacaaa tgcttttgca tttgaatatt tcataaatga aaggaatatg gttgttagtt   51660
acggttaata gtaaagaatg ggataggttt ctagatacta gaaatacagt gaggtggggg   51720
tagaccatca gttttctaaa taggtgctct cttagcttga aacagaaatt gaagtctcca   51780
ttagagaaaa tcatcaagtg tagtctgttc attccagaaa cattttttga gtgcctactg   51840 ttttttttgag acactgtgct gagtatcgtt tcaagacaga ggtgaagcca cacttggctc   51900
agctgctttt gccctcagag agcttatttc ttgtctctta gtgactctcg catgactcag   51960
aactgaggcg atgggatact ggggtatgac agaggtatgg gactggaagt agtacgtagt   52020
gctgcagcct gtgccttaat attttctgtg cttccataag ttctttctgt taatgggaaa   52080
aatcagctga cttcattcag aatttgcaga gtatttgctg tatcactaga gcaaccatag   52140
atgaagcaaa gccaatgctc cttctttgtc atagttgaaa actcattctc taacccttat   52200
```

```
gtgcgacttt ggagttaggt gttaaagcag gtgaataagt cagtcggaga ggcagcccac   52260
tccccattaa gctttcaaag cacttcttcc ttcagaagcc acagaattaa tttattcctg   52320
ccaaatgtta aaaaaatcgg aattttttt ttttaagaaa tgaaaattgt tttgtacttt    52380
aagtcactgg atagtatttg atactatcag tatcagtaat tatattcagt atattcggta   52440
attataagca cctccacccc caaatttacc cagttaagta gaaagaagga aagaagactt   52500
ggtagtatta ataagttgtt gttggaggag atgctcctat tacattatgt ctctattttc   52560
tttttttttt tttttttgag gcggggtctc ccgtcgtcac ccaggctgga gtgcagtggt   52620
gctgatcaca acttactgca gcctttgcct cccaggctca agtgatcctc ccacctcagc   52680
ccctcaagta gctgggacta caggcacgtg ctaccttgct gggctaattt tttgtgtgtt   52740
tttagtagag acagggtttc cccatgttgc ccaggctgga cttgaacttc tgggctcaag   52800
cgatctgccc gtcttggcct gccaaagtgc tgagattata cgcttgagcc actgtgccca   52860
gccatgtctc tgttttatat agtaaatact gcatggctgt aattgttatt ttaccccatg   52920
agcattgcaa gggcaagaac tacagtgcag taattaatta agctcacggg tgttgcagtc   52980
agactttaaa tccaggtttt aatcctggtt ttgtaatttg ctacctttct gactagacaa   53040
attgtataac ttctctgaac ctcagtgtcc tcatttgtga agttttgatg ctaaaactac   53100
accataaggt tgtaatgagg aataattaag ataatatata caagcactta gcacagtgcc   53160
tgcaacatag tacgtgctca ataaatgtta actgctgttt ttattggatt attggatgga   53220
tggatgaagg attgtatcag aggccaaata gcaggaaggg gaaagattgt gggctctgga   53280
gtgttagtaa actgttcaca ccttcttgtt tactcgagtt aagagcctta ttagtattat   53340
tacctttatc tttgcctttt tggaaagcaa attaatagat gaatcactgt cacagttctt   53400
cctaactact ccatccttaa accttttactt ccactaagga aggaattatt tttgtgctgc   53460
agtgactgtg atgattgaga gattatccca ctggcctgat gcaacccaat gctgagggtc   53520
aggtgtggcc catatgccag atttctactc tgaatttcac cacaactagt tctgctatt    53580 ttaagacatt ttaaataaaa aatttaaaca tttaatatgt gtgtgtgtgt gtgtgtgtgt   53640
gtgtgtgtat atatatatat ataatgattt ttcagtttca ttttactaca cttctttttt   53700
gctctatttt cattgattgt ggattatgaa tgtatgtcta ggatattttt gagaaggctc   53760
tggaggactt acacctgggc agtagtactc tttaaggaat ctcggattcg tagacagggt   53820
ggaaagtgct gtggttattt aggcacagag ttataccata tttcagagaa tcaaagatgc   53880 aaaattttc acattttaac attggaaaca acatgcatct tagaatcact gtgataagaa    53940
tggattatac ctttgtttag ttggcagcat ttttttcttag tgatacagaa gataatgatg   54000
taccttgaaa tcgctgtcat catagattgt atgaaatatg gtgtttcaag ggactatgtg   54060
cactgacaca tttttagcaat atggtatcat ggcaatataa ggagcgggaa gagcaggggc   54120
tccagagtca ggcttttgga gtttacattc tagcccgaga accatgcgca actttgggca   54180
agctacttat ccttctttt ctatagtttt ctcacctgta aaatgggggc taagagtagt    54240
acccatctta cagtgttgta atgaggatta aatagaagac atgtaatgtg tttaaaatag   54300
cctagcacat agaaagtact tagtaatcag ctaaatattat taattcagag attacagttt   54360
tgcagaatag acttaaattt actttgttgt gattgaaaca caacccatt acccttaata    54420 tttatgtatc atctgataat atcagcaatt gacacttaga ttttaaaaaa ggaagataag   54480
gaagattaac tgaacaagtt ttcttattct tttattttta ttttattttta tttttttttt   54540
```

```
ttttgagacg gagtttcgct ctgtcgccca ggctggagtg cagtggcgcg atctcgactc   54600
actgcaagct ccgcctcccg ggttcacgcc attctcctgc ctcagcctcc cgtgtagctg   54660
ggactacagg cgcgcgccac catgcctggc taattttttgt attttttagta gagacggggt   54720 ttcaccgtgt tagccaggat ggtctcgatc tcctgacctc gtgatccgcc cgtctcggcc   54780
tcccaaagtg ctgggattac aggcgtgagc caccgcgccc ggcccaagtt ttcttattct   54840
tattaagtaa gatttaagtg gcttatttgg tatacatatt actattctgt gtggttggaa   54900
tgtaagagaa atgaaggatg agctaggaaa taaatgtata ggaaaagcat ggaggagtta   54960
atcagatcgc tgaatctcat ataagtacag ttttttgattc ttactgatat tggtaagtat   55020
gggaagggtt ggaggttttg aaaatttgga aaatttgaag cattttttgca ccctaagtaa   55080 aagaaaagag agaatcctat ttggtttata tgaccacttt actgtcctag gtaaggactt   55140 tttttttcaaa attaaatatt tgggtaggca gcatctcttt acaatatgat ggctacagct   55200
taaggttgtc cttttattct taagagtcaa ttttattttt tctgttttag tgttcggtga   55260
ccagtgactt ggatttttcca acacaagtca tcccattaaa gactctgaat gcagttgctt   55320
cagtacccat aatgtattct tggtctcccc tacagcagaa ttttatggta tgtaaataag   55380
atatcttctg cttatttgat aataacttat ttgaagtaaa aaagcataga taattttatt   55440
gtcaaggtga atcaagacag tataaattct aaaagctat caaaataaca cttgaagtaa   55500
tttttaaaaa ttgattaagg tagttttttt aaggcctgtg cagtattact cttttcctat   55560
actctccaaa ggaaaagtgt taagcagtaa ccatacctag gattaaaaat atttaaaaga   55620
tgggctgggc attgtggctc atgcctgtaa tcccagcact ttgggaggct gaggcagatg   55680
gattacttga gtctgggaat tggagatcca cctgggcaat atggcaaaac gctgtgtcct   55740
caaaacaaaa gttagctggg tgtggcgcat gtctgtagtc ccaagctact caggaggctg   55800
aggtggaagg atggcttgag ggaggcggag gttgtagtga gctgagattg tgccattgta   55860
ctctagcttg ggtgacagcc agaccctgtc tgaaaaaaac aaaaggaatg aagcttatag   55920
ttcttatcct taaaaagtc agtgtcctgt aatctaagtc tgactttgag ttttttgttaa   55980 ttgagaactt attattttaaa acaactttag gtagcattttt attgtgataa tgtacattat   56040
ggtgtaaaat tcatagggct tgtgaaacat gagctgaaac atagttccat tgctaactct   56100
gacgcagcag ctttttgtaat aaaatgctaa agagaaactg aagcatgtgt tcttgacttg   56160
tattgctaaa taaaaaatat atagttgtat tacttaattg atatataaag tgggaaggct   56220
aataaaatgt tgatagaagt ccttggtgaa cctgctttgg ggaagttttt agtaactttt   56280
atactttgta cagtagagtc tcaacttcag ttactcttct gtagttgtat aaatttgagt   56340
gtagtttgag aattacattg catgaccttg agggaagttt catgttttca cagactgaaa   56400
ttctggaaga atatattatt taaatttgtc attaatttat gaatcaccca tggattttgc   56460
tggtctagcc tgggtgacag agccagaccc tgtctgattt tgctgaccaa agcagattag   56520
gcacacaatc tttattgtaa ctaagatacg ttttttggagag caggatgatg tggatatgat   56580
tgaaaagaca aaatatctaa gtgtcacttg attttggctt agatagaaag aaatcaaccc   56640
ctagtttaaa tgagattagt gcaagtgaaa tgagatgaaa acaggcctct agtgtgtaca   56700
taagcttgaa tttgaatata tgaatacatt aaaacctgca ttttaattat atgctccttt   56760
tatcccactt tttcttttcc ttgtctgtct acggtacttg ttatctttat gaactctcca   56820
gttgtcctaa atttgttacc tagggattat ttgagatttt ttccacattc cctggctgct   56880
actagtcctg tgtgtggcct ttcccagcgt gttcttacct gtgggccatg atcatagtgc   56940
```

```
tgggccgagc ctacgccatc tcacccttta aagagcttct gtgtcctccc agtcaggcat    57000
agccagtcca ttctgcttat tataattatc tttctaaaat tctgttttca accaatactc    57060
ttttcaaagg cctcttaaga cttagacttg tcttcacttg gaattagtct ctttaaacat    57120
gtacttcaga actgtccagt ctttatctat aactgctgtc atttttattc ttcattgaaa    57180
atgctcttcc tcctatgaat gtcaactttc tttaccttgt atgcttaact attctattct    57240
gtcttaactt ttgtttgatt ggctattctt ctttcttctc tgttgtcttc caaagcttga    57300
taaaaactca tctatcatct ttactagcac tgtcaacttt gatattcatc tcattcatct    57360
aaatattgaa atattttatg tttttgtaga atgttcttat tttacatata agtcacatatc    57420 cttttggcat aaactttaat ggactatcaa tactctgtat ccctagaatt ttattatatt    57480
ggatgtctta cattttttt tcattttacc ttaaactatt acaagttaat ggctgtttta    57540
ataactggat catcaagtgg agtttgggag tcttagggta gttttttggt atgggtcttt    57600
atagttgatc ttgatacacc atatttcatc atcctctatt aacatctaaa gtgcgcgtta    57660
aaactgatga tggctgggca tggtggctca tggtgtcaga cacctgttat cccagcactt    57720
tgggagccaa ggcgggtgga tcacttgagc tcaggagttc gagaccagcc tgggcagcat    57780
agtgagacac tcgtctcaat taaaaaacaa aaacagaaaa acagacgatg tcttctcata    57840
atctagagca tcttttttctt tcttagaggt atgtacaata atggtggtaa gttttaatga    57900
ttgatgacag actaagtgca ttatttttc tagaattaaa tttttttct gtcaacagtt    57960 ttctcagata tgcttattgg tgagagggg cttttatttt ttgataaatt ttagagtttg    58020
ctctctgact agtattttaa atctggagaa ctgggtaaag acatgtacac atgaaaaaaa    58080
ggttgtattt tagttatttc acatttgata cttagagtaa acctgctttt taaatatatt    58140
tttttctttt aggtggaaga tgaaactgtt ttacataaca ttccttatat gggagatgaa    58200 gtttagatc aggatggtac tttcattgaa gaactaataa aaaattatga tgggaaagta    58260
cacggggata gaggtgagcc atatgcttct tctcttggaa aaggggggcta aagaattgag    58320 agacactttt gttatgaag catatagggc atgagaaaaa ttttaatatt aaaattaagt    58380
tttgcactga actataaggg actgaacctg ggcccaggcc taagattttc agtattttcc    58440
ctaactattt ttgggaaaat tagttaggag gatcatgttt gccacctgat aattatgcat    58500
agttggttat aacataatgg caataacatg taaattaaat agaacttgag tgtatgtaga    58560
ttttaagatt ctttagtagt aaaattaatt aggattgggg ctctgcttct gtggcatata    58620
ggggctccaa cagcccctac tactaaaaaa taccgctcct ctaggacta cagtacctga    58680 aattcaatcc ttagagtcat ggtttcagtt ttttgtgtcc aggaggccct gttaaagtgt    58740
ctgaaaggat aatatttgta atatcatcat ccattgtcat tatcagcaga aagcagggtc    58800
tgaaatgatc agttaaagga cagatccatt gtttgggagg aggccaaagc cacaatcagt    58860
tcctagaaga ttcagttttc tactagaaag ttttggggag gggccattct acagaaagta    58920
gcaggtatta agataagtt tgcttccttt gcctaacacc agtcctgaaa atgatcttat    58980
cttttcctcc cctcatttca ataataatgt tttagtgcca gttactaggc tatgcctgtt    59040
ttgtccaagt agaaaagga tacataaact tttgacatta ttgcttctcc tgtgtgtttc    59100
tgacatttga tgcgtttcag aatgtgggtt tataaatgat gaaattttg tggagttggt    59160 gaatgccctt ggtcaatata atgatgatga cgatgatgat gatggagacg atcctgaaga    59220
aagagaagaa aagcagaaag atctggagga tcaccgagat ggtatgcctg attattagga    59280
```

```
ttctgtgtag ccattacagc tttctttcaa aaacagtaga aagagtagaa atagggctta    59340
gtttcttctt tctcttttc  tttctttgtt aaatatcaca ttgatagcag tataatcaaa    59400
attaacatat tatggccagg tagggtggct aactctgtaa tcctagcact tgggaggcta    59460
aggtgggcag attgcttgag cccaggagtt caagaccaac ctgggcaaca tagtgagacc    59520
ccatctctac taaaaagtaa aaaaatgaga cagggtgatt gcttgagccc aggaggtgta    59580
ggctgcattg agctgtgatt gtgccactgc acagtctggc tgggtgacag agtgagacct    59640
tgccttaaaa aagaaaaaaa aaagcataat acttgcaaca ttatcttcac ttgagtatct    59700
ttgtttcctt tggctagcaa agaacgtaat tttttgtgtg cttcactggg catcattata    59760
atatataaca ttgatattca ccgtgtacaa gttgtgtact aatcacttct tatgcaccag    59820
ctcacttaat cctcataatg gcttcatgag atggatgtta ttatcagatc cattttcttt    59880
ttcgagacgg agtctcgctc tgtcgcccag gctagagtac agtggcccca tctcagctta    59940
ctgcaagctt cgcctcctgg gttcacgcca ttctcctgcc tcagcctccc gagtagctgg    60000
gactataggc acctgccacc acacccagct aattttttgt atttttagt  agagacgggg    60060 tttcaccgtg ttagccagga tggtctctat ctcctgacct cgtgatccac ctgcctcggc    60120
ctcccaaagt gctaggatta caggcgtgag ccactgcgcc ccacctgtca gatccatttt    60180
ctatttgagg ggatagattt agagaggtta agtaacttat aagattacac tattgggaag    60240
aaacagagtc aatagttggt gttctctact tggcaaagct catgctaagg cagcatagaa    60300
tagaataatt tggcgggtga aatagcaatt tctaagaagc gtatttcaaa aaagagaaaa    60360
taacaaaaag gtaccttatt gaccttattg atcatctagt tcagctcctt cattttacag    60420
atgagtaaac agacccaaga ggtaaagtga tcactctaag tcacaaaatc agttagtagc    60480
agagctggga gtagaaccta ggttttctgc ttcccagtgc tcttaaagct tttcatattt    60540
gaatttgaat tttgtttttg actgactggc attccacaga catgtaaagt atgtgagaag    60600
taagtaaaac acaaaataga gatgatttct tagaaaatca gctttgttat agagacataa    60660
ttgggtagag aaaatgaaag atcaaaaact tgtttacttc cattctttt  ttcctttcat    60720 attctcctgt ttagataaag aaagccgccc acctcggaaa tttccttctg ataaaatttt    60780
tgaagccatt tcctcaatgt ttccagataa gggcacagca gaagaactaa aggaaaagta    60840
agaatttgtt cctttgaggc aatcttgccc tgtatggtat gtaactcacc attttggttt    60900
attacaaatg gaatcaatgt agcggatgag ccactacact ttgtttacag tgtttgcaag    60960
atacttgaag caacatgtgt acttgtggta ctctgcatta caaatatttt cctgtagata    61020
gaataaatac atatgtataa tttatatata cacataaaca cacacatata cataaaattt    61080
acagtagtac atttacagga aaattatctg gatactggta gaaatttgat gtttagttaa    61140
aactaatata atatcctttt ccatgatata tttgaatcat atcgatgaat ttgattcttg    61200
ataacaccat gcacaatatt tagttggctc tttatctaaa tagagccatt cctttatgtt    61260
ttaggcaaga taaacatcaa aagtaacaca tggaaacctt ttagaaactg ttttcaaaaa    61320
agtgattttt gtttcatgtt tacttaaatt tttcttggtt aatgtcagat ataagaact     61380 caccgaacag cagctcccag gcgcacttcc tcctgaatgt accccaaca  tagatggacc    61440 aaatgctaaa tctgttcaga gagagcaaag cttacactcc tttcatacgc ttttctgtag    61500
gcgatgtttt aaatatgact gcttcctaca tcgtaagtgc aattattgta cgttttcatt    61560
ttctatcttt gttgtggaat tatgtttaa  agcagcttgg agagtgctat catttattac    61620
aactagaatt tatcatttaa tcttgtagtt actttgacaa atatctttag atctcagtat    61680
```

```
tattattttt actttgttgc ttgaggattg ctctgaaatc ttttgcatgt atttcatttg   61740
gactactatt ttccactaac atggaattca ggtcagtgat ttttttttt ttccccgta    61800 agtgctaact aagcagttgt tttacaataa aactattatt atgaactggt agcccagagc   61860
aacattgctg atattgatga ataaattgtg ttaaataaga aattggccaa aaaaatgttc   61920
aggtaagtgc ttgtcgattt aatgtaattt tattttattt tattttattt ttttgccctc   61980
tgggtaagtt gttttttaaa aatacctgca tttgaataca agtaaaacgt aaaatgttct   62040
tagtgaaaat gtaagtatgg tatatacaaa atactttttt tcctctggca tttctaggga   62100
atgtggtttc ttagtaaatt ttcctggtaa ttgaaacttc taagcacagt ttaaaagcgt   62160
caactacttt tgaggcacat attttgaaaa tgtatttaat acttcctaat tttcctagag   62220
tagtttgctt attatagttt ggttttcct atattgtatt ttagtacgtc tgtctatggc    62280
atggtaattt ctttaggggc tttgacccat tgtaaaatcg ttttcccctg tactcaacgg   62340
ccccacattg ctttgttgtt ttgagttcct gtgcctacca ttgacagatt tattcctcct   62400
cgttcaccaa tgataacgtc tttttaagct tgcccaagca gctgtacctc acctcctcct   62460
aagtgtttgc tctacttgtt tttgctgcag ctaataatgt gttgagtgat gtaatacatt   62520
ggtctggaaa tgttaagttt tgttttgtg tgtgacatat tagtggttta gttatcttaa    62580
aatagaaaaa cttgaagtag ttttttagaa ttatcattat attgttacct ccttgctctt   62640
gttctaactc ctcatctagt ttaaattgat ttggtagttt taaaaattcg tagtaagtca   62700
tccatttgtt gcttcagcca ttggacagtt aagcccttga aatagttgtc ttgaatttca   62760
ttttaatttc cctttacaca ccatgaattt atgaattaca tcgagttttt attaagacta   62820
ttggacattg tatgtagata tcactatagc aaaagaattg agtggaagca ctattttgga   62880
gtcgctgaaa ggtccttcca atttgttgtt tatagatgta gcatttaata aagttttttt   62940
gctgtaaaaa tgaaccatag aagtaggaca ctacttttaa acattacaag tttttttattg   63000 tgccattcag agatgagtaa tttttttttt tgttaacttg aatcttgaac ctgttactta   63060
cctcattcta gctggggaga acagtggaat attttacttt aataaagttg gctttcatgg   63120
ggctaattgg ctgcctcctt gtagcatttg gtggccatgg gtccaactgt gctaggccca   63180
cttttacttc ttttttacagt agagccagtg tcttcatcat tcagtcctat tgagttctgt   63240
aggaacttca ttgttttacg ttaacttcga caaaatacca cacatggtat attttcttta   63300
ggtaaaataa gttactaaat aaatcattaa atatatataa tcatgcatta cttatggacg   63360
gagatgcatt ctgagaaatg tgttgttagg tgattttggc attatgtaaa cacagagtgt   63420
acttacacaa acctagatgg tacagcgcat gacacaccta ggccacatat ccctgcagca   63480
tgccactgta ctggatactg gaggcagttg tgacacattg gcaagtattt gtatgtttaa   63540
atcataataa acatagaaaa tatacagtaa aaatacaata ttatcttatg gtaccactgt   63600
tgtatatgcg gtccatcatt gactcagatg gtatgcagca catgactgtt tcttttttgt   63660
tgttgttgtt gttttttttt tttttgaga cgaagtctcg ttctgttgct cagtctgaag   63720
tgcagtggtg tgatttcagc tcgctgcaac ctccgcctgc tggattcaaa ggattctcct   63780
gtctcagcct cctgagtagc tgggattaca ggcgcccgcc accacgtcca gctaatttt   63840 gtattttag tagagatggg gtttcaccat gttggccagg ctggtcttga actcctgacc   63900
tcaagtgatc cacctgccct ggcctcccaa agtgttggga ctacaggtgt gagctaccac   63960
gcctggtcga ttttatgttg aatatagcat tttgtgcttt agttttctgg tctcttatct   64020
```

```
tggggatacg gtagtacttc ctttacagag ctgttgtgag gattagatga attaatgtgg    64080
ggaagatact taaaatggta cctggctctt gttagctatt gttgttttta aataggtca     64140 tcattcacat ggtttacgtt tccaaaaagt attaatatga agatgtgctg ggcgcggtgg    64200
ctcatccttt taatgccagt gctttgggag gcagaggtgg gaggactgct tgagcccaaa    64260
agtttgaggc tgcagtgagc tatgatcatg ccactgtact ccagctgggt gacagagtga    64320
gaccccatct cttaaaaaaa aaaaaaagt atgaaaatgt gtacaataaa gtctcccaat     64380
gactttctgt tccccatcct tcgaaatttt acctcactct tccactttta ttagtagtta    64440
accactttta ttggttctcg tattttttt acagtttctt tgacaagtat aaagataccc     64500
ttttttctga ccgtcttatt tacatggtgg catagcattc aggcttttcc ctttttttgg    64560
aataaggata ggatttaata ttgtagctat tagctttatc tgtatagctg catagcctgt    64620
gctgtaggag gttccagaac ttactggact ggtctctaat ggtgaccatt tggattattt    64680
tgagccttat gctgtaacga tgccacagca aatatctgta cccatttcat gcaagtttaa    64740
gtttacctga taaactctat ttaggtattg ccaaatgacc tgccatatgg ggatgcagca    64800
ctttaaagcc ctaccagcaa agtcagagag ccctgcccat agaaggtgtt accaaactaa    64860
tttttaaaat tgattttata agtgaaaaat ggcttttagc attattttta aattcttgtt    64920
tttctttgtt ttttaatctc tgcttcccac aggtgataag cattgtttta atatctggat    64980
ttaattcctt tgaatgaggg taggatcttc ctatatgttg aagagtgaac tattttatt     65040 ctttgttttt ttgattttgt gagacgggtc tcgctctgtc gcccaggctg gagtgcagtg    65100
gtgcagtctt ggctcacggc gacctctgcc tcctggattc aagtgattct cctgcctcag    65160
ccttctgagt agctgggatt acaggcgcgc accacctcac ctggctcata ttttattt     65220 tagtagaaac agggtttcac catgttggcc aggctggtct caaactcctg accttaggta    65280
atccacccac ctcagcctct cacagtgcta ggattactgg tgtgagccac tgcgcctggc    65340 ctattttat tcttggtctc atagatcttt ttgatgtctt aggagctttt tatataatca    65400
ggaaattagg ttttttgaaa tatgagttgc aattttttc aagtttattt ggtaaaagtc    65460
ccataagcaa agtttaaact tttttttttt tttgagacag tcttgctctg tcgctcaggc    65520
tggagtgcaa tggtgtgatc ttggctcatt gcagcctttg cctcctgggt tcaagggatt    65580
cttgtgcctc agcctctgga gtagctggga ctacaggcat gtgctaccac atccagctaa    65640 ttttctatt tttagtagag atgtggtttt gccatgttgg ccaggccggt ctcaaactcc    65700
tgacctcaag tgatctgccc gcctcagcct ctgaaagtgc tgagattaca ggtgtgagcc    65760
actgcacctg gtcagtttaa acatttttta aaagtagtt gaatttatca gttagctttc    65820
ccattccaag attataaagc gtttctcact ttttctagta tgttttaggc ttcatttta    65880 aaaacataaa tctttgatcc atttggaatt taatatgatg tggattataa atctgatcct    65940
cctcctcact tccaaagttg cctagttgtt tcatttactg aaaagttcat ctttcactac    66000
cttgagatat ttccttcatt gcctgttgcc atatgtattt gggtttctca acattgtgtt    66060
cctttagtct attcatgagg cggtattcag agatctcctg gcaattcttg ttttctata    66120 taaatttatt tatttagaga gagagatata tatacataca cacatacata catacacagg    66180
gtcttgctct gtcacccagg ccagagtggt gcagtggcac aatcatggct cactgcaacc    66240
ttgacttcct gagctcaagc tcttctccta tctcagcttc ctgcgtagct gggactacaa    66300
gcatgcacca ccattgctgg ttagttttct ttttcttttt ttgagatagg gtctcactat    66360
gttgcccagg ctggtcttaa actcctggcc tcaagtgatg ctcctacttt gggctcccaa    66420
```

```
agtgctggaa ttacaggcgt gagccactgc acccagccta tatacatttc aaaatctgtt   66480
tgtctagttc ttttttaaaaa aaattagtgg tatgttatt ggaatcccat taaatttata   66540
aattacctaa tttcttttta aaatataagg gttaagtcta actaaccata ccatcacctc   66600 tcttttttgtg tcctttaatt atctcccaag ttttctttat gtgactcttg tacatttttt   66660
gttgagtatt tctaggtatt aaacttgctg ctgctgttgg gcttttttcca cattttgtct   66720 tctgttttgt accctgctac cttactgcat tgtcttcatg ttttatcagt ttctcagtac   66780
attcttagga gttttccagc tgtgtaatta tactgtctgt agttattaat ggttttacct   66840
tctatccagt ctttataact gaagcttctt tctcttttct acctacttta tttatttatt   66900
ttttggttgg gcgggggagg ggagtgggga ggctttctga taaaaaccag aaagcctgct   66960
agacaaattc taaaagagct gtaactgtct tttctaccta ctttagcttg tagtttcagt   67020
acagtttaaa aattagtagt gctggtagat agagataaat gttctgtctc ttctggatga   67080
gttttagaaa attattcttt acatccaggt tttgagattt atttgtatga agtttatgtg   67140
ttctctaatg ttcgttttat ttttgttaat attcttgttc tctatatatt tcattgtcac   67200
ttttttgtta agaagtggtt tttgtatttt aaattatgta ttttttttctt cagagaacca   67260 gctacaatgt tagtttaact cataaacaga aaaacagttg tattagggtt ccttaacaaa   67320
cgtaatccag caccagatta gtattggtgt taggctgtct ggagcctaat tgctcacacg   67380
cttccaacag aatctgagcc ttgaatttt cttctttaaa aacacaactt tgtccttttt   67440
tttttttttc cttccttttc tcagtcttta aatatggctt tttacaaata tttaaaagat   67500
gatttgtttt gtggaaatgt cacttgtttt tctccaaatt aattttcatc ttgtataatt   67560
ctgaatagtc catttccagc atttcccttt tgtatatgag gaagtaagtt tttgcaagaa   67620
attctgtgaa gttagcactg ctgtcaatgt tcacactctt tcatgtagc agtgtacccg   67680 catttgaatc tttctgttac attattttgg aattttaggt ttcaaacagt gtatctttct   67740
aaaatccgtt ttttttgacat tgtaattttc tgtggcaaga cactataagc tctcaccagg   67800
ttcttggatt gggtatgatt cacaggaatt gaatgttagt aatctggggc tgtcctcttt   67860
atcattaaaa atgagttttt acaactggtg acaagctgat tgctgacctt tctttagaaa   67920
tcaagaaatt gtatgtcaga attaaaaata ggaaatctga tttaattgta gagggtctat   67980
caactgctta gacagagata gtaagattca atttaagtaa atgtttataa ccatagttat   68040
gcgcatcagt tttacttgca aggagaaaaa tgagaaatca cgactcattc cagaatttac   68100 tgttttttcct tcctgcttaa tggttggagg aggaggaatg gagaatacgt tgtgatcatt   68160
cagtaagagc ctgaaggaaa gttgtatgaa gtaacgtaaa ccacatatta gcaagattat   68220
aatccattaa ttgacttttc cagtggaact ggaagagtga aaaagtaagt atttttatagt   68280 tatattagat tctttgtttc atttattttg cagcttttca tgcaacaccc aacacttata   68340
agcggaagaa cacagaaaca gctctagaca acaaaccttg tggaccacag tgttaccagc   68400
atttggtaag acttagtgcc taattattgc agagggtact tgagaggact ttgcactttg   68460
gtggaggtga tcaagtcagc gttaatgttg tctgcaccca tgctgttatg ggccatatga   68520
tagacagagc tttctcaccc atgctgtttc ttccatagct catgtactgc acattttagt   68580
ccttcattaa tgtggtatta ttcttttaa aatctgtgtt atctcttcag caacatttca   68640
aggtctttag gatcaaggac ttttatgcct tccacaaagt ctatgagagt tgcaaggcac   68700
agatagtccg cttagaaagc aggcatgcag taatcatacg cagtagatcc caagcccctc   68760
```

```
tcatagccat atccctctac ttgagtttta gatgcactgt catttcagct atgtgatagg   68820
ttccacagat ttttttttt taaatgatgg agaacaggta aggggttagg aaaatatgag   68880
gtagaaaagt tgttttacg ggtactctct tattttacc atttcccctc tttgaaccaa    68940
gccactccta cctaggaact aaatgggtat atattgcctg ttggattttg gacagaagat  69000
tcattgaatg gcacctgcag aaggtatcct attttaagc aatttggttt ttgtagaatg   69060
aagtataaaa ctgttggctg ctgtcaaact tctcccttct atttccacta aaaaatgga   69120 attcttgagc acttgtttta taatattctt tacaaggcag aattttgttt ggctcatcta  69180
aaatgtttct gtggtctcta taaccatgc tcttaccatt gttttatact ttgagactgg   69240
attattgtac ttcataatgc aagatgtaac cctcacagtc ttattcctga agttcctttc  69300
atgtcttcct gtggctgtgt atccttcaca ggaaaaaaaa aaatgttgga tgttttaata  69360
gtaagacagg aagtgacaaa gtcaagcatg tttgtgtttt gtgttcttgt atagttgaaa  69420
tattaacacg aagaggtatg cattatctta aactctgcat aggtagtctg actccgtgca  69480
cattaggtat atgattcttt tgtaaagatt cacttttaaa tagactgtat gtccatagag  69540
ataattacct ttattacatg aagtatattt catactttat cttcttatat tttaacttaa  69600
ttataactag ctaatatatt ttacaaattc acaatataga actgtcttgc ctgattttttg 69660 taccattcta ggaatatata gaacccatat ttctctttct gaaatttttca gactatcaaa  69720 agcatatcaa aacaagtata ttagacatgc aaatgattat ttgtgataaa tggataatgt  69780
gatacatttt ttgactaacc tggcttatat agtatttttt tttctcttcc atcaaaatga  69840
gttttagaac tttgccctga tgttgacatt tttcatttcg taggagggag caaaggagtt  69900
tgctgctgct ctcaccgctg agcggataaa gaccccacca aaacgtccag gaggccgcag  69960
aagaggacgg cttcccaata acagtagcag gcccagcacc cccaccatta atgtgctgga  70020
atcaaaggat acagacagtg atagggaagc agggactgaa acgggggag agaacaatga    70080 taaagaagaa gaagagaaga aagatgaaac ttcgagctcc tctggtaaga cacgtctaat  70140
aactgggttt tactgttctg tgaaagttcg tgttgtgagg attaaggatg tataatgcat  70200
tgaataattt tcttagttgg ttagtttcag tataaagacc agagttatct caagaatgtg  70260
tagctgtgtt gtttctgttt cctgcctgca cccgtaccct agcttgtggt gtttgccctg  70320
cttggttgtt tgaaagctga tgatgcactt tattctcatt ctttgtgcca ttttctttt   70380 tcgatctttc tcaggtaggg aataatgaaa tttggatcat ttggtttaat attcttgacg  70440
ttctgtgagt agtttttgttg gaaaatgtga actacgatgg gttagtgttt tgccgattgg  70500
atttgagttg tcctcatctt ttcgcttttt tcttaagcac accctgaatt gtacttctta  70560
atattatttc caatcatttc ttgaccagtg cttacatttg gttttgtaga agcaaattct  70620
cggtgtcaaa caccaataaa gatgaagcca atattgaac ctcctgagaa tgtggagtgg    70680
agtggtgctg aagcctcaat gtttagagtc ctcattggca cttactatga caatttctgt  70740
gccattgcta ggttaattgg gaccaaaaca tgtagacagg taagatatcc gataaaaatg  70800
ttgttaaaag agcttcaaac atagagataa aactgtactc gttgtccaaa caagaaaat   70860 tcttggttat tactaagctc ctattcatct cctaaaaata atttttttt cttcccaaga   70920 gggaattgaa tgaaaattat tctccaggta tgttacagaa tttccccaat gtagactttt  70980
aaggttagat agcagtagct tttaaaagct agtaagaatt gaaatttagc atcacagttc  71040
ttgaccagaa tataattaca gctacccta atgtgagggt agggacagcg atgtgtgtta   71100
tatccccagc atctagcagt gtcacagaag agacaaagac attttctctgg tatgcatgag 71160
```

```
tataagaatg gtttgcctaa ataagactgt cctcatggct ctgtgactgt gcctcttgtc   71220
aggtgtatga gtttagagtc aaagaatcta gcatcatagc tccagctccc gctgaggatg   71280
tggatactcc tccaaggaaa aagaaggaga acaccggtg agtctgtcat gaagctcctt    71340
agagaagtca acatagatag acactgcagg caaggcccctt cctaagggct gttgttggtt  71400
tctacttagt ctattttaa aaaccttaa actgccatca aaaacagaac tatggaatct     71460
tatttccact gggaattgct agtatttttc tataagaata cagcagcctt cagtatattt   71520
ggtatgttaa gagtcataaa aattacggtt accagactgc atttgggtta agaaaaacat   71580
atttagtagc ttttgcagta aaggttacgt aaacaattac tttaacatca tgaaatgttc   71640
tgtgtttctg atgtgagctc tgggccagtt tttagaagta tcttttattc caggagcttg   71700
aatttctaag ttgtgtggca ttgcattccg atactcctaa tgggtaccct actttaagct   71760
tgtgtgaatg ttattttcac cttagcgaat gttttcaggc tgatttgatt tgtaaatgta   71820
gaaccagaaa aattgatgag tggactatct gctctaatct ccccataccct ctacctcaca  71880 tttttaaaaa tgagaaacct aattgggtag gtaagggtgc agttagatta tgcttcttaa   71940
attgtgtaca ggctcatgtt acatttctt actttaacaa aaataagtgt agggccaacc    72000
caatttagaa tttttttaaa gtcaagtttt tattttatt ttttaggctt taggagatgc    72060
ttctgaaatt ttggttgaat tatttctgac cacgtagttc acttgcttgg tttatgatgc   72120
ctgaaataag aggaagtgat cagtgtcatc cacatcagaa taaatcaaca ggcagacaca   72180
cctgctgctt tgtgcagcat tgggagctca ggagttctga ccaggagtca tggatgaaca   72240
caggaaatga cgtcttgcca cacctggggc agcctgagcc atcaagctgt ttgagttgct   72300
tcaaactgat ggcaaatata aactgggcag ggcatgactc ttggctttaa cgcattcctg   72360
tattcatggc acagatagat ccagttaagc agctctctgt tggatttgta gcttcccgca   72420
gaaatttggt ttaattttct ttgtgttttt gcaggttgtg ggctgcacac tgcagaaaga   72480
tacagctgaa aaagggttag catctttcca ttcctctcat tattagctta acaatatctg   72540
ctttgttttc atttgtttta gaatagtaac tggattagag cttgggttat tctaatataa   72600
ttgccttctg tatgttaaac caatttgaat ggaggacgtc tactgatgaa tccccagtca   72660
attctcttct gtaaagtgga ggctgactgg aaggtgtgag tccgagtcag ttgaaggaga   72720
agtgctttgg gatgggactg agatgtagcc gtgctttaga tggaactcat aagcacttgg   72780
gggtgggaga gtattttttg ccatcgttgt ggaaaccgga atatgtgtaa tgttatgcat   72840
tcagtaaagg caggccagct acactccaca ggtagtaggg aagaatgtac tcgtgttaat   72900
tgtgtatgat cgtttccatc tccctggatt cattggcctg catgatgtta tctttactca   72960
gacggctcct ctaaccatgt ttacaactat caaccctgtg atcatccacg gcagcctgt    73020 gacagttcgt gcccttgtgt gatagcacaa aattttgtg aaaagttttg tcaatgtagt    73080
tcagagtgta agtatttgtt gctttgatgc aattgcatga gaactaaata ggtctttggt   73140
tagcaattta aaaaatcaaa aataagaaca tgggagcact ccttgttta cttgacgaaa    73200 ctcatcaatt tgacaagtat ttattgagcc ccatacctgg ccctgtgcca gtggccagtc   73260
agtcgcctgg gtgttgtgtg tctgtgtgtg tgaggcaggc aaagttgtat taaaggaacc   73320 tgaatttat ttttttcttc tttgatcatt taaattaagt tgtattaaag ttggcacaga    73380
ttgtaagagg aatctagaag gagctaccca ataattttt gggcaccaga aatcgtcaga    73440
gttaggaggg ttttagtctt cagattaaag gaatgtagca taaacatagt agattttat    73500
```

```
aattgtttaa tgagactgca catgaagctt gggtattaag ggagtgttta gaactagggg   73560
ctattggaat ggtcaaggac catggatatt gttccatcca gacccttat tcacaccgac    73620 tttaaatata tacactattt aacaaatgaa aaatggaaaa acaactcagt ggtggtcttt   73680
ttcagtgcaa acagctataa cttcgctgtt aatacttcca tttccttgtc tatatagtag   73740
ggtaataagg tggttgtgag ggttgagagt cagtgagatg cccagtacag cccttgccac   73800
gtatctttct gcaagttttt gcatacggtg atgagtgaag aacctccaaa cctctctctg   73860
aaggtcaaaa ccgctttccg ggatgccgct gcaaagcaca gtgcaacacc aagcagtgcc   73920
cgtgctacct ggctgtccga gagtgtgacc ctgacctctg tcttacttgt ggagccgctg   73980
accattggga cagtaaaaat gtgtcctgca agaactgcag tattcagcgg ggctccaaaa   74040
aggtgagcaa caagtcactt ctggaagatt gtttgtagtt agctatttag tgatgcaaat   74100
gtcaggattg ccttagatga tttagctggg gcaaaaagta aaagtgatcc ttgaaaggtg   74160
caactgatga gaaagtgttc ataattttct ctgggtaatg caccctgggg cagtctcttc   74220
agttttatat agagcaccat actctgatag taggagaaac cagcaaattc tgagaagtag   74280
ccattcatgg tatcagattt aggaataaga ggtattttt ctacctgttt aatagattat   74340
ttgaatttgt cttttagtta atagtttatc tagtatcctt aatgcaaata aatggtgatt   74400
tctatcaaaa tatagactca ttctcatcaa agagtattta tagattcctt gctatgtaga   74460 gtaaagatg aaatttccca tggcaggttt ttatagactt acttcctgtt tgtttaataa    74520
ccttgaaaaa aacccagcta ggaactatat attttagtc tggggaattg tatgtaggtg    74580
agttaactct atcagccagg aagtaatgat tgagcaaaag acacttcagc agcatgtatt   74640
tgggaaattt cgtatctttt ttttttttt agggcagatg ataagttctt tcttcagtca    74700
gttcttttta taataatagc tgacattat taagcatgta aaaataggca ctgttgtgag    74760
tgctttagtg gatttgttca ttgattctcc taaccctgtg agtgaggagt aagtgttaac   74820
ccccatttta cgggtaagga aacccaaagt cacaagactt gtaaaggagc aggagatcaa   74880
atcctccagg ctcccattaa cctgctctta tgctctgtgt gtgtgtgtgt gtgtgtgtgt   74940
gtgtgtgtat gtggggtgta gagtagacat atctttgttg ttggaccatt tatttataat   75000
tgagaacaca cttcttacca gcaagtcccc ttctaccaga aattctgctc caggcaaaac   75060
attgaagttc tcttggtttt gtttgtgtct ttgaaccaaa gtctgtgttt atggcagaga   75120
gttgtgcagg gtggtgggct ttttgttttt agctttgact ttttcttt ctgttagaca    75180 tttagatgat tttactctag gcagttatat gtccatttag gtcattggat cacagtgact   75240
ctggttccgt ttccgatggc atacctgctc agacctaaaa atctcaattt ccccccccaaa  75300 caacttacca ttgtactcct tcctcacttt gttcagaaag tgggcaattc tattcatact   75360
gacatgtcct cttgtaaga cattttttaa ctcttaaaaa tgttaaacta tgtagatacc    75420
ttttaccagt tgggtttcat ttgcatagca gtatttagct aatttagttt ctgatcagaa   75480
ggctatttgg gaagttcaca tgacaggtga gtggtaagat ggtccagaat aggaatagat   75540
aggaagcctt tgtaaaggtc acaagaaaat tttggatgaa agcataatac tgagccgtga   75600
tgaaaaattg gcatatgttg gggaacacat ccctaaatac ataatttata gcaatgatca   75660
tcttggcatt tctgctgaaa atagactact ggactgacaa gatcatgata acacctcccg   75720
gtagtttctt gtgttatcct gaggaggtgg ggtggaagaa caaatccaaa gccaagctgc   75780
tatgggcttc agagggaacc aacgccagtg aagaatcagg gggtgtcctg gggctgaaaa   75840
tggaataact attaatagaa tcacttgggg aaagtagagg gaaaggtatg gagaggaaga   75900
```

```
gtgatttggt ggtgtcctta tattaaattc aggttgaaag tgaattactc gaggaaatca   75960
agggctgaag atacagggaa gccaaaagtg cagcaggcct agagcacctt gctgaacgat   76020
ggtcattgca gaggaccaac accaccaaaa ggttttctgt aagacagaga ttcttatctg   76080
ctgtataagg aaaacataat gttcatagcc attctcagca gctttcacgt tgactgaagc   76140
tgtgtgccca attactgcct tagaacaaac aggtctgagg atttacagtg atagcttttg   76200
ttttcattct gtagtctact ttgtccccag tccattttca ccctccttt ttgatgatgt     76260 gattgtgttt tattctctag catctattgc tggcaccatc tgacgtggca ggctggggga   76320
tttttatcaa agatcctgtg cagaaaaatg aattcatctc agaatactgt ggagaggtaa   76380
ggcactgata acctgtattc aggtggcatt gtatatacta actttacttt attttagatt   76440
gattttatta ggtaagtctg tgggtttgat tggaaatgaa ttgccataaa ctgccttttc   76500
agcctggact tctgcatgtt tgtggatttg catgcttagt aactggattg tgctgggcgc   76560
ggtggccgac tcctgcaatc ccagcacttt gggaggccga ggcaggtgga ttgcttgagc   76620
tcaggagttg agaccagca tgggcaacat ggcaagaccc cattgctaca aaaaatgcaa     76680
aaattagccg ggcgtggtgg tgcatacttg tagtcccagc tacttgggag ctgaggcagg   76740
aagatcgctt gagcctggaa gagcctggga ggttgaggct gcagtgagcc atgtttgtgc   76800
cactgcactc cggcctgggc gacaaagtga gaccctgtct cagaggggaa aaaagcaaa     76860 acaaaacagg attgcttggt tctagccaca tttagttttt ctcgtctagg gacaacaggg   76920
agaacaagag cttaccata gagtggcctg cttaatccac aacctagttg ataaggacct    76980
agaaacaaca acgtcattag ttattcacct tttaaattgt cgacagtgtt accgaaaaat   77040
cataggccta gcttcagttt ggaaccagct cacccaaatt tttttttttt tttttttttt   77100
ttttgagaca gagtttcgct cttgttgccc aggccggagt gcaatggcgt gattttggct   77160
caccgcaacc tcagcctccc gggttcaagc gattctcctg cctcagtgtc ccgagtagct   77220
gggattacag gcatgcgcca ccgcgcccag gtgatctgcc cgcctcggcc tcccaaagtg   77280
ctgggattac aggcgtgagc cactgcagcc ggctttttta aaaaactcag caaaaagact   77340
ttggttcctc actttctcca aggataatta cttcaggatg tggaaatatt tctgagttgg   77400
ggtccttagt atacagttat tctttattac tgcgcagacc gaatgggaaa gagaacttgg   77460
ctgtagtgac cctttttgtt gcgttttctc cagaaggtcc agtattcact ctgtgcgctt   77520
ttgtgtgttc tgtcaggctt gatcaccttt atccaaaaga attttctcct gtgtctttct   77580
ttttagatta tttctcaaga tgaagctgac agaagaggga aagtgtatga taaatacatg   77640
tgcagctttc tgttcaactt gaacaatggt atgtttcaga gctgggaggc agtgagttcc   77700
tgagttgcat gtggcagcct tctgccggcc gagtgttcag aaacgagggt agaggtcagt   77760
gaggtgacca gaaggaggat ctccttagag gcatggggggg ctgcttgctt gaaaggaact   77820
ggagcaagga attcctcagg gagcagatag actagatgtg caggaaaccg cctctctgga   77880
gtcccggctg tctgtgggtg gcactatccc agcatctggc tgtgaagggg acgttgtgct   77940
cttgctgctc acctcacctc ttgtgttcag gcagctcagc acacctcctc cagtcagtgc   78000
ctctgagcgg ggaaggaggg gaggagcact gcatttgcaa ccatcttcca gactcccctg   78060
gatattctca aaggactgag aggaaaggca gctgctttca tagctgatgt tctggggtag   78120
aatgtaaggc tgtgtaggga tgtttctggt gggattatgt gaaatggag gtaggcttaa     78180 catgtaagat attcagagaa actcttagtt ggaacaagta gaataggttt ttttctatga   78240
```

```
atgctttata gacattataa tgaaaaaaac taattttaaa tgtgaaaatg cctattcgtg    78300
atgtttggaa gaattttgtc agattttttt tttttttgc tatgttttgc tcagtaatgt    78360
atgtttatag ttgataatta atagcttttg agtcagataa ccatcttgaa ttataggtga    78420
ttaattttaa cctggaacaa tagtgtgttc ttccaaatgt catttcttac tgaatgaagc    78480
tgcttgattt atttgctttt gcaggcaaac cctgaagaac tgtaaccagt tgcatttaca    78540
aaatcataat aacttggttt acttataact gaaattattc actgggctgt gcttactttt    78600
ttctttttag attttgtggt ggatgcaacc cgcaagggta acaaaattcg ttttgcaaat    78660
cattcggtaa atccaaactg ctatgcaaaa ggtaggtacc tttgacgtga gaattggaac    78720 tccctttttca gtcctgtgat gatggacttg aatacttctg ggatagttgt tgttatgtg    78780 aacaagtcag ttaacccccc gtggcccgtc ttcatgctca ctgacaccag tgtgtctctt    78840
tgcagttatg atggttaacg gtgatcacag gataggtatt tttgccaaga gagccatcca    78900
gactggcgaa gagctgtttt ttgattacag gttggtaaag tacatttcta gcatgatctc    78960
taagggcttt ttctactgga ttgtgaactc tggacaaagg aggggttttta gttctttgct    79020 tcttttgatg ggtcactttg ccatgagcat tagtggggaa ttaggttaca ctttcctgtt    79080
atgtatttat tatccattta tatattatac aaggcatgct tatttttaaa atagagtaaa    79140
atccatgcag aaagccccat ttctcaccct gctgttgaca gctgggtgag tcctagacct    79200
tctcatatca tgccgcatgc tgcatgctca ctcgtggagc gttttccaga taagtgcgat    79260
cacactgtcc tatagatttt tctgcaacat ggttttactt gacaatatac tatgcatatc    79320
tttatggatt agatctactt aatttattgt ttgctataat acttattaca catatcatta    79380
ccattttaaa aggggctgtt ggcaaatcgc tgtctgatca ccctgtgggg atgcctggga    79440
cacgtgggcc accaatggta tctgtgtggt taggcattag gctgccagtt gacactgtca    79500
agctctgtgg gatacattta agtcagccat tgaatacaga tttaagtgca gtcagatgac    79560
tgtctagtta atgaactcct gtagccccgt gtacatccca tccagaagct gtctttgagt    79620
actgtgttct tgcatattca ggctggcctt taatggctgt tgcacagcag cgagctctca    79680
gtgaggcaga cagggtctga gtgaagggcc cactttagca aaggccgctg ccttcactcc    79740
aggctggctc tgaatgaaga gtgtggggtg gagcttcctt gggatgaccc ggtggcctca    79800
ccccccatgg tgggcttctt gtgctcctct ctgggtgtcc gctgcactcc agttcttgct    79860
tcacctgggg gagcaactgg cgggctgctc tttggccctc tttgctatgg tcatcatttt    79920
ttccagacca tggttctatt ttgccttccc agcgtcaggc ctaagcatcc tgatgtggac    79980
cagccttcct gggaccactt gcttcagagg catagggag gctggtcagg ctctgggaat    80040
gcttgtagac aggtttgttc acttcagaac ttggcagcgt ctcaattaga tggccagcaa    80100
cacagaccta tgcattgcct tctatgaatg tgccgttatg caggcagctg tgtaattgga    80160
tgggtttttt tttttttttt tttttaaag acatttaat gcacccacta tcttcagcag    80220
gctttgttgt gttaagtctc agcacatgtt ggatgggtgg ccatccagcg acatctcct    80280 tcctgttgtt tcagatacag ccaggctgat gccctgaagt atgtcggcat cgaaagagaa    80340
atggaaatcc cttgacatct gctacctcct cccccctcct ctgaaacagc tgccttagct    80400
tcaggaacct cgagtactgt gggcaattta gaaaaagaac atgcagtttg aaattctgaa    80460
tttgcaaagt actgtaagaa taatttatag taatgagttt aaaaatcaac ttttatgttc    80520
cttctcacca gctgcaaagt gttttgtacc agtgaatttt tgcaataatg cagtatggta    80580 cattttcaa cttttgaataa agaatacttg aacttgtcct tgttgaatca tctctcataa    80640
```

```
cgtgtcaata actgctttca ggactgctca acaaaaaact tttaaattta actccttggg    80700
ttttttagtt gtctttgtat gaatcttgat ttaactaata ctgcctgtga atatgtggaa    80760
gacatatatg aagaacactg ctgtgcatcc tgagggctta cccagtaaag ggcttgatct    80820
tatagacaag accagggtgg gtacgttcca gtcagctgtg caacctggag aaagagattt    80880
aacctccaag tctgttcccc atatataaac tgacagagta gacttttagg ttattttaa    80940 gaacgtacct agttctaaac tccattagtc tagatagagt tctttagaaa caaacacaat    81000
ataagttggg attccttacc taccttatca caaaaggtga ttgataggta taaccaaact    81060
gtagttttat atcttctcag aggtaaaaat cacaaactct gaaagcgtca aggaaacgac    81120
atgtaccttg catgccttat gataatgtgg tttgtcccag aatttgaggt aacttccctg    81180
caccctcccc aggtacattc accagcagca tcatgggaac cctgacaacc gctgcaaacc    81240
agtccatact gtcagttact tagcagttgc ctttgctaca gttagatttt tatttacaat    81300
gtggtagtat taatatgaaa cctaattaaa tggactcatc ttgctttcca gttccacagc    81360
atttgcggga tcaggtctct ctctgacaca tcagtgcaca ggcgcagcaa cttgagtcct    81420
acagttaatt tgccacttga tttgggattg aggagatccc tccctcagcc tcgtcccatg    81480
gtttcttaat gacagtgctg atctatttta catctaaata actatctcca ctctcaccca    81540
gaaaacggta ccattcactt cagagcttgt tgccctcgat gccctcatgt tccgctcggc    81600
actcagcagg accctgggca aactgggcag ccatcaatct cctgaggcag ttacttcatt    81660 atttggggtta ggtcattctc tagatggctc actggccttg cctaggcaca ggcgcatgga    81720
gcccatctgt tcatcatcgc ctgttcatga accccaaag attacttggg ctcaaaagta    81780
cctgttgaca tggctcattc cagctacagc cctcaaccca tcctcagagg aacagctggg    81840
aagcagatcc ttgaggcctc cagtgagctc aatgtaccag agcccaaat gcgtaggaaa    81900 gacaaggtgg cattgatgga aagcagtagt ttttgagccc tgtcgtgtat tctcattgca    81960
cagcaagctt tttataccat gatctgaaat gcgcttctct aaaagcctct tcagtgacgt    82020
ccgtgaacac agattttctg aacagaaatc cttgacgtta ataacccatt tgatacaacc    82080
ttctatcaag cttgtctggc ctgtggacag ccggttgcat acagcccaac acaaattcgt    82140
aaactttctt aaaacattga ggttttttgt gatttttttt tttttttaa agacagacag    82200 ggtcttgctc tgtcactaat cagcctggag tacagtggtg tgatcttggc tcactgcaac    82260
ctctgcctcc caggttcaag cgattctcct gcctcagcct tccgagtagc tgggattata    82320
ggcatgggct accaccccta attttgtgt ttttagtaga gatggggttt tgccttgttg    82380
gccaggctgg tcttgaactc ctgacctcaa gtgatccacc cgcctcggcc tcccaaagtg    82440
ctgggattac aggtgtgagc tgctccgccc agcgtttttt tttttttttt ttaagctcat    82500
cagctactta atagaaggct tgacatatac aataagcggg acctcaccca cagactaact    82560
actgtgggta aagttagagg cacctagaag ctgtgctagg tttcattat tgtctggttc    82620 atcccatctc cagtcttcac cgtatccatg ccaggtcctc acttccactt ctgcccaaga    82680
tgttcagcaa ctccaccaaa agtcaaatca aatgtaaacc cacacattta agcttgtaga    82740
tagctcatca agactggatc cgaaatgtaa acatttgaa aacagtattc tgttaaataa    82800
ttcttaatgg aactagttga aataattgcg tatccactca atcccttgat ataaataaac    82860
aattccagtg ggggctacac atggatacct ggcattagaa gtggtctaca ctcacctgtt    82920
acggcaaggg cattgttggg gttgcccctg gacagggtca tgaactggac agatgaacga    82980
```

| | |
|---|---:|
| tgatggtata aaaaatgaac ctgggcagcc aagtgactgt gattcctacg aacaagaagg | 83040 |
| tgtcttcatt agaaggggga ttcagttcaa atagctgaag gccagcaagc atgttttcca | 83100 |
| actgggggtg gtcatgctaa acttcacagg aaaattaggt accaatattc atcaaggagc | 83160 |
| agcatcttaa aatgctgtca gtaaaaatac atacatgaca ttacaggcac ctgttggtcc | 83220 |
| tgtagccact ttcttaccct tcagattcct gtcatgtggc gtgcctggcc agcatcccga | 83280 |
| gtctataccc tacgcttaac agagcccaac caggagactt accctcccag cgccgagat | 83340 |
| caaggtcctc ccttcccttg ttcccttagg tcacagcaat acatactcag cctgtgcatc | 83400 |
| tggtcttagt gcacagccca gctctgatta aaccacaatg aattttttcta aacccagga | 83460 |
| ggtaaaatat tgatttata aaatatgagt tcaagttgtc aatagattaa acctttgttg | 83520 |
| ctgtgatact gtttccaacc tctttggcca tgattccaag atagtaagcc tggtctcagt | 83580 |
| ggtaaccacc acaccgtgta gaccccccact aggatttggc agcaaatagt cccagatgtt | 83640 |
| tggtgttcta cagacaggct cccctatact tcaacaaagg gtaaaagcaa gagtgacaat | 83700 |
| gtgagtactc tggggctgga ttagttcagt gatactgcgc ttggtggttc tttgtaaact | 83760 |
| attttttgttt ttttttttttt tgacacggag tcttgctctg tcgcccaggc tggagtgcag | 83820 |
| tggcacgatc tcagctcact gcaacctctg cctcccaggt tcaagcgatc cgcctgcctc | 83880 |
| agcctcccaa gtggctggaa ctacaggcgt gtgctaccac aactggctaa ttttttgtat | 83940 |
| ttttagtaga gatggggttt caccatgttg gccaggctgg tcttgaactc ctgacctcaa | 84000 |

<210> SEQ ID NO 3
<211> LENGTH: 2723
<212> TYPE: DNA
<213> ORGANISM: Homo sapiens

<400> SEQUENCE: 3

| | |
|---|---:|
| ggcggcgctt gattgggctg gggggggccaa ataaaagcga tggcgattgg gctgccgcgt | 60 |
| ttggcgctcg gtccggtcgc gtccgacacc cggtgggact cagaaggcag tggagccccg | 120 |
| gcggcggcgg cggcggcgcg cggggggcgac gcgcgggaac aacgcgagtc ggcgcgcggg | 180 |
| acgaagaata atcatgggcc agactgggaa gaaatctgag aagggaccag tttgttggcg | 240 |
| gaagcgtgta aaatcagagt acatgcgact gagacagctc aagaggttca gacgagctga | 300 |
| tgaagtaaag agtatgttta gttccaatcg tcagaaaatt ttggaaagaa cggaaatctt | 360 |
| aaaccaagaa tggaaacagc gaaggataca gcctgtgcac atcctgactt ctgtgagctc | 420 |
| attgcgcggg actagggagt gttcggtgac cagtgacttg gattttccaa cacaagtcat | 480 |
| cccattaaag actctgaatg cagttgcttc agtacccata atgtattctt ggtctcccct | 540 |
| acagcagaat tttatggtgg aagatgaaac tgtttacat aacattcctt atatgggaga | 600 |
| tgaagtttta gatcaggatg gtactttcat tgaagaacta ataaaaatt atgatgggaa | 660 |
| agtacacggg gatagagaat gtgggtttat aaatgatgaa attttgtgg agttggtgaa | 720 |
| tgcccttggt caatataatg atgatgacga tgatgatgat ggagacgatc ctgaagaaag | 780 |
| agaagaaaag cagaaagatc tggaggatca ccgagatgat aagaaagcc gcccacctcg | 840 |
| gaaatttcct tctgataaaa ttttgaagc catttcctca atgttccag ataagggcac | 900 |
| agcagaagaa ctaaggaaa aatataaaga actcaccgaa cagcagctcc caggcgcact | 960 |
| tcctcctgaa tgtaccccca acatagatgg accaaatgct aaatctgttc agagagagca | 1020 |
| aagcttacac tcctttcata cgcttttctg taggcgatgt tttaaatatg actgcttcct | 1080 |
| acatcgtaag tgcaattatt cttttcatgc aacacccaac acttataagc ggaagaacac | 1140 |

```
agaaacagct ctagacaaca aaccttgtgg accacagtgt taccagcatt tggagggagc    1200
aaaggagttt gctgctgctc tcaccgctga gcggataaag accccaccaa aacgtccagg    1260
aggccgcaga agaggacggc ttcccaataa cagtagcagg cccagcaccc ccaccattaa    1320
tgtgctggaa tcaaaggata cagacagtga tagggaagca gggactgaaa cggggggaga    1380
gaacaatgat aaagaagaag aagagaagaa agatgaaact tcgagctcct ctgaagcaaa    1440
ttctcggtgt caaacaccaa taaagatgaa gccaaatatt gaacctcctg agaatgtgga    1500
gtggagtggt gctgaagcct caatgtttag agtcctcatt ggcacttact atgacaattt    1560
ctgtgccatt gctaggttaa ttgggaccaa aacatgtaga caggtgtatg agtttagagt    1620
caaagaatct agcatcatag ctccagctcc cgctgaggat gtggatactc ctccaaggaa    1680
aaagaagagg aaaacaccggt tgtgggctgc acactgcaga aagatacagc tgaaaaagga    1740
cggctcctct aaccatgttt acaactatca accctgtgat catccacggc agccttgtga    1800
cagttcgtgc ccttgtgtga tagcacaaaa ttttttgtgaa aagttttgtc aatgtagttc    1860
agagtgtcaa aaccgctttc cgggatgccg ctgcaaagca cagtgcaaca ccaagcagtg    1920
cccgtgctac ctggctgtcc gagagtgtga ccctgacctc tgtcttactt gtggagccgc    1980
tgaccattgg gacagtaaaa atgtgtcctg caagaactgc agtattcagc ggggctccaa    2040
aaagcatcta ttgctggcac catctgacgt ggcaggctgg gggatttttta tcaaagatcc    2100 tgtgcagaaa aatgaattca tctcagaata ctgtggagag attatttctc aagatgaagc    2160
tgacagaaga gggaaagtgt atgataaata catgtgcagc tttctgttca acttgaacaa    2220
tgattttgtg gtggatgcaa cccgcaaggg taacaaaatt cgttttgcaa atcattcggt    2280
aaatccaaac tgctatgcaa aagttatgat ggttaacggt gatcacagga taggtatttt    2340
tgccaagaga gccatccaga ctggcgaaga gctgtttttt gattacagat acagccaggc    2400
tgatgccctg aagtatgtcg gcatcgaaag agaaatggaa atcccttgac atctgctacc    2460
tcctcccccc tcctctgaaa cagctgcctt agcttcagga acctcgagta ctgtgggcaa    2520
tttagaaaaa gaacatgcag tttgaaattc tgaatttgca aagtactgta agaataattt    2580
atagtaatga gtttaaaaat caactttttta ttgccttctc accagctgca aagtgttttg    2640
taccagtgaa tttttgcaat aatgcagtat ggtacatttt tcaactttga ataaagaata    2700
cttgaacttg tccttgttga atc                                             2723
```

<210> SEQ ID NO 4
<211> LENGTH: 18
<212> TYPE: DNA
<213> ORGANISM: Artificial sequence
<220> FEATURE:
<223> OTHER INFORMATION: Primer

<400> SEQUENCE: 4

```
cctcctcccc cctcctct                                                    18
```

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5

```
tgttcttttt ctaaattgcc caca                                             24
```

```
<210> SEQ ID NO 6
<211> LENGTH: 29
<212> TYPE: DNA
<213> ORGANISM: Artificial sequence
<220> FEATURE:
<223> OTHER INFORMATION: Probe

<400> SEQUENCE: 6
aaacagctgc cttagcttca ggaacctcg                                    29

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
cccaccatta atgtgctgga a                                            21

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
ttgttctctc ccccgttt                                                19

<210> SEQ ID NO 9
<211> LENGTH: 32
<212> TYPE: DNA
<213> ORGANISM: Artificial sequence
<220> FEATURE:
<223> OTHER INFORMATION: Probe

<400> SEQUENCE: 9
aggatacaga cagtgatagg gaagcaggga ct                                32

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
cagcccaatc aagcgc                                                  16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
gcccaatcgc catcgc                                                  16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide
```

-continued

```
<400> SEQUENCE: 12
cgggtgtcgg acgcga                                               16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ccatgattat tcttcg                                               16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
gcttccgcca acaaac                                               16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
ctgtctcagt cgcatg                                               16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
attggaacta aacata                                               16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
atccttcgct gtttcc                                               16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
accgaacaag aagtca                                               16

<210> SEQ ID NO 19
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
ttaatgggat gacttg                                                    16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
atgggtactg aagcaa                                                    16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
gttatgtaaa acagtt                                                    16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
aatgaaagta ccatcc                                                    16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
acattctcta tccccg                                                    16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
tctttcttca ggatcg                                                    16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
```
gtgggcggct ttcttt                                                    16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
ttatctggaa acattg                                                    16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
gagctgctgt tcggtg                                                    16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
tggtccatct atgttg                                                    16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
ggagtgtaag ctttgc                                                    16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
atatttaaaa catcgc                                                    16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
tttgttgtct agagct                                                    16

<210> SEQ ID NO 32
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 32
gagcagcagc aaactc                                                    16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
tgcggcctcc tggacg                                                    16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
ctgttattgg gaagcc                                                    16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
gcttccctat cactgt                                                    16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
ttgcttcaga ggagct                                                    16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
ttctcaggag gttcaa                                                    16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
aggcttcagc accact                                                    16
```

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
gtaagtgcca atgagg                                                        16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gttttggtcc caatta                                                        16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
ctggagctat gatgct                                                        16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
ttggaggagt atccac                                                        16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
acatggttag aggagc                                                        16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
acgaactgtc acaagg                                                        16

<210> SEQ ID NO 45
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 45
tacattgaca aaactt                                                   16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
gcagcggcat cccgga                                                   16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
caggtagcac gggcac                                                   16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tccacaagta agacag                                                   16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
cttgcaggac acattt                                                   16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
tggagccccg ctgaat                                                   16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
cgtcagatgg tgccag                                                   16

```
<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
tcatacactt tccctc                                                       16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
acccttgcgg gttgca                                                       16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
agcagtttgg atttac                                                       16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
cctgtgatca ccgtta                                                       16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ctggatggct ctcttg                                                       16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
tctttcgatg ccgaca                                                       16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide
```

-continued

```
<400> SEQUENCE: 58
cagatgtcaa gggatt                                                    16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
ggcaataaaa agttga                                                    16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
gcaaaaattc actggt                                                    16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
gacaagttca agtatt                                                    16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
agctactccg agttcc                                                    16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
ggcgagggca gcccgc                                                    16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
gactcttccc tcaaac                                                    16

<210> SEQ ID NO 65
<211> LENGTH: 16
```

-continued

```
<212> TYPE: DNA
<213> ORGANISM: Artificial sequence
<220> FEATURE:
<223> OTHER INFORMATION: Synthetic oligonucleotide

<400> SEQUENCE: 65
gaattcaaca ggacgc                                                16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
cgctttcaaa aagtaa                                                16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
tcccaccaac ttgtgt                                                16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
atgacagttg atttcg                                                16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
tttcactcct tttatg                                                16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
acgagaactc actgtc                                                16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
```
tcccccagac ctcaac                                                        16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
agtgtggcct tgcctg                                                        16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
gagaaattgt tcattg                                                        16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
aaatgggagt ataagt                                                        16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
gttccaagta aaaact                                                        16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
cgactgtgtg gctgga                                                        16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
taggtaggag tggctt                                                        16

<210> SEQ ID NO 78
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 78
aacagtttta tacttc                                                      16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
cgagaatttg cttcta                                                      16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
tgaatccagg gagatg                                                      16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
ttctcatgca attgca                                                      16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
ccattgttca agttga                                                      16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tcataactgc aaagag                                                      16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
cccccccagc ccaatc                                                      16
```

```
<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
gcggcagccc aatcgc                                                       16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
tcccaccggg tgtcgg                                                       16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
ttcccagtct ggccca                                                       16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
acgcttccgc caacaa                                                       16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
ttgagctgtc tcagtc                                                       16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
aaattttctg acgatt                                                       16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 91
ggctgtatcc ttcgct                                              16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
ctggtcaccg aacaag                                              16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
gagtctttaa tgggat                                              16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
tacattatgg gtactg                                              16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
ccatataagg aatgtt                                              16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gttcttcaat gaaagt                                              16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
tcatttataa acccac                                              16

<210> SEQ ID NO 98
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
gtgatcctcc agatct                                                        16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
aatttccgag gtgggc                                                        16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
ctgtgccctt atctgg                                                        16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
gcgcctggga gctgct                                                        16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
agatttagca tttggt                                                        16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
atgaaaggag tgtaag                                                        16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
```
atgtaggaag cagtca                                                    16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
actgtggtcc acaagg                                                    16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
cggtgagagc agcagc                                                    16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
cctcttctgc ggcctc                                                    16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
gattccagca cattaa                                                    16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109 tcccccgtt tcagtc                                                     16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
tgacaccgag aatttg                                                    16

<210> SEQ ID NO 111
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 111
actccacatt ctcagg                                                    16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
aaacattgag gcttca                                                    16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
gtcatagtaa gtgcca                                                    16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
cacctgtcta catgtt                                                    16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
cgggagctgg agctat                                                    16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
cggtgtttcc tcttct                                                    16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
ttgatagttg taaaca                                                    16
```

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
agggcacgaa ctgtca                                                         16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
tgacactctg aactac                                                         16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
tgctttgcag cggcat                                                         16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
ggacagccag gtagca                                                         16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
agcggctcca caagta                                                         16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
gcagttcttg caggac                                                         16

<210> SEQ ID NO 124
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 124 gcttttttgga gccccg         16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
ctttgataaa aatccc         16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
cagaaagctg cacatg         16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
tttgttaccc ttgcgg         16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
ataacttttg catagc         16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
acctatcctg tgatca         16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
ctcttcgcca gtctgg         16

```
<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
catttctctt tcgatg                                                         16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
cagctggtga gaaggc                                                         16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
ctgcattatt gcaaaa                                                         16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
caatgagctc acagaa                                                         16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
aggcgaagct actccg                                                         16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
gccagaccag gcggcg                                                         16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 137
cagctcgact cttccc                                                        16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
tacacaatga agtggg                                                        16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
tcctcccgct ttcaaa                                                        16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140 cccttttca gctgta                                                         16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
tcctttgtct gagtgc                                                        16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
caaagctatt gttcac                                                        16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
aatttcactc cttta                                                         16

<210> SEQ ID NO 144
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 144
cacgagaact cactgt                                                       16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
agaccatgag agagga                                                       16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
cccatgatta ttctaa                                                       16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
aacctcccta gtcccg                                                       16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
caaatgggag tataag                                                       16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
agactcttgg cagaag                                                       16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
```

```
aagctgattt tctaag                                                       16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
aggcaatata taccca                                                       16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 152
attttagatg agccaa                                                       16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
tacctgtcta catgtt                                                       16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
ctgagtaaag ataaca                                                       16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
tcactgactc tcaacc                                                       16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
agcagcaaga gcacaa                                                       16

<210> SEQ ID NO 157
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 157
taccaacctg taatca                                                          16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
atttggcccc cccagc                                                          16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
ccaaacgcgg cagccc                                                          16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160 tcgccccgc gcgccg                                                           16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
gtcccttctc agattt                                                          16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
tctgatttta cacgct                                                          16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
gtctgaacct cttgag                                                          16
```

```
<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
cgttctttcc aaaatt                                                   16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
gcacaggctg tatcct                                                   16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
aagtcactgg tcaccg                                                   16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
cattcagagt ctttaa                                                   16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
agaccaagaa tacatt                                                   16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
atcctgatct aaaact                                                   16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 170
cccgtgtact ttccca                                               16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
aagggcattc accaac                                               16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 172
atctcggtga tcctcc                                               16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
aaggaaattt ccgagg                                               16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
gttcttctgc tgtgcc                                               16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
ggaagtgcgc ctggga                                               16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
ctgaacagat ttagca                                               16

<210> SEQ ID NO 177
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
cgcctacaga aaagcg                                                    16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
tgttgggtgt tgcatg                                                    16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
gctccctcca aatgct                                                    16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
ttatccgctc agcggt                                                    16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
agccgtcctc ttctgc                                                    16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
tcctttgatt ccagca                                                    16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
```
cattgttctc tccccc                                          16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
ctttattggt gtttga                                          16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
actccactcc acattc                                          16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
tgaggactct aaacat                                          16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
gcacagaaat tgtcat                                          16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
ctctaaactc atacac                                          16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
cctcagcggg agctgg                                          16

<210> SEQ ID NO 190
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 190
cacaaccggt gtttcc                                                   16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
tggatgatca cagggt                                                   16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
ctatcacaca agggca                                                   16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
cggaaagcgg ttttga                                                   16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
ttgcactgtg ctttgc                                                   16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
ctcggacagc caggta                                                   16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
atggtcagcg gctcca                                                   16
```

```
<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
gaatactgca gttctt                                                     16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
ccagcaatag atgctt                                                     16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
caggatcttt gataaa                                                     16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
tgttcaagtt gaacag                                                     16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
acgaattttg ttaccc                                                     16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
gttaaccatc ataact                                                     16

<210> SEQ ID NO 203
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 203
gcaaaaatac ctatcc                                                    16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
tcagggcatc agcctg                                                    16

<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
gggatttcca tttctc                                                    16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
gtacaaaaca ctttgc                                                    16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
aaaatgtacc atactg                                                    16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
ccctagtccc gcgcaa                                                    16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
ttccccgccg cgaacg                                                    16

```
<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
cgtcagaggc gaagct                                                    16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
cataaagcca gaccag                                                    16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
gcagagcagc tcgact                                                    16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
ccctgtggca cagatt                                                    16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
gttttccaaa agatcg                                                    16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
gcgcctcccc acgccc                                                    16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 216
aatttcttag gcaaca                                                    16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 217
gggcaaccat atatcc                                                    16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 218
tcacgagaac tcactg                                                    16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
taacgagtag cttgta                                                    16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
cctttacttc atcagc                                                    16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 221
atgggagtat aagttt                                                    16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
gagactttac caaagt                                                    16

<210> SEQ ID NO 223
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 223
acacaaccaa actgag                                                    16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
gttctttata tctgac                                                    16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
ctgtccaaaa tccaac                                                    16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
aggcaagaca gttcta                                                    16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
gcataatcta actgca                                                    16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
ttagaggagc cgtctg                                                    16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
```
aagcggtttt gacctt                                                    16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
tccaccacaa aatcta                                                    16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 231
gctccacccc acactc                                                    16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
cgccatcgct tttatt                                                    16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 233
cgaccggacc gagcgc                                                    16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
cgcgcgccga ctcgcg                                                    16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
acaaactggt cccttc                                                    16

<210> SEQ ID NO 236
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 236
cagtcgcatg tactct                                                   16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237
tttacttcat cagctc                                                   16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
cgctgtttcc attctt                                                   16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
caagaagtca ggatgt                                                   16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
aatccaagtc actggt                                                   16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
actgaagcaa ctgcat                                                   16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
aaattctgct gtaggg                                                   16
```

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
agtaccatcc tgatct                                                         16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
tctatccccg tgtact                                                         16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
cattatattg accaag                                                         16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 246
tttctttatc atctcg                                                         16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
ttgaggaaat ggcttc                                                         16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
ggtgagttct ttatat                                                         16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 249
gtacattcag gaggaa                                                    16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
taagctttgc tctctc                                                    16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 251
aaacatcgcc tacaga                                                    16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
cgcttataag tgttgg                                                    16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
gcagcaaact cctttg                                                    16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 254
gggtctttat ccgctc                                                    16

<210> SEQ ID NO 255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 255
ttgggaagcc gtcctc                                                    16

<210> SEQ ID NO 256
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
tgtctgtatc ctttga                                                       16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
ggagctcgaa gtttca                                                       16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
tcaatatttg gcttca                                                       16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 259
cttcagcacc actcca                                                       16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
gccaatgagg actcta                                                       16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
cctagcaatg gcacag                                                       16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
```

```
tgctagattc tttgac                                          16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 263
ccacatcctc agcggg                                          16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
agccgtcctt tttcag                                          16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
aaggctgccg tggatg                                          16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
cacaaaaatt ttgtgc                                          16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
gcatcccgga aagcgg                                          16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
gcactgcttg gtgttg                                          16

<210> SEQ ID NO 269
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 269
agtaagacag aggtca                                               16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
tgtcccaatg gtcagc                                               16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
cccgctgaat actgca                                               16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
atggtgccag caatag                                               16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
aatctctcca cagtat                                               16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 274
ggttgcatcc accaca                                               16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
tggatttacc gaatga                                               16
```

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
atcaccgtta accatc                                                      16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
ggctctcttg gcaaaa                                                      16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
gacatacttc agggca                                                      16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 279
aagggatttc catttc                                                      16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
cttacagtac tttgca                                                      16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
ttcactggta caaaac                                                      16

<210> SEQ ID NO 282
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 282
gttcaagtat tcttta                                               16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
cgatgtagga agcagt                                               16

<210> SEQ ID NO 284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
tccgagttcc ccgccg                                               16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
ccgccggagc tcaggg                                               16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
acttagcata aagcca                                               16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
caatagagag cagagc                                               16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
aagtaaccct gtggca                                               16

```
<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
cgttcaccaa gttttc                                                        16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290
gaaagcggtt ttgacc                                                        16

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291
caagttggcc aaaaca                                                        16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 292
ttcactcctt ttatgt                                                        16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 293
cgagaactca ctgtca                                                        16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
cctagccatc tctgtc                                                        16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 295
gactttccat gctgtt                                                        16

<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 296
tcacaatgac tttaga                                                        16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 297
aatgggagta taagtt                                                        16

<210> SEQ ID NO 298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 298
caccctacta tgtgcc                                                        16

<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 299
tagttgtagg agtaca                                                        16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 300
cttggttcaa agaggg                                                        16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 301
aataggatac cttctg                                                        16

<210> SEQ ID NO 302
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 302
tcttaccaga ggagct                                                     16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 303
ctttacagaa gagaat                                                     16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 304
tacactctga actaca                                                     16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 305
atggctactt ctcaga                                                     16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 306 cctttttgcat agcagt                                                    16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 307
gctgtatctg aaacaa                                                     16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 308
```

```
actccctagt cccgcg                                                        16

<210> SEQ ID NO 309
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 309
acactcccta gtcccg                                                        16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 310
cgaacactcc ctagtc                                                        16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 311
ggtcaccgaa cactcc                                                        16

<210> SEQ ID NO 312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 312
gaataattgc acttac                                                        16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 313
gtgttgcatg aaaaga                                                        16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 314
gtattctgag atgaat                                                        16

<210> SEQ ID NO 315
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 315
tattctgaga tgaatt                                                    16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 316
agtattctga gatgaa                                                    16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 317
cagtattctg agatga                                                    16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 318
acagtattct gagatg                                                    16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 319
cacagtattc tgagat                                                    16

<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 320
ccacagtatt ctgaga                                                    16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 321
tccacagtat tctgag                                                    16
```

```
<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 322
ctccacagta ttctga                                                       16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 323
tctccacagt attctg                                                       16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 324
ctctccacag tattct                                                       16

<210> SEQ ID NO 325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 325
tctctccaca gtattc                                                       16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 326
atctctccac agtatt                                                       16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 327
taatctctcc acagta                                                       16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 328
ataatctctc cacagt                                              16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 329
gcatccacca caaaat                                              16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
tgcatccacc acaaaa                                              16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
ttgcatccac cacaaa                                              16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
gttgcatcca ccacaa                                              16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
gggttgcatc caccac                                              16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
cgggttgcat ccacca                                              16

<210> SEQ ID NO 335
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
gcgggttgca tccacc                                                    16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
tgcgggttgc atccac                                                    16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
ttgcgggttg catcca                                                    16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
cttgcgggtt gcatcc                                                    16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
ccttgcgggt tgcatc                                                    16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
cccttgcggg ttgcat                                                    16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
```

```
taccccttgcg ggttgc                                                        16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
ttacccttgc gggttg                                                         16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
agtttcatct tccacc                                                         16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
gaatgttatg taaaac                                                         16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
taaggaatgt tatgta                                                         16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
tataaggaat gttatg                                                         16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
catataagga atgtta                                                         16

<210> SEQ ID NO 348
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 348
cccatataag gaatgt                                                    16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
ctaaaacttc atctcc                                                    16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
gatctaaaac ttcatc                                                    16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
ctgatctaaa acttca                                                    16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
catcctgatc taaaac                                                    16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
accatcctga tctaaa                                                    16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
gtaccatcct gatcta                                                    16
```

-continued

```
<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
aagtaccatc ctgatc                                                     16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
gaaagtacca tcctga                                                     16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
atgaaagtac catcct                                                     16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
caatgaaagt accatc                                                     16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
ttcaatgaaa gtacca                                                     16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
cttcaatgaa agtacc                                                     16

<210> SEQ ID NO 361
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 361
tcttcaatga aagtac                    16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
ttagttcttc aatgaa                    16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
attagttctt caatga                    16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
tattagttct tcaatg                    16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ccccgtgtac tttccc                    16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
atccccgtgt actttc                    16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
ctatccccgt gtactt                    16

```
<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
ctctatcccc gtgtac                                              16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
ttctctatcc ccgtgt                                              16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
cattctctat ccccgt                                              16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
cacattctct atcccc                                              16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
cccacattct ctatcc                                              16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
aacccacatt ctctat                                              16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 374
taaacccaca ttctct                                                    16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
tataaaccca cattct                                                    16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
ttataaaccc acattc                                                    16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
catcatttat aaaccc                                                    16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
tcatcattta taaacc                                                    16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
ttcaccaact ccacaa                                                    16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
cattcaccaa ctccac                                                    16

<210> SEQ ID NO 381
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 381
caagggcatt caccaa                                                   16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
accaagggca ttcacc                                                   16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
tgaccaaggg cattca                                                   16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
attgaccaag ggcatt                                                   16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
atattgacca agggca                                                   16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
ttatattgac caaggg                                                   16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
```
atcattatat tgacca                                                  16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
tcatcattat attgac                                                  16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
cgtcatcatc attata                                                  16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
cgtctccatc atcatc                                                  16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
ctctttcttc aggatc                                                  16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
ctccagatct ttctgc                                                  16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393
atcctccaga tctttc                                                  16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 394
tgatcctcca gatctt					16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
ggtgatcctc cagatc					16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
tcggtgatcc tccaga					16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
tctcggtgat cctcca					16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
catctcggtg atcctc					16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
atcatctcgg tgatcc					16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
ttatcatctc ggtgat					16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
ctttatcatc tcggtg                                                    16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
ttctttatca tctcgg                                                    16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 403
gctttcttta tcatct                                                    16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 404
cggctttctt tatcat                                                    16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 405
ggcggctttc tttatc                                                    16

<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 406
tgggcggctt tcttta                                                    16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 407
ggtgggcggc tttctt                                                     16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 408
gaggtgggcg gctttc                                                     16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 409
tccgaggtgg gcggct                                                     16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 410
tttccgaggt gggcgg                                                     16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 411
aaatttccga ggtggg                                                     16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 412
ggaaatttcc gaggtg                                                     16

<210> SEQ ID NO 413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 413
gaaggaaatt tccgag                                                     16

<210> SEQ ID NO 414
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 414
cagaaggaaa tttccg                                                       16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 415
gaggaaatgg cttcaa                                                       16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 416
attgaggaaa tggctt                                                       16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
ctggaaacat tgagga                                                       16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 418
tgcccttatc tggaaa                                                       16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 419
atctggaaac attgag                                                       16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 420
```
cttatctgga aacatt                                                16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 421
cccttatctg gaaaca                                                16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 422 tgtgcccctta tctgga                                               16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 423
gctgtgccct tatctg                                                16

<210> SEQ ID NO 424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 424
ctgctgtgcc cttatc                                                16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 425
ttctgctgtg cccta                                                 16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 426
tcttctgctg tgccct                                                16

<210> SEQ ID NO 427
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 427
agttcttctg ctgtgc                                                   16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 428
ttagttcttc tgctgt                                                   16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 429
ctttagttct tctgct                                                   16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 430
gtgagttctt tatatt                                                   16

<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 431
cggtgagttc tttata                                                   16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 432
ttcggtgagt tcttta                                                   16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 433
tgttcggtga gttctt                                                   16
```

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 434
gctgttcggt gagttc                                                     16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 435
ctgctgttcg gtgagt                                                     16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 436
agctgctgtt cggtga                                                     16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 437
ggagctgctg ttcggt                                                     16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 438
tgggagctgc tgttcg                                                     16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 439
cgcctgggag ctgctg                                                     16

<210> SEQ ID NO 440
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 440
tgcgcctggg agctgc                                                        16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 441
gtgcgcctgg gagctg                                                        16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 442
agtgcgcctg ggagct                                                        16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 443
aagtgcgcct gggagc                                                        16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 444
gaagtgcgcc tgggag                                                        16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 445
aggaagtgcg cctggg                                                        16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 446
gaggaagtgc gcctgg                                                        16

```
<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 447
ggaggaagtg cgcctg                                                    16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 448
aggaggaagt gcgcct                                                    16

<210> SEQ ID NO 449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 449
caggaggaag tgcgcc                                                    16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 450
ttcaggagga agtgcg                                                    16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 451
cattcaggag gaagtg                                                    16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 452
tacattcagg aggaag                                                    16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 453
ggtacattca ggagga                                                  16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 454
ttggtccatc tatgtt                                                  16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 455
atttggtcca tctatg                                                  16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 456
gcatttggtc catcta                                                  16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 457
tagcatttgg tccatc                                                  16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 458
ttagcatttg gtccat                                                  16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 459
tttagcattt ggtcca                                                  16

<210> SEQ ID NO 460
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 460
atttagcatt tggtcc                                                    16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 461
gatttagcat ttggtc                                                    16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 462
cagatttagc atttgg                                                    16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 463
acagatttag catttg                                                    16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 464
gaacagattt agcatt                                                    16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 465
tgaacagatt tagcat                                                    16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 466
```
tctgaacaga tttagc                                                        16

<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 467
ctctgaacag atttag                                                        16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 468
tctctgaaca gattta                                                        16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 469
ctctctgaac agattt                                                        16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 470
tctctctgaa cagatt                                                        16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 471
gctctctctg aacaga                                                        16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 472
ttgctctctc tgaaca                                                        16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 473
gctttgctct ctctga                                                    16

<210> SEQ ID NO 474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 474
agctttgctc tctctg                                                    16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 475
gtaagctttg ctctct                                                    16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 476
tgtaagcttt gctctc                                                    16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 477
gtgtaagctt tgctct                                                    16

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 478
agtgtaagct ttgctc                                                    16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 479
gagtgtaagc tttgct                                                    16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 480
aggagtgtaa gctttg                                              16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 481
aaggagtgta agcttt                                              16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 482
aaaggagtgt aagctt                                              16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 483
gaaaggagtg taagct                                              16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 484
tgaaaggagt gtaagc                                              16

<210> SEQ ID NO 485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 485
tatgaaagga gtgtaa                                              16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 486
cgtatgaaag gagtgt                                                    16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 487
tcgcctacag aaaagc                                                    16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 488
catcgcctac agaaaa                                                    16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 489
ttgcagctgg tgagaa                                                    16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 490
tttgcagctg gtgaga                                                    16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 491
ctttgcagct ggtgag                                                    16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 492
cactttgcag ctggtg                                                    16

<210> SEQ ID NO 493
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 493
aacactttgc agctgg                                                         16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 494
caaaacactt tgcagc                                                         16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 495
ggtacaaaac actttg                                                         16

<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 496
ctggtacaaa acactt                                                         16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 497
cactggtaca aaacac                                                         16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 498
attcactggt acaaaa                                                         16

<210> SEQ ID NO 499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 499
```
aaattcactg gtacaa            16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 500
caaaaattca ctggta            16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 501
tattgcaaaa attcac            16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 502
actgcattat tgcaaa            16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 503
atactgcatt attgca            16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 504
ccatactgca ttattg            16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 505
taccatactg cattat            16

<210> SEQ ID NO 506
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 506
tgtaccatac tgcatt                                                   16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 507
aatgtaccat actgca                                                   16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 508
gttgaaaaat gtacca                                                   16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 509
ctttattcaa agttga                                                   16

<210> SEQ ID NO 510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 510
tctttattca aagttg                                                   16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 511
aagttcaagt attctt                                                   16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 512
caagttcaag tattct                                                   16
```

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 513
ggacaagttc aagtat                                                      16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 514
aaggacaagt tcaagt                                                      16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 515
aacaaggaca agttca                                                      16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 516
tcaacaagga caagtt                                                      16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 517
attcaacaag gacaag                                                      16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 518
taagaaactg ctaacc                                                      16

<210> SEQ ID NO 519
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 519
gttttatact tcattc                                            16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 520
cagttttata cttcat                                            16

<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 521
acagttttat acttca                                            16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 522
caacagtttt atactt                                            16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 523
ccaacagttt tatact                                            16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 524
gccaacagtt ttatac                                            16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 525
agccaacagt tttata                                            16

```
<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 526
cgatacccgg gaccgg                                                      16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 527
aaagtggcaa ctcact                                                      16

<210> SEQ ID NO 528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 528
cttctaccac ctcatc                                                      16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 529
cgttaaattt cttagg                                                      16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 530
gatgacatca aaacgc                                                      16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 531
acacacttgt acagta                                                      16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 532
ttagatcttt atcata                                                       16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 533
cagaattaat agtaac                                                       16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 534
ccccaaagag atgttt                                                       16

<210> SEQ ID NO 535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 535
atgtatttgt gcaagg                                                       16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 536
cactgctcat gtaaag                                                       16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 537
aatctatcat gattta                                                       16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 538
ataaaaccct gtggga                                                       16

<210> SEQ ID NO 539
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 539
ctattctcta gcaaat                                                     16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 540
gatcatcaat atcaac                                                     16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
ttacactgtc gctaca                                                     16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
taccaagtag tggaac                                                     16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
cactggtaat accagt                                                     16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
acacaatggc tcagcc                                                     16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
attatcggag gctggg                                                    16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
aactgagatc acgcat                                                    16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
cacaaggtgg ttctta                                                    16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 548
catccatgta tcagaa                                                    16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
cattaaactc cccatt                                                    16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
tatgtagtga aacaga                                                    16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
atcaaacact ttttgc                                                    16

<210> SEQ ID NO 552
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 552
agcgaacaca tttaat                                                     16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
acttaatctc tccatc                                                     16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
gttcttcagg gaagtg                                                     16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
gcacattcat aaactg                                                     16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
caacacctat taaaac                                                     16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
aaccattata gatctt                                                     16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
cgcctaaaac tacaaa                                                     16
```

```
<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559
gacacaggaa aacccc                                                       16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
atccatgggt aaatga                                                       16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 561
cgagactgga agcaaa                                                       16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
acccaagact tttgtt                                                       16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
tctcataagg gtacca                                                       16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
ggtaaactgt atgcaa                                                       16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 565
aagtagtggc tatcag                                                    16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
ggccaagtta ctgcac                                                    16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
tccaagtaat aaacta                                                    16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
ccactttgag ggttgt                                                    16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
atcctatgcc tgaggg                                                    16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570
taagtaatat gattac                                                    16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
atttggtctg gccaaa                                                    16

<210> SEQ ID NO 572
```

-continued

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
gccaataact gaataa                                                       16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
caaatgtaga atccca                                                       16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
gattactaaa taccta                                                       16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
tttaaggagt gtgcaa                                                       16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
cataaggatg gccagg                                                       16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
acagagggta tctcag                                                       16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
```
cctcaaagaa cagagt                                          16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
ttagcagaat gtagtg                                          16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
actttatcca gaatac                                          16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 581
aactgtcttc acacca                                          16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582
cagattcaag gccacg                                          16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583
acacacttgg ttctgt                                          16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584
cttgtatctt atcagc                                          16

<210> SEQ ID NO 585
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 585
tagctagagt cttctc                                                    16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586
agatagtact aaactc                                                    16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587
actctattcc cactgt                                                    16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
atccaggtag ttcttt                                                    16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
taatgtgggt gttatt                                                    16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
gaccaaagga catcaa                                                    16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
gaactattcc aagtga                                                    16
```

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
aaagtctggc tggcag                                                     16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
gtttatacaa aagcac                                                     16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 594
agactcccat atactt                                                     16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
ggcgaagaaa ttcatt                                                     16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
cataaaaact tcatgc                                                     16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
caatttgtgc tttatc                                                     16

<210> SEQ ID NO 598
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 598
tgataaagtc tgtatt                                                    16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
ggaataatat aactga                                                    16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
taggaacatg atccca                                                    16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
ctaacaatca gtgaag                                                    16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
ccttaattgt atattc                                                    16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
ctaaacaaag actgat                                                    16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
aacgattgcc atcctt                                                    16
```

```
<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
ctgtaaagca ggttaa                                                   16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
atctacagca gtcatt                                                   16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 607
ctaaatagtg atctga                                                   16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
ctctcaacaa gaaatt                                                   16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
ttagactttt gccatt                                                   16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
ccatatttag acattc                                                   16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 611
cactgtataa tcaata                                                    16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
ctaaaaggtc accaaa                                                    16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
tataaaccta agttag                                                    16

<210> SEQ ID NO 614
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 614
gcaaactgac taaatg                                                    16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
aaatatccac ttgaac                                                    16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
tactgtggaa gtacta                                                    16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
taccaacacc agcaac                                                    16

<210> SEQ ID NO 618
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 618
ccaaacaaga atcact                                                      16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 619
gcacttacat ataatt                                                      16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 620
aactacaaat gggagt                                                      16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 621
aaacacatta agggac                                                      16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 622
taccaatatg aagacc                                                      16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 623
tgatatgaag tcagtg                                                      16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 624
```
cttacaagaa cattat                                                16

<210> SEQ ID NO 625
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 625
gaagagcaaa tctgta                                                16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 626
acatgtaaca ggtatt                                                16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 627
tcaaagaatg tatctg                                                16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 628
gagtaagaca gacact                                                16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 629
atacaggtgg gaatga                                                16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 630
agctaaccct ttggaa                                                16

<210> SEQ ID NO 631
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 631
gttttattag ttgcct                                                     16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 632
aaccaagcac ttttgt                                                     16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 633
tataaaatct gctaag                                                     16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 634
aatgatctgt tcagtg                                                     16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 635
tatctggcca ataatt                                                     16

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 636
actgattgca aaagta                                                     16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 637
gctggtaaca ctgtgg                                                     16
```

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 638
aacatcgcct acagaa					16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 639
aaaacatcgc ctacag					16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 640
ttaaaacatc gcctac					16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 641
atttaaaaca tcgcct					16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 642
catatttaaa acatcg					16

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 643
tgcatgaaaa ggatgt					16

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 644
tgttgcatga aaagga                                                    16

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 645
gggtgttgca tgaaaa                                                    16

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 646
ttgggtgttg catgaa                                                    16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 647
gtgttgggtg ttgcat                                                    16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 648
taagtgttgg gtgttg                                                    16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 649
tataagtgtt gggtgt                                                    16

<210> SEQ ID NO 650
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 650
ttataagtgt tgggtg                                                    16

<210> SEQ ID NO 651
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 651
cttataagtg ttgggt                                                       16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 652
gcttataagt gttggg                                                       16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 653
ccgcttataa gtgttg                                                       16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 654
tccgcttata agtgtt                                                       16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 655
ttccgcttat aagtgt                                                       16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 656
tcttccgctt ataagt                                                       16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 657
```
gttcttccgc ttataa                                                   16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 658
gtgttcttcc gcttat                                                   16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 659
ctgtgttctt ccgctt                                                   16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 660
ttctgtgttc ttccgc                                                   16

<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 661
gtttctgtgt tcttcc                                                   16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 662
gctgtttctg tgttct                                                   16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 663
gagctgtttc tgtgtt                                                   16

<210> SEQ ID NO 664
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 664
tagagctgtt tctgtg                                                    16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 665
tctagagctg tttctg                                                    16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 666
tgtctagagc tgtttc                                                    16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 667
gttgtctaga gctgtt                                                    16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 668
ttgttgtcta gagctg                                                    16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 669
gtttgttgtc tagagc                                                    16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 670
aggtttgttg tctaga                                                    16
```

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 671
caaggtttgt tgtcta                                                     16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 672
cacaaggttt gttgtc                                                     16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 673
tccacaaggt ttgttg                                                     16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 674
ggtccacaag gtttgt                                                     16

<210> SEQ ID NO 675
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 675
gtggtccaca aggttt                                                     16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 676
ctgtggtcca caaggt                                                     16

<210> SEQ ID NO 677
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 677
cactgtggtc cacaag					16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 678
aacactgtgg tccaca					16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 679
gtaacactgt ggtcca					16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 680
tggtaacact gtggtc					16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 681
atgctggtaa cactgt					16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 682
aaatgctggt aacact					16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 683
ccaaatgctg gtaaca					16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 684
ctccaaatgc tggtaa                                                 16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 685
ccctccaaat gctggt                                                 16

<210> SEQ ID NO 686
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 686
ctccctccaa atgctg                                                 16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 687
tgctccctcc aaatgc                                                 16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 688
ctttgctccc tccaaa                                                 16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 689
cagcaaactc ctttgc                                                 16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 690
agcagcaaac tccttt                                              16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 691
agagcagcag caaact                                              16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 692
gcggtgagag cagcag                                              16

<210> SEQ ID NO 693
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 693
cagcggtgag agcagc                                              16

<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 694
ctcagcggtg agagca                                              16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 695
cgctcagcgg tgagag                                              16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 696
tccgctcagc ggtgag                                              16

<210> SEQ ID NO 697
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 697
tatccgctca gcggtg                                                      16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 698
tttatccgct cagcgg                                                      16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 699
tctttatccg ctcagc                                                      16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 700
ggtctttatc cgctca                                                      16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 701
ctgcggcctc ctggac                                                      16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 702
ttctgcggcc tcctgg                                                      16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 703
```
tcttctgcgg cctcct                                                    16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 704
tcctcttctg cggcct                                                    16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 705
cgtcctcttc tgcggc                                                    16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 706
gccgtcctct tctgcg                                                    16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 707
aagccgtcct cttctg                                                    16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 708
ggaagccgtc ctcttc                                                    16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 709
tgggaagccg tcctct                                                    16

<210> SEQ ID NO 710
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 710
attgggaagc cgtcct                                                         16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 711
ttattgggaa gccgtc                                                         16

<210> SEQ ID NO 712
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 712
gtgtttgaca ccgaga                                                         16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 713
caatatttgg cttcat                                                         16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 714
gttcaatatt tggctt                                                         16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 715
ggttcaatat ttggct                                                         16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 716
aggttcaata tttggc                                                         16
```

```
<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 717
ggaggttcaa tatttg                                                    16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 718
caggaggttc aatatt                                                    16

<210> SEQ ID NO 719
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 719
ctcaggaggt tcaata                                                    16

<210> SEQ ID NO 720
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 720
acattctcag gaggtt                                                    16

<210> SEQ ID NO 721
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 721
cactccacat tctcag                                                    16

<210> SEQ ID NO 722
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 722
tccactccac attctc                                                    16

<210> SEQ ID NO 723
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 723
tgttattggg aagccg                                                    16

<210> SEQ ID NO 724
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 724
actgttattg ggaagc                                                    16

<210> SEQ ID NO 725
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 725
ctactgttat tgggaa                                                    16

<210> SEQ ID NO 726
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 726
tgctactgtt attggg                                                    16

<210> SEQ ID NO 727
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 727
cctgctactg ttattg                                                    16

<210> SEQ ID NO 728
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 728
ggcctgctac tgttat                                                    16

<210> SEQ ID NO 729
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 729
tgggcctgct actgtt                                                    16

<210> SEQ ID NO 730
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 730
gctgggcctg ctactg                                              16

<210> SEQ ID NO 731
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 731
gtgctgggcc tgctac                                              16

<210> SEQ ID NO 732
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 732
gcacattaat ggtggg                                              16

<210> SEQ ID NO 733
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 733
cagcacatta atggtg                                              16

<210> SEQ ID NO 734
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 734
tccagcacat taatgg                                              16

<210> SEQ ID NO 735
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 735
ttgattccag cacatt                                              16

<210> SEQ ID NO 736
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 736
```

```
ctttgattcc agcaca                                                  16

<210> SEQ ID NO 737
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 737
atcctttgat tccagc                                                  16

<210> SEQ ID NO 738
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 738
gtatcctttg attcca                                                  16

<210> SEQ ID NO 739
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 739
ctgtatcctt tgattc                                                  16

<210> SEQ ID NO 740
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 740
gtctgtatcc tttgat                                                  16

<210> SEQ ID NO 741
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 741
actgtctgta tccttt                                                  16

<210> SEQ ID NO 742
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 742
tcactgtctg tatcct                                                  16

<210> SEQ ID NO 743
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 743
tatcactgtc tgtatc                                                      16

<210> SEQ ID NO 744
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 744
cctatcactg tctgta                                                      16

<210> SEQ ID NO 745
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 745
cttccctatc actgtc                                                      16

<210> SEQ ID NO 746
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 746
tgcttcccta tcactg                                                      16

<210> SEQ ID NO 747
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 747
cctgcttccc tatcac                                                      16

<210> SEQ ID NO 748
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 748
gtccctgctt ccctat                                                      16

<210> SEQ ID NO 749
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 749
ttcagtccct gcttcc                                                      16
```

<210> SEQ ID NO 750
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 750
cgtttcagtc cctgct                                                  16

<210> SEQ ID NO 751
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 751
cccgtttcag tccctg                                                  16

<210> SEQ ID NO 752
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 752
cccccgtttc agtccc                                                  16

<210> SEQ ID NO 753
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 753 ctcccccgt ttcagt                                                   16

<210> SEQ ID NO 754
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 754 ctctccccc gtttca                                                   16

<210> SEQ ID NO 755
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 755
ttctctcccc ccgttt                                                  16

<210> SEQ ID NO 756
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 756
tgttctctcc ccccgt                                                    16

<210> SEQ ID NO 757
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 757
attgttctct cccccc                                                    16

<210> SEQ ID NO 758
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 758
tcattgttct ctcccc                                                    16

<210> SEQ ID NO 759
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 759
tatcattgtt ctctcc                                                    16

<210> SEQ ID NO 760
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 760
ctttatcatt gttctc                                                    16

<210> SEQ ID NO 761
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 761
cgaagtttca tctttc                                                    16

<210> SEQ ID NO 762
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 762
ctcgaagttt catctt                                                    16
```

```
<210> SEQ ID NO 763
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 763
agctcgaagt ttcatc                                                    16

<210> SEQ ID NO 764
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 764
aggagctcga agtttc                                                    16

<210> SEQ ID NO 765
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 765
agaggagctc gaagtt                                                    16

<210> SEQ ID NO 766
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 766
tcagaggagc tcgaag                                                    16

<210> SEQ ID NO 767
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 767
cttcagagga gctcga                                                    16

<210> SEQ ID NO 768
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 768
tgcttcagag gagctc                                                    16

<210> SEQ ID NO 769
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 769
tttgcttcag aggagc                                                   16

<210> SEQ ID NO 770
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 770
aatttgcttc agagga                                                   16

<210> SEQ ID NO 771
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 771
gagaatttgc ttcaga                                                   16

<210> SEQ ID NO 772
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 772
ccgagaattt gcttca                                                   16

<210> SEQ ID NO 773
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 773
caccgagaat ttgctt                                                   16

<210> SEQ ID NO 774
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 774
gacaccgaga atttgc                                                   16

<210> SEQ ID NO 775
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 775
ttgacaccga gaattt                                                   16

<210> SEQ ID NO 776
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 776
gtttgacacc gagaat                                                   16

<210> SEQ ID NO 777
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 777
tggtgtttga caccga                                                   16

<210> SEQ ID NO 778
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 778
attggtgttt gacacc                                                   16

<210> SEQ ID NO 779
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 779
ttattggtgt ttgaca                                                   16

<210> SEQ ID NO 780
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 780
tctttattgg tgtttg                                                   16

<210> SEQ ID NO 781
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 781
catctttatt ggtgtt                                                   16

<210> SEQ ID NO 782
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 782
```

-continued ttcatctttattggtg          16

<210> SEQ ID NO 783
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 783
gcttcatctt tattgg          16

<210> SEQ ID NO 784
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 784
aatatttggc ttcatc          16

<210> SEQ ID NO 785
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 785
attctcagga ggttca          16

<210> SEQ ID NO 786
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 786
tccacattct caggag          16

<210> SEQ ID NO 787
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 787
gcttcagcac cactcc          16

<210> SEQ ID NO 788
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 788
tcatacacct gtctac          16

<210> SEQ ID NO 789
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 789
cactccactc cacatt                                                  16

<210> SEQ ID NO 790
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 790
gaggcttcag caccac                                                  16

<210> SEQ ID NO 791
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 791
ttgaggcttc agcacc                                                  16

<210> SEQ ID NO 792
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 792
cattgaggct tcagca                                                  16

<210> SEQ ID NO 793
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 793
aacattgagg cttcag                                                  16

<210> SEQ ID NO 794
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 794
taaacattga ggcttc                                                  16

<210> SEQ ID NO 795
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 795
tctaaacatt gaggct                                                  16
```

<210> SEQ ID NO 796
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 796
actctaaaca ttgagg                                                    16

<210> SEQ ID NO 797
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 797
ggactctaaa cattga                                                    16

<210> SEQ ID NO 798
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 798
gaggactcta aacatt                                                    16

<210> SEQ ID NO 799
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 799
atgaggactc taaaca                                                    16

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
caatgaggac tctaaa                                                    16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
tgccaatgag gactct                                                    16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 802
gtgccaatga ggactc                                                   16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
agtgccaatg aggact                                                   16

<210> SEQ ID NO 804
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 804
aagtgccaat gaggac                                                   16

<210> SEQ ID NO 805
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 805
taagtgccaa tgagga                                                   16

<210> SEQ ID NO 806
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 806
agtaagtgcc aatgag                                                   16

<210> SEQ ID NO 807
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 807
tagtaagtgc caatga                                                   16

<210> SEQ ID NO 808
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 808
atagtaagtg ccaatg                                                   16

<210> SEQ ID NO 809

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 809
catagtaagt gccaat                                                    16

<210> SEQ ID NO 810
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 810
tcatagtaag tgccaa                                                    16

<210> SEQ ID NO 811
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 811
tgtcatagta agtgcc                                                    16

<210> SEQ ID NO 812
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 812
attgtcatag taagtg                                                    16

<210> SEQ ID NO 813
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 813
aaattgtcat agtaag                                                    16

<210> SEQ ID NO 814
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 814
agaaattgtc atagta                                                    16

<210> SEQ ID NO 815
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 815
```
acagaaattg tcatag                                                    16

<210> SEQ ID NO 816
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 816
ggcacagaaa ttgtca                                                    16

<210> SEQ ID NO 817
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 817
atggcacaga aattgt                                                    16

<210> SEQ ID NO 818
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 818
tagcaatggc acagaa                                                    16

<210> SEQ ID NO 819
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 819
acctagcaat ggcaca                                                    16

<210> SEQ ID NO 820
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 820
taacctagca atggca                                                    16

<210> SEQ ID NO 821
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 821
attaacctag caatgg                                                    16

<210> SEQ ID NO 822
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 822
caattaacct agcaat                                                    16

<210> SEQ ID NO 823
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 823
cccaattaac ctagca                                                    16

<210> SEQ ID NO 824
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 824
gtcccaatta acctag                                                    16

<210> SEQ ID NO 825
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 825
tggtcccaat taacct                                                    16

<210> SEQ ID NO 826
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 826
tttggtccca attaac                                                    16

<210> SEQ ID NO 827
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 827
tgttttggtc ccaatt                                                    16

<210> SEQ ID NO 828
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 828
catgttttgg tcccaa                                                    16
```

<210> SEQ ID NO 829
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 829
tacatgtttt ggtccc                                                    16

<210> SEQ ID NO 830
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 830
tctacatgtt ttggtc                                                    16

<210> SEQ ID NO 831
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 831
tgtctacatg ttttgg                                                    16

<210> SEQ ID NO 832
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 832
cctgtctaca tgtttt                                                    16

<210> SEQ ID NO 833
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 833
acacctgtct acatgt                                                    16

<210> SEQ ID NO 834
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 834
atacacctgt ctacat                                                    16

<210> SEQ ID NO 835
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 835
actcatacac ctgtct                                               16

<210> SEQ ID NO 836
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 836
aaactcatac acctgt                                               16

<210> SEQ ID NO 837
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 837
ctaaactcat acacct                                               16

<210> SEQ ID NO 838
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 838
actctaaact cataca                                               16

<210> SEQ ID NO 839
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 839
tgactctaaa ctcata                                               16

<210> SEQ ID NO 840
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 840
tttgactcta aactca                                               16

<210> SEQ ID NO 841
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 841
atgctagatt ctttga                                               16

```
<210> SEQ ID NO 842
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 842
tgatgctaga ttcttt                                                     16

<210> SEQ ID NO 843
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 843
tatgatgcta gattct                                                     16

<210> SEQ ID NO 844
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 844
gctatgatgc tagatt                                                     16

<210> SEQ ID NO 845
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 845
gagctatgat gctaga                                                     16

<210> SEQ ID NO 846
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 846
tggagctatg atgcta                                                     16

<210> SEQ ID NO 847
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 847
gctggagcta tgatgc                                                     16

<210> SEQ ID NO 848
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 848
gagctggagc tatgat                                                    16

<210> SEQ ID NO 849
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 849
gggagctgga gctatg                                                    16

<210> SEQ ID NO 850
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 850
gcgggagctg gagcta                                                    16

<210> SEQ ID NO 851
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 851
tcagcgggag ctggag                                                    16

<210> SEQ ID NO 852
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 852
tcctcagcgg gagctg                                                    16

<210> SEQ ID NO 853
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 853
catcctcagc gggagc                                                    16

<210> SEQ ID NO 854
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 854
cacatcctca gcggga                                                    16

<210> SEQ ID NO 855
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 855
tccacatcct cagcgg                                                       16

<210> SEQ ID NO 856
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 856
gtatccacat cctcag                                                       16

<210> SEQ ID NO 857
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 857
gagtatccac atcctc                                                       16

<210> SEQ ID NO 858
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 858
aggagtatcc acatcc                                                       16

<210> SEQ ID NO 859
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 859
ggaggagtat ccacat                                                       16

<210> SEQ ID NO 860
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 860
cttggaggag tatcca                                                       16

<210> SEQ ID NO 861
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 861
```
tccttggagg agtatc                                                16

<210> SEQ ID NO 862
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 862
tgtaaacatg gttaga                                                16

<210> SEQ ID NO 863
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 863
acacaagggc acgaac                                                16

<210> SEQ ID NO 864
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 864
tcacacaagg gcacga                                                16

<210> SEQ ID NO 865
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 865
tatcacacaa gggcac                                                16

<210> SEQ ID NO 866
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 866
gctatcacac aagggc                                                16

<210> SEQ ID NO 867
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 867
gtgctatcac acaagg                                                16

<210> SEQ ID NO 868
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 868
ttgtgctatc acacaa                                                      16

<210> SEQ ID NO 869
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 869
aattttgtgc tatcac                                                      16

<210> SEQ ID NO 870
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 870
ctgaactaca ttgaca                                                      16

<210> SEQ ID NO 871
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 871
tttccttgga ggagta                                                      16

<210> SEQ ID NO 872
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 872
cttttccctt ggagga                                                      16

<210> SEQ ID NO 873
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 873
ccggtgtttc ctcttc                                                      16

<210> SEQ ID NO 874
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 874
aaccggtgtt tcctct                                                      16
```

<210> SEQ ID NO 875
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 875
acaaccggtg tttcct                                                    16

<210> SEQ ID NO 876
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 876
ccacaaccgg tgtttc                                                    16

<210> SEQ ID NO 877
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 877
gcccacaacc ggtgtt                                                    16

<210> SEQ ID NO 878
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 878 cttttttcagc tgtatc                                                   16

<210> SEQ ID NO 879
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 879
gtcctttttc agctgt                                                    16

<210> SEQ ID NO 880
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 880
ccgtcctttt tcagct                                                    16

<210> SEQ ID NO 881
<211> LENGTH: 16
<212> TYPE: DNA
<213> ORGANISM: Artificial sequence
<220> FEATURE:
<223> OTHER INFORMATION: Synthetic oligonucleotide -continued

```
<400> SEQUENCE: 881
gagccgtcct ttttca                                                16

<210> SEQ ID NO 882
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 882
aggagccgtc cttttt                                                16

<210> SEQ ID NO 883
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 883
agaggagccg tccttt                                                16

<210> SEQ ID NO 884
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 884
ttagaggagc cgtcct                                                16

<210> SEQ ID NO 885
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 885
ggttagagga gccgtc                                                16

<210> SEQ ID NO 886
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 886
tggttagagg agccgt                                                16

<210> SEQ ID NO 887
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 887
atggttagag gagccg                                                16

<210> SEQ ID NO 888
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 888
catggttaga ggagcc                                                       16

<210> SEQ ID NO 889
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 889
aacatggtta gaggag                                                       16

<210> SEQ ID NO 890
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 890
aaacatggtt agagga                                                       16

<210> SEQ ID NO 891
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 891
taaacatggt tagagg                                                       16

<210> SEQ ID NO 892
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 892
gtaaacatgg ttagag                                                       16

<210> SEQ ID NO 893
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 893
gttgtaaaca tggtta                                                       16

<210> SEQ ID NO 894
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 894
```
tagttgtaaa catggt                                      16

<210> SEQ ID NO 895
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 895
gatagttgta aacatg                                      16

<210> SEQ ID NO 896
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 896
atcacagggt tgatag                                      16

<210> SEQ ID NO 897
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 897
tgatcacagg gttgat                                      16

<210> SEQ ID NO 898
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 898
atgatcacag ggttga                                      16

<210> SEQ ID NO 899
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 899
gatgatcaca gggttg                                      16

<210> SEQ ID NO 900
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 900
ggatgatcac agggtt                                      16

<210> SEQ ID NO 901
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 901
gtggatgatc acaggg    16

<210> SEQ ID NO 902
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 902
cgtggatgat cacagg    16

<210> SEQ ID NO 903
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 903
ccgtggatga tcacag    16

<210> SEQ ID NO 904
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 904
gccgtggatg atcaca    16

<210> SEQ ID NO 905
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 905
tgccgtggat gatcac    16

<210> SEQ ID NO 906
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 906
gctgccgtgg atgatc    16

<210> SEQ ID NO 907
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 907
aggctgccgt ggatga    16

```
<210> SEQ ID NO 908
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 908
caaggctgcc gtggat                                                   16

<210> SEQ ID NO 909
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 909
cacaaggctg ccgtgg                                                   16

<210> SEQ ID NO 910
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 910
gtcacaaggc tgccgt                                                   16

<210> SEQ ID NO 911
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 911
ctgtcacaag gctgcc                                                   16

<210> SEQ ID NO 912
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 912
actgtcacaa ggctgc                                                   16

<210> SEQ ID NO 913
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 913
aactgtcaca aggctg                                                   16

<210> SEQ ID NO 914
<211> LENGTH: 16
<212> TYPE: DNA
<213> ORGANISM: Artificial sequence
<220> FEATURE:
```

<223> OTHER INFORMATION: Synthetic oligonucleotide

<400> SEQUENCE: 914
gaactgtcac aaggct                                                      16

<210> SEQ ID NO 915
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 915
cgaactgtca caaggc                                                      16

<210> SEQ ID NO 916
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 916
cacgaactgt cacaag                                                      16

<210> SEQ ID NO 917
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 917
gcacgaactg tcacaa                                                      16

<210> SEQ ID NO 918
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 918
ggcacgaact gtcaca                                                      16

<210> SEQ ID NO 919
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 919
gggcacgaac tgtcac                                                      16

<210> SEQ ID NO 920
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 920
aagggcacga actgtc                                                      16

```
<210> SEQ ID NO 921
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 921
acaagggcac gaactg                                                      16

<210> SEQ ID NO 922
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 922
ttttgtgcta tcacac                                                      16

<210> SEQ ID NO 923
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 923
aaaattttgt gctatc                                                      16

<210> SEQ ID NO 924
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 924
gacaaaactt ttcaca                                                      16

<210> SEQ ID NO 925
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 925
ctacattgac aaaact                                                      16

<210> SEQ ID NO 926
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 926
gaactacatt gacaaa                                                      16

<210> SEQ ID NO 927
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 927
ctctgaacta cattga                                                   16

<210> SEQ ID NO 928
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 928
cactctgaac tacatt                                                   16

<210> SEQ ID NO 929
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 929
gacactctga actaca                                                   16

<210> SEQ ID NO 930
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 930
ttgacactct gaacta                                                   16

<210> SEQ ID NO 931
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 931
ttttgacact ctgaac                                                   16

<210> SEQ ID NO 932
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 932
ggttttgaca ctctga                                                   16

<210> SEQ ID NO 933
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 933
gcggttttga cactct                                                   16

<210> SEQ ID NO 934
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 934
aagcggtttt gacact                                                    16

<210> SEQ ID NO 935
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 935
agatgtcaag ggattt                                                    16

<210> SEQ ID NO 936
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 936
cctgaagcta aggcag                                                    16

<210> SEQ ID NO 937
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 937
gaatttcaaa ctgcat                                                    16

<210> SEQ ID NO 938
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 938
cagtactttg caaatt                                                    16

<210> SEQ ID NO 939
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 939
cttggcaaaa atacct                                                    16

<210> SEQ ID NO 940
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 940
```
gatggctctc ttggca 16

<210> SEQ ID NO 941
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 941
tggatggctc tcttgg 16

<210> SEQ ID NO 942
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 942
tctggatggc tctctt 16

<210> SEQ ID NO 943
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 943
agtctggatg gctctc 16

<210> SEQ ID NO 944
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 944
ccagtctgga tggctc 16

<210> SEQ ID NO 945
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 945
cgccagtctg gatggc 16

<210> SEQ ID NO 946
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 946
ttcgccagtc tggatg 16

<210> SEQ ID NO 947
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 947
tcttcgccag tctgga                                                    16

<210> SEQ ID NO 948
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 948
cagggcatca gcctgg                                                    16

<210> SEQ ID NO 949
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 949
ttcagggcat cagcct                                                    16

<210> SEQ ID NO 950
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 950
atacttcagg gcatca                                                    16

<210> SEQ ID NO 951
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 951
acatacttca gggcat                                                    16

<210> SEQ ID NO 952
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 952
cgacatactt cagggc                                                    16

<210> SEQ ID NO 953
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 953
gccgacatac ttcagg                                                    16
```

```
<210> SEQ ID NO 954
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 954
atgccgacat acttca                                                       16

<210> SEQ ID NO 955
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 955
cgatgccgac atactt                                                       16

<210> SEQ ID NO 956
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 956
ttcgatgccg acatac                                                       16

<210> SEQ ID NO 957
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 957
ctttcgatgc cgacat                                                       16

<210> SEQ ID NO 958
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 958
ctctttcgat gccgac                                                       16

<210> SEQ ID NO 959
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 959
ttctctttcg atgccg                                                       16

<210> SEQ ID NO 960
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 960
atttctcttt cgatgc                                                         16

<210> SEQ ID NO 961
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 961
ccatttctct ttcgat                                                         16

<210> SEQ ID NO 962
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 962
ttccatttct ctttcg                                                         16

<210> SEQ ID NO 963
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 963
gatttccatt tctctt                                                         16

<210> SEQ ID NO 964
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 964
ggatttccat ttctct                                                         16

<210> SEQ ID NO 965
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 965
agggatttcc atttct                                                         16

<210> SEQ ID NO 966
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 966
caagggattt ccattt                                                         16

<210> SEQ ID NO 967
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 967
tcaagggatt tccatt                                                  16

<210> SEQ ID NO 968
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 968
gtcaagggat ttccat                                                  16

<210> SEQ ID NO 969
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 969
tgtcaaggga tttcca                                                  16

<210> SEQ ID NO 970
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 970
atgtcaaggg atttcc                                                  16

<210> SEQ ID NO 971
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 971
gcagatgtca agggat                                                  16

<210> SEQ ID NO 972
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 972
tagcagatgt caaggg                                                  16

<210> SEQ ID NO 973
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 973
```
ggtagcagat gtcaag                                                    16

<210> SEQ ID NO 974
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 974
gaggtagcag atgtca                                                    16

<210> SEQ ID NO 975
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 975
aggaggtagc agatgt                                                    16

<210> SEQ ID NO 976
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 976
ggaggaggta gcagat                                                    16

<210> SEQ ID NO 977
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 977
ctgtttcaga ggaggg                                                    16

<210> SEQ ID NO 978
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 978
agctgtttca gaggag                                                    16

<210> SEQ ID NO 979
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 979
gcagctgttt cagagg                                                    16

<210> SEQ ID NO 980
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 980
ctaaggcagc tgtttc                                                    16

<210> SEQ ID NO 981
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 981
agctaaggca gctgtt                                                    16

<210> SEQ ID NO 982
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 982
tgaagctaag gcagct                                                    16

<210> SEQ ID NO 983
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 983
ttcctgaagc taaggc                                                    16

<210> SEQ ID NO 984
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 984
ggttcctgaa gctaag                                                    16

<210> SEQ ID NO 985
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 985
gaggttcctg aagcta                                                    16

<210> SEQ ID NO 986
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 986
tcgaggttcc tgaagc                                                    16
```

<210> SEQ ID NO 987
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 987
actcgaggtt cctgaa                                                    16

<210> SEQ ID NO 988
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 988
agtactcgag gttcct                                                    16

<210> SEQ ID NO 989
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 989
acagtactcg aggttc                                                    16

<210> SEQ ID NO 990
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 990
ccacagtact cgaggt                                                    16

<210> SEQ ID NO 991
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 991
gcccacagta ctcgag                                                    16

<210> SEQ ID NO 992
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 992
ttgcccacag tactcg                                                    16

<210> SEQ ID NO 993
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 993
aattgcccac agtact                                                    16

<210> SEQ ID NO 994
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 994
taaattgccc acagta                                                    16

<210> SEQ ID NO 995
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 995
tctaaattgc ccacag                                                    16

<210> SEQ ID NO 996
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 996
ttcaaactgc atgttc                                                    16

<210> SEQ ID NO 997
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 997
cagaatttca aactgc                                                    16

<210> SEQ ID NO 998
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 998
gtactttgca aattca                                                    16

<210> SEQ ID NO 999
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 999
tcttacagta ctttgc                                                    16
```

```
<210> SEQ ID NO 1000
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1000
ttattcttac agtact                                                    16

<210> SEQ ID NO 1001
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1001
ctcattacta taaatt                                                    16

<210> SEQ ID NO 1002
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1002
taaactcatt actata                                                    16

<210> SEQ ID NO 1003
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1003
gcaataaaaa gttgat                                                    16

<210> SEQ ID NO 1004
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1004
gtgagaaggc aataaa                                                    16

<210> SEQ ID NO 1005
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1005
tggtgagaag gcaata                                                    16

<210> SEQ ID NO 1006
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1006
ctggtgagaa ggcaat                                                     16

<210> SEQ ID NO 1007
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1007
agctggtgag aaggca                                                     16

<210> SEQ ID NO 1008
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1008
tatattgacc aagggc                                                     16

<210> SEQ ID NO 1009
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1009
attatattga ccaagg                                                     16

<210> SEQ ID NO 1010
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1010
tcattatatt gaccaa                                                     16

<210> SEQ ID NO 1011
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1011
catcattata ttgacc                                                     16

<210> SEQ ID NO 1012
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1012
atcatcatta tattga                                                     16

<210> SEQ ID NO 1013
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1013
catcatcatt atattg                                                        16

<210> SEQ ID NO 1014
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1014
tcatcatcat tatatt                                                        16

<210> SEQ ID NO 1015
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1015
aacagattta gcattt                                                        16

<210> SEQ ID NO 1016
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1016
ataagtgttg ggtgtt                                                        16

<210> SEQ ID NO 1017
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1017
cttccgctta taagtg                                                        16

<210> SEQ ID NO 1018
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1018
gatcacaggg ttgata                                                        16

<210> SEQ ID NO 1019
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1019
```
ttgcaaattc agaatt 16

<210> SEQ ID NO 1020
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1020
tttgcaaatt cagaat 16

<210> SEQ ID NO 1021
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1021
ctttgcaaat tcagaa 16

<210> SEQ ID NO 1022
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1022
actttgcaaa ttcaga 16

<210> SEQ ID NO 1023
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1023
tactttgcaa attcag 16

<210> SEQ ID NO 1024
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1024
agtactttgc aaattc 16

<210> SEQ ID NO 1025
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1025
acagtacttt gcaaat 16

<210> SEQ ID NO 1026
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1026
tacagtactt tgcaaa                                                         16

<210> SEQ ID NO 1027
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1027
ttacagtact ttgcaa                                                         16

<210> SEQ ID NO 1028
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1028
actttgcagc tggtga                                                         16

<210> SEQ ID NO 1029
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1029
acactttgca gctggt                                                         16

<210> SEQ ID NO 1030
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1030
aaacactttg cagctg                                                         16

<210> SEQ ID NO 1031
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1031 aaaacactttt gcagct                                                        16

<210> SEQ ID NO 1032
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1032
acaaaacact ttgcag                                                         16
```

<210> SEQ ID NO 1033
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1033
tacaaaacac tttgca                                                         16

<210> SEQ ID NO 1034
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1034
tttgtgcaag gcaaag                                                         16

<210> SEQ ID NO 1035
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1035
atttgtgcaa ggcaaa                                                         16

<210> SEQ ID NO 1036
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1036
tatttgtgca aggcaa                                                         16

<210> SEQ ID NO 1037
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1037
gtatttgtgc aaggca                                                         16

<210> SEQ ID NO 1038
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1038
tgtatttgtg caaggc                                                         16

<210> SEQ ID NO 1039
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1039
aatgtatttg tgcaag                                                    16

<210> SEQ ID NO 1040
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1040
aaatgtattt gtgcaa                                                    16

<210> SEQ ID NO 1041
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1041
taaatgtatt tgtgca                                                    16

<210> SEQ ID NO 1042
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1042
ttaaatgtat ttgtgc                                                    16

<210> SEQ ID NO 1043
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1043
cttaaatgta tttgtg                                                    16

<210> SEQ ID NO 1044
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1044
gttgttccat tattta                                                    16

<210> SEQ ID NO 1045
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1045
agttgttcca ttattt                                                    16

<210> SEQ ID NO 1046

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1046
aagttgttcc attatt                                                    16

<210> SEQ ID NO 1047
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1047
caagttgttc cattat                                                    16

<210> SEQ ID NO 1048
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1048
acaagttgtt ccatta                                                    16

<210> SEQ ID NO 1049
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1049
acacaagttg ttccat                                                    16

<210> SEQ ID NO 1050
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1050
aacacaagtt gttcca                                                    16

<210> SEQ ID NO 1051
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1051
aaacacaagt tgttcc                                                    16

<210> SEQ ID NO 1052
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1052
```
taaacacaag ttgttc                                              16

<210> SEQ ID NO 1053
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1053
gtaaacacaa gttgtt                                              16

<210> SEQ ID NO 1054
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1054
tttctgtgtt cttccg                                              16

<210> SEQ ID NO 1055
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1055
tgtttctgtg ttcttc                                              16

<210> SEQ ID NO 1056
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1056
ctgtttctgt gttctt                                              16

<210> SEQ ID NO 1057
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1057
agctgtttct gtgttc                                              16

<210> SEQ ID NO 1058
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1058
agagctgttt ctgtgt                                              16

<210> SEQ ID NO 1059
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1059
ctagagctgt ttctgt                                                    16

<210> SEQ ID NO 1060
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1060
atgttttggt cccaat                                                    16

<210> SEQ ID NO 1061
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1061
acatgttttg gtccca                                                    16

<210> SEQ ID NO 1062
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1062
ctacatgttt tggtcc                                                    16

<210> SEQ ID NO 1063
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1063
gtctacatgt tttggt                                                    16

<210> SEQ ID NO 1064
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1064
ctgtctacat gttttg                                                    16

<210> SEQ ID NO 1065
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1065
cacaagttgt tccatt                                                    16
```

<210> SEQ ID NO 1066
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1066
gtcgcatgta ctctga                                                     16

<210> SEQ ID NO 1067
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1067
agtcgcatgt actctg                                                     16

<210> SEQ ID NO 1068
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1068
aaacatttct ccatgc                                                     16

<210> SEQ ID NO 1069
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1069
actgtggaca gcacac                                                     16

<210> SEQ ID NO 1070
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1070
aggaagttta actgtg                                                     16

<210> SEQ ID NO 1071
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1071
cctgtgtgat aaagga                                                     16

<210> SEQ ID NO 1072
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1072
tgttacagat cctgtg                                                    16

<210> SEQ ID NO 1073
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1073
tagcaaagac acattt                                                    16

<210> SEQ ID NO 1074
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1074
tttaagtaaa tagcaa                                                    16

<210> SEQ ID NO 1075
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1075
aaagcaagcc tttaag                                                    16

<210> SEQ ID NO 1076
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1076
ttgaacccta aaaagc                                                    16

<210> SEQ ID NO 1077
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1077
aataacttgc ttgaac                                                    16

<210> SEQ ID NO 1078
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1078
ccacaaaatt aaacta                                                    16

```
<210> SEQ ID NO 1079
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1079
ttttatgatg acatca                                                  16

<210> SEQ ID NO 1080
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1080
gtttattaaa tgctgt                                                  16

<210> SEQ ID NO 1081
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1081
gtttttcaaa ggttta                                                  16

<210> SEQ ID NO 1082
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1082
attgtgacag cattcg                                                  16

<210> SEQ ID NO 1083
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1083
actacattca attgtg                                                  16

<210> SEQ ID NO 1084
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1084
cctaaaagta taaact                                                  16

<210> SEQ ID NO 1085
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1085
ctccaaaacc cctaaa                                                    16

<210> SEQ ID NO 1086
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1086
tgaagagtaa tagaaa                                                    16

<210> SEQ ID NO 1087
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1087
ctaatgctta tgaaga                                                    16

<210> SEQ ID NO 1088
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1088
gaattagttg ctaatg                                                    16

<210> SEQ ID NO 1089
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1089
tcctaaacat gaatta                                                    16

<210> SEQ ID NO 1090
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1090
ttgtacagta ttccta                                                    16

<210> SEQ ID NO 1091
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1091
aggattacac acttgt                                                    16

<210> SEQ ID NO 1092
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1092
taaacaagtt aggatt                                                     16

<210> SEQ ID NO 1093
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1093
ctgcaaataa aattac                                                     16

<210> SEQ ID NO 1094
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1094
atacttgttt tcctgc                                                     16

<210> SEQ ID NO 1095
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1095
ccatgaatag aaaatt                                                     16

<210> SEQ ID NO 1096
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1096
actttagaga ccatga                                                     16

<210> SEQ ID NO 1097
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1097
cctattccta acttta                                                     16

<210> SEQ ID NO 1098
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1098
```

-continued

| | |
|---|---|
| tagaatccta cctatt | 16 |

<210> SEQ ID NO 1099
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1099

| | |
|---|---|
| tatctatgac tagaat | 16 |

<210> SEQ ID NO 1100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1100

| | |
|---|---|
| agagagaaca agacgc | 16 |

<210> SEQ ID NO 1101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1101

| | |
|---|---|
| acctccgaaa agagag | 16 |

<210> SEQ ID NO 1102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1102

| | |
|---|---|
| cacccaacac acctcc | 16 |

<210> SEQ ID NO 1103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1103

| | |
|---|---|
| aatattacat caccca | 16 |

<210> SEQ ID NO 1104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1104

| | |
|---|---|
| ggaaacctta aatatt | 16 |

<210> SEQ ID NO 1105
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1105
cctgtttccg ggaaac                                                     16

<210> SEQ ID NO 1106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1106
atgcagtgtt cctgtt                                                     16

<210> SEQ ID NO 1107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1107
agaatttaag atgcag                                                     16

<210> SEQ ID NO 1108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1108
cacaaaaacg agaatt                                                     16

<210> SEQ ID NO 1109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1109
attcactttc cacaaa                                                     16

<210> SEQ ID NO 1110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1110
cttggaatat attcac                                                     16

<210> SEQ ID NO 1111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1111
aacttgtttt cttgga                                                     16
```

```
<210> SEQ ID NO 1112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1112
atgtttttct aacttg                                                    16

<210> SEQ ID NO 1113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1113
gcaaccagaa gaacgc                                                    16

<210> SEQ ID NO 1114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1114
ataggacagt gcaacc                                                    16

<210> SEQ ID NO 1115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1115
tgcacattag atcttt                                                    16

<210> SEQ ID NO 1116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1116
agttagcaga tgcaca                                                    16

<210> SEQ ID NO 1117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1117 tgaaaccttaagttag                                                    16

<210> SEQ ID NO 1118
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1118
atttatttgt ctccat                                                     16

<210> SEQ ID NO 1119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1119
ctctccaaaa tatatg                                                     16

<210> SEQ ID NO 1120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1120
acagtggtgt caacac                                                     16

<210> SEQ ID NO 1121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1121
gaatgcccgt acagtg                                                     16

<210> SEQ ID NO 1122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1122
ccagcacctg gaatgc                                                     16

<210> SEQ ID NO 1123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1123
aacacttaga ccagca                                                     16

<210> SEQ ID NO 1124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1124
ataatgtctc aacact                                                     16

<210> SEQ ID NO 1125
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1125
gtaactaata taaacg                                                    16

<210> SEQ ID NO 1126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1126
attattaata ggattt                                                    16

<210> SEQ ID NO 1127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1127
aatggacaag attatt                                                    16

<210> SEQ ID NO 1128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1128
cttatctcat aatgga                                                    16

<210> SEQ ID NO 1129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1129
gcataactac cttatc                                                    16

<210> SEQ ID NO 1130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1130
ccaaaaatct gcataa                                                    16

<210> SEQ ID NO 1131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1131
```
cgaatttctg ccaaaa                                              16

<210> SEQ ID NO 1132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1132
ctaaaatatc cgaatt                                              16

<210> SEQ ID NO 1133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1133
acatatgtat cctaaa                                              16

<210> SEQ ID NO 1134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1134
gtacatcact tcaggt                                              16

<210> SEQ ID NO 1135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1135
gcggaggcgg gtacat                                              16

<210> SEQ ID NO 1136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1136
gatcagcatt ttggga                                              16

<210> SEQ ID NO 1137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1137
tttatcctag gctggg                                              16

<210> SEQ ID NO 1138
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1138
gttagaaatt tttatc                                                     16

<210> SEQ ID NO 1139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1139
caagggcaaa gttaga                                                     16

<210> SEQ ID NO 1140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1140
agagaacact caaggg                                                     16

<210> SEQ ID NO 1141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1141
tatcaaatac agagaa                                                     16

<210> SEQ ID NO 1142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1142
gaatagtaat tatcaa                                                     16

<210> SEQ ID NO 1143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1143
caagtacaaa gaatag                                                     16

<210> SEQ ID NO 1144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1144
tatctcatgg caagta                                                     16
```

<210> SEQ ID NO 1145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1145
ccaattcccc aaagag                                                     16

<210> SEQ ID NO 1146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1146
gtaccagaaa ataatt                                                     16

<210> SEQ ID NO 1147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1147
attctcaatt gtacca                                                     16

<210> SEQ ID NO 1148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1148
gactaaatac attctc                                                     16

<210> SEQ ID NO 1149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1149
tacttaaact gactaa                                                     16

<210> SEQ ID NO 1150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1150
aagtcactgc tactta                                                     16

<210> SEQ ID NO 1151
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1151
caagtgtgtt ttaagt                                                    16

<210> SEQ ID NO 1152
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1152
actagatcaa caagtg                                                    16

<210> SEQ ID NO 1153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1153
ttctaactac actaga                                                    16

<210> SEQ ID NO 1154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1154
tcagaacttt ttctaa                                                    16

<210> SEQ ID NO 1155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1155
tatcaaagta tcagaa                                                    16

<210> SEQ ID NO 1156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1156
caaagctagg tatcaa                                                    16

<210> SEQ ID NO 1157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1157
gcaaggcaaa gctagg                                                    16
```

```
<210> SEQ ID NO 1158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1158
tattcactta aatgta                                                    16

<210> SEQ ID NO 1159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1159
caacataaag atattc                                                    16

<210> SEQ ID NO 1160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1160
tttaaatggc caacat                                                    16

<210> SEQ ID NO 1161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1161
gaaatttgcc taaaat                                                    16

<210> SEQ ID NO 1162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1162
atgacttgga gaaatt                                                    16

<210> SEQ ID NO 1163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1163
aaattccagt atgact                                                    16

<210> SEQ ID NO 1164
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1164
tatcctggga aaattc                                                16

<210> SEQ ID NO 1165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1165
agaaggaagg tatcct                                                16

<210> SEQ ID NO 1166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1166
ctacctcaaa agaagg                                                16

<210> SEQ ID NO 1167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1167
cttgagcaca ctacct                                                16

<210> SEQ ID NO 1168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1168
attcagaatc cttgag                                                16

<210> SEQ ID NO 1169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1169
ggtaatactg aaataa                                                16

<210> SEQ ID NO 1170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1170
tcatgtaaag ggtaat                                                16

<210> SEQ ID NO 1171
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1171
ctcaatcact gctcat                                                    16

<210> SEQ ID NO 1172
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1172
gatcaacttt ctcaat                                                    16

<210> SEQ ID NO 1173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1173
gtccttgttg gttttt                                                    16

<210> SEQ ID NO 1174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1174
attggaggat ttgtcc                                                    16

<210> SEQ ID NO 1175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1175
aatacattat attgga                                                    16

<210> SEQ ID NO 1176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1176
ttaaccacag aataca                                                    16

<210> SEQ ID NO 1177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1177
```
atcattgcta attaac                              16

<210> SEQ ID NO 1178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1178
taatccataa atcatt                              16

<210> SEQ ID NO 1179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1179
acttcaaggc taatcc                              16

<210> SEQ ID NO 1180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1180
tgatataaag acttca                              16

<210> SEQ ID NO 1181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1181
tgtcatctat actgat                              16

<210> SEQ ID NO 1182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1182
acagaaaatt tgtcat                              16

<210> SEQ ID NO 1183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1183
atatagaatc tatcat                              16

<210> SEQ ID NO 1184
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1184
tcacctactc atatag                                                     16

<210> SEQ ID NO 1185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1185
cccgaagatt tcacct                                                     16

<210> SEQ ID NO 1186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1186
acttatgctc tccccc                                                     16

<210> SEQ ID NO 1187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1187
attgctgctg ttcact                                                     16

<210> SEQ ID NO 1188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1188
aatttaatga attgct                                                     16

<210> SEQ ID NO 1189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1189
cctttctctg aattta                                                     16

<210> SEQ ID NO 1190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1190
tgaccatgaa cctttc                                                     16
```

```
<210> SEQ ID NO 1191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1191
atgtatcatc tgacca                                                    16

<210> SEQ ID NO 1192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1192
aaggtaaagt atgtat                                                    16

<210> SEQ ID NO 1193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1193
agacctccag aaggta                                                    16

<210> SEQ ID NO 1194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1194
aattcaggga agacct                                                    16

<210> SEQ ID NO 1195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1195
caagagtggg aattca                                                    16

<210> SEQ ID NO 1196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1196
ccctgtggga acacaa                                                    16

<210> SEQ ID NO 1197
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1197
aaatatgata aaaccc                                                    16

<210> SEQ ID NO 1198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1198
catgctacaa taaaat                                                    16

<210> SEQ ID NO 1199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1199
acaattgagt catgct                                                    16

<210> SEQ ID NO 1200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1200
tgattacaat acaatt                                                    16

<210> SEQ ID NO 1201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1201
cataaacaag tgatta                                                    16

<210> SEQ ID NO 1202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1202
agagagggat gcataa                                                    16

<210> SEQ ID NO 1203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1203
actgtaggga agagag                                                    16

<210> SEQ ID NO 1204
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1204
aggcactttg actgta                                              16

<210> SEQ ID NO 1205
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1205
ctctaccagg aggcac                                              16

<210> SEQ ID NO 1206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1206
taagacagag cctcta                                              16

<210> SEQ ID NO 1207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1207
ctaggtatac aaagaa                                              16

<210> SEQ ID NO 1208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1208
ctagcaaata ccaacg                                              16

<210> SEQ ID NO 1209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1209 aaaccctat tctcta                                               16

<210> SEQ ID NO 1210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1210
```
actatattta aaaccc                                          16

<210> SEQ ID NO 1211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1211
aattcattca actata                                          16

<210> SEQ ID NO 1212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1212
catatttcct taattc                                          16

<210> SEQ ID NO 1213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1213
ccctacattt ttcata                                          16

<210> SEQ ID NO 1214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1214
caaattattt ccctac                                          16

<210> SEQ ID NO 1215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1215
gttcctttgt caaatt                                          16

<210> SEQ ID NO 1216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1216
cactttgcaa gttcct                                          16

<210> SEQ ID NO 1217
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 1217
catatcctgt tcactt                                                  16

<210> SEQ ID NO 1218
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1218
accattccaa acagaa                                                  16

<210> SEQ ID NO 1219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1219
gttcaaccat cactat                                                  16

<210> SEQ ID NO 1220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1220
gtgtaaaatt taccat                                                  16

<210> SEQ ID NO 1221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1221
gtaagatata tagata                                                  16

<210> SEQ ID NO 1222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1222
aaaggttttc ggagtg                                                  16

<210> SEQ ID NO 1223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1223
cttaactcct cccctg                                                  16

<210> SEQ ID NO 1224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1224
ccgaatgcaa attccc                                                   16

<210> SEQ ID NO 1225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1225
gtagataata tgtagt                                                   16

<210> SEQ ID NO 1226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1226
cagaaagcca gcagat                                                   16

<210> SEQ ID NO 1227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1227
aactcattct tctcgg                                                   16

<210> SEQ ID NO 1228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1228
acctactttt aaatgt                                                   16

<210> SEQ ID NO 1229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1229
ctttagtctg tctagg                                                   16

<210> SEQ ID NO 1230
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1230
ctattaccac tctggc                                                        16

<210> SEQ ID NO 1231
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1231
atccttagaa ctctac                                                        16

<210> SEQ ID NO 1232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1232
cagggactgg aaccca                                                        16

<210> SEQ ID NO 1233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1233
catcaagagg ataaca                                                        16

<210> SEQ ID NO 1234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1234
tcattatcct caccaa                                                        16

<210> SEQ ID NO 1235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1235
atcaattcct ttaatc                                                        16

<210> SEQ ID NO 1236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1236
cactttttgc caggta                                                        16

```
<210> SEQ ID NO 1237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1237
aataatattg gcacaa                                                    16

<210> SEQ ID NO 1238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1238
aagtgtttgg ttccat                                                    16

<210> SEQ ID NO 1239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1239
tttgtaactt accagt                                                    16

<210> SEQ ID NO 1240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1240
gacatttcta aattga                                                    16

<210> SEQ ID NO 1241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1241
attgtttcag tagttt                                                    16

<210> SEQ ID NO 1242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1242
aacagggatc aatacg                                                    16

<210> SEQ ID NO 1243
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1243
agaatataca ccaaac                                                   16

<210> SEQ ID NO 1244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1244
taacttggtc ccattt                                                   16

<210> SEQ ID NO 1245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1245
ttgtattgac cttaaa                                                   16

<210> SEQ ID NO 1246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1246
ctaaaggaat atcaat                                                   16

<210> SEQ ID NO 1247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1247
aataatgact tagaag                                                   16

<210> SEQ ID NO 1248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1248
aactagttgt tactta                                                   16

<210> SEQ ID NO 1249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1249
gactttgaag ctaacg                                                   16

<210> SEQ ID NO 1250
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1250
cagctcacag gcctta                                                      16

<210> SEQ ID NO 1251
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1251
ttatatgttc ttcagg                                                      16

<210> SEQ ID NO 1252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1252
tggtaagtat tttagg                                                      16

<210> SEQ ID NO 1253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1253
atggcttaga gcaagg                                                      16

<210> SEQ ID NO 1254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1254
tactatgcac ccccct                                                      16

<210> SEQ ID NO 1255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1255
acagattggt ttgctg                                                      16

<210> SEQ ID NO 1256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1256
```
gttcacttct tttcag                                                16

<210> SEQ ID NO 1257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1257
gaaaattgtc acacaa                                                16

<210> SEQ ID NO 1258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1258
ctagaaatgt tcataa                                                16

<210> SEQ ID NO 1259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1259
gttgttttaa ctaaaa                                                16

<210> SEQ ID NO 1260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1260
tcaaatgtgt gctttt                                                16

<210> SEQ ID NO 1261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1261
gtgcaggtgc atacat                                                16

<210> SEQ ID NO 1262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1262
gatgatggca accatt                                                16

<210> SEQ ID NO 1263
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1263
gttgagagaa tgactg                                                   16

<210> SEQ ID NO 1264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1264
gaggtgagag gttcga                                                   16

<210> SEQ ID NO 1265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1265
aaccatcctg ggcgac                                                   16

<210> SEQ ID NO 1266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1266
aagtcaggtg ccgcgg                                                   16

<210> SEQ ID NO 1267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1267
atgcctacaa tggaat                                                   16

<210> SEQ ID NO 1268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1268
gtcctatgtg tccatc                                                   16

<210> SEQ ID NO 1269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1269
acaaatggtg atagca                                                   16
```

```
<210> SEQ ID NO 1270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1270
atcaatattt accact                                                     16

<210> SEQ ID NO 1271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1271
ctattttgga aaagag                                                     16

<210> SEQ ID NO 1272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1272
acagttacaa ctgtaa                                                     16

<210> SEQ ID NO 1273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1273
aagtgtcaat gaaaat                                                     16

<210> SEQ ID NO 1274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1274
ctcatttgat ggccaa                                                     16

<210> SEQ ID NO 1275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1275
atcatctgag aaacac                                                     16

<210> SEQ ID NO 1276
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1276
aagtacacaa atggcc                                              16

<210> SEQ ID NO 1277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1277
cagacaaaca atccaa                                              16

<210> SEQ ID NO 1278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1278
atgtacccag aacata                                              16

<210> SEQ ID NO 1279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1279
taacttgatc tttata                                              16

<210> SEQ ID NO 1280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1280
acataattta tctgat                                              16

<210> SEQ ID NO 1281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1281
ctaattaaat gactcg                                              16

<210> SEQ ID NO 1282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1282
agtttacaag tttctg                                              16

<210> SEQ ID NO 1283
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1283
catccataca cctaac                                                     16

<210> SEQ ID NO 1284
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1284
gaattactaa atacaa                                                     16

<210> SEQ ID NO 1285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1285
actcactaat aaatga                                                     16

<210> SEQ ID NO 1286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1286
ttctaagatc aaggtc                                                     16

<210> SEQ ID NO 1287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1287
gggaaactaa gtttgg                                                     16

<210> SEQ ID NO 1288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1288 aaaaaattt acggga                                                      16

<210> SEQ ID NO 1289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1289
```
aagtatatat aatctg                                                    16

<210> SEQ ID NO 1290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1290
aactgctact ttacaa                                                    16

<210> SEQ ID NO 1291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1291
aaaaatttat tgtggg                                                    16

<210> SEQ ID NO 1292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1292
ggaaaagtta tgtatt                                                    16

<210> SEQ ID NO 1293
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1293
cagcttgctt tatata                                                    16

<210> SEQ ID NO 1294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1294
acctacagtg gtggta                                                    16

<210> SEQ ID NO 1295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1295
ccacagccat gagaag                                                    16

<210> SEQ ID NO 1296
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1296
actacctgga atgcta                                                     16

<210> SEQ ID NO 1297
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1297
agataatact aattca                                                     16

<210> SEQ ID NO 1298
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1298
agctcaggaa tcttga                                                     16

<210> SEQ ID NO 1299
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1299
taccagggcc aggcac                                                     16

<210> SEQ ID NO 1300
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1300
caagtgagat caacag                                                     16

<210> SEQ ID NO 1301
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1301
aggcacagaa tctcca                                                     16

<210> SEQ ID NO 1302
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1302
gagatgctaa aataag                                                     16
```

<210> SEQ ID NO 1303
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1303
aacttggttg ggatgg                                                   16

<210> SEQ ID NO 1304
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1304
gattaataca catgtt                                                   16

<210> SEQ ID NO 1305
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1305
gagcttaaaa tgaagg                                                   16

<210> SEQ ID NO 1306
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1306 aaccttttc taagct                                                    16

<210> SEQ ID NO 1307
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1307
atcaacttca caaata                                                   16

<210> SEQ ID NO 1308
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1308
attgagttgc ttacag                                                   16

<210> SEQ ID NO 1309
<211> LENGTH: 16
<212> TYPE: DNA
<213> ORGANISM: Artificial sequence
<220> FEATURE:

```
<223> OTHER INFORMATION: Synthetic oligonucleotide

<400> SEQUENCE: 1309
cagtacactg ggtgag                                                     16

<210> SEQ ID NO 1310
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1310
caaggatata ctttaa                                                     16

<210> SEQ ID NO 1311
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1311
agagtttctc aagctt                                                     16

<210> SEQ ID NO 1312
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1312
tttcatgctc ttcatt                                                     16

<210> SEQ ID NO 1313
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1313
ctgtgtacaa aaaaga                                                     16

<210> SEQ ID NO 1314
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1314
gtctgaggat gtagtg                                                     16

<210> SEQ ID NO 1315
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1315
cagctttggg aggaca                                                     16
```

```
<210> SEQ ID NO 1316
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1316
gataaagatc actggg                                                    16

<210> SEQ ID NO 1317
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1317
actatgtatg aattta                                                    16

<210> SEQ ID NO 1318
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1318
gtctttttga tacctt                                                    16

<210> SEQ ID NO 1319
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1319
aactaagaga ctaaaa                                                    16

<210> SEQ ID NO 1320
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1320
tgttaaagca tttctc                                                    16

<210> SEQ ID NO 1321
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1321
aaataattaa ctgtct                                                    16

<210> SEQ ID NO 1322
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1322
tgacatcaaa aaatac                                                    16

<210> SEQ ID NO 1323
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1323
atctacaaac agaata                                                    16

<210> SEQ ID NO 1324
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1324
aattagttct attatg                                                    16

<210> SEQ ID NO 1325
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1325
atgtatatta ggtaca                                                    16

<210> SEQ ID NO 1326
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1326
attaatttac tatggg                                                    16

<210> SEQ ID NO 1327
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1327
atctgttgtg caacaa                                                    16

<210> SEQ ID NO 1328
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1328
ctcaatgggt acagaa                                                    16

<210> SEQ ID NO 1329
<211> LENGTH: 16
```

<212> TYPE: DNA
<213> ORGANISM: Artificial sequence
<220> FEATURE:
<223> OTHER INFORMATION: Synthetic oligonucleotide

<400> SEQUENCE: 1329
ctgccaagaa tttggg                                                    16

<210> SEQ ID NO 1330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1330
acagtcaaaa atcatg                                                    16

<210> SEQ ID NO 1331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1331
gcaaatactg tttaat                                                    16

<210> SEQ ID NO 1332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1332
tgacattatg ctaagc                                                    16

<210> SEQ ID NO 1333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1333
gcctttacag aaaaga                                                    16

<210> SEQ ID NO 1334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1334
caccaataga taaatg                                                    16

<210> SEQ ID NO 1335
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1335
aatagtgaat caccaa 16

<210> SEQ ID NO 1336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1336
taccaacatt tactgc 16

<210> SEQ ID NO 1337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1337
ccatatatcc aaaaga 16

<210> SEQ ID NO 1338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1338
gatccacata gttcaa 16

<210> SEQ ID NO 1339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1339
ttctatctat ggctgg 16

<210> SEQ ID NO 1340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1340
atggcatgaa taacag 16

<210> SEQ ID NO 1341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1341
ttttgagcag ggtctt 16

<210> SEQ ID NO 1342
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1342
ttcacatccc acaaat                                                       16

<210> SEQ ID NO 1343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1343
ctgcatatac aaaaag                                                       16

<210> SEQ ID NO 1344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1344
attcactcat actcaa                                                       16

<210> SEQ ID NO 1345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1345
gaataagact ggttcc                                                       16

<210> SEQ ID NO 1346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1346
gacgaataat taaaaa                                                       16

<210> SEQ ID NO 1347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1347
ccacagcata tgcaga                                                       16

<210> SEQ ID NO 1348
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1348
cattaaaata gaacta                                                       16
```

```
<210> SEQ ID NO 1349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1349
taggactgta aaaatc                                                     16

<210> SEQ ID NO 1350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1350
gtgcactgtg ggtagg                                                     16

<210> SEQ ID NO 1351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1351
cgaaaccttt gtgcac                                                     16

<210> SEQ ID NO 1352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1352
gcagagacat cgaaac                                                     16

<210> SEQ ID NO 1353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1353
ctaccaaaag aaacag                                                     16

<210> SEQ ID NO 1354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1354
attatgttgg ccacta                                                     16

<210> SEQ ID NO 1355
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1355
tgttaatgca aatcaa                                              16

<210> SEQ ID NO 1356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1356
gatactcaac attgtt                                              16

<210> SEQ ID NO 1357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1357
aaacatgaag gatact                                              16

<210> SEQ ID NO 1358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1358
gattttcaat aaattc                                              16

<210> SEQ ID NO 1359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1359
tgagttttac ataatt                                              16

<210> SEQ ID NO 1360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1360
caaatgatgc atggta                                              16

<210> SEQ ID NO 1361
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1361
cttttcccat ttaaca                                              16

<210> SEQ ID NO 1362
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1362
gacaaattct cctttt                                                       16

<210> SEQ ID NO 1363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1363
tagtcataag gacaaa                                                       16

<210> SEQ ID NO 1364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1364
ccttattaga atattt                                                       16

<210> SEQ ID NO 1365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1365
aaaaggttca ccttat                                                       16

<210> SEQ ID NO 1366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1366
gactctataa aaatgc                                                       16

<210> SEQ ID NO 1367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1367
ttaccagcca ggccaa                                                       16

<210> SEQ ID NO 1368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1368
```

```
gttcatctta ttacca                                              16

<210> SEQ ID NO 1369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1369
aaagtataaa gttcat                                              16

<210> SEQ ID NO 1370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1370
gcacctaggt gacaga                                              16

<210> SEQ ID NO 1371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1371
atcccagata cctgag                                              16

<210> SEQ ID NO 1372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1372
tcctaggagt tctaga                                              16

<210> SEQ ID NO 1373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1373
gagatcactt gatcct                                              16

<210> SEQ ID NO 1374
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1374
tccaaggtgg gagatc                                              16

<210> SEQ ID NO 1375
<211> LENGTH: 16
<212> TYPE: DNA
```

<213> ORGANISM: Artificial sequence
<220> FEATURE:
<223> OTHER INFORMATION: Synthetic oligonucleotide

<400> SEQUENCE: 1375
aagttctggc ccaatg                                                     16

<210> SEQ ID NO 1376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1376
aataagtata aagttc                                                     16

<210> SEQ ID NO 1377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1377
catactgttt aataag                                                     16

<210> SEQ ID NO 1378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1378
ctatcatcag catact                                                     16

<210> SEQ ID NO 1379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1379
acagtttttt cctatc                                                     16

<210> SEQ ID NO 1380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1380
taaggattgc acagtt                                                     16

<210> SEQ ID NO 1381
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1381
aattttatga ataagg                                                     16

<210> SEQ ID NO 1382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1382
tttagatcag aattt                                                    16

<210> SEQ ID NO 1383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1383
attttaatat aacacg                                                   16

<210> SEQ ID NO 1384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1384
gcattattaa ttaatt                                                   16

<210> SEQ ID NO 1385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1385
aattttgctt gcatta                                                   16

<210> SEQ ID NO 1386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1386
caaataaatt tgccaa                                                   16

<210> SEQ ID NO 1387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1387
agtagcccaa aatggg                                                   16

<210> SEQ ID NO 1388
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1388
taattttcga agtagc                                                         16

<210> SEQ ID NO 1389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1389
gatccataaa taattt                                                         16

<210> SEQ ID NO 1390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1390
aaccttttct gatcca                                                         16

<210> SEQ ID NO 1391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1391
aagtatttcc caacct                                                         16

<210> SEQ ID NO 1392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1392
tactctagaa aagtat                                                         16

<210> SEQ ID NO 1393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1393
tacagggcct gctcaa                                                         16

<210> SEQ ID NO 1394
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1394
cttctgccat ctacag                                                         16

```
<210> SEQ ID NO 1395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1395
ttcaagcaac acttct                                                       16

<210> SEQ ID NO 1396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1396
ctctacgcca gttcaa                                                       16

<210> SEQ ID NO 1397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1397
acactttctt cctcta                                                       16

<210> SEQ ID NO 1398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1398
gggcaattca acactt                                                       16

<210> SEQ ID NO 1399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1399
taaggaatta agtggg                                                       16

<210> SEQ ID NO 1400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1400
caaaattact taagga                                                       16

<210> SEQ ID NO 1401
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1401
ctccaaagag gcaaaa                                                    16

<210> SEQ ID NO 1402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1402
ggcaaatatt ctccaa                                                    16

<210> SEQ ID NO 1403
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1403
ctctatttca ggcaaa                                                    16

<210> SEQ ID NO 1404
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1404
aacttgagtt ctctat                                                    16

<210> SEQ ID NO 1405
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1405
ttcatagcat aacttg                                                    16

<210> SEQ ID NO 1406
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1406
caaaaagaat cttcat                                                    16

<210> SEQ ID NO 1407
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1407
gcaatgtgag accctg                                                    16

<210> SEQ ID NO 1408
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1408
aaggtgaaag ggtcac                                              16

<210> SEQ ID NO 1409
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1409
ccaaaatatc ttcttg                                              16

<210> SEQ ID NO 1410
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1410
atgtagccct ccaaaa                                              16

<210> SEQ ID NO 1411
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1411
tactggtggg atgtag                                              16

<210> SEQ ID NO 1412
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1412
aacatcaagc tactgg                                              16

<210> SEQ ID NO 1413
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1413
ctctttgtac aacatc                                              16

<210> SEQ ID NO 1414
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1414
```

```
ccagagccta ccactc                                                  16

<210> SEQ ID NO 1415
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1415
gcagagcctc gcccag                                                  16

<210> SEQ ID NO 1416
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1416
tagtataatg gcagag                                                  16

<210> SEQ ID NO 1417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1417
gaaatacaac tagtat                                                  16

<210> SEQ ID NO 1418
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1418
atccacaaaa gctacg                                                  16

<210> SEQ ID NO 1419
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1419
aagaggagag atccac                                                  16

<210> SEQ ID NO 1420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1420
tgtcaccatg aagagg                                                  16

<210> SEQ ID NO 1421
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1421
atctcattca tgtcac                                                    16

<210> SEQ ID NO 1422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1422
ccattattta ttcatc                                                    16

<210> SEQ ID NO 1423
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1423
tactcagtaa acacaa                                                    16

<210> SEQ ID NO 1424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1424
tacatggtag atactc                                                    16

<210> SEQ ID NO 1425
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1425
ctgcaggcac atacat                                                    16

<210> SEQ ID NO 1426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1426
agacatcctc tctgca                                                    16

<210> SEQ ID NO 1427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1427
attacttcat ctgcaa                                                    16
```

<210> SEQ ID NO 1428
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1428
agttatttac taatta                                                 16

<210> SEQ ID NO 1429
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1429
aacctaggca agttat                                                 16

<210> SEQ ID NO 1430
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1430
tacctgaggg aaccta                                                 16

<210> SEQ ID NO 1431
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1431
aagggcccac tacctg                                                 16

<210> SEQ ID NO 1432
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1432
gcccattctt caaggg                                                 16

<210> SEQ ID NO 1433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1433
ggccataaaa gcccat                                                 16

<210> SEQ ID NO 1434
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 1434
caatgcactt ggccat                                                    16

<210> SEQ ID NO 1435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1435
aatgccacca catgtg                                                    16

<210> SEQ ID NO 1436
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1436
actctcccat gcagct                                                    16

<210> SEQ ID NO 1437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1437
accctctcac ctcact                                                    16

<210> SEQ ID NO 1438
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1438
cagtctctac cttctg                                                    16

<210> SEQ ID NO 1439
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1439
ccctataggc agcaat                                                    16

<210> SEQ ID NO 1440
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1440
ctaaaaagga ccctat                                                    16

<210> SEQ ID NO 1441
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1441
agtatttgca ctaaaa                                                       16

<210> SEQ ID NO 1442
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1442
ttagaatcct agtatt                                                       16

<210> SEQ ID NO 1443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1443
aaccaagtgc ttagaa                                                       16

<210> SEQ ID NO 1444
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1444
gggtaacaga aaccaa                                                       16

<210> SEQ ID NO 1445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1445
atagtttgac ctgggt                                                       16

<210> SEQ ID NO 1446
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1446
ctccaaagaa atagtt                                                       16

<210> SEQ ID NO 1447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1447
```
taatcaaact ctccaa                                                      16

<210> SEQ ID NO 1448
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1448
acctgtgatg gtaatc                                                      16

<210> SEQ ID NO 1449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1449
atcttaccat cacctg                                                      16

<210> SEQ ID NO 1450
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1450
agctagggag aatctt                                                      16

<210> SEQ ID NO 1451
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1451
attaaatgcc agctag                                                      16

<210> SEQ ID NO 1452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1452
taaccactgg attaaa                                                      16

<210> SEQ ID NO 1453
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1453
atttgggaaa gatgca                                                      16

<210> SEQ ID NO 1454
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1454
ttgataaaga atttgg                                                     16

<210> SEQ ID NO 1455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1455
attgaccaac ttgata                                                     16

<210> SEQ ID NO 1456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1456
atgttctatg aattga                                                     16

<210> SEQ ID NO 1457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1457
tcagcattag atgttc                                                     16

<210> SEQ ID NO 1458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1458
aggcttataa tcagca                                                     16

<210> SEQ ID NO 1459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1459
gcaagataat aggctt                                                     16

<210> SEQ ID NO 1460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1460
cagagacaca agcaag                                                     16
```

<210> SEQ ID NO 1461
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1461
gcccatagtg cagaga                                              16

<210> SEQ ID NO 1462
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1462
gtgctattat gcccat                                              16

<210> SEQ ID NO 1463
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1463
aagcttttag gtgcta                                              16

<210> SEQ ID NO 1464
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1464
attatagcaa aagctt                                              16

<210> SEQ ID NO 1465
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1465
atcatagtcc attata                                              16

<210> SEQ ID NO 1466
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1466
attcagatac atcata                                              16

<210> SEQ ID NO 1467
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1467
aaggtaattt attcag                                                    16

<210> SEQ ID NO 1468
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1468
agatttgatt gtttat                                                    16

<210> SEQ ID NO 1469
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1469
ttgccaattt agattt                                                    16

<210> SEQ ID NO 1470
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1470
aaatttgaac ttgcca                                                    16

<210> SEQ ID NO 1471
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1471
taagaaaaat tgggta                                                    16

<210> SEQ ID NO 1472
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1472
gtaaattcta taagaa                                                    16

<210> SEQ ID NO 1473
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1473
aactgcaaag gtaaat                                                    16

```
<210> SEQ ID NO 1474
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1474
caattatttc tttaac                                                   16

<210> SEQ ID NO 1475
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1475
acaaatggta aaaac                                                    16

<210> SEQ ID NO 1476
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1476
gtcatactag acaaat                                                   16

<210> SEQ ID NO 1477
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1477
taaataacaa gtcata                                                   16

<210> SEQ ID NO 1478
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1478
catgctattt gtaaat                                                   16

<210> SEQ ID NO 1479
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1479
agctggccag ttacat                                                   16

<210> SEQ ID NO 1480
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 1480
tgtatagtac agctgg                                                    16

<210> SEQ ID NO 1481
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1481
ctagaaaatg tgtata                                                    16

<210> SEQ ID NO 1482
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1482
aggcacccaa taagaa                                                    16

<210> SEQ ID NO 1483
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1483
taaaagacta aggcac                                                    16

<210> SEQ ID NO 1484
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1484
ccctaatggg taaaag                                                    16

<210> SEQ ID NO 1485
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1485
atttgaatag ccctaa                                                    16

<210> SEQ ID NO 1486
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1486
ctcattcttt atttga                                                    16

<210> SEQ ID NO 1487
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 1487
taagagaata tctcat                                                 16

<210> SEQ ID NO 1488
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1488
ttctagagaa taagag                                                 16

<210> SEQ ID NO 1489
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1489
tatagaatgt ctcttt                                                 16

<210> SEQ ID NO 1490
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1490
tttccattag tataga                                                 16

<210> SEQ ID NO 1491
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1491
aaaagttggt atttcc                                                 16

<210> SEQ ID NO 1492
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1492
gtctagattt aaaagt                                                 16

<210> SEQ ID NO 1493
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1493
``` tttttttggta gtctag                                                  16

<210> SEQ ID NO 1494
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1494
gtagaaaaac atgact                                                   16

<210> SEQ ID NO 1495
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1495
atctatagcc tctagg                                                   16

<210> SEQ ID NO 1496
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1496
gacattaaga atctat                                                   16

<210> SEQ ID NO 1497
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1497
atgagtggct gacatt                                                   16

<210> SEQ ID NO 1498
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1498
agagggccag gatgag                                                   16

<210> SEQ ID NO 1499
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1499
catatgggaa aagaag                                                   16

<210> SEQ ID NO 1500
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 1500
ctagaacttc catatg                                                    16

<210> SEQ ID NO 1501
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1501
ctatatcacc ctagaa                                                    16

<210> SEQ ID NO 1502
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1502
ccacagagcc aaacta                                                    16

<210> SEQ ID NO 1503
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1503
attacaattt gacgcg                                                    16

<210> SEQ ID NO 1504
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1504
ctcctccaac tttggg                                                    16

<210> SEQ ID NO 1505
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1505
ttcccaccag acccct                                                    16

<210> SEQ ID NO 1506
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1506
caagggaaaa gtctgc                                                    16
```

```
<210> SEQ ID NO 1507
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1507
gtcaggagaa cagcaa                                                    16

<210> SEQ ID NO 1508
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1508
agaactcact gtcagg                                                    16

<210> SEQ ID NO 1509
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1509
cactgtcacg agaact                                                    16

<210> SEQ ID NO 1510
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1510
gtgctacata atttta                                                    16

<210> SEQ ID NO 1511
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1511
aaagtggcag gtgcta                                                    16

<210> SEQ ID NO 1512
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1512
gaagagagag caaagt                                                    16

<210> SEQ ID NO 1513
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1513
agccagcaca ttatac                                                           16

<210> SEQ ID NO 1514
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1514
acttatcatc acagtg                                                           16

<210> SEQ ID NO 1515
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1515
cagcaggcta tacagg                                                           16

<210> SEQ ID NO 1516
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1516
gcttacagtt cagcag                                                           16

<210> SEQ ID NO 1517
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1517
ggtttaattt gcttac                                                           16

<210> SEQ ID NO 1518
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1518
tgaatactaa catatc                                                           16

<210> SEQ ID NO 1519
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1519
agttcctcac atgaat                                                           16

<210> SEQ ID NO 1520

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1520
cacatttcaa agttcc                                                       16

<210> SEQ ID NO 1521
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1521
tattaaagag ggagaa                                                       16

<210> SEQ ID NO 1522
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1522
aatcattccc tattaa                                                       16

<210> SEQ ID NO 1523
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1523
gacaactatt tttctt                                                       16

<210> SEQ ID NO 1524
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1524
acttgttcac cttgac                                                       16

<210> SEQ ID NO 1525
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1525
aaaacttgga acttgt                                                       16

<210> SEQ ID NO 1526
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1526
```
ataactagga aaaact                                        16

<210> SEQ ID NO 1527
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1527
actacagatt ataact                                        16

<210> SEQ ID NO 1528
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1528
aatgtttagt actaca                                        16

<210> SEQ ID NO 1529
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1529
aaggatatct aatgtt                                        16

<210> SEQ ID NO 1530
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1530
gttgcatcta aaggat                                        16

<210> SEQ ID NO 1531
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1531
tccgagtgta atagtt                                        16

<210> SEQ ID NO 1532
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1532
tctccagttg tccgag                                        16

<210> SEQ ID NO 1533
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 1533
catcaagttc tctcca                                                       16

<210> SEQ ID NO 1534
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1534
ccagatgatt catcaa                                                       16

<210> SEQ ID NO 1535
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1535
tactaaatat ccagat                                                       16

<210> SEQ ID NO 1536
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1536
caaatactat tactaa                                                       16

<210> SEQ ID NO 1537
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1537
taaatcaaat taagca                                                       16

<210> SEQ ID NO 1538
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1538
atatcaacat taaatc                                                       16

<210> SEQ ID NO 1539
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1539
caaagagatc atcaat                                                       16
```

<210> SEQ ID NO 1540
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1540
ccttatattt ttgcaa                                               16

<210> SEQ ID NO 1541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1541
accctctctc gccctt                                               16

<210> SEQ ID NO 1542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1542
aagatctact accctc                                               16

<210> SEQ ID NO 1543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1543
tttcagttaa aagatc                                               16

<210> SEQ ID NO 1544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1544
caaaacagct tttcag                                               16

<210> SEQ ID NO 1545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1545
tgaattataa caaaac                                               16

<210> SEQ ID NO 1546
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 1546
aaagaactca tgaatt                                                    16

<210> SEQ ID NO 1547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1547
ttactccaat aaagaa                                                    16

<210> SEQ ID NO 1548
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1548
ctacctcaat ttactc                                                    16

<210> SEQ ID NO 1549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1549
gctccaaaac ctacct                                                    16

<210> SEQ ID NO 1550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1550
ttcagtttta gctcca                                                    16

<210> SEQ ID NO 1551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1551
cgctacatcc ttcagt                                                    16

<210> SEQ ID NO 1552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1552
atccaattac actgtc                                                    16

```
<210> SEQ ID NO 1553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1553
ccaataaatg atccaa                                                         16

<210> SEQ ID NO 1554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1554
gaaaagcatc ccaata                                                         16

<210> SEQ ID NO 1555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1555
ctgtatttaa atcatt                                                         16

<210> SEQ ID NO 1556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1556
atttgctaat ctgtat                                                         16

<210> SEQ ID NO 1557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1557
gtatcactaa atttgc                                                         16

<210> SEQ ID NO 1558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1558
aacttttgag gtatca                                                         16

<210> SEQ ID NO 1559
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 1559
taccagctgt aacttt                                                    16

<210> SEQ ID NO 1560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1560
cttagaaatt taccag                                                    16

<210> SEQ ID NO 1561
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1561
gtgcaactat cttaga                                                    16

<210> SEQ ID NO 1562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1562
atatggaatg gtgcaa                                                    16

<210> SEQ ID NO 1563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1563
cagtggcaag atatgg                                                    16

<210> SEQ ID NO 1564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1564
tttttatacc aagtag                                                    16

<210> SEQ ID NO 1565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1565
acaaatttgt catatt                                                    16

<210> SEQ ID NO 1566
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 1566
taatctaaac acaaat                                                 16

<210> SEQ ID NO 1567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1567
tgctaaccac ataatc                                                 16

<210> SEQ ID NO 1568
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1568
caattattaa gaaact                                                 16

<210> SEQ ID NO 1569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1569
gaaaacaaga ccaatt                                                 16

<210> SEQ ID NO 1570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1570
attgttaatg gaaaac                                                 16

<210> SEQ ID NO 1571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1571
gttctgtctt gctatt                                                 16

<210> SEQ ID NO 1572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1572
```

```
ctatgatctt gttctg                                                    16

<210> SEQ ID NO 1573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1573
aatggtgtgc actggt                                                    16

<210> SEQ ID NO 1574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1574
aagtcaccac aatggt                                                    16

<210> SEQ ID NO 1575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1575
aagcaggatc ccatct                                                    16

<210> SEQ ID NO 1576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1576
atccctgtac tttaag                                                    16

<210> SEQ ID NO 1577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1577
aaaaagtatc tgggtc                                                    16

<210> SEQ ID NO 1578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1578
taaataaatt agccga                                                    16

<210> SEQ ID NO 1579
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 1579
tacttgagag gtgagg                                                        16

<210> SEQ ID NO 1580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1580
ataaaaatta tcggag                                                        16

<210> SEQ ID NO 1581
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1581
gacgaggcag gtcaat                                                        16

<210> SEQ ID NO 1582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1582
acacagcagg gtgtgg                                                        16

<210> SEQ ID NO 1583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1583
aagtatccag gccagg                                                        16

<210> SEQ ID NO 1584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1584
tgacaacaag accctg                                                        16

<210> SEQ ID NO 1585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1585
caaaagctgg gtgcag                                                        16
```

```
<210> SEQ ID NO 1586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1586
ctgttggcag acacaa                                                      16

<210> SEQ ID NO 1587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1587
ctccttttat gttttc                                                      16

<210> SEQ ID NO 1588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1588
ttatgtctga attatt                                                      16

<210> SEQ ID NO 1589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1589
tattctccag ctccat                                                      16

<210> SEQ ID NO 1590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1590
tacaaaaggt tgtatc                                                      16

<210> SEQ ID NO 1591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1591
acctcatata aatgag                                                      16
```

```
<210> SEQ ID NO 1592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1592
attcacctct ccccctc                                                      16
```

MODULATORS OF EZH2 EXPRESSION

SEQUENCE LISTING

The present application is being filed along with a Sequence Listing in electronic format. The Sequence Listing is provided as a file entitled BIOL0334USASEQ_ST25.txt created Oct. 1, 2020, which is 426 kb in size. The information in the electronic format of the sequence listing is incorporated herein by reference in its entirety.

FIELD

The present embodiments provide methods, compounds, and compositions useful for inhibiting EZH2 expression, which can be useful for treating, preventing, or ameliorating a cancer associated with EZH2.

BACKGROUND

Enhancer of Zeste Homologue 2 (EZH2) is an epigenetic regulator of gene expression that is overexpressed or activated by mutations in several human cancers. EZH2 is the catalytic subunit of the Polycomb Repressive Complex 2 (PRC2) that functions as a histone methyltransferase, which catalyzes the mono—through trimethylation of K27 of H3 (H3K27me3) and suppresses the transcription of specific genes. Increased EZH2 expression or activity correlates with poor prognosis in multiple solid tumors (cancers of prostate, ovarian, breast, liver and rhabdomyosarcoma) as well as hematological malignancies. Aberrant expression of EZH2 through multiple mechanisms drives tumorigenesis.

SUMMARY

Certain embodiments provided herein are directed to potent and tolerable compounds and compositions useful for inhibiting EZH2 expression, which can be useful for treating, preventing, ameliorating, or slowing progression of cancer associated with EZH2.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION number indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of EZH2", it is implied that EZH2 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating EZH2 RNA can mean to increase or decrease the level of EZH2 RNA and/or EZH2 protein in a cell, tissue, organ or organism. A "modulator" effects the change in the cell, tissue, organ or organism. For example, a EZH2 compound can be a modulator that decreases the amount of EZH2 RNA and/or EZH2 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Synergy" or "synergize" refers to an effect of a combination that is greater than additive of the effects of each component alone at the same doses.

"EZH2" means any nucleic acid or protein of EZH2. "EZH2 nucleic acid" means any nucleic acid encoding EZH2. For example, in certain embodiments, a EZH2 nucleic acid includes a DNA sequence encoding EZH2, an RNA sequence transcribed from DNA encoding EZH2 (including genomic DNA comprising introns and exons), and an mRNA sequence encoding EZH2. "EZH2 mRNA" means an mRNA encoding a EZH2 protein. The target may be referred to in either upper or lower case.

"EZH2 specific inhibitor" refers to any agent capable of specifically inhibiting EZH2 RNA and/or EZH2 protein expression or activity at the molecular level. For example, EZH2 specific inhibitors include nucleic acids (including antisense compounds), peptides, antibodies, small molecules, and other agents capable of inhibiting the expression of EZH2 RNA and/or EZH2 protein.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds and compositions for inhibiting EZH2 expression.

Certain embodiments provide compounds targeted to a EZH2 nucleic acid. In certain embodiments, the EZH2 nucleic acid has the sequence set forth in RefSeq or GENBANK Accession No. NM_001203248.1 (SEQ ID NO: 1), NC_000007.14_TRUNC_148804001_148888000_COMP (SEQ ID NO: 2), or NM_004456.4 (SEQ ID NO: 3), each of which is incorporated by reference in its entirety. In certain embodiments, the compound is an antisense compound or oligomeric compound. In certain embodiments, the compound is single-stranded. In certain embodiments, the compound is double-stranded.

Certain embodiments provide a compound comprising a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 10 to 30 linked nucleosides.

Certain embodiments provide a compound comprising a modified oligonucleotide consisting of 9 to 80 linked nucleosides and having a nucleobase sequence comprising at least 9 contiguous nucleobases of any of the nucleobase sequences of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 10 to 30 linked nucleosides.

Certain embodiments provide a compound comprising a modified oligonucleotide consisting of 10 to 80 linked nucleosides and having a nucleobase sequence comprising at least 10 contiguous nucleobases of any of the nucleobase sequences of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 10 to 30 linked nucleosides.

Certain embodiments provide a compound comprising a modified oligonucleotide consisting of 11 to 80 linked nucleosides and having a nucleobase sequence comprising at least 11 contiguous nucleobases of any of the nucleobase sequences of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 11 to 30 linked nucleosides.

Certain embodiments provide a compound comprising a modified oligonucleotide consisting of 12 to 80 linked nucleosides and having a nucleobase sequence comprising at least 12 contiguous nucleobases of any of the nucleobase sequences of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 12 to 30 linked nucleosides.

Certain embodiments provide a compound comprising a modified oligonucleotide consists of 16 to 80 linked nucleosides and having a nucleobase sequence comprising the nucleobase sequence of any one of SEQ ID NOs: 10-1592. In certain embodiments, the compound is an antisense compound or oligomeric compound. In certain embodiments, the compound is single-stranded. In certain embodiments, the compound is double-stranded. In certain embodiments, the modified oligonucleotide consists of 16 to 30 linked nucleosides.

Certain embodiments provide a compound comprising a modified oligonucleotide having a nucleobase sequence consisting of the nucleobase sequence of any one of SEQ ID NOs: 10-1592. In certain embodiments, the compound is an antisense compound or oligomeric compound. In certain embodiments, the compound is single-stranded. In certain embodiments, the compound is double-stranded.

In certain embodiments, a compound comprises a modified oligonucleotide consisting of 8 to 80 linked nucleosides and having at least an 8, 9, 10, 11, 12, 13, 14, 15, or 16 contiguous nucleobase portion complementary to an equal length portion within nucleotides 700-715, 964-979, 1074-1089, or 2509-2524 of SEQ ID NO: 1. In certain embodiments, the modified oligonucleotide consists of 10 to 30 linked nucleosides. In certain embodiments, the modified oligonucleotide consists of 16 to 30 linked nucleosides.

In certain embodiments, a compound comprises a modified oligonucleotide consisting of 8 to 80 linked nucleosides and having at least an 8, 9, 10, 11, 12, 13, 14, 15, or 16 contiguous nucleobase portion complementary to an equal length portion within nucleotides 6589-6604, 59170-59185, 61438-61453, 68329-68344, or 80457-80472 of SEQ ID NO: 2. In certain embodiments, the modified oligonucleotide consists of 10 to 30 linked nucleosides. In certain embodiments, the modified oligonucleotide consists of 16 to 30 linked nucleosides.

In certain embodiments, a compound comprises a modified oligonucleotide consisting of 8 to 80 linked nucleosides wherein the modified oligonucleotide is complementary within nucleotides 700-715, 964-979, 1074-1089, or 2509-2524 of SEQ ID NO: 1. In certain embodiments, the modified oligonucleotide consists of 10 to 30 linked nucleosides. In certain embodiments, the modified oligonucleotide consists of 16 to 30 linked nucleosides.

In certain embodiments, a compound comprises a modified oligonucleotide consists of 8 to 80 linked nucleosides wherein the modified oligonucleotide is complementary within nucleotides 6589-6604, 59170-59185, 61438-61453, 68329-68344, or 80457-80472 of SEQ ID NO: 2. In certain embodiments, the modified oligonucleotide consists of 10 to 30 linked nucleosides. In certain embodiments, the modified oligonucleotide consists of 16 to 30 linked nucleosides.

In certain embodiments, a compound comprises a modified oligonucleotide consisting of 8 to 80 linked nucleosides and having a nucleobase sequence comprising at least an 8, 9, 10, 11, 12, 13, 14, 15, or 16 contiguous nucleobase portion of the nucleobase sequence of any one of SEQ ID NOs: 102, 252, 387, 998, or 1038. In certain embodiments, the modified oligonucleotide consists of 10 to 30 linked nucleosides. In certain embodiments, the modified oligonucleotide consists of 16 to 30 linked nucleosides.

In certain embodiments, a compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the modified oligonucleotide consists of 16 to 30 linked nucleosides.

In certain embodiments, a compound comprises a modified oligonucleotide consisting of 16 linked nucleosides and having a nucleobase sequence consisting of the nucleobase sequence of any one of SEQ ID NOs: 102, 252, 387, 998, or 1038.

In certain embodiments, a compound targeted to EZH2 is ION 633365. Out of over 2,800 compounds that were screened as described in the Examples section below, ION 633365, 662368, 662950, 702334, 702366, and 754175 emerged as the top lead compounds. In particular, ION 633365 exhibited the best combination of properties in terms of potency and tolerability out of over 2,800 compounds.

In certain embodiments, any of the foregoing modified oligonucleotides has at least one modified internucleoside linkage, at least one modified sugar, and/or at least one modified nucleobase.

In certain embodiments, at least one nucleoside of any of the foregoing modified oligonucleotides comprises a modified sugar. In certain embodiments, the modified sugar comprises a 2'-O-methoxyethyl group. In certain embodiments, the modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one internucleoside linkage of the modified oligonucleotide is a modified internucleoside linkage, such as a phosphorothioate internucleoside linkage.

In certain embodiments, at least one nucleobase of any of the foregoing modified oligonucleotides is a modified nucleobase, such as 5-methylcytosine.

In certain embodiments, any of the foregoing modified oligonucleotides has:
 a gap segment consisting of linked 2'-deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide consists of 16 to 80 linked nucleosides and has a nucleobase sequence comprising the nucleobase sequence recited in any one of SEQ ID NOs: 102, 252, 387, 998, or 1038. In certain embodiments, the modified oligonucleotide consists of 16 to 30 linked nucleosides and has a nucleobase sequence comprising the nucleobase sequence recited in any one of SEQ ID NOs: 102, 252, 387, 998, or 1038. In certain embodiments, the modified oligonucleotide consists of 16 linked nucleosides and has a nucleobase sequence consisting of the nucleobase sequence recited in any one of SEQ ID NOs: 102, 252, 387, 998, or 1038.

In certain embodiments, a compound comprises or consists of a modified oligonucleotide consisting of 16-80 linked nucleosides and having a nucleobase sequence comprising the nucleobase sequence recited in any one of SEQ ID NOs: 10-1592, wherein the modified oligonucleotide has:
 a gap segment consisting of linked 2'-deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in any one of SEQ ID NOs: 102, 252, 387, 998, or 1038, wherein the modified oligonucleotide has:
 a gap segment consisting of linked 2'-deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in any one of SEQ ID NOs: 252, 387, or 998, wherein the modified oligonucleotide has:
 a gap segment consisting of ten linked 2'-deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in SEQ ID NO: 252, wherein the modified oligonucleotide has:
 a gap segment consisting of ten linked 2'-deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in SEQ ID NO: 1038, wherein the modified oligonucleotide has:
 a gap segment consisting of ten linked 2'-deoxynucleosides;
 a 5' wing segment consisting of one linked nucleoside; and
 a 3' wing segment consisting of five linked nucleosides;
 wherein the gap segment is positioned between the 5' wing segment and the 3' wing segment; wherein the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in SEQ ID NO: 252, wherein the modified oligonucleotide has:
 a gap segment consisting of ten linked 2'-deoxynucleosides;
 a 5' wing segment consisting of two linked nucleosides; and
 a 3' wing segment consisting of four linked nucleosides;
 wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound comprises or consists of a modified oligonucleotide consisting of 16-80 linked nucleosides and having a nucleobase sequence comprising the nucleobase sequence recited in SEQ ID NO: 102, wherein the modified oligonucleotide has:
 a gap segment consisting of nine linked 2'-deoxynucleosides;
 a 5' wing segment consisting of two linked nucleosides; and
 a 3' wing segment consisting of five linked nucleosides;
 wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In certain embodiments, a compound has the structure:
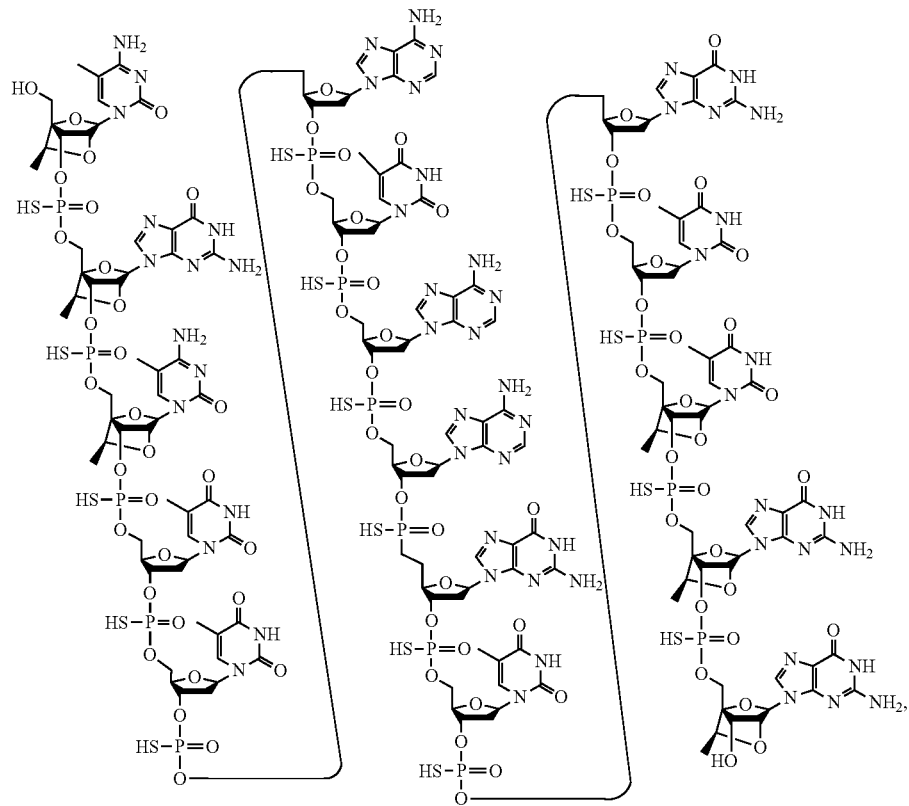
or a salt thereof.
In certain embodiments, a compound has the structure:
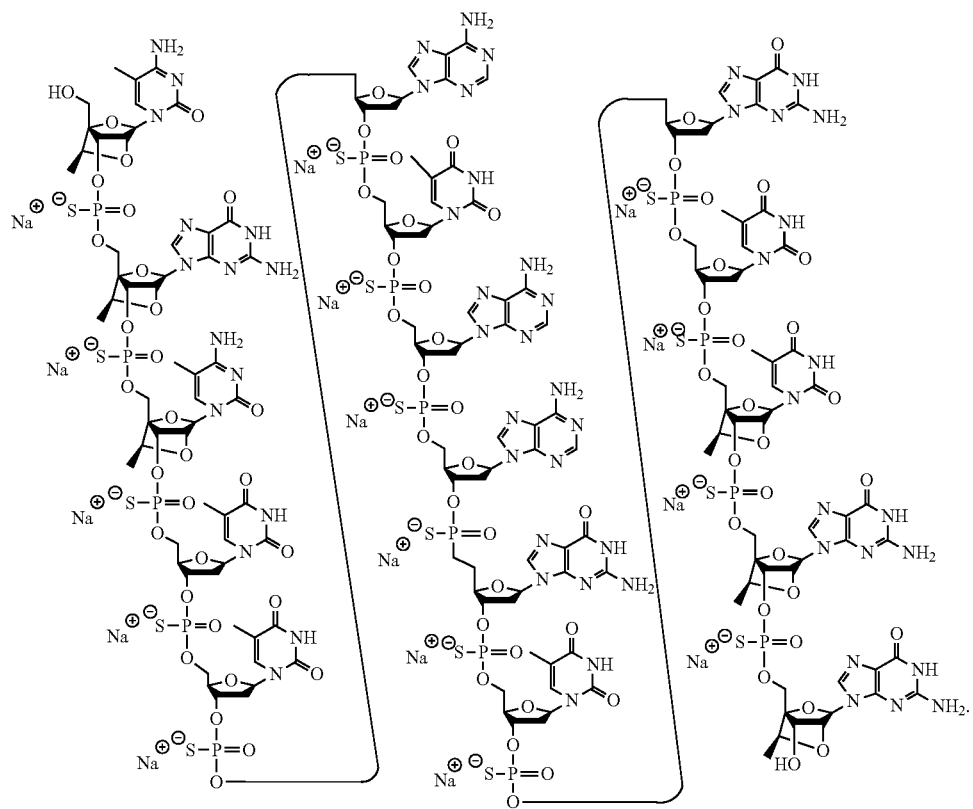

In any of the foregoing embodiments, the compound or oligonucleotide can be at least 85%, at least 90%, at least 95%, at least 98%, at least 99%, or 100% complementary to a nucleic acid encoding EZH2.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can consist of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain embodiments, the compound comprises or consists of an oligonucleotide.

In certain embodiments, compounds or compositions provided herein comprise a salt of the modified oligonucleotide. In certain embodiments, the salt is a sodium salt. In certain embodiments, the salt is a potassium salt.

In certain embodiments, the compounds or compositions as described herein are highly tolerable as demonstrated by having at least one of an increase an alanine transaminase (ALT) or aspartate transaminase (AST) value of no more than 4 fold, 3 fold, or 2 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or salt thereof and at least one of a pharmaceutically acceptable carrier or diluent. In certain embodiments, the composition has a viscosity less than about 40 centipoise (cP), less than about 30 centipoise (cP), less than about 20 centipoise (cP), less than about 15 centipoise (cP), or less than about 10 centipoise (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Non-limiting numbered embodiments include:

E1. A compound comprising a modified oligonucleotide 8 to 80 linked nucleosides in length having a nucleobase sequence comprising at least 8 contiguous nucleobases of any of the nucleobase sequences of SEQ ID NOs: 10-1592.

E2. A compound comprising a modified oligonucleotide 9 to 80 linked nucleosides in length having a nucleobase sequence comprising at least 9 contiguous nucleobases of any of the nucleobase sequences of SEQ ID NOs: 10-1592.

E3. A compound comprising a modified oligonucleotide 10 to 80 linked nucleosides in length having a nucleobase sequence comprising at least 10 contiguous nucleobases of any of the nucleobase sequences of SEQ ID NOs: 10-1592.

E4. A compound comprising a modified oligonucleotide 11 to 80 linked nucleosides in length having a nucleobase sequence comprising at least 11 contiguous nucleobases of any of the nucleobase sequences of SEQ ID NOs: 10-1592.

E5. A compound comprising a modified oligonucleotide 12 to 80 linked nucleosides in length having a nucleobase sequence comprising at least 12 contiguous nucleobases of any of the nucleobase sequences of SEQ ID NOs: 10-1592.

E6. A compound comprising a modified oligonucleotide 16 to 80 linked nucleosides in length having a nucleobase sequence comprising the nucleobase sequence of any one of SEQ ID NOs: 10-1592.

E7. A compound comprising a modified oligonucleotide having a nucleobase sequence consisting of any one of SEQ ID NOs: 10-1592.

E8. A compound comprising a modified oligonucleotide 8 to 80 linked nucleosides in length complementary within nucleotides 700-715, 964-979, 1074-1089, or 2509-2524 of SEQ ID NO: 1 or within nucleotides 6589-6604, 59170-59185, 61438-61453, 68329-68344, or 80457-80472 of SEQ ID NO: 2.

E9. A compound comprising a modified oligonucleotide 8 to 80 linked nucleosides in length having a nucleobase sequence comprising any one of SEQ ID NOs: 102, 252, 387, 998, or 1038.

E10. A compound comprising a modified oligonucleotide having a nucleobase sequence consisting of any one of SEQ ID NOs: 102, 252, 387, 998, or 1038.

E11. The compound of any one of claims 1-10, wherein the modified oligonucleotide comprises at least one modified internucleoside linkage, at least one modified sugar, or at least one modified nucleobase.

E12. The compound of claim 11, wherein the modified internucleoside linkage is a phosphorothioate internucleoside linkage.

E13. The compound of claim 11 or 12, wherein the modified sugar is a bicyclic sugar.

E14. The compound of claim 13, wherein the bicyclic sugar is selected from the group consisting of: 4'-($CH_2$)—O-2' (LNA); 4'-($CH_2$)$_2$—O-2' (ENA); and 4'-CH($CH_3$)—O-2' (cEt).

E15. The compound of claim 11 or 12, wherein the modified sugar is 2'-O-methoxyethyl.

E16. The compound of any one of claims 11-15, wherein the modified nucleobase is a 5-methylcytosine.

E17. The compound of any one of claims 1-16, wherein the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar.

E18. A compound comprising a modified oligonucleotide 16 to 80 linked nucleosides in length having a nucleobase sequence comprising any one of SEQ ID NOs: 102, 252, 387, 998, or 1038, wherein the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar.

E19. A compound comprising a modified oligonucleotide 16-80 linked nucleobases in length having a nucleobase sequence comprising the sequence recited in any one of SEQ ID NOs: 252, 387, or 998, wherein the modified oligonucleotide comprises:
 a gap segment consisting of ten linked deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine.

E20. A compound comprising a modified oligonucleotide 16-80 linked nucleobases in length having a nucleobase sequence comprising the sequence recited in SEQ ID NO: 1038, wherein the modified oligonucleotide comprises:
 a gap segment consisting of ten linked deoxynucleosides;
 a 5' wing segment consisting of one linked nucleoside; and
 a 3' wing segment consisting of five linked nucleosides;
 wherein the gap segment is positioned between the 5' wing segment and the 3' wing segment; wherein the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine.

E21. A compound comprising a modified oligonucleotide 16-80 linked nucleobases in length having a nucleobase sequence comprising the sequence recited in SEQ ID NO: 252, wherein the modified oligonucleotide comprises:
 a gap segment consisting of ten linked deoxynucleosides;
 a 5' wing segment consisting of two linked nucleosides; and
 a 3' wing segment consisting of four linked nucleosides;
 wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine.

E22. A compound comprising a modified oligonucleotide 16-80 linked nucleobases in length having a nucleobase sequence comprising the sequence recited in SEQ ID NO: 102, wherein the modified oligonucleotide comprises:
 a gap segment consisting of nine linked deoxynucleosides;
 a 5' wing segment consisting of two linked nucleosides; and
 a 3' wing segment consisting of five linked nucleosides;
 wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine.

E23. The compound of any one of claims 1-22, wherein the oligonucleotide is at least 80%, 85%, 90%, 95% or 100% complementary to any of SEQ ID NOs: 1-3.

E24. The compound of any one of claims 1-23, wherein the compound is single-stranded.

E25. The compound of any one of claims 1-23, wherein the compound is double-stranded.

E26. The compound of any one of claims 1-25, wherein the compound comprises ribonucleotides.

E27. The compound of any one of claims 1-25, wherein the compound comprises deoxyribonucleotides.

E28. The compound of any one of claims 1-27, wherein the modified oligonucleotide consists of 16 to 30 linked nucleosides.

E29. The compound of any preceding claim, wherein the compound consists of the modified oligonucleotide.

E30. A compound consisting of a pharmaceutically acceptable salt of any of the compounds of claims 1-29.

E31. The compound of claim 30, wherein the pharmaceutically acceptable salt is a sodium salt.

E32. The compound of claim 30, wherein the pharmaceutically acceptable salt is a potassium salt.

E33. A compound having the formula:
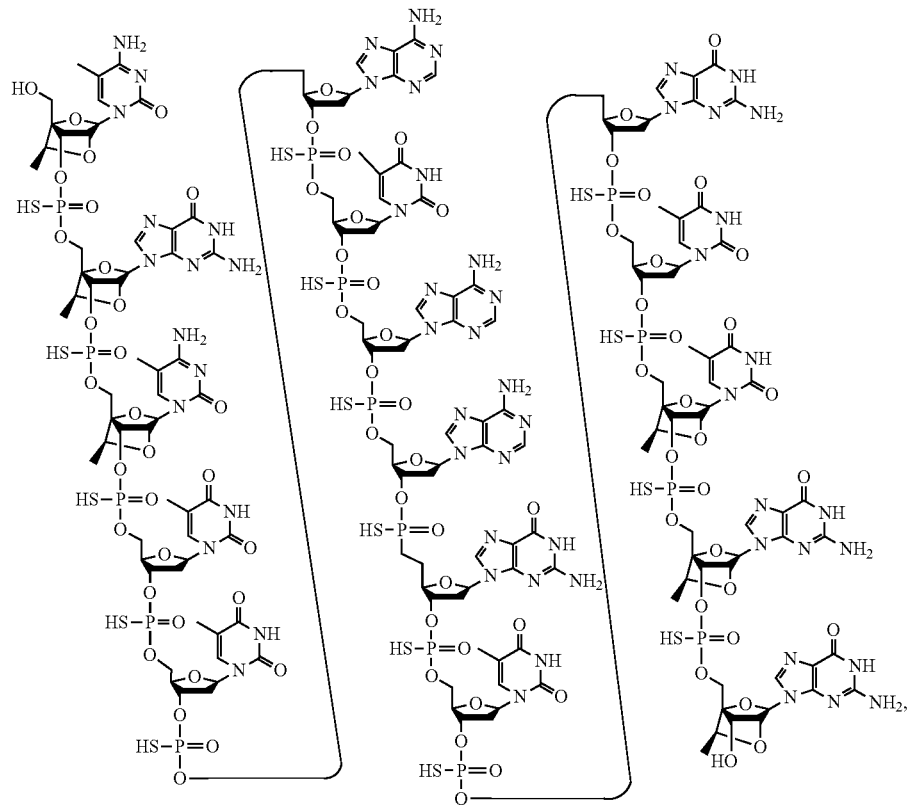
or a salt thereof.
E34. A compound having the formula:
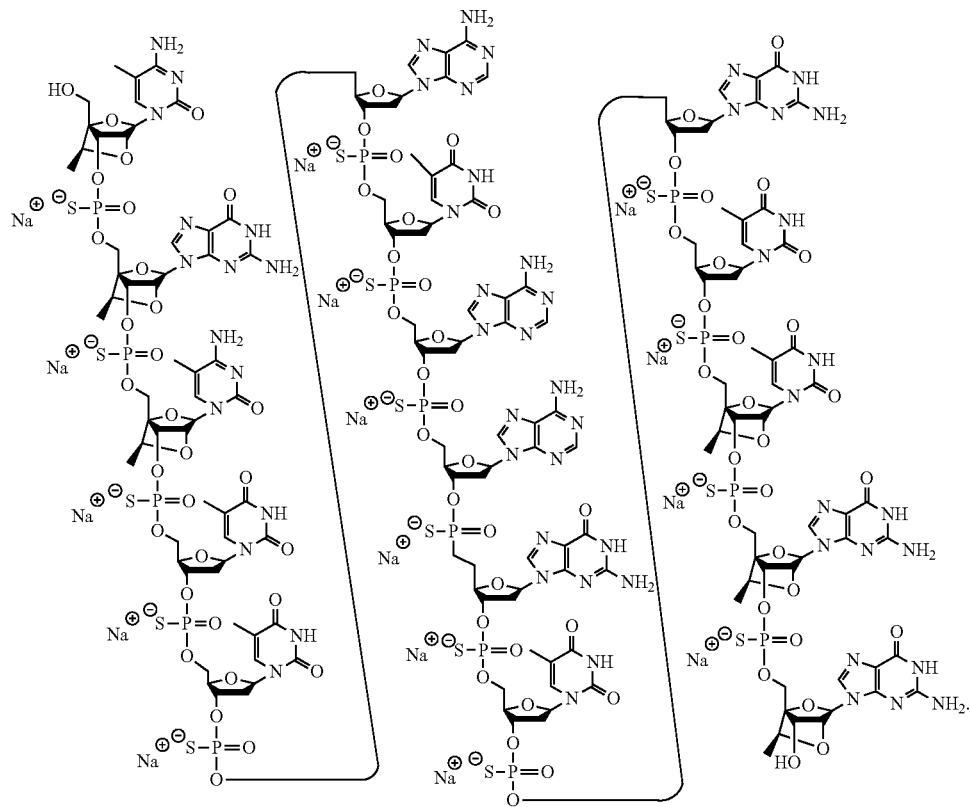

E35. A composition comprising the compound of any one of claims 1-34 and a pharmaceutically acceptable carrier.

E36. A composition comprising a compound or modified oligonucleotide of any preceding claim, for use in therapy.

E37. A method of treating or ameliorating cancer in an individual comprising administering to the individual a compound targeted to EZH2, thereby treating or ameliorating the cancer.

E38. The method of claim 37, wherein the compound is an antisense compound targeted to EZH2.

E39. The method of claim 37 or 38, wherein the cancer is a blood cancer, myeloma, multiple myeloma (MM), B cell malignancy, lymphoma, B cell lymphoma, DLBCL, GC-DLBCL, T cell lymphoma, or leukemia.

E40. The method of any of claims 42-44, wherein administering the compound inhibits or reduces cancer cell proliferation, tumor growth, or metastasis.

E41. A method of inhibiting expression of EZH2 in a cell comprising contacting the cell with a compound targeted to EZH2, thereby inhibiting expression of EZH2 in the cell.

E42. The method of claim 41, wherein the cell a cancer cell.

E43. The method of claim 42, wherein the individual has a blood cancer, myeloma, multiple myeloma (MM), B cell malignancy, lymphoma, B cell lymphoma, DLBCL, GC DLBCL, T cell lymphoma, or leukemia.

E44. A method of reducing or inhibiting cancer cell proliferation, tumor growth, or metastasis in an individual having cancer comprising administering a compound targeted to EZH2 to the individual, thereby reducing or inhibiting cancer cell proliferation, tumor growth, or metastasis in the individual.

E45. The method of claim 44, wherein the individual has a blood cancer, myeloma, multiple myeloma (MM), B cell malignancy, B cell lymphoma, T cell lymphoma, or leukemia.

E46. The method of any one of claims 37-45, wherein the compound is an antisense compound targeted to EZH2.

E47. The method of any one of claims 37-46, wherein the compound is the compound of any one of claims 1-34 or composition of claim 35 or 36.

E48. The method of any of claims 37-47, wherein the compound is administered parenterally.

E49. Use of a compound targeted to EZH2 for treating, preventing, or ameliorating a cancer associated with EZH2.

E50. The use of claim 49, wherein the cancer is a blood cancer, myeloma, multiple myeloma (MM), B cell malignancy, lymphoma, B cell lymphoma, DLBCL, GC DLBCL, T cell lymphoma, or leukemia.

E51. The use of claim 49 or 50, wherein the compound is an antisense compound targeted to EZH2.

E52. The use of any one of claims 49-51, wherein the compound is the compound of any one of claims 1-34 or composition of claim 35 or 36.

E53. Use of a compound targeted to EZH2 in the manufacture of a medicament for treating or ameliorating a cancer associated with EZH2.

E54. The use of claim 53, wherein the cancer is a blood cancer, myeloma, multiple myeloma (MM), B cell malignancy, lymphoma, B cell lymphoma, DLBCL, GC DLBCL, T cell lymphoma, or leukemia.

E55. The use of claim 53 or 54, wherein the compound is an antisense compound targeted to EZH2.

E56. The use of any one of claims 53-55, wherein the compound is the compound of any one of claims 1-34 or composition of claim 35 or 36.

E57. Use of a compound targeted to EZH2 in the preparation of a medicament for treating or ameliorating a cancer associated with EZH2.

E58. The use of claim 57, wherein the cancer is a blood cancer, myeloma, multiple myeloma (MM), B cell malignancy, lymphoma, B cell lymphoma, DLBCL, GC DLBCL, T cell lymphoma, or leukemia.

E59. The use of claim 57 or 58, wherein the compound is an antisense compound targeted to EZH2.

E60. The use of any one of claims 57-59, wherein the compound is the compound of any one of claims 1-34 or composition of claim 35 or 36.

Certain Indications

Certain embodiments provided herein relate to methods of inhibiting EZH2 expression, which can be useful for treating, preventing, or ameliorating a cancer associated with EZH2 in an individual, by administration of a compound that targets EZH2. In certain embodiments, the compound can be a EZH2 specific inhibitor. In certain embodiments, the compound can be an antisense compound, oligomeric compound, or oligonucleotide targeted to EZH2.

Examples of cancers associated with EZH2 treatable, preventable, and/or ameliorable with the compounds and methods provided herein include blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma).

In certain embodiments, a method of treating, preventing, or ameliorating a cancer associated with EZH2 in an individual comprises administering to the individual a compound comprising a EZH2 specific inhibitor, thereby treating, preventing, or ameliorating the cancer. In certain embodiments, the compound comprises an antisense compound targeted to EZH2. In certain embodiments, the compound comprises an oligonucleotide targeted to EZH2. In certain embodiments, a compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, a compound comprises a modified oligonucleotide consisting of 16 to 80 linked nucleosides and having a nucleobase sequence comprising the nucleobase sequence of any one of SEQ ID NOs: 10-1592. In certain embodiments, a compound comprises a modified oligonucleotide having a nucleobase sequence consisting of the nucleobase sequence of any one of SEQ ID NOs: 10-1592. In certain embodiments, a compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, a compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis.

In certain embodiments, a method of treating or ameliorating caner comprises administering to the individual a compound comprising a EZH2 specific inhibitor, thereby treating or ameliorating the cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

In certain embodiments, a method of inhibiting expression of EZH2 in an individual having, or at risk of having, a cancer associated with EZH2 comprises administering to the individual a compound comprising a EZH2 specific inhibitor, thereby inhibiting expression of EZH2 in the individual. In certain embodiments, administering the compound inhibits expression of EZH2 in the bone marrow, lymphoid tissue, or lymph node. In certain embodiments, the individual has, or is at risk of having blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

In certain embodiments, a method of inhibiting expression of EZH2 in a cell comprises contacting the cell with a compound comprising a EZH2 specific inhibitor, thereby inhibiting expression of EZH2 in the cell. In certain embodiments, the cell is a cancer cell. In certain embodiments, the cell is a bone marrow, lymphoid tissue, or lymph node cell. In certain embodiments, the cell is in the bone marrow, lymphoid tissue, or lymph node. In certain embodiments, the cell is in the bone marrow, lymphoid tissue, or lymph node of an individual who has, or is at risk of having cancer, such as blood cancer, myeloma, multiple myeloma (MM), B cell malignancies, lymphoma, B cell lymphoma, T cell lymphoma, or leukemia. In certain embodiments, the compound comprises an antisense compound targeted to EZH2. In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound.

In certain embodiments, a method of reducing or inhibiting cancer cell proliferation, tumor growth, or metastasis of an individual having, or at risk of having, a cancer associated with EZH2 comprises administering to the individual a compound comprising a EZH2 specific inhibitor, thereby reducing or inhibiting cancer cell proliferation, tumor growth, or metastasis in the individual. In certain embodiments, the individual has, or is at risk of having, blood cancer, myeloma, multiple myeloma (MM), B cell malignancies, lymphoma, B cell lymphoma, T cell lymphoma, or leukemia. Examples of cancers associated with EZH2 treatable, preventable, and/or ameliorable with the methods provided herein include blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

Certain embodiments are drawn to a compound comprising a EZH2 specific inhibitor for use in treating cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

Certain embodiments are drawn to a compound comprising a EZH2 specific inhibitor for use in reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound.

Certain embodiments are drawn to use of a compound comprising a EZH2 specific inhibitor for the manufacture or preparation of a medicament for treating cancer. Certain embodiments are drawn to use of a compound comprising a EZH2 specific inhibitor for the preparation of a medicament for treating a cancer associated with EZH2. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

Certain embodiments are drawn to use of a compound comprising a EZH2 specific inhibitor for the manufacture or preparation of a medicament for reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. Certain embodiments are drawn to use of a compound comprising a EZH2 specific inhibitor for the preparation of a medicament for reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma includes, but is not limited to, peripheral T-cell lymphoma, adult T cell leukemia/lymphoma (ATLL), and anaplastic large cell lymphoma (ALCL). In certain embodiments, the leukemia includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, the compound comprises an antisense compound targeted to EZH2. In certain embodiments, the compound comprises an oligonucleotide targeted to EZH2. In certain embodiments, the compound comprises a modified oligonucleotide consisting of 8 to 80 linked nucleosides and having a nucleobase sequence comprising at least 8 contiguous nucleobases of any of the nucleobase sequences of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 10-1592. In certain embodiments, the compound comprises a modified oligonucleotide having a nucleobase sequence consisting of the nucleobase sequence of any one of SEQ ID NOs: 10-1592. In certain embodiments, the compound comprises a modified oligonucleotide consisting of 16 to 80 linked nucleosides and having a nucleobase sequence comprising the nucleobase sequence of any one of SEQ ID NOs: 102, 252, 387, 998, or 1038. In certain embodiments, the compound comprises a modified oligonucleotide having a nucleobase sequence consisting of the nucleobase sequence of any one of SEQ ID NOs: 102, 252, 387, 998, or 1038. In any of the foregoing embodiments, the modified oligonucleotide can consist of 10 to 30 linked nucleosides. In certain embodiments, the compound is ION 633365, 662368, 662950, 702334, 702366, and 754175. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with EZH2.

In any of the foregoing methods or uses, the compound can be targeted to EZH2. In certain embodiments, the compound comprises or consists of a modified oligonucleotide, for example a modified oligonucleotide consisting of 8 to 80 linked nucleosides, 10 to 30 linked nucleosides, 12 to 30 linked nucleosides, or 20 linked nucleosides. In certain embodiments, the modified oligonucleotide is at least 80%, 85%, 90%, 95% or 100% complementary to any of the nucleobase sequences recited in SEQ ID NOs: 1-3. In certain embodiments, at least one internucleoside linkage of the modified oligonucleotide is a modified internucleoside linkage, at least one nucleoside of the modified oligonucleotide comprises a modified sugar and/or at least one nucleobase of the modified oligonucleotide is a modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide has a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide can consist of 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides. In certain embodiments, the modified oligonucleotide is at least 80%, 85%, 90%, 95% or 100% complementary to any of the nucleobase sequences recited in SEQ ID NOs: 1-3. In certain embodiments, at least one internucleoside linkage of the modified oligonucleotide is a modified internucleoside linkage, at least one nucleoside of the modified oligonucleotide comprises a modified sugar and/or at least one nucleobase of the modified oligonucleotide is a modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide has a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound can comprise or consist of a modified oligonucleotide consisting of 16 to 80 linked nucleosides and having a nucleobase sequence comprising the nucleobase sequence of any one of SEQ ID NOs: 10-1592, wherein the modified oligonucleotide has:
 a gap segment consisting of linked 2'-deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in any one of SEQ ID NOs: 102, 252, 387, 998, or 1038, wherein the modified oligonucleotide has:
 a gap segment consisting of linked 2'-deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in any one of SEQ ID NOs: 252, 387, or 998, wherein the modified oligonucleotide has:
 a gap segment consisting of ten linked 2'-deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in SEQ ID NO: 252, wherein the modified oligonucleotide has:
 a gap segment consisting of ten linked 2'-deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in SEQ ID NO: 1038, wherein the modified oligonucleotide has:

a gap segment consisting of ten linked 2'-deoxynucleosides;

a 5' wing segment consisting of one linked nucleoside; and a 3' wing segment consisting of five linked nucleosides;

wherein the gap segment is positioned between the 5' wing segment and the 3' wing segment; wherein the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in SEQ ID NO: 252, wherein the modified oligonucleotide comprises:

a gap segment consisting of ten linked 2'-deoxynucleosides;

a 5' wing segment consisting of two linked nucleosides; and a 3' wing segment consisting of four linked nucleosides;

wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In any of the foregoing methods or uses, the compound can comprise or consist of a modified oligonucleotide consisting of 16-80 linked nucleosides and having a nucleobase sequence comprising the nucleobase sequence recited in SEQ ID NO: 102, wherein the modified oligonucleotide has:

a gap segment consisting of nine linked 2'-deoxynucleosides;

a 5' wing segment consisting of two linked nucleosides; and a 3' wing segment consisting of five linked nucleosides;

wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide consists of 16-30 linked nucleosides. In certain embodiments, the modified oligonucleotide consists of 16 linked nucleosides.

In any of the foregoing methods or uses, the compound can have the structure:

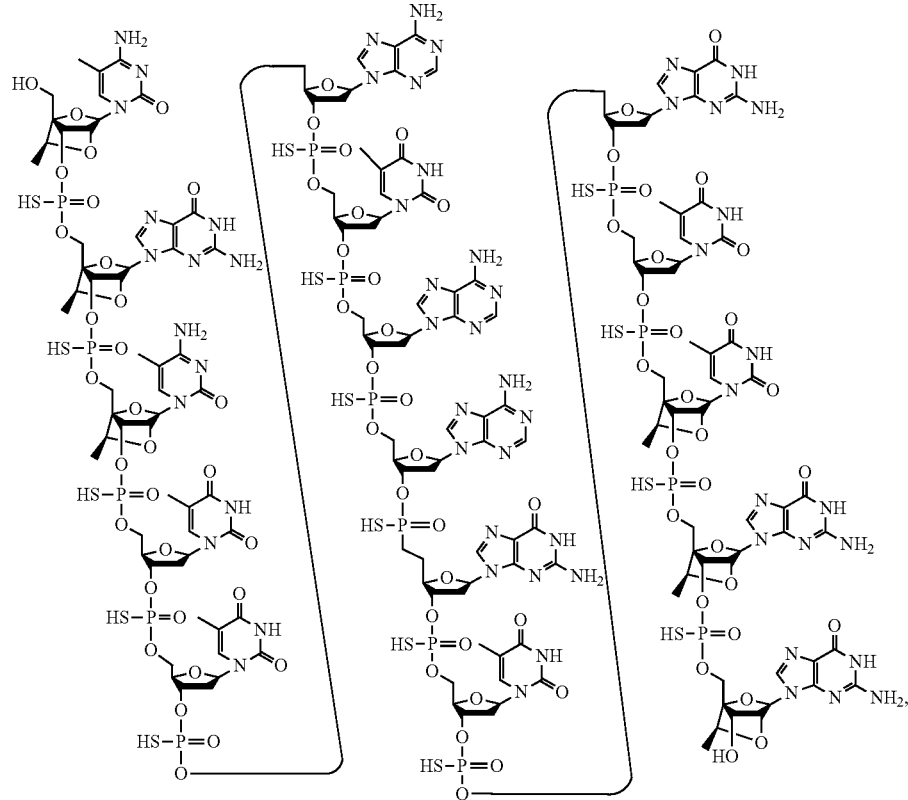

or a salt thereof.

In any of the foregoing methods or uses, the compound can have the structure:

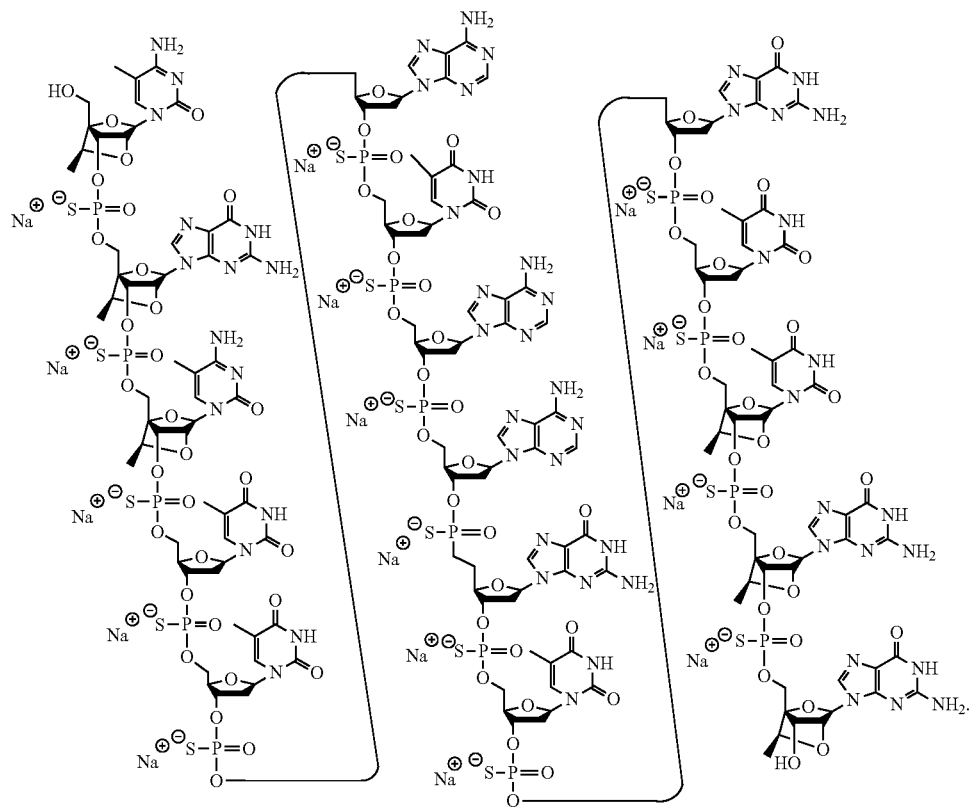

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Combinations and Combination Therapies

In certain embodiments, a first agent comprising a compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more secondary agents. In certain embodiments, one or more compounds or compositions provided herein and one or more secondary agents, are administered at different times. In certain embodiments, one or more compounds or compositions provided herein and one or more secondary agents, are prepared together in a single formulation. In certain embodiments, one or more compounds or compositions provided herein and one or more secondary agents, are prepared separately. In certain embodiments, a secondary agent is selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide. In certain embodiments, a secondary agent is selected from tazemetostat, EPZ-6438, E7438, GSK2816126, CPI-1205, CPI-360, CPI-169, and CPI-1205.

Certain embodiments are directed to the use of a compound targeted to EZH2 as described herein in combination with a secondary agent. In particular embodiments such use is in a method of treating a patient suffering from cancer including, but not limited to, blood cancer, myeloma, multiple myeloma (MM), B cell malignancies, lymphoma, B cell lymphoma, T cell lymphoma, or leukemia. In certain embodiments, such use is in the preparation or manufacture of a medicament for treating cancer including, but not limited to, blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL) (GC DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma includes, but is not limited to, peripheral T-cell lymphoma, adult T cell leukemia/lymphoma (ATLL), and anaplastic large cell lymphoma (ALCL). In certain embodiments, the leukemia includes, but is not limited to, acute lymphocytic leukemia (ALL). Additional examples of cancers associated with EZH2 treatable, preventable, and/or ameliorable with the compounds and methods provided herein include include but are not limited to lung cancer (e.g. non-small cell lung carcinoma (NSCLC) and small-cell lung carcinoma (SCLC)), gastrointestinal cancer (e.g. large intestinal cancer, small intestinal cancer, and stomach cancer), colon cancer, colorectal cancer, bladder cancer, liver cancer, esophageal cancer, pancreatic cancer, biliary tract cancer, breast cancer, ovarian cancer, endometrial cancer, cervical cancer, prostate cancer, mesothelioma, sarcomas (e.g. epitheloid, rhabdoid and synovial), chordoma, renal cancer, neuroblastoma, and brain cancer (e.g. glioblastoma). In certain embodiments, a secondary agent is selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide. In certain embodiments, a secondary agent is selected from tazemetostat, EPZ-6438, E7438, GSK2816126, CPI-1205, CPI-360, CPI-169, and CPI-1205.

Certain embodiments are drawn to a combination of a compound targeted to EZH2 as described herein and a secondary agent, such as a secondary agent selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; dexamethasone, thalidomide, cisplatin, doxorubicin, cyclophosphamide, and etoposide. In certain embodiments, such a combination of a compound targeted to EZH2 as described herein and a secondary agent, such as a secondary agent selected from: proteasome inhibitors including but not limited to bortezomib, carfilzomib, and ixazomib; BTK inhibitors including but not limited to ibrutinib; IMiDs including but not limited to lenalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide. In certain embodiments, a secondary agent is selected from tazemetostat, EPZ-6438, E7438, GSK2816126, CPI-1205, CPI-360, CPI-169, and CPI-1205. Such combinations can be useful for reducing or inhibiting cancer cell proliferation, tumor growth, or metastasis and/or treating cancer including, but not limited to, blood cancer, myeloma, multiple myeloma (MM), B cell malignancies, lymphoma, B cell lymphoma, T cell lymphoma, or leukemia.

In certain embodiments the compound targeted to EZH2 as described herein and the secondary agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, one of the modified oligonucleotides has a nucleobase sequence comprising at least 8 contiguous nucleobases of any of SEQ ID NOs: 10-1592.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to an EZH2 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al.

Proc. Natl. Acad. Sci. USA 1992, 89:7305-7309; Gautschi et al. *J. Natl. Cancer Inst. March* 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to EZH2 described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 10-1592 and a second strand. In certain embodiments, the compound comprises a first strand comprising the nucleobase sequence of any one of SEQ ID NOs: 10-1592 and a second strand. In certain embodiments, the compound comprises ribonucleotides in which the first strand has uracil (U) in place of thymine (T) in any one of SEQ ID NOs: 10-1592. In certain embodiments, the compound comprises (i) a first strand comprising a nucleobase sequence complementary to the site on EZH2 to which any of SEQ ID NOs: 10-1592 is targeted, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to EZH2 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 10-1592. In certain embodiments, the compound comprises the nucleobase sequence of any one of SEQ ID NOs: 10-1592. In certain embodiments, the compound comprises ribonucleotides in which uracil (U) is in place of thymine (T) in any one of SEQ ID NOs: 10-1592. In certain embodiments, the compound comprises a nucleobase sequence complementary to the site on EZH2 to which any of SEQ ID NOs: 10-1592 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the compound that are beneficial for use as a therapeutic or research tool. In certain embodiments, radioactive isotopic substitutions may make the compound suitable for research or diagnostic purposes, such as an imaging assay.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode EZH2 include, without limitation, the following: Ref SEQ No. NM_001203248.1 (SEQ ID NO: 1), NC_000007.14 TRUNC_148804001_148888000_COMP (SEQ ID NO: 2), or NM_004456.4 (SEQ ID NO: 3), each of which is incorporated by reference in its entirety.

Hybridization

In some embodiments, hybridization occurs between a compound disclosed herein and a EZH2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a EZH2 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a EZH2 nucleic acid may be tolerated provided that the compound remains able to specifically hybridize to a target nucleic acid. Moreover, a compound may hybridize over one or more segments of a EZH2 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a EZH2 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a EZH2 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a EZH2 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a EZH2 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a EZH2 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., US2010/190837 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, $OCH_3$, and $OCH_2CH_2OCH_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., J. Org. Chem., 2009, 74, 118-134), 4'-$CH_2$—C(=$CH_2$)-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)$=$C(R_b)$—, —$C(R_a)$=N—, —C(=$NR_a$)—, —C(=O)—, —C(=S)—, —O—, —$Si(R_a)_2$—, —$S(=O)_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129, 8362-8379; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

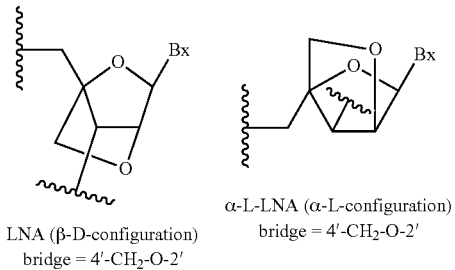

LNA (β-D-configuration)
bridge = 4'-$CH_2$-O-2'

α-L-LNA (α-L-configuration)
bridge = 4'-$CH_2$-O-2'

α-L-methyleneoxy (4'-$CH_2$—O-2') or α-L-LNA bicyclic nucleosides have been incorporated into oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), mannitol nucleic acid ("MNA") (see e.g., Leumann, C J. *Bioorg. & Med. Chem.* 2002, 10, 841-854), fluoro HNA:

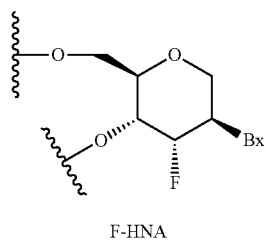

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906, F-HNA can also be referred to as a F-THP or 3'-fluoro tetrahydropyran), and nucleosides comprising additional modified THP compounds having the formula:

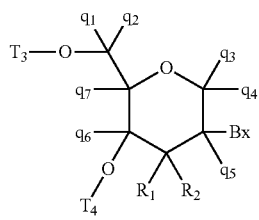

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

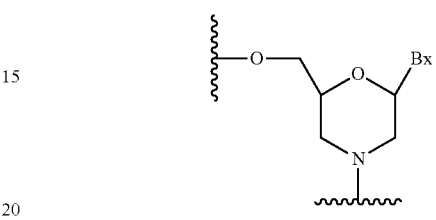

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi¬dines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a EZH2 nucleic acid comprise one or more modified nucleobases. In certain embodiments, the modified nucleobase is 5-methylcytosine. In certain embodiments, each cytosine is a 5-methylcytosine.

3. Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

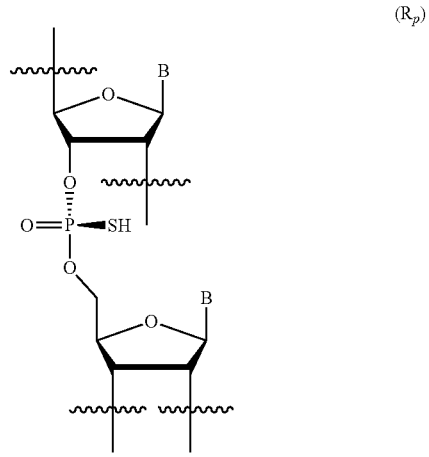

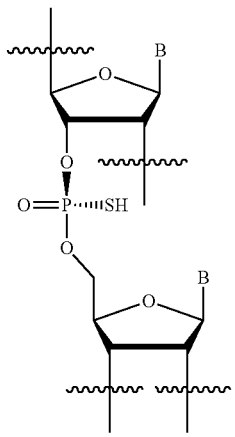

($S_p$)

Unless otherwise indicated, chiral internucleoside linkages of modified oligonucleotides described herein can be stereorandom or in a particular stereochemical configuration.

In certain embodiments, compounds targeted to an EZH2 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

In certain embodiments, a modified oligonucleotide can comprise a sugar motif described in Swayze et al., US2010/0197762; Freier et al., US2014/0107330; Freier et al., US2015/0184153; and Seth et al., US2015/0267195, each of which is incorporated by reference in its entirety herein.

Certain embodiments provided herein are directed to modified oligomeric compounds useful for inhibiting target nucleic acid expression, which can be useful for treating, preventing, ameliorating, or slowing progression of a disease associated with such a target nucleic acid. In certain embodiments, the modified oligomeric compounds comprise antisense oligonucleotides that are gapmers having certain sugar motifs. In certain embodiments, the gapmer sugar motifs provided herein can be combined with any nucleobase sequence and any internucleoside linkage motif to form potent antisense oligonucleotides.

In certain embodiments, a method comprises contacting a cell or administering to a subject a compound comprising a modified oligonucleotide 16 linked nucleosides in length having the motif: ekk-d9-kkee, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: k-d9-kekeke, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kkk-d8-kekek, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kkk-d9-keke, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kk-d9-kdkdk, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a compound comprises a modified oligonucleotide 16 linked nucleosides in length having the motif: kk-d9-eeekk, wherein 'd' represents a 2'-deoxyribose sugar, 'k' represents a cEt nucleoside, and 'e' represents a 2'-MOE nucleoside. In certain embodiments, a method comprises contacting a cell or administering to a subject a compound comprising a modified oligonucleotide 16 linked nucleosides in length having the motif: kk-d9-eeekk, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kk-d9-ekeke, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

4. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to EZH2 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to EZH2 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

EXAMPLES

The Examples below describe the screening process to identify lead compounds targeted to EZH2. Out of over 2,800 oligonucleotides that were screened, ION 633365, 662368, 662950, 702334, 702366, and 754175 emerged as the top lead compounds. In particular, ION 633365 exhibited the best combination of properties in terms of potency and tolerability out of over 2,800 oligonucleotides.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Effect of 3-10-3 cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured HepG2 cells at a density of 20,000 cells per well were transfected using electroporation with 2,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (forward sequence CCTCCTCCCCCCTCCTCT, designated herein as SEQ ID NO: 4; reverse sequence TGTTCTTTTTCTAAATTGCCCACA, designated herein as SEQ ID NO: 5; probe sequence AAACAGCTGCCTTAGCTTCAGGAACCTCG, designated herein as SEQ ID NO: 6) was used to measure mRNA levels. EZH2 mRNA levels were adjusted according to total RNA content, as measured by RiboGreen®. Results are presented in the tables below as percent control of the amount of EZH2 mRNA, relative to untreated control (UTC) cells.

The modified oligonucleotides in the tables below are 3-10-3 cEt gapmers. The gapmers are 16 nucleobases in length, wherein the central gap segment comprises ten 2'-deoxynucleosides flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human EZH2 nucleic acid sequences SEQ ID NO: 1 (Ref SEQ No. NM_001203248.1), SEQ ID NO: 2 (Ref SEQ No. NC_000007.14_TRUNC148804001_148888000_COMP), or SEQ ID NO: 3 (Ref SEQ No. NM_004456.4) as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 1

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633282 | 5 | 20 | 3656 | 3671 | CAGCCCAATCAAGCGC | 115 | 10 |
| 633286 | 37 | 52 | 3688 | 3703 | GCCCAATCGCCATCGC | 109 | 11 |
| 633290 | 77 | 92 | 3728 | 3743 | CGGGTGTCGGACGCGA | 61 | 12 |
| 633294 | 182 | 197 | N/A | N/A | CCATGATTATTCTTCG | 52 | 13 |
| 633298 | 230 | 245 | 40739 | 40754 | GCTTCCGCCAACAAAC | 32 | 14 |
| 633302 | 262 | 277 | 40771 | 40786 | CTGTCTCAGTCGCATG | 18 | 15 |
| 633306 | 313 | 328 | 41405 | 41420 | ATTGGAACTAAACATA | 44 | 16 |
| 633310 | 372 | 387 | 41464 | 41479 | ATCCTTCGCTGTTTCC | 23 | 17 |
| 633314 | 405 | 420 | N/A | N/A | ACCGAACAAGAAGTCA | 42 | 18 |
| 633318 | 446 | 461 | 55284 | 55299 | TTAATGGGATGACTTG | 36 | 19 |
| 633322 | 477 | 492 | 55315 | 55330 | ATGGGTACTGAAGCAA | 17 | 20 |
| 633326 | 541 | 556 | 58164 | 58179 | GTTATGTAAAACAGTT | 25 | 21 |
| 633330 | 589 | 604 | 58212 | 58227 | AATGAAAGTACCATCC | 30 | 22 |
| 633334 | 640 | 655 | N/A | N/A | ACATTCTCTATCCCCG | 29 | 23 |
| 633338 | 739 | 754 | 59209 | 59224 | TCTTTCTTCAGGATCG | 29 | 24 |
| 633342 | 794 | 809 | 60737 | 60752 | GTGGGCGGCTTTCTTT | 55 | 25 |
| 633346 | 852 | 867 | 60795 | 60810 | TTATCTGGAAACATTG | 57 | 26 |
| 633350 | 907 | 922 | 61381 | 61396 | GAGCTGCTGTTCGGTG | 34 | 27 |
| 633354 | 952 | 967 | 61426 | 61441 | TGGTCCATCTATGTTG | 30 | 28 |
| 633358 | 991 | 1006 | 61465 | 61480 | GGAGTGTAAGCTTTGC | 11 | 29 |
| 633362 | 1027 | 1042 | 61501 | 61516 | ATATTTAAAACATCGC | 54 | 30 |
| 633366 | 1105 | 1120 | 68360 | 68375 | TTTGTTGTCTAGAGCT | 39 | 31 |
| 633370 | 1163 | 1178 | 69896 | 69911 | GAGCAGCAGCAAACTC | 77 | 32 |
| 633374 | 1211 | 1226 | 69944 | 69959 | TGCGGCCTCCTGGACG | 41 | 33 |
| 633378 | 1236 | 1251 | 69969 | 69984 | CTGTTATTGGGAAGCC | 29 | 34 |
| 633382 | 1302 | 1317 | 70035 | 70050 | GCTTCCCTATCACTGT | 38 | 35 |
| 633386 | 1382 | 1397 | N/A | N/A | TTGCTTCAGAGGAGCT | 95 | 36 |
| 633390 | 1437 | 1452 | 70655 | 70670 | TTCTCAGGAGGTTCAA | 32 | 37 |
| 633394 | 1463 | 1478 | 70681 | 70696 | AGGCTTCAGCACCACT | 110 | 38 |
| 633398 | 1492 | 1507 | 70710 | 70725 | GTAAGTGCCAATGAGG | 12 | 39 |
| 633402 | 1536 | 1551 | 70754 | 70769 | GTTTTGGTCCCAATTA | 23 | 40 |

TABLE 1-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633406 | 1589 | 1604 | 71250 | 71265 | CTGGAGCTATGATGCT | 29 | 41 |
| 633410 | 1619 | 1634 | 71280 | 71295 | TTGGAGGAGTATCCAC | 29 | 42 |
| 633414 | 1701 | 1716 | 72965 | 72980 | ACATGGTTAGAGGAGC | 20 | 43 |
| 633418 | 1751 | 1766 | 73015 | 73030 | ACGAACTGTCACAAGG | 18 | 44 |
| 633422 | 1799 | 1814 | 73063 | 73078 | TACATTGACAAAACTT | 43 | 45 |
| 633426 | 1837 | 1852 | 73877 | 73892 | GCAGCGGCATCCCGGA | 30 | 46 |
| 633430 | 1876 | 1891 | 73916 | 73931 | CAGGTAGCACGGGCAC | 27 | 47 |
| 633434 | 1918 | 1933 | 73958 | 73973 | TCCACAAGTAAGACAG | 45 | 48 |
| 633438 | 1957 | 1972 | 73997 | 74012 | CTTGCAGGACACATTT | 24 | 49 |
| 633442 | 1982 | 1997 | 74022 | 74037 | TGGAGCCCCGCTGAAT | 39 | 50 |
| 633446 | 2012 | 2027 | 76290 | 76305 | CGTCAGATGGTGCCAG | 27 | 51 |
| 633450 | 2127 | 2142 | 77615 | 77630 | TCATACACTTTCCCTC | 29 | 52 |
| 633454 | 2194 | 2209 | 78624 | 78639 | ACCCTTGCGGGTTGCA | 64 | 53 |
| 633458 | 2237 | 2252 | 78667 | 78682 | AGCAGTTTGGATTTAC | 45 | 54 |
| 633462 | 2272 | 2287 | 78856 | 78871 | CCTGTGATCACCGTTA | 20 | 55 |
| 633466 | 2302 | 2317 | 78886 | 78901 | CTGGATGGCTCTCTTG | 29 | 56 |
| 633470 | 2374 | 2389 | 80322 | 80337 | TCTTTCGATGCCGACA | 31 | 57 |
| 633474 | 2398 | 2413 | 80346 | 80361 | CAGATGTCAAGGGATT | 26 | 58 |
| 633482 | 2558 | 2573 | 80506 | 80521 | GGCAATAAAAAGTTGA | 26 | 59 |
| 633486 | 2600 | 2615 | 80548 | 80563 | GCAAAAATTCACTGGT | 17 | 60 |
| 633490 | 2655 | 2670 | 80603 | 80618 | GACAAGTTCAAGTATT | 78 | 61 |
| 633502 | N/A | N/A | 4509 | 4524 | AGCTACTCCGAGTTCC | 52 | 62 |
| 633506 | N/A | N/A | 4581 | 4596 | GGCGAGGGCAGCCCGC | 29 | 63 |
| 633510 | N/A | N/A | 4619 | 4634 | GACTCTTCCCTCAAAC | 60 | 64 |
| 633514 | N/A | N/A | 4672 | 4687 | GAATTCAACAGGACGC | 37 | 65 |
| 633518 | N/A | N/A | 4742 | 4757 | CGCTTTCAAAAAGTAA | 81 | 66 |
| 633526 | N/A | N/A | 4259 | 4274 | TCCCACCAACTTGTGT | 77 | 67 |
| 633530 | N/A | N/A | 4901 | 4916 | ATGACAGTTGATTTCG | 19 | 68 |
| 633534 | N/A N/A | N/A N/A | 9466 9543 | 9481 9558 | TTTCACTCCTTTTATG | 39 | 69 |
| 633538 | N/A N/A | N/A N/A | 19518 19534 | 19533 19549 | ACGAGAACTCACTGTC | 17 | 70 |
| 633542 | N/A | N/A | 30887 | 30902 | TCCCCCAGACCTCAAC | 94 | 71 |
| 633546 | N/A | N/A | 38437 | 38452 | AGTGTGGCCTTGCCTG | 27 | 72 |
| 633550 | N/A | N/A | 41358 | 41373 | GAGAAATTGTTCATTG | 82 | 73 |
| 633554 | N/A N/A | N/A N/A | 44091 44417 | 44106 44432 | AAATGGGAGTATAAGT | 41 | 74 |

TABLE 1-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633558 | N/A | N/A | 51041 | 51056 | GTTCCAAGTAAAAACT | 80 | 75 |
| 633562 | N/A | N/A | 51142 | 51157 | CGACTGTGTGGCTGGA | 20 | 76 |
| 633566 | N/A | N/A | 68939 | 68954 | TAGGTAGGAGTGGCTT | 45 | 77 |
| 633570 | N/A | N/A | 69060 | 69075 | AACAGTTTTATACTTC | 19 | 78 |
| 633574 | N/A | N/A | 70607 | 70622 | CGAGAATTTGCTTCTA | 41 | 79 |
| 633578 | N/A | N/A | 72917 | 72932 | TGAATCCAGGGAGATG | 55 | 80 |
| 633582 | N/A | N/A | 73108 | 73123 | TTCTCATGCAATTGCA | 33 | 81 |
| 633586 | N/A | N/A | 77654 | 77669 | CCATTGTTCAAGTTGA | 46 | 82 |
| 633590 | N/A | N/A | 78836 | 78851 | TCATAACTGCAAAGAG | 89 | 83 |

TABLE 2

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633283 | 11 | 26 | 3662 | 3677 | CCCCCCCAGCCCAATC | 150 | 84 |
| 633287 | 43 | 58 | 3694 | 3709 | GCGGCAGCCCAATCGC | 87 | 85 |
| 633291 | 83 | 98 | 3734 | 3749 | TCCCACCGGGTGTCGG | 103 | 86 |
| 633295 | 195 | 210 | 40704 | 40719 | TTCCCAGTCTGGCCCA | 47 | 87 |
| 633299 | 232 | 247 | 40741 | 40756 | ACGCTTCCGCCAACAA | 13 | 88 |
| 633303 | 267 | 282 | 40776 | 40791 | TTGAGCTGTCTCAGTC | 21 | 89 |
| 633307 | 326 | 341 | 41418 | 41433 | AAATTTTCTGACGATT | 81 | 90 |
| 633311 | 378 | 393 | 41470 | 41485 | GGCTGTATCCTTCGCT | 39 | 91 |
| 633315 | 411 | 426 | N/A | N/A | CTGGTCACCGAACAAG | 26 | 92 |
| 633319 | 452 | 467 | 55290 | 55305 | GAGTCTTTAATGGGAT | 21 | 93 |
| 633323 | 483 | 498 | 55321 | 55336 | TACATTATGGGTACTG | 11 | 94 |
| 633327 | 554 | 569 | 58177 | 58192 | CCATATAAGGAATGTT | 50 | 95 |
| 633331 | 596 | 611 | 58219 | 58234 | GTTCTTCAATGAAAGT | 15 | 96 |
| 633335 | 654 | 669 | 59124 | 59139 | TCATTTATAAACCCAC | 16 | 97 |
| 633339 | 769 | 784 | 59239 | 59254 | GTGATCCTCCAGATCT | 133 | 98 |
| 633343 | 804 | 819 | 60747 | 60762 | AATTTCCGAGGTGGGC | 19 | 99 |
| 633347 | 860 | 875 | 60803 | 60818 | CTGTGCCCTTATCTGG | 22 | 100 |
| 633351 | 915 | 930 | 61389 | 61404 | GCGCCTGGGAGCTGCT | 42 | 101 |
| 633355 | 964 | 979 | 61438 | 61453 | AGATTTAGCATTTGGT | 7 | 102 |
| 633359 | 997 | 1012 | 61471 | 61486 | ATGAAAGGAGTGTAAG | 44 | 103 |
| 633363 | 1042 | 1057 | 61516 | 61531 | ATGTAGGAAGCAGTCA | 28 | 104 |

TABLE 2-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633367 | 1121 | 1136 | 68376 | 68391 | ACTGTGGTCCACAAGG | 22 | 105 |
| 633371 | 1169 | 1184 | 69902 | 69917 | CGGTGAGAGCAGCAGC | 16 | 106 |
| 633375 | 1218 | 1233 | 69951 | 69966 | CCTCTTCTGCGGCCTC | 73 | 107 |
| 633379 | 1275 | 1290 | 70008 | 70023 | GATTCCAGCACATTAA | 75 | 108 |
| 633383 | 1321 | 1336 | 70054 | 70069 | TCCCCCCGYTTCAGTC | 57 | 109 |
| 633387 | 1395 | 1410 | 70613 | 70628 | TGACACCGAGAATTTG | 86 | 110 |
| 633391 | 1445 | 1460 | 70663 | 70678 | ACTCCACATTCTCAGG | 22 | 111 |
| 633395 | 1471 | 1486 | 70689 | 70704 | AAACATTGAGGCTTCA | 25 | 112 |
| 633399 | 1498 | 1513 | 70716 | 70731 | GTCATAGTAAGTGCCA | 23 | 113 |
| 633403 | 1549 | 1564 | 71256 | 71271 | CACCTGTCTACATGTT | 72 | 114 |
| 633407 | 1595 | 1610 | 71302 | 71317 | CGGGAGCTGGAGCTAT | 50 | 115 |
| 633411 | 1641 | 1656 | N/A | N/A | CGGTGTTTCCTCTTCT | 45 | 116 |
| 633415 | 1714 | 1729 | 72978 | 72993 | TTGATAGTTGTAAACA | 48 | 117 |
| 633419 | 1756 | 1771 | 73020 | 73035 | AGGGCACGAACTGTCA | 53 | 118 |
| 633423 | 1812 | 1827 | N/A | N/A | TGACACTCTGAACTAC | 34 | 119 |
| 633427 | 1843 | 1858 | 73883 | 73898 | TGCTTTGCAGCGGCAT | 63 | 120 |
| 633431 | 1883 | 1898 | 73923 | 73938 | GGACAGCCAGGTAGCA | 41 | 121 |
| 633435 | 1924 | 1939 | 73964 | 73979 | AGCGGCTCCACAAGTA | 43 | 122 |
| 633439 | 1963 | 1978 | 74003 | 74018 | GCAGTTCTTGCAGGAC | 21 | 123 |
| 633443 | 1988 | 2003 | N/A | N/A | GCTTTTTGGAGCCCCG | 57 | 124 |
| 633447 | 2039 | 2054 | 76317 | 76332 | CTTTGATAAAAATCCC | 41 | 125 |
| 633451 | 2149 | 2164 | 77637 | 77652 | CAGAAAGCTGCACATG | 38 | 126 |
| 633455 | 2200 | 2215 | 78630 | 78645 | TTTGTTACCCTTGCGG | 14 | 127 |
| 633459 | 2250 | 2265 | N/A | N/A | ATAACTTTGCATAGC | 43 | 128 |
| 633463 | 2278 | 2293 | 78862 | 78877 | ACCTATCCTGTGATCA | 23 | 129 |
| 633467 | 2314 | 2329 | 78898 | 78913 | CTCTTCGCCAGTCTGG | 47 | 130 |
| 633471 | 2380 | 2395 | 80328 | 80343 | CATTTCTCTTTCGATG | 57 | 131 |
| 633483 | 2571 | 2586 | 80519 | 80534 | CAGCTGGTGAGAAGGC | 15 | 132 |
| 633487 | 2610 | 2625 | 80558 | 80573 | CTGCATTATTGCAAAA | 92 | 133 |
| 633491 | N/A | N/A | 41501 | 41516 | CAATGAGCTCACAGAA | 93 | 134 |
| 633503 | N/A | N/A | 4515 | 4530 | AGGCGAAGCTACTCCG | 47 | 135 |
| 633507 | N/A | N/A | 4593 | 4608 | GCCAGACCAGGCGGCG | 132 | 136 |
| 633511 | N/A | N/A | 4625 | 4640 | CAGCTCGACTCTTCCC | 28 | 137 |
| 633515 | N/A | N/A | 4687 | 4702 | TACACAATGAAGTGGG | 23 | 138 |
| 633519 | N/A | N/A | 4748 | 4763 | TCCTCCCGCTTTCAAA | 67 | 139 |
| 633523 | N/A | N/A | 72481 | 72496 | CCCTTTTTCAGCTGTA | 49 | 140 |

TABLE 2-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633527 | N/A | N/A | 4291 | 4306 | TCCTTTGTCTGAGTGC | 54 | 141 |
| 633531 | N/A | N/A | 5057 | 5072 | CAAAGCTATTGTTCAC | 43 | 142 |
| 633535 | N/A | N/A | 9490 9545 | 9505 9560 | AATTTCACTCCTTTTA | 20 | 143 |
| 633539 | N/A | N/A | 19519 19535 | 19534 19550 | CACGAGAACTCACTGT | 25 | 144 |
| 633543 | N/A | N/A | 32953 | 32968 | AGACCATGAGAGAGGA | 34 | 145 |
| 633547 | N/A | N/A | 40692 | 40707 | CCCATGATTATTCTAA | 25 | 146 |
| 633551 | N/A | N/A | 41519 | 41534 | AACCTCCCTAGTCCCG | 39 | 147 |
| 633555 | N/A | N/A | 44092 44418 | 44107 44433 | CAAATGGGAGTATAAG | 71 | 148 |
| 633559 | N/A | N/A | 51061 | 51076 | AGACTCTTGGCAGAAG | 25 | 149 |
| 633563 | N/A | N/A | 60629 | 60644 | AAGCTGATTTTCTAAG | 86 | 150 |
| 633567 | N/A | N/A | 68964 | 68979 | AGGCAATATATACCCA | 44 | 151 |
| 633571 | N/A | N/A | 69169 | 69184 | ATTTTAGATGAGCCAA | 31 | 152 |
| 633575 | N/A | N/A | 70767 | 70782 | TACCTGTCTACATGTT | 52 | 153 |
| 633579 | N/A | N/A | 72946 | 72961 | CTGAGTAAAGATAACA | 90 | 154 |
| 633583 | N/A | N/A | 73761 | 73776 | TCACTGACTCTCAACC | 104 | 155 |
| 633587 | N/A | N/A | 77934 | 77949 | AGCAGCAAGAGCACAA | 126 | 156 |
| 633591 | N/A | N/A | 78922 | 78937 | TACCAACCTGTAATCA | 158 | 157 |

TABLE 3

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633284 | 17 | 32 | 3668 | 3683 | ATTTGGCCCCCCCAGC | 107 | 158 |
| 633288 | 49 | 64 | 3700 | 3715 | CCAAACGCGGCAGCCC | 85 | 159 |
| 633292 | 134 | 149 | 3785 | 3800 | TCGCCCCGCGCGCCG | 48 | 160 |
| 633296 | 212 | 227 | 40721 | 40736 | GTCCCTTCTCAGATTT | 40 | 161 |
| 633300 | 243 | 258 | 40752 | 40767 | TCTGATTTACACGCT | 28 | 162 |
| 633304 | 278 | 293 | 40787 | 40802 | GTCTGAACCTCTTGAG | 47 | 163 |
| 633308 | 337 | 352 | 41429 | 41444 | CGTTCTTTCCAAAATT | 29 | 164 |
| 633312 | 383 | 398 | 41475 | 41490 | GCACAGGCTGTATCCT | 29 | 165 |
| 633316 | 417 | 432 | 55255 | 55270 | AAGTCACTGGTCACCG | 27 | 166 |
| 633320 | 458 | 473 | 55296 | 55311 | CATTCAGAGTCTTTAA | 45 | 167 |
| 633324 | 493 | 508 | 55331 | 55346 | AGACCAAGAATACATT | 49 | 168 |

TABLE 3-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633328 | 577 | 592 | 58200 | 58215 | ATCCTGATCTAAAACT | 40 | 169 |
| 633332 | 628 | 643 | 58251 | 58266 | CCCGTGTACTTTCCCA | 63 | 170 |
| 633336 | 685 | 700 | 59155 | 59170 | AAGGGCATTCACCAAC | 28 | 171 |
| 633340 | 775 | 790 | 59245 | 59260 | ATCTCGGTGATCCTCC | 31 | 172 |
| 633344 | 809 | 824 | 60752 | 60767 | AAGGAAATTTCCGAGG | 15 | 173 |
| 633348 | 869 | 884 | 60812 | 60827 | GTTCTTCTGCTGTGCC | 21 | 174 |
| 633352 | 921 | 936 | 61395 | 61410 | GGAAGTGCGCCTGGGA | 11 | 175 |
| 633356 | 970 | 985 | 61444 | 61459 | CTGAACAGATTTAGCA | 18 | 176 |
| 633360 | 1014 | 1029 | 61488 | 61503 | CGCCTACAGAAAAGCG | 81 | 177 |
| 633364 | 1064 | 1079 | 68319 | 68334 | TGTTGGGTGTTGCATG | 42 | 178 |
| 633368 | 1143 | 1158 | N/A | N/A | GCTCCCTCCAAATGCT | 97 | 179 |
| 633372 | 1181 | 1196 | 69914 | 69929 | TTATCCGCTCAGCGGT | 82 | 180 |
| 633376 | 1224 | 1239 | 69957 | 69972 | AGCCGTCCTCTTCTGC | 60 | 181 |
| 633380 | 1281 | 1296 | 70014 | 70029 | TCCTTTGATTCCAGCA | 30 | 182 |
| 633384 | 1331 | 1346 | 70064 | 70079 | CATTGTTCTCTCCCCC | 22 | 183 |
| 633388 | 1408 | 1423 | 70626 | 70641 | CTTTATTGGTGTTTGA | 59 | 184 |
| 633392 | 1450 | 1465 | 70668 | 70683 | ACTCCACTCCACATTC | 28 | 185 |
| 633396 | 1481 | 1496 | 70699 | 70714 | TGAGGACTCTAAACAT | 34 | 186 |
| 633400 | 1509 | 1524 | 70727 | 70742 | GCACAGAAATTGTCAT | 44 | 187 |
| 633404 | 1562 | 1577 | 71223 | 71238 | CTCTAAACTCATACAC | 51 | 188 |
| 633408 | 1601 | 1616 | 71262 | 71277 | CCTCAGCGGGAGCTGG | 108 | 189 |
| 633412 | 1647 | 1662 | N/A | N/A | CACAACCGGTGTTTCC | 77 | 190 |
| 633416 | 1729 | 1744 | 72993 | 73008 | TGGATGATCACAGGGT | 13 | 191 |
| 633420 | 1766 | 1781 | 73030 | 73045 | CTATCACACAAGGGCA | 14 | 192 |
| 633424 | 1825 | 1840 | 73865 | 73880 | CGGAAAGCGGTTTTGA | 39 | 193 |
| 633428 | 1851 | 1866 | 73891 | 73906 | TTGCACTGTGCTTTGC | 37 | 194 |
| 633432 | 1886 | 1901 | 73926 | 73941 | CTCGGACAGCCAGGTA | 46 | 195 |
| 633436 | 1930 | 1945 | 73970 | 73985 | ATGGTCAGCGGCTCCA | 43 | 196 |
| 633440 | 1970 | 1985 | 74010 | 74025 | GAATACTGCAGTTCTT | 93 | 197 |
| 633444 | 2000 | 2015 | N/A | N/A | CCAGCAATAGATGCTT | 61 | 198 |
| 633448 | 2045 | 2060 | 76323 | 76338 | CAGGATCTTTGATAAA | 45 | 199 |
| 633452 | 2162 | 2177 | 77650 | 77665 | TGTTCAAGTTGAACAG | 61 | 200 |
| 633456 | 2206 | 2221 | 78636 | 78651 | ACGAATTTTGTTACCC | 19 | 201 |
| 633460 | 2260 | 2275 | 78844 | 78859 | GTTAACCATCATAACT | 79 | 202 |

TABLE 3-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633464 | 2286 | 2301 | 78870 | 78885 | GCAAAAATACCTATCC | 29 | 203 |
| 633468 | 2354 | 2369 | 80302 | 80317 | TCAGGGCATCAGCCTG | 69 | 204 |
| 633472 | 2388 | 2403 | 80336 | 80351 | GGGATTTCCATTTCTC | 36 | 205 |
| 633484 | 2586 | 2601 | 80534 | 80549 | GTACAAAACACTTTGC | 47 | 206 |
| 633488 | 2623 | 2638 | 80571 | 80586 | AAAATGTACCATACTG | 56 | 207 |
| 633492 | N/A | N/A | 41514 | 41529 | CCCTAGTCCCGCGCAA | 39 | 208 |
| 633500 | N/A | N/A | 4497 | 4512 | TTCCCCGCCGCGAACG | 42 | 209 |
| 633504 | N/A | N/A | 4521 | 4536 | CGTCAGAGGCGAAGCT | 33 | 210 |
| 633508 | N/A | N/A | 4599 | 4614 | CATAAAGCCAGACCAG | 52 | 211 |
| 633512 | N/A | N/A | 4631 | 4646 | GCAGAGCAGCTCGACT | 39 | 212 |
| 633516 | N/A | N/A | 4726 | 4741 | CCCTGTGGCACAGATT | 22 | 213 |
| 633520 | N/A | N/A | 4775 | 4790 | GTTTTCCAAAAGATCG | 24 | 214 |
| 633528 | N/A | N/A | 4380 | 4395 | GCGCCTCCCCACGCCC | 145 | 215 |
| 633532 | N/A | N/A | 5105 | 5120 | AATTTCTTAGGCAACA | 27 | 216 |
| 633536 | N/A | N/A | 16028 19520 | 16043 19535 | GGGCAACCATATATCC | 21 | 217 |
| 633540 | N/A | N/A | 19536 | 19551 | TCACGAGAACTCACTG | 37 | 218 |
| 633544 | N/A | N/A | 36889 | 36904 | TAACGAGTAGCTTGTA | 38 | 219 |
| 633548 | N/A | N/A | 40805 | 40820 | CCTTTACTTCATCAGC | 25 | 220 |
| 633552 | N/A | N/A | 44089 44415 | 44104 44430 | ATGGGAGTATAAGTTT | 24 | 221 |
| 633556 | N/A | N/A | 50930 | 50945 | GAGACTTTACCAAAGT | 35 | 222 |
| 633560 | N/A | N/A | 51075 | 51090 | ACACAACCAAACTGAG | 81 | 223 |
| 633564 | N/A | N/A | 61364 | 61379 | GTTCTTTATATCTGAC | 34 | 224 |
| 633568 | N/A | N/A | 68980 | 68995 | CTGTCCAAAATCCAAC | 49 | 225 |
| 633572 | N/A | N/A | 69637 | 69652 | AGGCAAGACAGTTCTA | 27 | 226 |
| 633576 | N/A | N/A | 71918 | 71933 | GCATAATCTAACTGCA | 101 | 227 |
| 633580 | N/A | N/A | 72959 | 72974 | TTAGAGGAGCCGTCTG | 60 | 228 |
| 633584 | N/A | N/A | 73861 | 73876 | AAGCGGTTTTGACCTT | 52 | 229 |
| 633588 | N/A | N/A | 78608 | 78623 | TCCACCACAAAATCTA | 42 | 230 |
| 633592 | N/A | N/A | 79759 | 79774 | GCTCCACCCCACACTC | 98 | 231 |

TABLE 4

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633285 | 30 | 45 | 3681 | 3696 | CGCCATCGCTTTTATT | 105 | 232 |
| 633289 | 64 | 79 | 3715 | 3730 | CGACCGGACCGAGCGC | 70 | 233 |
| 633293 | 163 | 178 | 3814 | 3829 | CGCGCGCCGACTCGCG | 85 | 234 |
| 633297 | 220 | 235 | 40729 | 40744 | ACAAACTGGTCCCTTC | 35 | 235 |
| 633301 | 256 | 271 | 40765 | 40780 | CAGTCGCATGTACTCT | 21 | 236 |
| 633305 | 294 | 309 | 40803 | 40818 | TTTACTTCATCAGCTC | 28 | 237 |
| 633309 | 366 | 381 | 41458 | 41473 | CGCTGTTTCCATTCTT | 33 | 238 |
| 633313 | 399 | 414 | N/A | N/A | CAAGAAGTCAGGATGT | 67 | 239 |
| 633317 | 422 | 437 | 55260 | 55275 | AATCCAAGTCACTGGT | 42 | 240 |
| 633321 | 471 | 486 | 55309 | 55324 | ACTGAAGCAACTGCAT | 34 | 241 |
| 633325 | 510 | 525 | 55348 | 55363 | AAATTCTGCTGTAGGG | 30 | 242 |
| 633329 | 583 | 598 | 58206 | 58221 | AGTACCATCCTGATCT | 20 | 243 |
| 633333 | 634 | 649 | 58257 | 58272 | TCTATCCCCGTGTACT | 38 | 244 |
| 633337 | 698 | 713 | 59168 | 59183 | CATTATATTGACCAAG | 25 | 245 |
| 633341 | 785 | 800 | N/A | N/A | TTTCTTTATCATCTCG | 32 | 246 |
| 633345 | 839 | 854 | 60782 | 60797 | TTGAGGAAATGGCTTC | 34 | 247 |
| 633349 | 895 | 910 | 61369 | 61384 | GGTGAGTTCTTTATAT | 44 | 248 |
| 633353 | 933 | 948 | 61407 | 61422 | GTACATTCAGGAGGAA | 37 | 249 |
| 633357 | 985 | 1000 | 61459 | 61474 | TAAGCTTTGCTCTCTC | 13 | 250 |
| 633361 | 1020 | 1035 | 61494 | 61509 | AAACATCGCCTACAGA | 44 | 251 |
| 633365 | 1074 | 1089 | 68329 | 68344 | CGCTTATAAGTGTTGG | 15 | 252 |
| 633369 | 1158 | 1173 | 69891 | 69906 | GCAGCAAACTCCTTTG | 32 | 253 |
| 633373 | 1187 | 1202 | 69920 | 69935 | GGGTCTTTATCCGCTC | 55 | 254 |
| 633377 | 1230 | 1245 | 69963 | 69978 | TTGGGAAGCCGTCCTC | 44 | 255 |
| 633381 | 1289 | 1304 | 70022 | 70037 | TGTCTGTATCCTTTGA | 25 | 256 |
| 633385 | 1372 | 1387 | 70105 | 70120 | GGAGCTCGAAGTTTCA | 53 | 257 |
| 633389 | 1425 | 1440 | 70643 | 70658 | TCAATATTTGGCTTCA | 20 | 258 |
| 633393 | 1460 | 1475 | 70678 | 70693 | CTTCAGCACCACTCCA | 33 | 259 |
| 633397 | 1486 | 1501 | 70704 | 70719 | GCCAATGAGGACTCTA | 27 | 260 |
| 633401 | 1519 | 1534 | 70737 | 70752 | CCTAGCAATGGCACAG | 29 | 261 |
| 633405 | 1577 | 1592 | 71238 | 71253 | TGCTAGATTCTTTGAC | 37 | 262 |
| 633409 | 1607 | 1622 | 71268 | 71283 | CCACATCCTCAGCGGG | 42 | 263 |
| 633413 | 1688 | 1703 | N/A | N/A | AGCCGTCCTTTTTCAG | 80 | 264 |
| 633417 | 1739 | 1754 | 73003 | 73018 | AAGGCTGCCGTGGATG | 34 | 265 |
| 633421 | 1781 | 1796 | 73045 | 73060 | CACAAAAATTTTGTGC | 98 | 266 |
| 633425 | 1831 | 1846 | 73871 | 73886 | GCATCCCGGAAAGCGG | 33 | 267 |

TABLE 4-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633429 | 1864 | 1879 | 73904 | 73919 | GCACTGCTTGGTGTTG | 36 | 268 |
| 633433 | 1912 | 1927 | 73952 | 73967 | AGTAAGACAGAGGTCA | 26 | 269 |
| 633437 | 1937 | 1952 | 73977 | 73992 | TGTCCCAATGGTCAGC | 33 | 270 |
| 633441 | 1976 | 1991 | 74016 | 74031 | CCCGCTGAATACTGCA | 65 | 271 |
| 633445 | 2006 | 2021 | 76284 | 76299 | ATGGTGCCAGCAATAG | 33 | 272 |
| 633449 | 2086 | 2101 | N/A | N/A | AATCTCTCCACAGTAT | 30 | 273 |
| 633453 | 2185 | 2200 | 78615 | 78630 | GGTTGCATCCACCACA | 34 | 274 |
| 633457 | 2230 | 2245 | 78660 | 78675 | TGGATTTACCGAATGA | 36 | 275 |
| 633461 | 2266 | 2281 | 78850 | 78865 | ATCACCGTTAACCATC | 23 | 276 |
| 633465 | 2296 | 2311 | 78880 | 78895 | GGCTCTCTTGGCAAAA | 34 | 277 |
| 633469 | 2362 | 2377 | 80310 | 80325 | GACATACTTCAGGGCA | 38 | 278 |
| 633473 | 2390 | 2405 | 80338 | 80353 | AAGGGATTTCCATTTC | 18 | 279 |
| 633481 | 2515 | 2530 | 80463 | 80478 | CTTACAGTACTTTGCA | 21 | 280 |
| 633485 | 2593 | 2608 | 80541 | 80556 | TTCACTGGTACAAAAC | 29 | 281 |
| 633489 | 2650 | 2665 | 80598 | 80613 | GTTCAAGTATTCTTTA | 51 | 282 |
| 633497 | N/A | N/A | 61518 | 61533 | CGATGTAGGAAGCAGT | 21 | 283 |
| 633501 | N/A | N/A | 4503 | 4518 | TCCGAGTTCCCCGCCG | 46 | 284 |
| 633505 | N/A | N/A | 4563 | 4578 | CCGCCGGAGCTCAGGG | 53 | 285 |
| 633509 | N/A | N/A | 4605 | 4620 | ACTTAGCATAAAGCCA | 46 | 286 |
| 633513 | N/A | N/A | 4640 | 4655 | CAATAGAGAGCAGAGC | 51 | 287 |
| 633517 | N/A | N/A | 4732 | 4747 | AAGTAACCCTGTGGCA | 27 | 288 |
| 633521 | N/A | N/A | 4785 | 4800 | CGTTCACCAAGTTTTC | 17 | 289 |
| 633525 | N/A | N/A | 73863 | 73878 | GAAAGCGGTTTTGACC | 54 | 290 |
| 633529 | N/A | N/A | 4852 | 4867 | CAAGTTGGCCAAAACA | 38 | 291 |
| 633533 | N/A | N/A | 9465 9542 | 9480 9557 | TTCACTCCTTTTATGT | 25 | 292 |
| 633537 | N/A | N/A | 19517 19533 | 19532 19548 | CGAGAACTCACTGTCA | 21 | 293 |
| 633541 | N/A | N/A | 19979 | 19994 | CCTAGCCATCTCTGTC | 39 | 294 |
| 633545 | N/A | N/A | 37567 | 37582 | GACTTTCCATGCTGTT | 34 | 295 |
| 633549 | N/A | N/A | 41088 | 41103 | TCACAATGACTTTAGA | 39 | 296 |
| 633553 | N/A | N/A | 44090 44416 | 44105 44431 | AATGGGAGTATAAGTT | 24 | 297 |
| 633557 | N/A | N/A | 50959 | 50974 | CACCCTACTATGTGCC | 47 | 298 |
| 633561 | N/A | N/A | 51088 | 51103 | TAGTTGTAGGAGTACA | 39 | 299 |
| 633565 | N/A | N/A | 68926 | 68941 | CTTGGTTCAAAGAGGG | 43 | 300 |
| 633569 | N/A | N/A | 69018 | 69033 | AATAGGATACCTTCTG | 69 | 301 |
| 633573 | N/A | N/A | 70115 | 70130 | TCTTACCAGAGGAGCT | 89 | 302 |

TABLE 4-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633577 | N/A | N/A | 72661 | 72676 | CTTTACAGAAGAGAAT | 73 | 303 |
| 633581 | N/A | N/A | 73075 | 73090 | TACACTCTGAACTACA | 32 | 304 |
| 633585 | N/A | N/A | 74269 | 74284 | ATGGCTACTTCTCAGA | 37 | 305 |
| 633589 | N/A | N/A | 78677 | 78692 | CCTTTTGCATAGCAGT | 27 | 306 |
| 633593 | N/A | N/A | 80286 | 80301 | GCTGTATCTGAAACAA | 69 | 307 |

TABLE 5

Percent control of human EZH2 mRNA with 3-10-3 cEt gapmers with phosphorothioate internucleoside linkages

| ION Number | SEQ ID NO: 3 Start Site | SEQ ID NO: 3 Stop Site | Sequence (5' to 3') | EZH2 (% UTC) | SEQ ID NO |
|---|---|---|---|---|---|
| 633493 | 425 | 440 | ACTCCCTAGTCCCGCG | 31 | 308 |
| 633494 | 427 | 442 | ACACTCCCTAGTCCCG | 42 | 309 |
| 633495 | 430 | 445 | CGAACACTCCCTAGTC | 65 | 310 |
| 633496 | 436 | 451 | GGTCACCGAACACTCC | 40 | 311 |
| 633498 | 1086 | 1101 | GAATAATTGCACTTAC | 112 | 312 |
| 633499 | 1100 | 1115 | GTGTTGCATGAAAAGA | 19 | 313 |

Example 2: Effect of 3-10-3 cEt Gapmers and Mixed MOE and cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured HepG2 cells at a density of 20,000 cells per well were transfected using electroporation with 2,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (described hereinabove in Example 1) was used to measure mRNA levels. EZH2 mRNA levels were adjusted according to total RNA content, as measured by RiboGreen®. Results are presented in the table below as percent control of the amount of EZH2 mRNA, relative to untreated control cells (UTC).

The modified oligonucleotides in the table below are cEt and/or MOE containing gapmers. The gapmers have a central gap segment comprises 2'-deoxynucleosides which is flanked by wing segments on both the 5' end and on the 3' end. At least one nucleoside in the 5' wing segment and/or one nucleoside in the 3' wing segment has a MOE and/or cEt sugar modification. The "Chemistry" column describes the sugar modifications of each oligonucleotide. "k" indicates a cEt sugar modification; "d" indicates deoxyribose; and "e" indicates a MOE modification. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 6

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633355 | 964 | 979 | 61438 | 61453 | AGATTTAGCATTTGGT | kkk-d10-kkk | 12 | 102 |
| 633449 | 2086 | 2101 | N/A | N/A | AATCTCTCCACAGTAT | kkk-d10-kkk | 43 | 273 |
| 633453 | 2185 | 2200 | 78615 | 78630 | GGTTGCATCCACCACA | kkk-d10-kkk | 39 | 274 |
| 633454 | 2194 | 2209 | 78624 | 78639 | ACCCTTGCGGGTTGCA | kkk-d10-kkk | 59 | 53 |

TABLE 6-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 640732 | 2074 | 2089 | 76352 | 76367 | GTATTCTGAGATGAAT | kkk-d10-kkk | 93 | 314 |
| 652281 | 2073 | 2088 | 76351 | 76366 | TATTCTGAGATGAATT | kkk-d10-kkk | 77 | 315 |
| 652282 | 2075 | 2090 | 76353 | 76368 | AGTATTCTGAGATGAA | kkk-d10-kkk | 77 | 316 |
| 652283 | 2076 | 2091 | 76354 | 76369 | CAGTATTCTGAGATGA | kkk-d10-kkk | 76 | 317 |
| 652284 | 2077 | 2092 | 76355 | 76370 | ACAGTATTCTGAGATG | kkk-d10-kkk | 52 | 318 |
| 652285 | 2078 | 2093 | 76356 | 76371 | CACAGTATTCTGAGAT | kkk-d10-kkk | 46 | 319 |
| 652286 | 2079 | 2094 | 76357 | 76372 | CCACAGTATTCTGAGA | kkk-d10-kkk | 36 | 320 |
| 652287 | 2080 | 2095 | 76358 | 76373 | TCCACAGTATTCTGAG | kkk-d10-kkk | 41 | 321 |
| 652288 | 2081 | 2096 | 76359 | 76374 | CTCCACAGTATTCTGA | kkk-d10-kkk | 50 | 322 |
| 652289 | 2082 | 2097 | 76360 | 76375 | TCTCCACAGTATTCTG | kkk-d10-kkk | 36 | 323 |
| 652290 | 2083 | 2098 | 76361 | 76376 | CTCTCCACAGTATTCT | kkk-d10-kkk | 29 | 324 |
| 652291 | 2084 | 2099 | N/A | N/A | TCTCTCCACAGTATTC | kkk-d10-kkk | 32 | 325 |
| 652292 | 2085 | 2100 | N/A | N/A | ATCTCTCCACAGTATT | kkk-d10-kkk | 36 | 326 |
| 652293 | 2087 | 2102 | N/A | N/A | TAATCTCTCCACAGTA | kkk-d10-kkk | 40 | 327 |
| 652294 | 2088 | 2103 | N/A | N/A | ATAATCTCTCCACAGT | kkk-d10-kkk | 33 | 328 |
| 652295 | 2181 | 2196 | 78611 | 78626 | GCATCCACCACAAAAT | kkk-d10-kkk | 24 | 329 |
| 652296 | 2182 | 2197 | 78612 | 78627 | TGCATCCACCACAAAA | kkk-d10-kkk | 28 | 330 |
| 652297 | 2183 | 2198 | 78613 | 78628 | TTGCATCCACCACAAA | kkk-d10-kkk | 32 | 331 |
| 652298 | 2184 | 2199 | 78614 | 78629 | GTTGCATCCACCACAA | kkk-d10-kkk | 42 | 332 |
| 652299 | 2186 | 2201 | 78616 | 78631 | GGGTTGCATCCACCAC | kkk-d10-kkk | 49 | 333 |
| 652300 | 2187 | 2202 | 78617 | 78632 | CGGGTTGCATCCACCA | kkk-d10-kkk | 69 | 334 |
| 652301 | 2188 | 2203 | 78618 | 78633 | GCGGGTTGCATCCACC | kkk-d10-kkk | 33 | 335 |
| 652302 | 2189 | 2204 | 78619 | 78634 | TGCGGGTTGCATCCAC | kkk-d10-kkk | 27 | 336 |
| 652303 | 2190 | 2205 | 78620 | 78635 | TTGCGGGTTGCATCCA | kkk-d10-kkk | 25 | 337 |
| 652304 | 2191 | 2206 | 78621 | 78636 | CTTGCGGGTTGCATCC | kkk-d10-kkk | 28 | 338 |
| 652305 | 2192 | 2207 | 78622 | 78637 | CCTTGCGGGTTGCATC | kkk-d10-kkk | 36 | 339 |
| 652306 | 2193 | 2208 | 78623 | 78638 | CCCTTGCGGGTTGCAT | kkk-d10-kkk | 52 | 340 |
| 652307 | 2195 | 2210 | 78625 | 78640 | TACCCTTGCGGGTTGC | kkk-d10-kkk | 57 | 341 |
| 652308 | 2196 | 2211 | 78626 | 78641 | TTACCCTTGCGGGTTG | kkk-d10-kkk | 88 | 342 |
| 652341 | 2074 | 2089 | 76352 | 76367 | GTATTCTGAGATGAAT | ekkk-d8-kkke | 98 | 318 |
| 652342 | 2075 | 2090 | 76353 | 76368 | AGTATTCTGAGATGAA | ekkk-d8-kkke | 88 | 320 |
| 652343 | 2076 | 2091 | 76354 | 76369 | CAGTATTCTGAGATGA | ekkk-d8-kkke | 63 | 321 |
| 652344 | 2077 | 2092 | 76355 | 76370 | ACAGTATTCTGAGATG | ekkk-d8-kkke | 63 | 322 |
| 652345 | 2078 | 2093 | 76356 | 76371 | CACAGTATTCTGAGAT | ekkk-d8-kkke | 56 | 323 |
| 652346 | 2079 | 2094 | 76357 | 76372 | CCACAGTATTCTGAGA | ekkk-d8-kkke | 49 | 324 |
| 652347 | 2080 | 2095 | 76358 | 76373 | TCCACAGTATTCTGAG | ekkk-d8-kkke | 49 | 325 |

TABLE 6-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 652348 | 2081 | 2096 | 76359 | 76374 | CTCCACAGTATTCTGA | ekkk-d8-kkke | 57 | 326 |
| 652349 | 2082 | 2097 | 76360 | 76375 | TCTCCACAGTATTCTG | ekkk-d8-kkke | 66 | 327 |
| 652350 | 2083 | 2098 | 76361 | 76376 | CTCTCCACAGTATTCT | ekkk-d8-kkke | 42 | 328 |
| 652351 | 2084 | 2099 | N/A | N/A | TCTCTCCACAGTATTC | ekkk-d8-kkke | 41 | 329 |
| 652352 | 2085 | 2100 | N/A | N/A | ATCTCTCCACAGTATT | ekkk-d8-kkke | 54 | 330 |
| 652353 | 2086 | 2101 | N/A | N/A | AATCTCTCCACAGTAT | ekkk-d8-kkke | 37 | 273 |

Example 3: Effect of 3-10-3 cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured HepG2 cells at a density of 20,000 cells per well were transfected using electroporation with 2,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC).

The modified oligonucleotides in the tables below are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 7

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633331 | 596 | 611 | 58219 | 58234 | GTTCTTCAATGAAAGT | 24 | 96 |
| 633335 | 654 | 669 | 59124 | 59139 | TCATTTATAAACCCAC | 13 | 97 |
| 633355 | 964 | 979 | 61438 | 61453 | AGATTTAGCATTTGGT | 17 | 102 |
| 633473 | 2390 | 2405 | 80338 | 80353 | AAGGGATTTCCATTTC | 18 | 279 |
| 662324 | 529 | 544 | 58152 | 58167 | AGTTTCATCTTCCACC | 22 | 343 |
| 662325 | 545 | 560 | 58168 | 58183 | GAATGTTATGTAAAAC | 81 | 344 |
| 662326 | 549 | 564 | 58172 | 58187 | TAAGGAATGTTATGTA | 56 | 345 |
| 662327 | 551 | 566 | 58174 | 58189 | TATAAGGAATGTTATG | 81 | 346 |
| 662328 | 553 | 568 | 58176 | 58191 | CATATAAGGAATGTTA | 82 | 347 |
| 662329 | 555 | 570 | 58178 | 58193 | CCCATATAAGGAATGT | 29 | 348 |
| 662330 | 569 | 584 | 58192 | 58207 | CTAAAACTTCATCTCC | 40 | 349 |

TABLE 7-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662331 | 572 | 587 | 58195 | 58210 | GATCTAAAACTTCATC | 58 | 350 |
| 662332 | 574 | 589 | 58197 | 58212 | CTGATCTAAAACTTCA | 39 | 351 |
| 662333 | 578 | 593 | 58201 | 58216 | CATCCTGATCTAAAAC | 49 | 352 |
| 662334 | 580 | 595 | 58203 | 58218 | ACCATCCTGATCTAAA | 24 | 353 |
| 662335 | 582 | 597 | 58205 | 58220 | GTACCATCCTGATCTA | 24 | 354 |
| 662336 | 584 | 599 | 58207 | 58222 | AAGTACCATCCTGATC | 38 | 355 |
| 662337 | 586 | 601 | 58209 | 58224 | GAAAGTACCATCCTGA | 28 | 356 |
| 662338 | 588 | 603 | 58211 | 58226 | ATGAAAGTACCATCCT | 23 | 357 |
| 662339 | 590 | 605 | 58213 | 58228 | CAATGAAAGTACCATC | 43 | 358 |
| 662340 | 592 | 607 | 58215 | 58230 | TTCAATGAAAGTACCA | 22 | 359 |
| 662341 | 593 | 608 | 58216 | 58231 | CTTCAATGAAAGTACC | 24 | 360 |
| 662342 | 594 | 609 | 58217 | 58232 | TCTTCAATGAAAGTAC | 40 | 361 |
| 662343 | 599 | 614 | 58222 | 58237 | TTAGTTCTTCAATGAA | 51 | 362 |
| 662344 | 600 | 615 | 58223 | 58238 | ATTAGTTCTTCAATGA | 46 | 363 |
| 662345 | 601 | 616 | 58224 | 58239 | TATTAGTTCTTCAATG | 87 | 364 |
| 662346 | 629 | 644 | 58252 | 58267 | CCCCGTGTACTTTCCC | 51 | 365 |
| 662347 | 631 | 646 | 58254 | 58269 | ATCCCCGTGTACTTTC | 30 | 366 |
| 662348 | 633 | 648 | 58256 | 58271 | CTATCCCCGTGTACTT | 38 | 367 |
| 662349 | 635 | 650 | 58258 | 58273 | CTCTATCCCCGTGTAC | 58 | 368 |
| 662350 | 637 | 652 | N/A | N/A | TTCTCTATCCCCGTGT | 40 | 369 |
| 662351 | 639 | 654 | N/A | N/A | CATTCTCTATCCCCGT | 34 | 370 |
| 662352 | 641 | 656 | N/A | N/A | CACATTCTCTATCCCC | 32 | 371 |
| 662353 | 643 | 658 | N/A | N/A | CCCACATTCTCTATCC | 46 | 372 |
| 662354 | 645 | 660 | N/A | N/A | AACCCACATTCTCTAT | 61 | 373 |
| 662355 | 647 | 662 | N/A | N/A | TAAACCCACATTCTCT | 43 | 374 |
| 662356 | 649 | 664 | 59119 | 59134 | TATAAACCCACATTCT | 52 | 375 |
| 662357 | 650 | 665 | 59120 | 59135 | TTATAAACCCACATTC | 56 | 376 |
| 662358 | 656 | 671 | 59126 | 59141 | CATCATTTATAAACCC | 16 | 377 |
| 662359 | 657 | 672 | 59127 | 59142 | TCATCATTTATAAACC | 37 | 378 |
| 662360 | 678 | 693 | 59148 | 59163 | TTCACCAACTCCACAA | 39 | 379 |
| 662361 | 680 | 695 | 59150 | 59165 | CATTCACCAACTCCAC | 24 | 380 |
| 662362 | 686 | 701 | 59156 | 59171 | CAAGGGCATTCACCAA | 19 | 381 |
| 662363 | 688 | 703 | 59158 | 59173 | ACCAAGGGCATTCACC | 24 | 382 |
| 662364 | 690 | 705 | 59160 | 59175 | TGACCAAGGGCATTCA | 21 | 383 |
| 662365 | 692 | 707 | 59162 | 59177 | ATTGACCAAGGGCATT | 14 | 384 |
| 662366 | 694 | 709 | 59164 | 59179 | ATATTGACCAAGGGCA | 18 | 385 |

TABLE 7-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662367 | 696 | 711 | 59166 | 59181 | TTATATTGACCAAGGG | 27 | 386 |
| 662368 | 700 | 715 | 59170 | 59185 | ATCATTATATTGACCA | 12 | 387 |
| 662369 | 702 | 717 | 59172 | 59187 | TCATCATTATATTGAC | 41 | 388 |
| 662370 | 707 | 722 | 59177 | 59192 | CGTCATCATCATTATA | 30 | 389 |
| 662371 | 725 | 740 | 59195 | 59210 | CGTCTCCATCATCATC | 27 | 390 |
| 662372 | 740 | 755 | 59210 | 59225 | CTCTTTCTTCAGGATC | 42 | 391 |
| 662373 | 763 | 778 | 59233 | 59248 | CTCCAGATCTTTCTGC | 93 | 392 |
| 662374 | 766 | 781 | 59236 | 59251 | ATCCTCCAGATCTTTC | 89 | 393 |
| 662375 | 768 | 783 | 59238 | 59253 | TGATCCTCCAGATCTT | 102 | 394 |
| 662376 | 770 | 785 | 59240 | 59255 | GGTGATCCTCCAGATC | 49 | 395 |
| 662377 | 772 | 787 | 59242 | 59257 | TCGGTGATCCTCCAGA | 35 | 396 |
| 662378 | 774 | 789 | 59244 | 59259 | TCTCGGTGATCCTCCA | 36 | 397 |
| 662379 | 776 | 791 | 59246 | 59261 | CATCTCGGTGATCCTC | 25 | 398 |
| 662380 | 778 | 793 | N/A | N/A | ATCATCTCGGTGATCC | 13 | 399 |
| 662381 | 780 | 795 | N/A | N/A | TTATCATCTCGGTGAT | 49 | 400 |
| 662382 | 782 | 797 | N/A | N/A | CTTTATCATCTCGGTG | 42 | 401 |
| 662383 | 784 | 799 | N/A | N/A | TTCTTTATCATCTCGG | 33 | 402 |
| 662384 | 787 | 802 | N/A | N/A | GCTTTCTTTATCATCT | 50 | 403 |
| 662385 | 789 | 804 | N/A | N/A | CGGCTTTCTTTATCAT | 49 | 404 |
| 662386 | 791 | 806 | 60734 | 60749 | GGCGGCTTTCTTTATC | 70 | 405 |
| 662387 | 793 | 808 | 60736 | 60751 | TGGGCGGCTTTCTTTA | 62 | 406 |
| 662388 | 795 | 810 | 60738 | 60753 | GGTGGGCGGCTTTCTT | 44 | 407 |
| 662389 | 797 | 812 | 60740 | 60755 | GAGGTGGGCGGCTTTC | 32 | 408 |
| 662390 | 800 | 815 | 60743 | 60758 | TCCGAGGTGGGCGGCT | 31 | 409 |
| 662391 | 802 | 817 | 60745 | 60760 | TTTCCGAGGTGGGCGG | 26 | 410 |
| 662392 | 805 | 820 | 60748 | 60763 | AAATTTCCGAGGTGGG | 28 | 411 |
| 662393 | 807 | 822 | 60750 | 60765 | GGAAATTTCCGAGGTG | 28 | 412 |
| 662394 | 810 | 825 | 60753 | 60768 | GAAGGAAATTTCCGAG | 35 | 413 |
| 662395 | 812 | 827 | 60755 | 60770 | CAGAAGGAAATTTCCG | 51 | 414 |
| 662396 | 837 | 852 | 60780 | 60795 | GAGGAAATGGCTTCAA | 27 | 415 |
| 662397 | 840 | 855 | 60783 | 60798 | ATTGAGGAAATGGCTT | 29 | 416 |
| 662398 | 848 | 863 | 60791 | 60806 | CTGGAAACATTGAGGA | 30 | 417 |

TABLE 8

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 17 | 97 |
| 633352 | 921 | 936 | 61395 | 61410 | GGAAGTGCGCCTGGGA | 8 | 175 |
| 633355 | 964 | 979 | 61438 | 61453 | AGATTTAGCATTTGGT | 12 | 102 |
| 633356 | 970 | 985 | 61444 | 61459 | CTGAACAGATTTAGCA | 18 | 176 |
| 633357 | 985 | 1000 | 61459 | 61474 | TAAGCTTTGCTCTCTC | 9 | 250 |
| 633358 | 991 | 1006 | 61465 | 61480 | GGAGTGTAAGCTTTGC | 7 | 29 |
| 633473 | 2390 | 2405 | 80338 | 80353 | AAGGGATTTCCATTTC | 19 | 279 |
| 640640 | 857 | 872 | 60800 | 60815 | TGCCCTTATCTGGAAA | 74 | 418 |
| 662399 | 850 | 865 | 60793 | 60808 | ATCTGGAAACATTGAG | 40 | 419 |
| 662400 | 853 | 868 | 60796 | 60811 | CTTATCTGGAAACATT | 63 | 420 |
| 662401 | 855 | 870 | 60798 | 60813 | CCCTTATCTGGAAACA | 45 | 421 |
| 662402 | 859 | 874 | 60802 | 60817 | TGTGCCCTTATCTGGA | 49 | 422 |
| 662403 | 861 | 876 | 60804 | 60819 | GCTGTGCCCTTATCTG | 16 | 423 |
| 662404 | 863 | 878 | 60806 | 60821 | CTGCTGTGCCCTTATC | 29 | 424 |
| 662405 | 865 | 880 | 60808 | 60823 | TTCTGCTGTGCCCTTA | 35 | 425 |
| 662406 | 867 | 882 | 60810 | 60825 | TCTTCTGCTGTGCCCT | 28 | 426 |
| 662407 | 870 | 885 | 60813 | 60828 | AGTTCTTCTGCTGTGC | 31 | 427 |
| 662408 | 872 | 887 | 60815 | 60830 | TTAGTTCTTCTGCTGT | 54 | 428 |
| 662409 | 874 | 889 | 60817 | 60832 | CTTTAGTTCTTCTGCT | 63 | 429 |
| 662410 | 894 | 909 | N/A | N/A | GTGAGTTCTTTATATT | 47 | 430 |
| 662411 | 896 | 911 | 61370 | 61385 | CGGTGAGTTCTTTATA | 22 | 431 |
| 662412 | 898 | 913 | 61372 | 61387 | TTCGGTGAGTTCTTTA | 24 | 432 |
| 662413 | 900 | 915 | 61374 | 61389 | TGTTCGGTGAGTTCTT | 22 | 433 |
| 662414 | 902 | 917 | 61376 | 61391 | GCTGTTCGGTGAGTTC | 17 | 434 |
| 662415 | 904 | 919 | 61378 | 61393 | CTGCTGTTCGGTGAGT | 26 | 435 |
| 662416 | 906 | 921 | 61380 | 61395 | AGCTGCTGTTCGGTGA | 24 | 436 |
| 662417 | 908 | 923 | 61382 | 61397 | GGAGCTGCTGTTCGGT | 12 | 437 |
| 662418 | 910 | 925 | 61384 | 61399 | TGGGAGCTGCTGTTCG | 18 | 438 |
| 662419 | 914 | 929 | 61388 | 61403 | CGCCTGGGAGCTGCTG | 33 | 439 |
| 662420 | 916 | 931 | 61390 | 61405 | TGCGCCTGGGAGCTGC | 27 | 440 |
| 662421 | 917 | 932 | 61391 | 61406 | GTGCGCCTGGGAGCTG | 17 | 441 |
| 662422 | 918 | 933 | 61392 | 61407 | AGTGCGCCTGGGAGCT | 11 | 442 |
| 662423 | 919 | 934 | 61393 | 61408 | AAGTGCGCCTGGGAGC | 20 | 443 |
| 662424 | 920 | 935 | 61394 | 61409 | GAAGTGCGCCTGGGAG | 12 | 444 |
| 662425 | 922 | 937 | 61396 | 61411 | AGGAAGTGCGCCTGGG | 9 | 445 |
| 662426 | 923 | 938 | 61397 | 61412 | GAGGAAGTGCGCCTGG | 12 | 446 |

TABLE 8-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662427 | 924 | 939 | 61398 | 61413 | GGAGGAAGTGCGCCTG | 16 | 447 |
| 662428 | 925 | 940 | 61399 | 61414 | AGGAGGAAGTGCGCCT | 41 | 448 |
| 662429 | 926 | 941 | 61400 | 61415 | CAGGAGGAAGTGCGCC | 25 | 449 |
| 662430 | 928 | 943 | 61402 | 61417 | TTCAGGAGGAAGTGCG | 28 | 450 |
| 662431 | 930 | 945 | 61404 | 61419 | CATTCAGGAGGAAGTG | 33 | 451 |
| 662432 | 932 | 947 | 61406 | 61421 | TACATTCAGGAGGAAG | 30 | 452 |
| 662433 | 934 | 949 | 61408 | 61423 | GGTACATTCAGGAGGA | 13 | 453 |
| 662434 | 953 | 968 | 61427 | 61442 | TTGGTCCATCTATGTT | 15 | 454 |
| 662435 | 955 | 970 | 61429 | 61444 | ATTTGGTCCATCTATG | 46 | 455 |
| 662436 | 957 | 972 | 61431 | 61446 | GCATTTGGTCCATCTA | 17 | 456 |
| 662437 | 959 | 974 | 61433 | 61448 | TAGCATTTGGTCCATC | 61 | 457 |
| 662438 | 960 | 975 | 61434 | 61449 | TTAGCATTTGGTCCAT | 17 | 458 |
| 662439 | 961 | 976 | 61435 | 61450 | TTTAGCATTTGGTCCA | 22 | 459 |
| 662440 | 962 | 977 | 61436 | 61451 | ATTTAGCATTTGGTCC | 28 | 460 |
| 662441 | 963 | 978 | 61437 | 61452 | GATTTAGCATTTGGTC | 19 | 461 |
| 662442 | 965 | 980 | 61439 | 61454 | CAGATTTAGCATTTGG | 9 | 462 |
| 662443 | 966 | 981 | 61440 | 61455 | ACAGATTTAGCATTTG | 22 | 463 |
| 662444 | 968 | 983 | 61442 | 61457 | GAACAGATTTAGCATT | 37 | 464 |
| 662445 | 969 | 984 | 61443 | 61458 | TGAACAGATTTAGCAT | 33 | 465 |
| 662446 | 971 | 986 | 61445 | 61460 | TCTGAACAGATTTAGC | 22 | 466 |
| 662447 | 972 | 987 | 61446 | 61461 | CTCTGAACAGATTTAG | 24 | 467 |
| 662448 | 973 | 988 | 61447 | 61462 | TCTCTGAACAGATTTA | 26 | 468 |
| 662449 | 974 | 989 | 61448 | 61463 | CTCTCTGAACAGATTT | 21 | 469 |
| 662450 | 975 | 990 | 61449 | 61464 | TCTCTCTGAACAGATT | 39 | 470 |
| 662451 | 977 | 992 | 61451 | 61466 | GCTCTCTCTGAACAGA | 31 | 471 |
| 662452 | 979 | 994 | 61453 | 61468 | TTGCTCTCTCTGAACA | 22 | 472 |
| 662453 | 982 | 997 | 61456 | 61471 | GCTTTGCTCTCTCTGA | 8 | 473 |
| 662454 | 983 | 998 | 61457 | 61472 | AGCTTTGCTCTCTCTG | 9 | 474 |
| 662455 | 986 | 1001 | 61460 | 61475 | GTAAGCTTTGCTCTCT | 9 | 475 |
| 662456 | 987 | 1002 | 61461 | 61476 | TGTAAGCTTTGCTCTC | 8 | 476 |
| 662457 | 988 | 1003 | 61462 | 61477 | GTGTAAGCTTTGCTCT | 13 | 477 |
| 662458 | 989 | 1004 | 61463 | 61478 | AGTGTAAGCTTTGCTC | 17 | 478 |
| 662459 | 990 | 1005 | 61464 | 61479 | GAGTGTAAGCTTTGCT | 56 | 479 |
| 662460 | 992 | 1007 | 61466 | 61481 | AGGAGTGTAAGCTTTG | 9 | 480 |
| 662461 | 993 | 1008 | 61467 | 61482 | AAGGAGTGTAAGCTTT | 28 | 481 |
| 662462 | 994 | 1009 | 61468 | 61483 | AAAGGAGTGTAAGCTT | 25 | 482 |

TABLE 8-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662463 | 995 | 1010 | 61469 | 61484 | GAAAGGAGTGTAAGCT | 13 | 483 |
| 662464 | 996 | 1011 | 61470 | 61485 | TGAAAGGAGTGTAAGC | 28 | 484 |
| 662465 | 998 | 1013 | 61472 | 61487 | TATGAAAGGAGTGTAA | 44 | 485 |
| 662466 | 1000 | 1015 | 61474 | 61489 | CGTATGAAAGGAGTGT | 15 | 486 |
| 662467 | 1015 | 1030 | 61489 | 61504 | TCGCCTACAGAAAGC | 34 | 487 |
| 662468 | 1017 | 1032 | 61491 | 61506 | CATCGCCTACAGAAAA | 62 | 488 |

TABLE 9

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 15 | 97 |
| 633473 | 2390 | 2405 | 80338 | 80353 | AAGGGATTTCCATTTC | 14 | 279 |
| 633483 | 2571 | 2586 | 80519 | 80534 | CAGCTGGTGAGAAGGC | 14 | 132 |
| 633486 | 2600 | 2615 | 80548 | 80563 | GCAAAAATTCACTGGT | 20 | 60 |
| 633489 | 2650 | 2665 | 80598 | 80613 | GTTCAAGTATTCTTTA | 40 | 282 |
| 633570 | N/A | N/A | 69060 | 69075 | AACAGTTTTATACTTC | 19 | 78 |
| 662960 | 2574 | 2589 | 80522 | 80537 | TTGCAGCTGGTGAGAA | 34 | 489 |
| 662961 | 2575 | 2590 | 80523 | 80538 | TTTGCAGCTGGTGAGA | 23 | 490 |
| 662962 | 2576 | 2591 | 80524 | 80539 | CTTTGCAGCTGGTGAG | 10 | 491 |
| 662963 | 2578 | 2593 | 80526 | 80541 | CACTTTGCAGCTGGTG | 24 | 492 |
| 662964 | 2580 | 2595 | 80528 | 80543 | AACACTTTGCAGCTGG | 6 | 493 |
| 662965 | 2583 | 2598 | 80531 | 80546 | CAAAACACTTTGCAGC | 36 | 494 |
| 662966 | 2587 | 2602 | 80535 | 80550 | GGTACAAAACACTTTG | 26 | 495 |
| 662967 | 2589 | 2604 | 80537 | 80552 | CTGGTACAAAACACTT | 35 | 496 |
| 662968 | 2591 | 2606 | 80539 | 80554 | CACTGGTACAAAACAC | 45 | 497 |
| 662969 | 2594 | 2609 | 80542 | 80557 | ATTCACTGGTACAAAA | 55 | 498 |
| 662970 | 2596 | 2611 | 80544 | 80559 | AAATTCACTGGTACAA | 42 | 499 |
| 662971 | 2599 | 2614 | 80547 | 80562 | CAAAAATTCACTGGTA | 68 | 500 |
| 662972 | 2604 | 2619 | 80552 | 80567 | TATTGCAAAAATTCAC | 92 | 501 |
| 662973 | 2611 | 2626 | 80559 | 80574 | ACTGCATTATTGCAAA | 30 | 502 |
| 662974 | 2613 | 2628 | 80561 | 80576 | ATACTGCATTATTGCA | 28 | 503 |
| 662975 | 2615 | 2630 | 80563 | 80578 | CCATACTGCATTATTG | 41 | 504 |
| 662976 | 2617 | 2632 | 80565 | 80580 | TACCATACTGCATTAT | 52 | 505 |
| 662977 | 2619 | 2634 | 80567 | 80582 | TGTACCATACTGCATT | 33 | 506 |

TABLE 9-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662978 | 2621 | 2636 | 80569 | 80584 | AATGTACCATACTGCA | 25 | 507 |
| 662979 | 2628 | 2643 | 80576 | 80591 | GTTGAAAAATGTACCA | 24 | 508 |
| 662980 | 2639 | 2654 | 80587 | 80602 | CTTTATTCAAAGTTGA | 39 | 509 |
| 662981 | 2640 | 2655 | 80588 | 80603 | TCTTTATTCAAAGTTG | 25 | 510 |
| 662982 | 2652 | 2667 | 80600 | 80615 | AAGTTCAAGTATTCTT | 62 | 511 |
| 662983 | 2653 | 2668 | 80601 | 80616 | CAAGTTCAAGTATTCT | 57 | 512 |
| 662984 | 2656 | 2671 | 80604 | 80619 | GGACAAGTTCAAGTAT | 84 | 513 |
| 662985 | 2658 | 2673 | 80606 | 80621 | AAGGACAAGTTCAAGT | 89 | 514 |
| 662986 | 2661 | 2676 | 80609 | 80624 | AACAAGGACAAGTTCA | 80 | 515 |
| 662987 | 2663 | 2678 | 80611 | 80626 | TCAACAAGGACAAGTT | 70 | 516 |
| 662988 | 2665 | 2680 | 80613 | 80628 | ATTCAACAAGGACAAG | 60 | 517 |
| 662989 | N/A | N/A | 5022 | 5037 | TAAGAAACTGCTAACC | 33 | 518 |
|  |  |  | 7879 | 7894 |  |  |  |
| 662990 | N/A | N/A | 69056 | 69071 | GTTTTATACTTCATTC | 40 | 519 |
| 662991 | N/A | N/A | 69058 | 69073 | CAGTTTTATACTTCAT | 31 | 520 |
| 662992 | N/A | N/A | 69059 | 69074 | ACAGTTTTATACTTCA | 10 | 521 |
| 662993 | N/A | N/A | 69061 | 69076 | CAACAGTTTTATACTT | 86 | 522 |
| 662994 | N/A | N/A | 69062 | 69077 | CCAACAGTTTTATACT | 35 | 523 |
| 662995 | N/A | N/A | 69063 | 69078 | GCCAACAGTTTTATAC | 59 | 524 |
| 662996 | N/A | N/A | 69064 | 69079 | AGCCAACAGTTTTATA | 61 | 525 |
| 663088 | N/A | N/A | 3932 | 3947 | CGATACCCGGGACCGG | 95 | 526 |
| 663089 | N/A | N/A | 4804 | 4819 | AAAGTGGCAACTCACT | 52 | 527 |
| 663090 | N/A | N/A | 4957 | 4972 | CTTCTACCACCTCATC | 44 | 528 |
| 663091 | N/A | N/A | 5110 | 5125 | CGTTAAATTTCTTAGG | 52 | 529 |
| 663092 | N/A | N/A | 5268 | 5283 | GATGACATCAAAACGC | 15 | 530 |
| 663093 | N/A | N/A | 5418 | 5433 | ACACACTTGTACAGTA | 24 | 531 |
| 663094 | N/A | N/A | 5718 | 5733 | TTAGATCTTTATCATA | 53 | 532 |
| 663095 | N/A | N/A | 5893 | 5908 | CAGAATTAATAGTAAC | 87 | 533 |
| 663096 | N/A | N/A | 6433 | 6448 | CCCCAAAGAGATGTTT | 56 | 534 |
| 663097 | N/A | N/A | 6590 | 6605 | ATGTATTTGTGCAAGG | 5 | 535 |
| 663098 | N/A | N/A | 6741 | 6756 | CACTGCTCATGTAAAG | 62 | 536 |
| 663099 | N/A | N/A | 6891 | 6906 | AATCTATCATGATTTA | 68 | 537 |
| 663100 | N/A | N/A | 7042 | 7057 | ATAAACCCTGTGGGA | 84 | 538 |
| 663101 | N/A | N/A | 7193 | 7208 | CTATTCTCTAGCAAAT | 81 | 539 |
| 663102 | N/A | N/A | 7530 | 7545 | GATCATCAATATCAAC | 14 | 540 |
| 663103 | N/A | N/A | 7680 | 7695 | TTACACTGTCGCTACA | 69 | 541 |

TABLE 9-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 663104 | N/A | N/A | 7830 | 7845 | TACCAAGTAGTGGAAC | 41 | 542 |
| 663105 | N/A | N/A | 8005 | 8020 | CACTGGTAATACCAGT | 108 | 543 |
| 663106 | N/A | N/A | 8156 | 8171 | ACACAATGGCTCAGCC | 46 | 544 |
| 663107 | N/A | N/A | 8586 | 8601 | ATTATCGGAGGCTGGG | 63 | 545 |
| 663108 | N/A | N/A | 9142 | 9157 | AACTGAGATCACGCAT | 86 | 546 |
| 663109 | N/A | N/A | 9402 | 9417 | CACAAGGTGGTTCTTA | 26 | 547 |
| 663110 | N/A | N/A | 9559 | 9574 | CATCCATGTATCAGAA | 17 | 548 |
| 663111 | N/A | N/A | 9734 | 9749 | CATTAAACTCCCCATT | 88 | 549 |
| 663112 | N/A | N/A | 10070 | 10085 | TATGTAGTGAAACAGA | 23 | 550 |
| 663113 | N/A | N/A | 10520 | 10535 | ATCAAACACTTTTTGC | 44 | 551 |
| 663114 | N/A | N/A | 10696 | 10711 | AGCGAACACATTTAAT | 31 | 552 |
| 663115 | N/A | N/A | 11019 | 11034 | ACTTAATCTCTCCATC | 44 | 553 |
| 663116 | N/A | N/A | 11180 | 11195 | GTTCTTCAGGGAAGTG | 9 | 554 |
| 663117 | N/A | N/A | 11330 | 11345 | GCACATTCATAAACTG | 14 | 555 |
| 663118 | N/A | N/A | 11482 | 11497 | CAACACCTATTAAAAC | 103 | 556 |
| 663119 | N/A | N/A | 11632 | 11647 | AACCATTATAGATCTT | 19 | 557 |
| 663120 | N/A | N/A | 11866 | 11881 | CGCCTAAAACTACAAA | 59 | 558 |
| 663121 | N/A | N/A | 12017 | 12032 | GACACAGGAAAACCCC | 27 | 559 |
| 663122 | N/A | N/A | 12182 | 12197 | ATCCATGGGTAAATGA | 24 | 560 |

TABLE 10

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 15 | 97 |
| 633473 | 2390 | 2405 | 80338 | 80353 | AAGGGATTTCCATTTC | 21 | 279 |
| 663199 | N/A | N/A | 31298 | 31313 | CGAGACTGGAAGCAAA | 72 | 561 |
| 663200 | N/A | N/A | 31452 | 31467 | ACCCAAGACTTTTGTT | 61 | 562 |
| 663201 | N/A | N/A | 31776 | 31791 | TCTCATAAGGGTACCA | 34 | 563 |
| 663202 | N/A | N/A | 31964 | 31979 | GGTAAACTGTATGCAA | 30 | 564 |
| 663203 | N/A | N/A | 32382 | 32397 | AAGTAGTGGCTATCAG | 44 | 565 |
| 663204 | N/A | N/A | 32533 | 32548 | GGCCAAGTTACTGCAC | 68 | 566 |
| 663205 | N/A | N/A | 32687 | 32702 | TCCAAGTAATAAACTA | 67 | 567 |
| 663206 | N/A | N/A | 32837 | 32852 | CCACTTTGAGGGTTGT | 71 | 568 |

TABLE 10-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 663207 | N/A | N/A | 33001 | 33016 | ATCCTATGCCTGAGGG | 76 | 569 |
| 663208 | N/A | N/A | 33333 | 33348 | TAAGTAATATGATTAC | 94 | 570 |
| 663209 | N/A | N/A | 33491 | 33506 | ATTTGGTCTGGCCAAA | 61 | 571 |
| 663210 | N/A | N/A | 33896 | 33911 | GCCAATAACTGAATAA | 68 | 572 |
| 663211 | N/A | N/A | 34200 | 34215 | CAAATGTAGAATCCCA | 54 | 573 |
| 663212 | N/A | N/A | 34353 | 34368 | GATTACTAAATACCTA | 86 | 574 |
| 663213 | N/A | N/A | 34552 | 34567 | TTTAAGGAGTGTGCAA | 51 | 575 |
| 663214 | N/A | N/A | 34858 | 34873 | CATAAGGATGGCCAGG | 61 | 576 |
| 663215 | N/A | N/A | 35170 | 35185 | ACAGAGGGTATCTCAG | 30 | 577 |
| 663216 | N/A | N/A | 35326 | 35341 | CCTCAAAGAACAGAGT | 75 | 578 |
| 663217 | N/A | N/A | 35800 | 35815 | TTAGCAGAATGTAGTG | 28 | 579 |
| 663218 | N/A | N/A | 35956 | 35971 | ACTTTATCCAGAATAC | 52 | 580 |
| 663219 | N/A | N/A | 36170 | 36185 | AACTGTCTTCACACCA | 70 | 581 |
| 663220 | N/A | N/A | 36409 | 36424 | CAGATTCAAGGCCACG | 26 | 582 |
| 663221 | N/A | N/A | 36568 | 36583 | ACACACTTGGTTCTGT | 56 | 583 |
| 663222 | N/A | N/A | 36879 | 36894 | CTTGTATCTTATCAGC | 30 | 584 |
| 663223 | N/A | N/A | 37044 | 37059 | TAGCTAGAGTCTTCTC | 41 | 585 |
| 663224 | N/A | N/A | 37194 | 37209 | AGATAGTACTAAACTC | 87 | 586 |
| 663225 | N/A | N/A | 37348 | 37363 | ACTCTATTCCCACTGT | 58 | 587 |
| 663226 | N/A | N/A | 37502 | 37517 | ATCCAGGTAGTTCTTT | 44 | 588 |
| 663227 | N/A | N/A | 37982 | 37997 | TAATGTGGGTGTTATT | 81 | 589 |
| 663228 | N/A | N/A | 38307 | 38322 | GACCAAAGGACATCAA | 72 | 590 |
| 663229 | N/A | N/A | 38463 | 38478 | GAACTATTCCAAGTGA | 76 | 591 |
| 663230 | N/A | N/A | 38616 | 38631 | AAAGTCTGGCTGGCAG | 87 | 592 |
| 663231 | N/A | N/A | 38788 | 38803 | GTTTATACAAAAGCAC | 69 | 593 |
| 663232 | N/A | N/A | 39027 | 39042 | AGACTCCCATATACTT | 50 | 594 |
| 663233 | N/A | N/A | 39352 | 39367 | GGCGAAGAAATTCATT | 71 | 595 |
| 663234 | N/A | N/A | 39502 | 39517 | CATAAAAACTTCATGC | 82 | 596 |
| 663235 | N/A | N/A | 39806 | 39821 | CAATTTGTGCTTTATC | 52 | 597 |
| 663236 | N/A | N/A | 40135 | 40150 | TGATAAAGTCTGTATT | 79 | 598 |
| 663237 | N/A | N/A | 40285 | 40300 | GGAATAATATAACTGA | 34 | 599 |
| 663238 | N/A | N/A | 40435 | 40450 | TAGGAACATGATCCCA | 37 | 600 |
| 663239 | N/A | N/A | 40601 | 40616 | CTAACAATCAGTGAAG | 63 | 601 |
| 663240 | N/A | N/A | 40845 | 40860 | CCTTAATTGTATATTC | 109 | 602 |
| 663241 | N/A | N/A | 40997 | 41012 | CTAAACAAAGACTGAT | 86 | 603 |
| 663242 | N/A | N/A | 41174 | 41189 | AACGATTGCCATCCTT | 26 | 604 |

TABLE 10-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 663243 | N/A | N/A | 41324 | 41339 | CTGTAAAGCAGGTTAA | 94 | 605 |
| 663244 | N/A | N/A | 41674 | 41689 | ATCTACAGCAGTCATT | 58 | 606 |
| 663245 | N/A | N/A | 41824 | 41839 | CTAAATAGTGATCTGA | 61 | 607 |
| 663246 | N/A | N/A | 41977 | 41992 | CTCTCAACAAGAAATT | 79 | 608 |
| 663247 | N/A | N/A | 42143 | 42158 | TTAGACTTTTGCCATT | 41 | 609 |
| 663248 | N/A | N/A | 42296 | 42311 | CCATATTTAGACATTC | 39 | 610 |
| 663249 | N/A | N/A | 42607 | 42622 | CACTGTATAATCAATA | 66 | 611 |
| 663250 | N/A | N/A | 42769 | 42784 | CTAAAAGGTCACCAAA | 70 | 612 |
| 663251 | N/A | N/A | 42919 | 42934 | TATAAACCTAAGTTAG | 94 | 613 |
| 663252 | N/A | N/A | 43073 | 43088 | GCAAACTGACTAAATG | 87 | 614 |
| 663253 | N/A | N/A | 43223 | 43238 | AAATATCCACTTGAAC | 64 | 615 |
| 663254 | N/A | N/A | 43376 | 43391 | TACTGTGGAAGTACTA | 61 | 616 |
| 663255 | N/A | N/A | 43526 | 43541 | TACCAACACCAGCAAC | 77 | 617 |
| 663256 | N/A | N/A | 43852 | 43867 | CCAAACAAGAATCACT | 46 | 618 |
| 663257 | N/A | N/A | 44002 | 44017 | GCACTTACATATAATT | 52 | 619 |
| 663258 | N/A | N/A | 44423 | 44438 | AACTACAAATGGGAGT | 50 | 620 |
| 663259 | N/A | N/A | 45214 | 45229 | AAACACATTAAGGGAC | 73 | 621 |
| 663260 | N/A | N/A | 45562 | 45577 | TACCAATATGAAGACC | 76 | 622 |
| 663261 | N/A | N/A | 45717 | 45732 | TGATATGAAGTCAGTG | 49 | 623 |
| 663262 | N/A | N/A | 45869 | 45884 | CTTACAAGAACATTAT | 80 | 624 |
| 663263 | N/A | N/A | 46026 | 46041 | GAAGAGCAAATCTGTA | 34 | 625 |
| 663264 | N/A | N/A | 46191 | 46206 | ACATGTAACAGGTATT | 44 | 626 |
| 663265 | N/A | N/A | 46341 | 46356 | TCAAAGAATGTATCTG | 58 | 627 |
| 663266 | N/A | N/A | 46493 | 46508 | GAGTAAGACAGACACT | 69 | 628 |
| 663267 | N/A | N/A | 46643 | 46658 | ATACAGGTGGGAATGA | 82 | 629 |
| 663268 | N/A | N/A | 46793 | 46808 | AGCTAACCCTTTGGAA | 70 | 630 |
| 663269 | N/A | N/A | 46944 | 46959 | GTTTTATTAGTTGCCT | 44 | 631 |
| 663270 | N/A | N/A | 47115 | 47130 | AACCAAGCACTTTTGT | 65 | 632 |
| 663271 | N/A | N/A | 47266 | 47281 | TATAAAATCTGCTAAG | 98 | 633 |
| 663272 | N/A | N/A | 47419 | 47434 | AATGATCTGTTCAGTG | 33 | 634 |
| 663273 | N/A | N/A | 47582 | 47597 | TATCTGGCCAATAATT | 88 | 635 |
| 663274 | N/A | N/A | 47738 | 47753 | ACTGATTGCAAAAGTA | 74 | 636 |

TABLE 11

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 8 | 97 |
| 633365 | 1074 | 1089 | 68329 | 68344 | CGCTTATAAGTGTTGG | 13 | 252 |
| 633473 | 2390 | 2405 | 80338 | 80353 | AAGGGATTTCCATTTC | 12 | 279 |
| 640656 | 1130 | 1145 | 68385 | 68400 | GCTGGTAACACTGTGG | 31 | 637 |
| 662469 | 1019 | 1034 | 61493 | 61508 | AACATCGCCTACAGAA | 28 | 638 |
| 662470 | 1021 | 1036 | 61495 | 61510 | AAACATCGCCTACAG | 36 | 639 |
| 662471 | 1023 | 1038 | 61497 | 61512 | TTAAACATCGCCTAC | 75 | 640 |
| 662472 | 1025 | 1040 | 61499 | 61514 | ATTTAAAACATCGCCT | 79 | 641 |
| 662473 | 1028 | 1043 | 61502 | 61517 | CATATTTAAAACATCG | 22 | 642 |
| 662474 | 1054 | 1069 | N/A | N/A | TGCATGAAAAGGATGT | 47 | 643 |
| 662475 | 1057 | 1072 | N/A | N/A | TGTTGCATGAAAAGGA | 40 | 644 |
| 662476 | 1060 | 1075 | 68315 | 68330 | GGGTGTTGCATGAAAA | 31 | 645 |
| 662477 | 1062 | 1077 | 68317 | 68332 | TTGGGTGTTGCATGAA | 15 | 646 |
| 662478 | 1065 | 1080 | 68320 | 68335 | GTGTTGGGTGTTGCAT | 15 | 647 |
| 662479 | 1068 | 1083 | 68323 | 68338 | TAAGTGTTGGGTGTTG | 36 | 648 |
| 662480 | 1070 | 1085 | 68325 | 68340 | TATAAGTGTTGGGTGT | 32 | 649 |
| 662481 | 1071 | 1086 | 68326 | 68341 | TTATAAGTGTTGGGTG | 40 | 650 |
| 662482 | 1072 | 1087 | 68327 | 68342 | CTTATAAGTGTTGGGT | 20 | 651 |
| 662483 | 1073 | 1088 | 68328 | 68343 | GCTTATAAGTGTTGGG | 16 | 652 |
| 662484 | 1075 | 1090 | 68330 | 68345 | CCGCTTATAAGTGTTG | 18 | 653 |
| 662485 | 1076 | 1091 | 68331 | 68346 | TCCGCTTATAAGTGTT | 36 | 654 |
| 662486 | 1077 | 1092 | 68332 | 68347 | TTCCGCTTATAAGTGT | 41 | 655 |
| 662487 | 1079 | 1094 | 68334 | 68349 | TCTTCCGCTTATAAGT | 40 | 656 |
| 662488 | 1081 | 1096 | 68336 | 68351 | GTTCTTCCGCTTATAA | 21 | 657 |
| 662489 | 1083 | 1098 | 68338 | 68353 | GTGTTCTTCCGCTTAT | 12 | 658 |
| 662490 | 1085 | 1100 | 68340 | 68355 | CTGTGTTCTTCCGCTT | 18 | 659 |
| 662491 | 1087 | 1102 | 68342 | 68357 | TTCTGTGTTCTTCCGC | 18 | 660 |
| 662492 | 1089 | 1104 | 68344 | 68359 | GTTTCTGTGTTCTTCC | 16 | 661 |
| 662493 | 1092 | 1107 | 68347 | 68362 | GCTGTTTCTGTGTTCT | 13 | 662 |
| 662494 | 1094 | 1109 | 68349 | 68364 | GAGCTGTTTCTGTGTT | 22 | 663 |
| 662495 | 1096 | 1111 | 68351 | 68366 | TAGAGCTGTTTCTGTG | 20 | 664 |
| 662496 | 1098 | 1113 | 68353 | 68368 | TCTAGAGCTGTTTCTG | 27 | 665 |
| 662497 | 1100 | 1115 | 68355 | 68370 | TGTCTAGAGCTGTTTC | 22 | 666 |
| 662498 | 1102 | 1117 | 68357 | 68372 | GTTGTCTAGAGCTGTT | 14 | 667 |
| 662499 | 1104 | 1119 | 68359 | 68374 | TTGTTGTCTAGAGCTG | 11 | 668 |
| 662500 | 1106 | 1121 | 68361 | 68376 | GTTTGTTGTCTAGAGC | 16 | 669 |

TABLE 11-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662501 | 1108 | 1123 | 68363 | 68378 | AGGTTTGTTGTCTAGA | 11 | 670 |
| 662502 | 1110 | 1125 | 68365 | 68380 | CAAGGTTTGTTGTCTA | 21 | 671 |
| 662503 | 1112 | 1127 | 68367 | 68382 | CACAAGGTTTGTTGTC | 55 | 672 |
| 662504 | 1114 | 1129 | 68369 | 68384 | TCCACAAGGTTTGTTG | 82 | 673 |
| 662505 | 1116 | 1131 | 68371 | 68386 | GGTCCACAAGGTTTGT | 40 | 674 |
| 662506 | 1118 | 1133 | 68373 | 68388 | GTGGTCCACAAGGTTT | 47 | 675 |
| 662507 | 1120 | 1135 | 68375 | 68390 | CTGTGGTCCACAAGGT | 41 | 676 |
| 662508 | 1122 | 1137 | 68377 | 68392 | CACTGTGGTCCACAAG | 31 | 677 |
| 662509 | 1124 | 1139 | 68379 | 68394 | AACACTGTGGTCCACA | 49 | 678 |
| 662510 | 1126 | 1141 | 68381 | 68396 | GTAACACTGTGGTCCA | 30 | 679 |
| 662511 | 1128 | 1143 | 68383 | 68398 | TGGTAACACTGTGGTC | 34 | 680 |
| 662512 | 1132 | 1147 | 68387 | 68402 | ATGCTGGTAACACTGT | 29 | 681 |
| 662513 | 1134 | 1149 | 68389 | 68404 | AAATGCTGGTAACACT | 51 | 682 |
| 662514 | 1136 | 1151 | 68391 | 68406 | CCAAATGCTGGTAACA | 46 | 683 |
| 662515 | 1138 | 1153 | N/A | N/A | CTCCAAATGCTGGTAA | 57 | 684 |
| 662516 | 1140 | 1155 | N/A | N/A | CCCTCCAAATGCTGGT | 68 | 685 |
| 662517 | 1142 | 1157 | N/A | N/A | CTCCCTCCAAATGCTG | 67 | 686 |
| 662518 | 1144 | 1159 | N/A | N/A | TGCTCCCTCCAAATGC | 73 | 687 |
| 662519 | 1147 | 1162 | N/A | N/A | CTTTGCTCCCTCCAAA | 48 | 688 |
| 662520 | 1157 | 1172 | 69890 | 69905 | CAGCAAACTCCTTTGC | 67 | 689 |
| 662521 | 1159 | 1174 | 69892 | 69907 | AGCAGCAAACTCCTTT | 31 | 690 |
| 662522 | 1164 | 1179 | 69897 | 69912 | AGAGCAGCAGCAAACT | 39 | 691 |
| 662523 | 1170 | 1185 | 69903 | 69918 | GCGGTGAGAGCAGCAG | 37 | 692 |
| 662524 | 1172 | 1187 | 69905 | 69920 | CAGCGGTGAGAGCAGC | 28 | 693 |
| 662525 | 1174 | 1189 | 69907 | 69922 | CTCAGCGGTGAGAGCA | 54 | 694 |
| 662526 | 1176 | 1191 | 69909 | 69924 | CGCTCAGCGGTGAGAG | 51 | 695 |
| 662527 | 1178 | 1193 | 69911 | 69926 | TCCGCTCAGCGGTGAG | 60 | 696 |
| 662528 | 1180 | 1195 | 69913 | 69928 | TATCCGCTCAGCGGTG | 43 | 697 |
| 662529 | 1182 | 1197 | 69915 | 69930 | TTTATCCGCTCAGCGG | 63 | 698 |
| 662530 | 1184 | 1199 | 69917 | 69932 | TCTTTATCCGCTCAGC | 25 | 699 |
| 662531 | 1186 | 1201 | 69919 | 69934 | GGTCTTTATCCGCTCA | 22 | 700 |
| 662532 | 1212 | 1227 | 69945 | 69960 | CTGCGGCCTCCTGGAC | 25 | 701 |
| 662533 | 1214 | 1229 | 69947 | 69962 | TTCTGCGGCCTCCTGG | 54 | 702 |
| 662534 | 1216 | 1231 | 69949 | 69964 | TCTTCTGCGGCCTCCT | 58 | 703 |
| 662535 | 1219 | 1234 | 69952 | 69967 | TCCTCTTCTGCGGCCT | 62 | 704 |
| 662536 | 1221 | 1236 | 69954 | 69969 | CGTCCTCTTCTGCGGC | 32 | 705 |

TABLE 11-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662537 | 1223 | 1238 | 69956 | 69971 | GCCGTCCTCTTCTGCG | 65 | 706 |
| 662538 | 1225 | 1240 | 69958 | 69973 | AAGCCGTCCTCTTCTG | 66 | 707 |
| 662539 | 1227 | 1242 | 69960 | 69975 | GGAAGCCGTCCTCTTC | 51 | 708 |
| 662540 | 1229 | 1244 | 69962 | 69977 | TGGGAAGCCGTCCTCT | 51 | 709 |
| 662541 | 1231 | 1246 | 69964 | 69979 | ATTGGGAAGCCGTCCT | 41 | 710 |
| 662542 | 1233 | 1248 | 69966 | 69981 | TTATTGGGAAGCCGTC | 57 | 711 |

TABLE 12

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 10 | 97 |
| 633473 | 2390 | 2405 | 80338 | 80353 | AAGGGATTTCCATTTC | 10 | 279 |
| 640672 | 1400 | 1415 | 70618 | 70633 | GTGTTTGACACCGAGA | 15 | 712 |
| 640675 | 1424 | 1439 | 70642 | 70657 | CAATATTTGGCTTCAT | 22 | 713 |
| 640677 | 1427 | 1442 | 70645 | 70660 | GTTCAATATTTGGCTT | 11 | 714 |
| 640678 | 1428 | 1443 | 70646 | 70661 | GGTTCAATATTTGGCT | 10 | 715 |
| 640679 | 1429 | 1444 | 70647 | 70662 | AGGTTCAATATTTGGC | 6 | 716 |
| 640681 | 1431 | 1446 | 70649 | 70664 | GGAGGTTCAATATTTG | 31 | 717 |
| 640682 | 1433 | 1448 | 70651 | 70666 | CAGGAGGTTCAATATT | 28 | 718 |
| 640683 | 1435 | 1450 | 70653 | 70668 | CTCAGGAGGTTCAATA | 20 | 719 |
| 640684 | 1440 | 1455 | 70658 | 70673 | ACATTCTCAGGAGGTT | 12 | 720 |
| 640687 | 1446 | 1461 | 70664 | 70679 | CACTCCACATTCTCAG | 19 | 721 |
| 640688 | 1448 | 1463 | 70666 | 70681 | TCCACTCCACATTCTC | 23 | 722 |
| 662543 | 1235 | 1250 | 69968 | 69983 | TGTTATTGGGAAGCCG | 27 | 723 |
| 662544 | 1237 | 1252 | 69970 | 69985 | ACTGTTATTGGGAAGC | 20 | 724 |
| 662545 | 1239 | 1254 | 69972 | 69987 | CTACTGTTATTGGGAA | 22 | 725 |
| 662546 | 1241 | 1256 | 69974 | 69989 | TGCTACTGTTATTGGG | 16 | 726 |
| 662547 | 1243 | 1258 | 69976 | 69991 | CCTGCTACTGTTATTG | 33 | 727 |
| 662548 | 1245 | 1260 | 69978 | 69993 | GGCCTGCTACTGTTAT | 54 | 728 |
| 662549 | 1247 | 1262 | 69980 | 69995 | TGGGCCTGCTACTGTT | 28 | 729 |
| 662550 | 1249 | 1264 | 69982 | 69997 | GCTGGGCCTGCTACTG | 25 | 730 |
| 662551 | 1251 | 1266 | 69984 | 69999 | GTGCTGGGCCTGCTAC | 30 | 731 |
| 662552 | 1268 | 1283 | 70001 | 70016 | GCACATTAATGGTGGG | 23 | 732 |
| 662553 | 1270 | 1285 | 70003 | 70018 | CAGCACATTAATGGTG | 45 | 733 |

TABLE 12-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662554 | 1272 | 1287 | 70005 | 70020 | TCCAGCACATTAATGG | 63 | 734 |
| 662556 | 1277 | 1292 | 70010 | 70025 | TTGATTCCAGCACATT | 20 | 735 |
| 662557 | 1279 | 1294 | 70012 | 70027 | CTTTGATTCCAGCACA | 35 | 736 |
| 662558 | 1282 | 1297 | 70015 | 70030 | ATCCTTTGATTCCAGC | 14 | 737 |
| 662559 | 1284 | 1299 | 70017 | 70032 | GTATCCTTTGATTCCA | 12 | 738 |
| 662560 | 1286 | 1301 | 70019 | 70034 | CTGTATCCTTTGATTC | 16 | 739 |
| 662561 | 1288 | 1303 | 70021 | 70036 | GTCTGTATCCTTTGAT | 24 | 740 |
| 662562 | 1291 | 1306 | 70024 | 70039 | ACTGTCTGTATCCTTT | 9 | 741 |
| 662563 | 1293 | 1308 | 70026 | 70041 | TCACTGTCTGTATCCT | 12 | 742 |
| 662564 | 1295 | 1310 | 70028 | 70043 | TATCACTGTCTGTATC | 34 | 743 |
| 662565 | 1297 | 1312 | 70030 | 70045 | CCTATCACTGTCTGTA | 8 | 744 |
| 662566 | 1301 | 1316 | 70034 | 70049 | CTTCCCTATCACTGTC | 23 | 745 |
| 662567 | 1303 | 1318 | 70036 | 70051 | TGCTTCCCTATCACTG | 32 | 746 |
| 662568 | 1305 | 1320 | 70038 | 70053 | CCTGCTTCCCTATCAC | 22 | 747 |
| 662569 | 1308 | 1323 | 70041 | 70056 | GTCCCTGCTTCCCTAT | 33 | 748 |
| 662570 | 1312 | 1327 | 70045 | 70060 | TTCAGTCCCTGCTTCC | 12 | 749 |
| 662571 | 1315 | 1330 | 70048 | 70063 | CGTTTCAGTCCCTGCT | 14 | 750 |
| 662572 | 1317 | 1332 | 70050 | 70065 | CCCGTTTCAGTCCCTG | 34 | 751 |
| 662573 | 1319 | 1334 | 70052 | 70067 | CCCCCGTTTCAGTCCC | 50 | 752 |
| 662574 | 1322 | 1337 | 70055 | 70070 | CTCCCCCCGTTTCAGT | 38 | 753 |
| 662575 | 1324 | 1339 | 70057 | 70072 | CTCTCCCCCCGTTTCA | 19 | 754 |
| 662576 | 1326 | 1341 | 70059 | 70074 | TTCTCTCCCCCCGTTT | 20 | 755 |
| 662577 | 1328 | 1343 | 70061 | 70076 | TGTTCTCTCCCCCCGT | 5 | 756 |
| 662578 | 1330 | 1345 | 70063 | 70078 | ATTGTTCTCTCCCCCC | 7 | 757 |
| 662579 | 1332 | 1347 | 70065 | 70080 | TCATTGTTCTCTCCCC | 9 | 758 |
| 662580 | 1334 | 1349 | 70067 | 70082 | TATCATTGTTCTCTCC | 24 | 759 |
| 662581 | 1337 | 1352 | 70070 | 70085 | CTTTATCATTGTTCTC | 26 | 760 |
| 662582 | 1366 | 1381 | 70099 | 70114 | CGAAGTTTCATCTTTC | 70 | 761 |
| 662583 | 1368 | 1383 | 70101 | 70116 | CTCGAAGTTTCATCTT | 72 | 762 |
| 662584 | 1370 | 1385 | 70103 | 70118 | AGCTCGAAGTTTCATC | 57 | 763 |
| 662585 | 1373 | 1388 | 70106 | 70121 | AGGAGCTCGAAGTTTC | 35 | 764 |
| 662586 | 1375 | 1390 | 70108 | 70123 | AGAGGAGCTCGAAGTT | 28 | 765 |
| 662587 | 1377 | 1392 | N/A | N/A | TCAGAGGAGCTCGAAG | 56 | 766 |
| 662588 | 1379 | 1394 | N/A | N/A | CTTCAGAGGAGCTCGA | 61 | 767 |
| 662589 | 1381 | 1396 | N/A | N/A | TGCTTCAGAGGAGCTC | 65 | 768 |
| 662590 | 1383 | 1398 | N/A | N/A | TTTGCTTCAGAGGAGC | 44 | 769 |

TABLE 12-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662591 | 1385 | 1400 | N/A | N/A | AATTTGCTTCAGAGGA | 56 | 770 |
| 662592 | 1388 | 1403 | N/A | N/A | GAGAATTTGCTTCAGA | 19 | 771 |
| 662593 | 1390 | 1405 | N/A | N/A | CCGAGAATTTGCTTCA | 17 | 772 |
| 662594 | 1392 | 1407 | 70610 | 70625 | CACCGAGAATTTGCTT | 28 | 773 |
| 662595 | 1394 | 1409 | 70612 | 70627 | GACACCGAGAATTTGC | 12 | 774 |
| 662596 | 1396 | 1411 | 70614 | 70629 | TTGACACCGAGAATTT | 30 | 775 |
| 662597 | 1398 | 1413 | 70616 | 70631 | GTTTGACACCGAGAAT | 29 | 776 |
| 662598 | 1402 | 1417 | 70620 | 70635 | TGGTGTTTGACACCGA | 58 | 777 |
| 662599 | 1404 | 1419 | 70622 | 70637 | ATTGGTGTTTGACACC | 36 | 778 |
| 662600 | 1406 | 1421 | 70624 | 70639 | TTATTGGTGTTTGACA | 53 | 779 |
| 662601 | 1409 | 1424 | 70627 | 70642 | TCTTTATTGGTGTTTG | 23 | 780 |
| 662602 | 1411 | 1426 | 70629 | 70644 | CATCTTTATTGGTGTT | 14 | 781 |
| 662603 | 1413 | 1428 | 70631 | 70646 | TTCATCTTTATTGGTG | 28 | 782 |
| 662604 | 1415 | 1430 | 70633 | 70648 | GCTTCATCTTTATTGG | 19 | 783 |
| 662605 | 1423 | 1438 | 70641 | 70656 | AATATTTGGCTTCATC | 21 | 784 |
| 662606 | 1438 | 1453 | 70656 | 70671 | ATTCTCAGGAGGTTCA | 9 | 785 |
| 662607 | 1443 | 1458 | 70661 | 70676 | TCCACATTCTCAGGAG | 58 | 786 |

TABLE 13

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 10 | 97 |
| 633398 | 1492 | 1507 | 70710 | 70725 | GTAAGTGCCAATGAGG | 15 | 39 |
| 633473 | 2390 | 2405 | 80338 | 80353 | AAGGGATTTCCATTTC | 16 | 279 |
| 640692 | 1461 | 1476 | 70679 | 70694 | GCTTCAGCACCACTCC | 8 | 787 |
| 640698 | 1554 | 1569 | N/A | N/A | TCATACACCTGTCTAC | 68 | 788 |
| 662608 | 1451 | 1466 | 70669 | 70684 | CACTCCACTCCACATT | 30 | 789 |
| 662609 | 1464 | 1479 | 70682 | 70697 | GAGGCTTCAGCACCAC | 9 | 790 |
| 662610 | 1466 | 1481 | 70684 | 70699 | TTGAGGCTTCAGCACC | 7 | 791 |
| 662611 | 1468 | 1483 | 70686 | 70701 | CATTGAGGCTTCAGCA | 24 | 792 |
| 662612 | 1470 | 1485 | 70688 | 70703 | AACATTGAGGCTTCAG | 20 | 793 |
| 662613 | 1472 | 1487 | 70690 | 70705 | TAAACATTGAGGCTTC | 18 | 794 |
| 662614 | 1474 | 1489 | 70692 | 70707 | TCTAAACATTGAGGCT | 20 | 795 |

TABLE 13-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662615 | 1476 | 1491 | 70694 | 70709 | ACTCTAAACATTGAGG | 35 | 796 |
| 662616 | 1478 | 1493 | 70696 | 70711 | GGACTCTAAACATTGA | 12 | 797 |
| 662617 | 1480 | 1495 | 70698 | 70713 | GAGGACTCTAAACATT | 23 | 798 |
| 662618 | 1482 | 1497 | 70700 | 70715 | ATGAGGACTCTAAACA | 21 | 799 |
| 662619 | 1484 | 1499 | 70702 | 70717 | CAATGAGGACTCTAAA | 84 | 800 |
| 662620 | 1487 | 1502 | 70705 | 70720 | TGCCAATGAGGACTCT | 36 | 801 |
| 662621 | 1488 | 1503 | 70706 | 70721 | GTGCCAATGAGGACTC | 15 | 802 |
| 662622 | 1489 | 1504 | 70707 | 70722 | AGTGCCAATGAGGACT | 52 | 803 |
| 662623 | 1490 | 1505 | 70708 | 70723 | AAGTGCCAATGAGGAC | 33 | 804 |
| 662624 | 1491 | 1506 | 70709 | 70724 | TAAGTGCCAATGAGGA | 44 | 805 |
| 662625 | 1493 | 1508 | 70711 | 70726 | AGTAAGTGCCAATGAG | 24 | 806 |
| 662626 | 1494 | 1509 | 70712 | 70727 | TAGTAAGTGCCAATGA | 55 | 807 |
| 662627 | 1495 | 1510 | 70713 | 70728 | ATAGTAAGTGCCAATG | 55 | 808 |
| 662628 | 1496 | 1511 | 70714 | 70729 | CATAGTAAGTGCCAAT | 59 | 809 |
| 662629 | 1497 | 1512 | 70715 | 70730 | TCATAGTAAGTGCCAA | 51 | 810 |
| 662630 | 1499 | 1514 | 70717 | 70732 | TGTCATAGTAAGTGCC | 24 | 811 |
| 662631 | 1501 | 1516 | 70719 | 70734 | ATTGTCATAGTAAGTG | 26 | 812 |
| 662632 | 1503 | 1518 | 70721 | 70736 | AAATTGTCATAGTAAG | 64 | 813 |
| 662633 | 1505 | 1520 | 70723 | 70738 | AGAAATTGTCATAGTA | 40 | 814 |
| 662634 | 1507 | 1522 | 70725 | 70740 | ACAGAAATTGTCATAG | 40 | 815 |
| 662635 | 1510 | 1525 | 70728 | 70743 | GGCACAGAAATTGTCA | 67 | 816 |
| 662636 | 1512 | 1527 | 70730 | 70745 | ATGGCACAGAAATTGT | 40 | 817 |
| 662637 | 1517 | 1532 | 70735 | 70750 | TAGCAATGGCACAGAA | 52 | 818 |
| 662638 | 1520 | 1535 | 70738 | 70753 | ACCTAGCAATGGCACA | 29 | 819 |
| 662639 | 1522 | 1537 | 70740 | 70755 | TAACCTAGCAATGGCA | 52 | 820 |
| 662640 | 1524 | 1539 | 70742 | 70757 | ATTAACCTAGCAATGG | 52 | 821 |
| 662641 | 1526 | 1541 | 70744 | 70759 | CAATTAACCTAGCAAT | 78 | 822 |
| 662642 | 1528 | 1543 | 70746 | 70761 | CCCAATTAACCTAGCA | 36 | 823 |
| 662643 | 1530 | 1545 | 70748 | 70763 | GTCCCAATTAACCTAG | 49 | 824 |
| 662644 | 1532 | 1547 | 70750 | 70765 | TGGTCCCAATTAACCT | 68 | 825 |
| 662645 | 1534 | 1549 | 70752 | 70767 | TTTGGTCCCAATTAAC | 24 | 826 |
| 662646 | 1537 | 1552 | 70755 | 70770 | TGTTTTGGTCCCAATT | 22 | 827 |
| 662647 | 1539 | 1554 | 70757 | 70772 | CATGTTTTGGTCCCAA | 11 | 828 |
| 662648 | 1541 | 1556 | 70759 | 70774 | TACATGTTTTGGTCCC | 10 | 829 |
| 662649 | 1543 | 1558 | 70761 | 70776 | TCTACATGTTTTGGTC | 14 | 830 |
| 662650 | 1545 | 1560 | 70763 | 70778 | TGTCTACATGTTTTGG | 22 | 831 |

TABLE 13-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662651 | 1547 | 1562 | 70765 | 70780 | CCTGTCTACATGTTTT | 38 | 832 |
| 662652 | 1550 | 1565 | N/A | N/A | ACACCTGTCTACATGT | 52 | 833 |
| 662653 | 1552 | 1567 | N/A | N/A | ATACACCTGTCTACAT | 70 | 834 |
| 662654 | 1556 | 1571 | N/A | N/A | ACTCATACACCTGTCT | 48 | 835 |
| 662655 | 1558 | 1573 | N/A | N/A | AAACTCATACACCTGT | 48 | 836 |
| 662656 | 1560 | 1575 | 71221 | 71236 | CTAAACTCATACACCT | 66 | 837 |
| 662657 | 1563 | 1578 | 71224 | 71239 | ACTCTAAACTCATACA | 25 | 838 |
| 662658 | 1565 | 1580 | 71226 | 71241 | TGACTCTAAACTCATA | 16 | 839 |
| 662659 | 1567 | 1582 | 71228 | 71243 | TTTGACTCTAAACTCA | 22 | 840 |
| 662660 | 1578 | 1593 | 71239 | 71254 | ATGCTAGATTCTTTGA | 30 | 841 |
| 662661 | 1580 | 1595 | 71241 | 71256 | TGATGCTAGATTCTTT | 34 | 842 |
| 662662 | 1582 | 1597 | 71243 | 71258 | TATGATGCTAGATTCT | 31 | 843 |
| 662663 | 1584 | 1599 | 71245 | 71260 | GCTATGATGCTAGATT | 42 | 844 |
| 662664 | 1586 | 1601 | 71247 | 71262 | GAGCTATGATGCTAGA | 27 | 845 |
| 662665 | 1588 | 1603 | 71249 | 71264 | TGGAGCTATGATGCTA | 34 | 846 |
| 662666 | 1590 | 1605 | 71251 | 71266 | GCTGGAGCTATGATGC | 51 | 847 |
| 662667 | 1592 | 1607 | 71253 | 71268 | GAGCTGGAGCTATGAT | 45 | 848 |
| 662668 | 1594 | 1609 | 71255 | 71270 | GGGAGCTGGAGCTATG | 52 | 849 |
| 662669 | 1596 | 1611 | 71257 | 71272 | GCGGGAGCTGGAGCTA | 38 | 850 |
| 662670 | 1599 | 1614 | 71260 | 71275 | TCAGCGGGAGCTGGAG | 59 | 851 |
| 662671 | 1602 | 1617 | 71263 | 71278 | TCCTCAGCGGGAGCTG | 54 | 852 |
| 662672 | 1604 | 1619 | 71265 | 71280 | CATCCTCAGCGGGAGC | 23 | 853 |
| 662673 | 1606 | 1621 | 71267 | 71282 | CACATCCTCAGCGGGA | 47 | 854 |
| 662674 | 1608 | 1623 | 71269 | 71284 | TCCACATCCTCAGCGG | 53 | 855 |
| 662675 | 1611 | 1626 | 71272 | 71287 | GTATCCACATCCTCAG | 29 | 856 |
| 662676 | 1613 | 1628 | 71274 | 71289 | GAGTATCCACATCCTC | 59 | 857 |
| 662677 | 1615 | 1630 | 71276 | 71291 | AGGAGTATCCACATCC | 64 | 858 |
| 662678 | 1617 | 1632 | 71278 | 71293 | GGAGGAGTATCCACAT | 54 | 859 |
| 662679 | 1620 | 1635 | 71281 | 71296 | CTTGGAGGAGTATCCA | 65 | 860 |
| 662680 | 1622 | 1637 | 71283 | 71298 | TCCTTGGAGGAGTATC | 72 | 861 |

TABLE 14

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633335 | 654 | 669 | 59124 | 59139 | TCATTTATAAACCCAC | 12 | 97 |
| 633414 | 1701 | 1716 | 72965 | 72980 | ACATGGTTAGAGGAGC | 17 | 43 |
| 633416 | 1729 | 1744 | 72993 | 73008 | TGGATGATCACAGGGT | 12 | 191 |
| 633418 | 1751 | 1766 | 73015 | 73030 | ACGAACTGTCACAAGG | 11 | 44 |
| 633473 | 2390 | 2405 | 80338 | 80353 | AAGGGATTTCCATTTC | 17 | 279 |
| 640708 | 1706 | 1721 | 72970 | 72985 | TGTAAACATGGTTAGA | 18 | 862 |
| 640710 | 1761 | 1776 | 73025 | 73040 | ACACAAGGGCACGAAC | 49 | 863 |
| 640711 | 1763 | 1778 | 73027 | 73042 | TCACACAAGGGCACGA | 21 | 864 |
| 640712 | 1765 | 1780 | 73029 | 73044 | TATCACACAAGGGCAC | 24 | 865 |
| 640713 | 1767 | 1782 | 73031 | 73046 | GCTATCACACAAGGGC | 22 | 866 |
| 640714 | 1769 | 1784 | 73033 | 73048 | GTGCTATCACACAAGG | 12 | 867 |
| 640715 | 1771 | 1786 | 73035 | 73050 | TTGTGCTATCACACAA | 59 | 868 |
| 640716 | 1775 | 1790 | 73039 | 73054 | AATTTTGTGCTATCAC | 29 | 869 |
| 640717 | 1805 | 1820 | 73069 | 73084 | CTGAACTACATTGACA | 14 | 870 |
| 662681 | 1624 | 1639 | 71285 | 71300 | TTTCCTTGGAGGAGTA | 49 | 871 |
| 662682 | 1627 | 1642 | 71288 | 71303 | CTTTTTCCTTGGAGGA | 85 | 872 |
| 662683 | 1642 | 1657 | 71303 | 71318 | CCGGTGTTTCCTCTTC | 44 | 873 |
| 662684 | 1644 | 1659 | N/A | N/A | AACCGGTGTTTCCTCT | 59 | 874 |
| 662685 | 1646 | 1661 | N/A | N/A | ACAACCGGTGTTTCCT | 49 | 875 |
| 662686 | 1648 | 1663 | N/A | N/A | CCACAACCGGTGTTTC | 71 | 876 |
| 662687 | 1650 | 1665 | N/A | N/A | GCCCACAACCGGTGTT | 74 | 877 |
| 662688 | 1681 | 1696 | 72479 | 72494 | CTTTTTCAGCTGTATC | 42 | 878 |
| 662689 | 1684 | 1699 | N/A | N/A | GTCCTTTTTCAGCTGT | 53 | 879 |
| 662690 | 1686 | 1701 | N/A | N/A | CCGTCCTTTTTCAGCT | 66 | 880 |
| 662691 | 1689 | 1704 | N/A | N/A | GAGCCGTCCTTTTTCA | 63 | 881 |
| 662692 | 1691 | 1706 | N/A | N/A | AGGAGCCGTCCTTTTT | 64 | 882 |
| 662693 | 1693 | 1708 | N/A | N/A | AGAGGAGCCGTCCTTT | 48 | 883 |
| 662694 | 1695 | 1710 | N/A | N/A | TTAGAGGAGCCGTCCT | 48 | 884 |
| 662695 | 1697 | 1712 | 72961 | 72976 | GGTTAGAGGAGCCGTC | 12 | 885 |
| 662696 | 1698 | 1713 | 72962 | 72977 | TGGTTAGAGGAGCCGT | 17 | 886 |
| 662697 | 1699 | 1714 | 72963 | 72978 | ATGGTTAGAGGAGCCG | 23 | 887 |
| 662698 | 1700 | 1715 | 72964 | 72979 | CATGGTTAGAGGAGCC | 16 | 888 |
| 662699 | 1702 | 1717 | 72966 | 72981 | AACATGGTTAGAGGAG | 19 | 889 |
| 662700 | 1703 | 1718 | 72967 | 72982 | AAACATGGTTAGAGGA | 27 | 890 |
| 662701 | 1704 | 1719 | 72968 | 72983 | TAAACATGGTTAGAGG | 16 | 891 |
| 662702 | 1705 | 1720 | 72969 | 72984 | GTAAACATGGTTAGAG | 18 | 892 |

TABLE 14-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662703 | 1708 | 1723 | 72972 | 72987 | GTTGTAAACATGGTTA | 12 | 893 |
| 662704 | 1710 | 1725 | 72974 | 72989 | TAGTTGTAAACATGGT | 11 | 894 |
| 662705 | 1712 | 1727 | 72976 | 72991 | GATAGTTGTAAACATG | 18 | 895 |
| 662706 | 1723 | 1738 | 72987 | 73002 | ATCACAGGGTTGATAG | 57 | 896 |
| 662707 | 1725 | 1740 | 72989 | 73004 | TGATCACAGGGTTGAT | 34 | 897 |
| 662708 | 1726 | 1741 | 72990 | 73005 | ATGATCACAGGGTTGA | 17 | 898 |
| 662709 | 1727 | 1742 | 72991 | 73006 | GATGATCACAGGGTTG | 15 | 899 |
| 662710 | 1728 | 1743 | 72992 | 73007 | GGATGATCACAGGGTT | 9 | 900 |
| 662711 | 1730 | 1745 | 72994 | 73009 | GTGGATGATCACAGGG | 17 | 901 |
| 662712 | 1731 | 1746 | 72995 | 73010 | CGTGGATGATCACAGG | 13 | 902 |
| 662713 | 1732 | 1747 | 72996 | 73011 | CCGTGGATGATCACAG | 17 | 903 |
| 662714 | 1733 | 1748 | 72997 | 73012 | GCCGTGGATGATCACA | 18 | 904 |
| 662715 | 1734 | 1749 | 72998 | 73013 | TGCCGTGGATGATCAC | 23 | 905 |
| 662716 | 1736 | 1751 | 73000 | 73015 | GCTGCCGTGGATGATC | 50 | 906 |
| 662717 | 1738 | 1753 | 73002 | 73017 | AGGCTGCCGTGGATGA | 20 | 907 |
| 662718 | 1740 | 1755 | 73004 | 73019 | CAAGGCTGCCGTGGAT | 29 | 908 |
| 662719 | 1742 | 1757 | 73006 | 73021 | CACAAGGCTGCCGTGG | 25 | 909 |
| 662720 | 1744 | 1759 | 73008 | 73023 | GTCACAAGGCTGCCGT | 13 | 910 |
| 662721 | 1746 | 1761 | 73010 | 73025 | CTGTCACAAGGCTGCC | 12 | 911 |
| 662722 | 1747 | 1762 | 73011 | 73026 | ACTGTCACAAGGCTGC | 11 | 912 |
| 662723 | 1748 | 1763 | 73012 | 73027 | AACTGTCACAAGGCTG | 14 | 913 |
| 662724 | 1749 | 1764 | 73013 | 73028 | GAACTGTCACAAGGCT | 15 | 914 |
| 662725 | 1750 | 1765 | 73014 | 73029 | CGAACTGTCACAAGGC | 10 | 915 |
| 662726 | 1752 | 1767 | 73016 | 73031 | CACGAACTGTCACAAG | 16 | 916 |
| 662727 | 1753 | 1768 | 73017 | 73032 | GCACGAACTGTCACAA | 20 | 917 |
| 662728 | 1754 | 1769 | 73018 | 73033 | GGCACGAACTGTCACA | 21 | 918 |
| 662729 | 1755 | 1770 | 73019 | 73034 | GGGCACGAACTGTCAC | 44 | 919 |
| 662730 | 1757 | 1772 | 73021 | 73036 | AAGGGCACGAACTGTC | 16 | 920 |
| 662731 | 1759 | 1774 | 73023 | 73038 | ACAAGGGCACGAACTG | 14 | 921 |
| 662732 | 1773 | 1788 | 73037 | 73052 | TTTTGTGCTATCACAC | 17 | 922 |
| 662733 | 1777 | 1792 | 73041 | 73056 | AAAATTTTGTGCTATC | 49 | 923 |
| 662734 | 1793 | 1808 | 73057 | 73072 | GACAAAACTTTTCACA | 41 | 924 |
| 662735 | 1800 | 1815 | 73064 | 73079 | CTACATTGACAAAACT | 60 | 925 |
| 662736 | 1803 | 1818 | 73067 | 73082 | GAACTACATTGACAAA | 37 | 926 |
| 662737 | 1807 | 1822 | 73071 | 73086 | CTCTGAACTACATTGA | 27 | 927 |
| 662738 | 1809 | 1824 | 73073 | 73088 | CACTCTGAACTACATT | 31 | 928 |

TABLE 14-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662739 | 1811 | 1826 | N/A | N/A | GACACTCTGAACTACA | 26 | 929 |
| 662740 | 1813 | 1828 | N/A | N/A | TTGACACTCTGAACTA | 45 | 930 |
| 662741 | 1815 | 1830 | N/A | N/A | TTTTGACACTCTGAAC | 63 | 931 |
| 662742 | 1817 | 1832 | N/A | N/A | GGTTTTGACACTCTGA | 31 | 932 |
| 662743 | 1819 | 1834 | N/A | N/A | GCGGTTTTGACACTCT | 26 | 933 |
| 662744 | 1821 | 1836 | N/A | N/A | AAGCGGTTTTGACACT | 46 | 934 |

Example 4: Effect of 3-10-3 cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured HepG2 cells at a density of 20,000 cells per well were transfected using electroporation with 2,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1985 (forward sequence CCCACCAT-TAATGTGCTGGAA, designated herein as SEQ ID NO: 7; reverse sequence TTGTTCTCTCCCCCCGTTT, designated herein as SEQ ID NO: 8; probe sequence AGGATACA-GACAGTGATAGGGAAGCAGGGACT, designated herein as SEQ ID NO: 9) was used to measure mRNA levels. EZH2 mRNA levels were adjusted according to total RNA content, as measured by RiboGreen®. Results are presented in the table below as percent control of the amount of EZH2 mRNA, relative to untreated control cells (UTC).

The modified oligonucleotides in the table below are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 15

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633355 | 964 | 979 | 61438 | 61453 | AGATTTAGCATTTGGT | 6 | 102 |
| 633472 | 2388 | 2403 | 80336 | 80351 | GGGATTTCCATTTCTC | 37 | 205 |
| 633473 | 2390 | 2405 | 80338 | 80353 | AAGGGATTTCCATTTC | 17 | 279 |
| 633481 | 2515 | 2530 | 80463 | 80478 | CTTACAGTACTTTGCA | 14 | 280 |
| 640748 | 2397 | 2412 | 80345 | 80360 | AGATGTCAAGGGATTT | 23 | 935 |
| 640749 | 2442 | 2457 | 80390 | 80405 | CCTGAAGCTAAGGCAG | 26 | 936 |
| 640753 | 2493 | 2508 | 80441 | 80456 | GAATTTCAAACTGCAT | 32 | 937 |
| 640755 | 2511 | 2526 | 80459 | 80474 | CAGTACTTTGCAAATT | 35 | 938 |
| 662891 | 2290 | 2305 | 78874 | 78889 | CTTGGCAAAAATACCT | 26 | 939 |

TABLE 15-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662892 | 2299 | 2314 | 78883 | 78898 | GATGGCTCTCTTGGCA | 20 | 940 |
| 662893 | 2301 | 2316 | 78885 | 78900 | TGGATGGCTCTCTTGG | 16 | 941 |
| 662894 | 2303 | 2318 | 78887 | 78902 | TCTGGATGGCTCTCTT | 27 | 942 |
| 662895 | 2305 | 2320 | 78889 | 78904 | AGTCTGGATGGCTCTC | 13 | 943 |
| 662896 | 2307 | 2322 | 78891 | 78906 | CCAGTCTGGATGGCTC | 17 | 944 |
| 662897 | 2309 | 2324 | 78893 | 78908 | CGCCAGTCTGGATGGC | 65 | 945 |
| 662898 | 2311 | 2326 | 78895 | 78910 | TTCGCCAGTCTGGATG | 63 | 946 |
| 662899 | 2313 | 2328 | 78897 | 78912 | TCTTCGCCAGTCTGGA | 53 | 947 |
| 662900 | 2353 | 2368 | 80301 | 80316 | CAGGGCATCAGCCTGG | 57 | 948 |
| 662901 | 2355 | 2370 | 80303 | 80318 | TTCAGGGCATCAGCCT | 43 | 949 |
| 662902 | 2359 | 2374 | 80307 | 80322 | ATACTTCAGGGCATCA | 70 | 950 |
| 662903 | 2361 | 2376 | 80309 | 80324 | ACATACTTCAGGGCAT | 56 | 951 |
| 662904 | 2363 | 2378 | 80311 | 80326 | CGACATACTTCAGGGC | 39 | 952 |
| 662905 | 2365 | 2380 | 80313 | 80328 | GCCGACATACTTCAGG | 40 | 953 |
| 662906 | 2367 | 2382 | 80315 | 80330 | ATGCCGACATACTTCA | 65 | 954 |
| 662907 | 2369 | 2384 | 80317 | 80332 | CGATGCCGACATACTT | 49 | 955 |
| 662908 | 2371 | 2386 | 80319 | 80334 | TTCGATGCCGACATAC | 47 | 956 |
| 662909 | 2373 | 2388 | 80321 | 80336 | CTTTCGATGCCGACAT | 50 | 957 |
| 662910 | 2375 | 2390 | 80323 | 80338 | CTCTTTCGATGCCGAC | 29 | 958 |
| 662911 | 2377 | 2392 | 80325 | 80340 | TTCTCTTTCGATGCCG | 32 | 959 |
| 662912 | 2379 | 2394 | 80327 | 80342 | ATTTCTCTTTCGATGC | 35 | 960 |
| 662913 | 2381 | 2396 | 80329 | 80344 | CCATTTCTCTTTCGAT | 30 | 961 |
| 662914 | 2383 | 2398 | 80331 | 80346 | TTCCATTTCTCTTTCG | 35 | 962 |
| 662915 | 2386 | 2401 | 80334 | 80349 | GATTTCCATTTCTCTT | 30 | 963 |
| 662916 | 2387 | 2402 | 80335 | 80350 | GGATTTCCATTTCTCT | 22 | 964 |
| 662917 | 2389 | 2404 | 80337 | 80352 | AGGGATTTCCATTTCT | 20 | 965 |
| 662918 | 2391 | 2406 | 80339 | 80354 | CAAGGGATTTCCATTT | 27 | 966 |
| 662919 | 2392 | 2407 | 80340 | 80355 | TCAAGGGATTTCCATT | 30 | 967 |
| 662920 | 2393 | 2408 | 80341 | 80356 | GTCAAGGGATTTCCAT | 27 | 968 |
| 662921 | 2394 | 2409 | 80342 | 80357 | TGTCAAGGGATTTCCA | 24 | 969 |
| 662922 | 2395 | 2410 | 80343 | 80358 | ATGTCAAGGGATTTCC | 23 | 970 |
| 662923 | 2399 | 2414 | 80347 | 80362 | GCAGATGTCAAGGGAT | 19 | 971 |
| 662924 | 2401 | 2416 | 80349 | 80364 | TAGCAGATGTCAAGGG | 21 | 972 |
| 662925 | 2403 | 2418 | 80351 | 80366 | GGTAGCAGATGTCAAG | 22 | 973 |
| 662926 | 2405 | 2420 | 80353 | 80368 | GAGGTAGCAGATGTCA | 18 | 974 |
| 662927 | 2407 | 2422 | 80355 | 80370 | AGGAGGTAGCAGATGT | 25 | 975 |

TABLE 15-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 662928 | 2409 | 2424 | 80357 | 80372 | GGAGGAGGTAGCAGAT | 45 | 976 |
| 662929 | 2426 | 2441 | 80374 | 80389 | CTGTTTCAGAGGAGGG | 19 | 977 |
| 662930 | 2428 | 2443 | 80376 | 80391 | AGCTGTTTCAGAGGAG | 18 | 978 |
| 662931 | 2430 | 2445 | 80378 | 80393 | GCAGCTGTTTCAGAGG | 13 | 979 |
| 662932 | 2435 | 2450 | 80383 | 80398 | CTAAGGCAGCTGTTTC | 139 | 980 |
| 662933 | 2437 | 2452 | 80385 | 80400 | AGCTAAGGCAGCTGTT | 34 | 981 |
| 662934 | 2440 | 2455 | 80388 | 80403 | TGAAGCTAAGGCAGCT | 24 | 982 |
| 662935 | 2444 | 2459 | 80392 | 80407 | TTCCTGAAGCTAAGGC | 18 | 983 |
| 662936 | 2446 | 2461 | 80394 | 80409 | GGTTCCTGAAGCTAAG | 17 | 984 |
| 662937 | 2448 | 2463 | 80396 | 80411 | GAGGTTCCTGAAGCTA | 11 | 985 |
| 662938 | 2450 | 2465 | 80398 | 80413 | TCGAGGTTCCTGAAGC | 21 | 986 |
| 662939 | 2452 | 2467 | 80400 | 80415 | ACTCGAGGTTCCTGAA | 23 | 987 |
| 662940 | 2455 | 2470 | 80403 | 80418 | AGTACTCGAGGTTCCT | 14 | 988 |
| 662941 | 2457 | 2472 | 80405 | 80420 | ACAGTACTCGAGGTTC | 10 | 989 |
| 662942 | 2459 | 2474 | 80407 | 80422 | CCACAGTACTCGAGGT | 24 | 990 |
| 662943 | 2461 | 2476 | 80409 | 80424 | GCCCACAGTACTCGAG | 39 | 991 |
| 662944 | 2463 | 2478 | 80411 | 80426 | TTGCCCACAGTACTCG | 14 | 992 |
| 662945 | 2465 | 2480 | 80413 | 80428 | AATTGCCCACAGTACT | 39 | 993 |
| 662946 | 2467 | 2482 | 80415 | 80430 | TAAATTGCCCACAGTA | 30 | 994 |
| 662947 | 2469 | 2484 | 80417 | 80432 | TCTAAATTGCCCACAG | 20 | 995 |
| 662948 | 2489 | 2504 | 80437 | 80452 | TTCAAACTGCATGTTC | 18 | 996 |
| 662949 | 2495 | 2510 | 80443 | 80458 | CAGAATTTCAAACTGC | 19 | 997 |
| 662950 | 2509 | 2524 | 80457 | 80472 | GTACTTTGCAAATTCA | 12 | 998 |
| 662951 | 2516 | 2531 | 80464 | 80479 | TCTTACAGTACTTTGC | 16 | 999 |
| 662952 | 2520 | 2535 | 80468 | 80483 | TTATTCTTACAGTACT | 21 | 1000 |
| 662953 | 2534 | 2549 | 80482 | 80497 | CTCATTACTATAAATT | 38 | 1001 |
| 662954 | 2538 | 2553 | 80486 | 80501 | TAAACTCATTACTATA | 36 | 1002 |
| 662955 | 2557 | 2572 | 80505 | 80520 | GCAATAAAAAGTTGAT | 50 | 1003 |
| 662956 | 2565 | 2580 | 80513 | 80528 | GTGAGAAGGCAATAAA | 19 | 1004 |
| 662957 | 2567 | 2582 | 80515 | 80530 | TGGTGAGAAGGCAATA | 9 | 1005 |
| 662958 | 2568 | 2583 | 80516 | 80531 | CTGGTGAGAAGGCAAT | 22 | 1006 |
| 662959 | 2570 | 2585 | 80518 | 80533 | AGCTGGTGAGAAGGCA | 10 | 1007 |

Example 5: Effect of 3-10-3 cEt Gapmers and Mixed MOE and cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured A431 cells at a density of 5,000 cells per well were transfected via free uptake with 1,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC).

The modified oligonucleotides in the tables below are cEt and/or MOE containing gapmers. The gapmers have a central gap segment comprises 2'-deoxynucleosides which is flanked by wing segments on both the 5' end and on the 3' end. At least one nucleoside in the 5' wing segment and/or one nucleoside in the 3' wing segment has a MOE and/or cEt sugar modification. The "Chemistry" column describes the sugar modifications of each oligonucleotide. "k" indicates a cEt sugar modification; "d" indicates deoxyribose; and "e" indicates a MOE modification. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 16

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633335 | 654 | 669 | 59124 | 59139 | TCATTTATAAACCCAC | kkk-d10-kkk | 59 | 97 |
| 633365 | 1074 | 1089 | 68329 | 68344 | CGCTTATAAGTGTTGG | kkk-d10-kkk | 33 | 252 |
| 633473 | 2390 | 2405 | 80338 | 80353 | AAGGGATTTCCATTTC | kkk-d10-kkk | 61 | 279 |
| 663097 | N/A | N/A | 6590 | 6605 | ATGTATTTGTGCAAGG | kkk-d10-kkk | 20 | 535 |
| 702201 | 695 | 710 | 59165 | 59180 | TATATTGACCAAGGGC | kkk-d10-kkk | 69 | 1008 |
| 702202 | 697 | 712 | 59167 | 59182 | ATTATATTGACCAAGG | kkk-d10-kkk | 65 | 1009 |
| 702203 | 699 | 714 | 59169 | 59184 | TCATTATATTGACCAA | kkk-d10-kkk | 60 | 1010 |
| 702204 | 701 | 716 | 59171 | 59186 | CATCATTATATTGACC | kkk-d10-kkk | 64 | 1011 |
| 702205 | 703 | 718 | 59173 | 59188 | ATCATCATTATATTGA | kkk-d10-kkk | 108 | 1012 |
| 702206 | 704 | 719 | 59174 | 59189 | CATCATCATTATATTG | kkk-d10-kkk | 93 | 1013 |
| 702207 | 705 | 720 | 59175 | 59190 | TCATCATCATTATATT | kkk-d10-kkk | 97 | 1014 |
| 702210 | 967 | 982 | 61441 | 61456 | AACAGATTTAGCATTT | kkk-d10-kkk | 74 | 1015 |
| 702211 | 1069 | 1084 | 68324 | 68339 | ATAAGTGTTGGGTGTT | kkk-d10-kkk | 46 | 1016 |
| 702212 | 1078 | 1093 | 68333 | 68348 | CTTCCGCTTATAAGTG | kkk-d10-kkk | 99 | 1017 |
| 702213 | 1724 | 1739 | 72988 | 73003 | GATCACAGGGTTGATA | kkk-d10-kkk | 112 | 1018 |
| 702214 | 2504 | 2519 | 80452 | 80467 | TTGCAAATTCAGAATT | kkk-d10-kkk | 99 | 1019 |
| 702215 | 2505 | 2520 | 80453 | 80468 | TTTGCAAATTCAGAAT | kkk-d10-kkk | 93 | 1020 |
| 702216 | 2506 | 2521 | 80454 | 80469 | CTTTGCAAATTCAGAA | kkk-d10-kkk | 77 | 1021 |
| 702217 | 2507 | 2522 | 80455 | 80470 | ACTTTGCAAATTCAGA | kkk-d10-kkk | 35 | 1022 |
| 702218 | 2508 | 2523 | 80456 | 80471 | TACTTTGCAAATTCAG | kkk-d10-kkk | 53 | 1023 |
| 702219 | 2510 | 2525 | 80458 | 80473 | AGTACTTTGCAAATTC | kkk-d10-kkk | 87 | 1024 |
| 702220 | 2512 | 2527 | 80460 | 80475 | ACAGTACTTTGCAAAT | kkk-d10-kkk | 91 | 1025 |

TABLE 16-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702221 | 2513 | 2528 | 80461 | 80476 | TACAGTACTTTGCAAA | kkk-d10-kkk | 65 | 1026 |
| 702222 | 2514 | 2529 | 80462 | 80477 | TTACAGTACTTTGCAA | kkk-d10-kkk | 95 | 1027 |
| 702223 | 2577 | 2592 | 80525 | 80540 | ACTTTGCAGCTGGTGA | kkk-d10-kkk | 42 | 1028 |
| 702224 | 2579 | 2594 | 80527 | 80542 | ACACTTTGCAGCTGGT | kkk-d10-kkk | 83 | 1029 |
| 702225 | 2581 | 2596 | 80529 | 80544 | AAACACTTTGCAGCTG | kkk-d10-kkk | 88 | 1030 |
| 702226 | 2582 | 2597 | 80530 | 80545 | AAAACACTTTGCAGCT | kkk-d10-kkk | 80 | 1031 |
| 702227 | 2584 | 2599 | 80532 | 80547 | ACAAAACACTTTGCAG | kkk-d10-kkk | 77 | 1032 |
| 702228 | 2585 | 2600 | 80533 | 80548 | TACAAAACACTTTGCA | kkk-d10-kkk | 90 | 1033 |
| 702229 | N/A | N/A | 6585 | 6600 | TTTGTGCAAGGCAAAG | kkk-d10-kkk | 80 | 1034 |
| 702230 | N/A | N/A | 6586 | 6601 | ATTTGTGCAAGGCAAA | kkk-d10-kkk | 103 | 1035 |
| 702231 | N/A | N/A | 6587 | 6602 | TATTTGTGCAAGGCAA | kkk-d10-kkk | 85 | 1036 |
| 702232 | N/A | N/A | 6588 | 6603 | GTATTTGTGCAAGGCA | kkk-d10-kkk | 25 | 1037 |
| 702233 | N/A | N/A | 6589 | 6604 | TGTATTTGTGCAAGGC | kkk-d10-kkk | 12 | 1038 |
| 702234 | N/A | N/A | 6591 | 6606 | AATGTATTTGTGCAAG | kkk-d10-kkk | 48 | 1039 |
| 702235 | N/A | N/A | 6592 | 6607 | AAATGTATTTGTGCAA | kkk-d10-kkk | 79 | 1040 |
| 702236 | N/A | N/A | 6593 | 6608 | TAAATGTATTTGTGCA | kkk-d10-kkk | 66 | 1041 |
| 702237 | N/A | N/A | 6594 | 6609 | TTAAATGTATTTGTGC | kkk-d10-kkk | 70 | 1042 |
| 702238 | N/A | N/A | 6595 | 6610 | CTTAAATGTATTTGTG | kkk-d10-kkk | 97 | 1043 |
| 702249 | N/A | N/A | 18219 | 18234 | GTTGTTCCATTATTTA | kkk-d10-kkk | 38 | 1044 |
| 702250 | N/A | N/A | 18220 | 18235 | AGTTGTTCCATTATTT | kkk-d10-kkk | 23 | 1045 |
| 702251 | N/A | N/A | 18221 | 18236 | AAGTTGTTCCATTATT | kkk-d10-kkk | 59 | 1046 |
| 702252 | N/A | N/A | 18222 | 18237 | CAAGTTGTTCCATTAT | kkk-d10-kkk | 44 | 1047 |
| 702253 | N/A | N/A | 18223 | 18238 | ACAAGTTGTTCCATTA | kkk-d10-kkk | 32 | 1048 |
| 702254 | N/A | N/A | 18225 | 18240 | ACACAAGTTGTTCCAT | kkk-d10-kkk | 57 | 1049 |
| 702255 | N/A | N/A | 18226 | 18241 | AACACAAGTTGTTCCA | kkk-d10-kkk | 66 | 1050 |
| 702256 | N/A | N/A | 18227 | 18242 | AAACACAAGTTGTTCC | kkk-d10-kkk | 81 | 1051 |
| 702257 | N/A | N/A | 18228 | 18243 | TAAACACAAGTTGTTC | kkk-d10-kkk | 97 | 1052 |
| 702258 | N/A | N/A | 18229 | 18244 | GTAAACACAAGTTGTT | kkk-d10-kkk | 64 | 1053 |
| 702267 | N/A | N/A | 6590 | 6605 | ATGTATTTGTGCAAGG | k-d10-kekek | 40 | 535 |
| 702278 | N/A | N/A | 6588 | 6603 | GTATTTGTGCAAGGCA | k-d10-kekek | 44 | 1037 |
| 702289 | N/A | N/A | 6590 | 6605 | ATGTATTTGTGCAAGG | k-d9-kekeke | 66 | 535 |
| 702300 | N/A | N/A | 6588 | 6603 | GTATTTGTGCAAGGCA | k-d9-kekeke | 63 | 1037 |
| 702311 | N/A | N/A | 6590 | 6605 | ATGTATTTGTGCAAGG | kk-d8-kekekk | 81 | 535 |
| 702338 | N/A | N/A | 6590 | 6605 | ATGTATTTGTGCAAGG | kk-d10-keke | 16 | 535 |
| 702349 | N/A | N/A | 6589 | 6604 | TGTATTTGTGCAAGGC | kk-d10-keke | 22 | 1038 |
| 702360 | N/A | N/A | 6590 | 6605 | ATGTATTTGTGCAAGG | kk-d9-kekek | 55 | 535 |

TABLE 16-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702371 | N/A | N/A | 6589 | 6604 | TGTATTTGTGCAAGGC | kk-d9-kekek | 34 | 1038 |
| 702382 | N/A | N/A | 6590 | 6605 | ATGTATTTGTGCAAGG | kkk-d9-kkke | 22 | 535 |
| 702393 | N/A | N/A | 6589 | 6604 | TGTATTTGTGCAAGGC | kkk-d9-kkke | 23 | 1038 |
| 702404 | N/A | N/A | 6590 | 6605 | ATGTATTTGTGCAAGG | kkk-d8-kekek | 49 | 535 |
| 702415 | N/A | N/A | 6590 | 6605 | ATGTATTTGTGCAAGG | kkk-d9-keke | 18 | 535 |
| 702441 | N/A | N/A | 6590 | 6605 | ATGTATTTGTGCAAGG | kkk-d8-kdkdk | 52 | 535 |
| 702467 | N/A | N/A | 6589 | 6604 | TGTATTTGTGCAAGGC | kk-d9-kdkdk | 29 | 1038 |
| 702828 | 1088 | 1103 | 68343 | 68358 | TTTCTGTGTTCTTCCG | kkk-d10-kkk | 59 | 1054 |
| 702829 | 1090 | 1105 | 68345 | 68360 | TGTTTCTGTGTTCTTC | kkk-d10-kkk | 57 | 1055 |
| 702830 | 1091 | 1106 | 68346 | 68361 | CTGTTTCTGTGTTCTT | kkk-d10-kkk | 32 | 1056 |
| 702831 | 1093 | 1108 | 68348 | 68363 | AGCTGTTTCTGTGTTC | kkk-d10-kkk | 73 | 1057 |
| 702832 | 1095 | 1110 | 68350 | 68365 | AGAGCTGTTTCTGTGT | kkk-d10-kkk | 72 | 1058 |
| 702833 | 1097 | 1112 | 68352 | 68367 | CTAGAGCTGTTTCTGT | kkk-d10-kkk | 75 | 1059 |
| 702834 | 1538 | 1553 | 70756 | 70771 | ATGTTTTGGTCCCAAT | kkk-d10-kkk | 66 | 1060 |
| 702835 | 1540 | 1555 | 70758 | 70773 | ACATGTTTTGGTCCCA | kkk-d10-kkk | 64 | 1061 |
| 702836 | 1542 | 1557 | 70760 | 70775 | CTACATGTTTTGGTCC | kkk-d10-kkk | 56 | 1062 |
| 702837 | 1544 | 1559 | 70762 | 70777 | GTCTACATGTTTTGGT | kkk-d10-kkk | 77 | 1063 |
| 702838 | 1546 | 1561 | 70764 | 70779 | CTGTCTACATGTTTTG | kkk-d10-kkk | 55 | 1064 |
| 702923 | 2579 | 2594 | 80527 | 80542 | ACACTTTGCAGCTGGT | kkk-d8-kekek | 79 | 1029 |
| 702924 | N/A | N/A | 6589 | 6604 | TGTATTTGTGCAAGGC | kkk-d8-kekek | 50 | 1038 |
| 702941 | N/A | N/A | 6589 | 6604 | TGTATTTGTGCAAGGC | kk-d8-kekekk | 59 | 1038 |

TABLE 17

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633301 | 256 | 271 | 40765 | 40780 | CAGTCGCATGTACTCT | kkk-d10-kkk | 92 | 236 |
| 633335 | 654 | 669 | 59124 | 59139 | TCATTTATAAACCCAC | kkk-d10-kkk | 54 | 97 |
| 633365 | 1074 | 1089 | 68329 | 68344 | CGCTTATAAGTGTTGG | kkk-d10-kkk | 31 | 252 |
| 633473 | 2390 | 2405 | 80338 | 80353 | AAGGGATTTCCATTTC | kkk-d10-kkk | 54 | 279 |
| 662368 | 700 | 715 | 59170 | 59185 | ATCATTATATTGACCA | kkk-d10-kkk | 29 | 387 |
| 662423 | 919 | 934 | 61393 | 61408 | AAGTGCGCCTGGGAGC | kkk-d10-kkk | 59 | 443 |
| 663144 | N/A | N/A | 18224 | 18239 | CACAAGTTGTTCCATT | kkk-d10-kkk | 41 | 1065 |
| 702259 | 700 | 715 | 59170 | 59185 | ATCATTATATTGACCA | k-d10-kekek | 77 | 387 |
| 702260 | 919 | 934 | 61393 | 61408 | AAGTGCGCCTGGGAGC | k-d10-kekek | 82 | 443 |

TABLE 17-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702269 | N/A | N/A | 18224 | 18239 | CACAAGTTGTTCCATT | k-d10-kekek | 69 | 1065 |
| 702270 | 698 | 713 | 59168 | 59183 | CATTATATTGACCAAG | k-d10-kekek | 59 | 245 |
| 702271 | 917 | 932 | 61391 | 61406 | GTGCGCCTGGGAGCTG | k-d10-kekek | 98 | 441 |
| 702280 | N/A | N/A | 18222 | 18237 | CAAGTTGTTCCATTAT | k-d10-kekek | 73 | 1047 |
| 702281 | 700 | 715 | 59170 | 59185 | ATCATTATATTGACCA | k-d9-kekeke | 71 | 387 |
| 702282 | 919 | 934 | 61393 | 61408 | AAGTGCGCCTGGGAGC | k-d9-kekeke | 91 | 443 |
| 702291 | N/A | N/A | 18224 | 18239 | CACAAGTTGTTCCATT | k-d9-kekeke | 73 | 1065 |
| 702292 | 698 | 713 | 59168 | 59183 | CATTATATTGACCAAG | k-d9-kekeke | 67 | 245 |
| 702293 | 917 | 932 | 61391 | 61406 | GTGCGCCTGGGAGCTG | k-d9-kekeke | 96 | 441 |
| 702302 | N/A | N/A | 18222 | 18237 | CAAGTTGTTCCATTAT | k-d9-kekeke | 57 | 1047 |
| 702303 | 700 | 715 | 59170 | 59185 | ATCATTATATTGACCA | kk-d8-kekekk | 95 | 387 |
| 702304 | 919 | 934 | 61393 | 61408 | AAGTGCGCCTGGGAGC | kk-d8-kekekk | 85 | 443 |
| 702310 | 2580 | 2595 | 80528 | 80543 | AACACTTTGCAGCTGG | kk-d8-kekekk | 90 | 493 |
| 702313 | N/A | N/A | 18224 | 18239 | CACAAGTTGTTCCATT | kk-d8-kekekk | 77 | 1065 |
| 702330 | 700 | 715 | 59170 | 59185 | ATCATTATATTGACCA | kk-d10-keke | 75 | 387 |
| 702331 | 919 | 934 | 61393 | 61408 | AAGTGCGCCTGGGAGC | kk-d10-keke | 64 | 443 |
| 702340 | N/A | N/A | 18224 | 18239 | CACAAGTTGTTCCATT | kk-d10-keke | 43 | 1065 |
| 702341 | 699 | 714 | 59169 | 59184 | TCATTATATTGACCAA | kk-d10-keke | 98 | 1010 |
| 702342 | 918 | 933 | 61392 | 61407 | AGTGCGCCTGGGAGCT | kk-d10-keke | 67 | 442 |
| 702351 | N/A | N/A | 18223 | 18238 | ACAAGTTGTTCCATTA | kk-d10-keke | 61 | 1048 |
| 702352 | 700 | 715 | 59170 | 59185 | ATCATTATATTGACCA | kk-d9-kekek | 56 | 387 |
| 702353 | 919 | 934 | 61393 | 61408 | AAGTGCGCCTGGGAGC | kk-d9-kekek | 81 | 443 |
| 702362 | N/A | N/A | 18224 | 18239 | CACAAGTTGTTCCATT | kk-d9-kekek | 52 | 1065 |
| 702363 | 699 | 714 | 59169 | 59184 | TCATTATATTGACCAA | kk-d9-kekek | 51 | 1010 |
| 702364 | 918 | 933 | 61392 | 61407 | AGTGCGCCTGGGAGCT | kk-d9-kekek | 65 | 442 |
| 702373 | N/A | N/A | 18223 | 18238 | ACAAGTTGTTCCATTA | kk-d9-kekek | 34 | 1048 |
| 702374 | 700 | 715 | 59170 | 59185 | ATCATTATATTGACCA | kkk-d9-kkke | 73 | 387 |
| 702375 | 919 | 934 | 61393 | 61408 | AAGTGCGCCTGGGAGC | kkk-d9-kkke | 70 | 443 |
| 702384 | N/A | N/A | 18224 | 18239 | CACAAGTTGTTCCATT | kkk-d9-kkke | 33 | 1065 |
| 702385 | 699 | 714 | 59169 | 59184 | TCATTATATTGACCAA | kkk-d9-kkke | 61 | 1010 |
| 702386 | 918 | 933 | 61392 | 61407 | AGTGCGCCTGGGAGCT | kkk-d9-kkke | 101 | 442 |
| 702395 | N/A | N/A | 18223 | 18238 | ACAAGTTGTTCCATTA | kkk-d9-kkke | 30 | 1048 |
| 702396 | 700 | 715 | 59170 | 59185 | ATCATTATATTGACCA | kkk-d8-kekek | 87 | 387 |
| 702397 | 919 | 934 | 61393 | 61408 | AAGTGCGCCTGGGAGC | kkk-d8-kekek | 80 | 443 |
| 702406 | N/A | N/A | 18224 | 18239 | CACAAGTTGTTCCATT | kkk-d8-kekek | 49 | 1065 |
| 702407 | 700 | 715 | 59170 | 59185 | ATCATTATATTGACCA | kkk-d9-keke | 66 | 387 |

TABLE 17-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702408 | 919 | 934 | 61393 | 61408 | AAGTGCGCCTGGGAGC | kkk-d9-keke | 65 | 443 |
| 702417 | N/A | N/A | 18224 | 18239 | CACAAGTTGTTCCATT | kkk-d9-keke | 28 | 1065 |
| 702433 | 700 | 715 | 59170 | 59185 | ATCATTATATTGACCA | kkk-d8-kdkdk | 70 | 387 |
| 702434 | 919 | 934 | 61393 | 61408 | AAGTGCGCCTGGGAGC | kkk-d8-kdkdk | 79 | 443 |
| 702440 | 2580 | 2595 | 80528 | 80543 | AACACTTTGCAGCTGG | kkk-d8-kdkdk | 71 | 493 |
| 702443 | N/A | N/A | 18224 | 18239 | CACAAGTTGTTCCATT | kkk-d8-kdkdk | 51 | 1065 |
| 702459 | 699 | 714 | 59169 | 59184 | TCATTATATTGACCAA | kk-d9-kdkdk | 68 | 1010 |
| 702460 | 918 | 933 | 61392 | 61407 | AGTGCGCCTGGGAGCT | kk-d9-kdkdk | 56 | 442 |
| 702466 | 2579 | 2594 | 80527 | 80542 | ACACTTTGCAGCTGGT | kk-d9-kdkdk | 71 | 1029 |
| 702469 | N/A | N/A | 18223 | 18238 | ACAAGTTGTTCCATTA | kk-d9-kdkdk | 37 | 1048 |
| 702861 | 256 | 271 | 40765 | 40780 | CAGTCGCATGTACTCT | k-d10-kekek | 58 | 236 |
| 702866 | 254 | 269 | 40763 | 40778 | GTCGCATGTACTCTGA | k-d10-kekek | 72 | 1066 |
| 702871 | 256 | 271 | 40765 | 40780 | CAGTCGCATGTACTCT | k-d9-kekeke | 75 | 236 |
| 702876 | 254 | 269 | 40763 | 40778 | GTCGCATGTACTCTGA | k-d9-kekeke | 68 | 1066 |
| 702881 | 256 | 271 | 40765 | 40780 | CAGTCGCATGTACTCT | kk-d10-keke | 83 | 236 |
| 702885 | 255 | 270 | 40764 | 40779 | AGTCGCATGTACTCTG | kk-d10-keke | 73 | 1067 |
| 702890 | 256 | 271 | 40765 | 40780 | CAGTCGCATGTACTCT | kk-d9-kekek | 72 | 236 |
| 702894 | 255 | 270 | 40764 | 40779 | AGTCGCATGTACTCTG | kk-d9-kekek | 91 | 1067 |
| 702899 | 256 | 271 | 40765 | 40780 | CAGTCGCATGTACTCT | kkk-d9-kkke | 96 | 236 |
| 702903 | 255 | 270 | 40764 | 40779 | AGTCGCATGTACTCTG | kkk-d9-kkke | 65 | 1067 |
| 702908 | 256 | 271 | 40765 | 40780 | CAGTCGCATGTACTCT | kkk-d8-kekek | 77 | 236 |
| 702913 | 255 | 270 | 40764 | 40779 | AGTCGCATGTACTCTG | kkk-d8-kekek | 85 | 1067 |
| 702914 | 699 | 714 | 59169 | 59184 | TCATTATATTGACCAA | kkk-d8-kekek | 69 | 1010 |
| 702915 | 918 | 933 | 61392 | 61407 | AGTGCGCCTGGGAGCT | kkk-d8-kekek | 79 | 442 |
| 702925 | N/A | N/A | 18223 | 18238 | ACAAGTTGTTCCATTA | kkk-d8-kekek | 26 | 1048 |
| 702926 | 256 | 271 | 40765 | 40780 | CAGTCGCATGTACTCT | kk-d8-kekekk | 74 | 236 |
| 702931 | 255 | 270 | 40764 | 40779 | AGTCGCATGTACTCTG | kk-d8-kekekk | 92 | 1067 |
| 702932 | 699 | 714 | 59169 | 59184 | TCATTATATTGACCAA | kk-d8-kekekk | 90 | 1010 |
| 702933 | 918 | 933 | 61392 | 61407 | AGTGCGCCTGGGAGCT | kk-d8-kekekk | 98 | 442 |
| 702940 | 2579 | 2594 | 80527 | 80542 | ACACTTTGCAGCTGGT | kk-d8-kekekk | 101 | 1029 |
| 702942 | N/A | N/A | 18223 | 18238 | ACAAGTTGTTCCATTA | kk-d8-kekekk | 58 | 1048 |
| 702948 | 255 | 270 | 40764 | 40779 | AGTCGCATGTACTCTG | kk-d9-kdkdk | 72 | 1067 |
| 702953 | 256 | 271 | 40765 | 40780 | CAGTCGCATGTACTCT | kkk-d8-kdkdk | 70 | 236 |
| 702958 | 256 | 271 | 40765 | 40780 | CAGTCGCATGTACTCT | kkk-d9-keke | 94 | 236 |

TABLE 18

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633335 | 654 | 669 | 59124 | 59139 | TCATTTATAAACCCAC | kkk-d10-kkk | 32 | 97 |
| 633355 | 964 | 979 | 61438 | 61453 | AGATTTAGCATTTGGT | kkk-d10-kkk | 26 | 102 |
| 633365 | 1074 | 1089 | 68329 | 68344 | CGCTTATAAGTGTTGG | kkk-d10-kkk | 38 | 252 |
| 633473 | 2390 | 2405 | 80338 | 80353 | AAGGGATTTCCATTTC | kkk-d10-kkk | 60 | 279 |
| 633473 | 2390 | 2405 | 80338 | 80353 | AAGGGATTTCCATTTC | kkk-d10-kkk | 42 | 279 |
| 662442 | 965 | 980 | 61439 | 61454 | CAGATTTAGCATTTGG | kkk-d10-kkk | 72 | 462 |
| 662493 | 1092 | 1107 | 68347 | 68362 | GCTGTTTCTGTGTTCT | kkk-d10-kkk | 48 | 662 |
| 662964 | 2580 | 2595 | 80528 | 80543 | AACACTTTGCAGCTGG | kkk-d10-kkk | 36 | 493 |
| 702262 | 965 | 980 | 61439 | 61454 | CAGATTTAGCATTTGG | k-d10-kekek | 63 | 462 |
| 702263 | 1074 | 1089 | 68329 | 68344 | CGCTTATAAGTGTTGG | k-d10-kekek | 41 | 252 |
| 702273 | 963 | 978 | 61437 | 61452 | GATTTAGCATTTGGTC | k-d10-kekek | 27 | 461 |
| 702274 | 1072 | 1087 | 68327 | 68342 | CTTATAAGTGTTGGGT | k-d10-kekek | 61 | 651 |
| 702284 | 965 | 980 | 61439 | 61454 | CAGATTTAGCATTTGG | k-d9-kekeke | 48 | 462 |
| 702285 | 1074 | 1089 | 68329 | 68344 | CGCTTATAAGTGTTGG | k-d9-kekeke | 54 | 252 |
| 702295 | 963 | 978 | 61437 | 61452 | GATTTAGCATTTGGTC | k-d9-kekeke | 41 | 461 |
| 702296 | 1072 | 1087 | 68327 | 68342 | CTTATAAGTGTTGGGT | k-d9-kekeke | 90 | 651 |
| 702306 | 965 | 980 | 61439 | 61454 | CAGATTTAGCATTTGG | kk-d8-kekekk | 76 | 462 |
| 702307 | 1074 | 1089 | 68329 | 68344 | CGCTTATAAGTGTTGG | kk-d8-kekekk | 94 | 252 |
| 702317 | 963 | 978 | 61437 | 61452 | GATTTAGCATTTGGTC | kk-d8-kekekk | 71 | 461 |
| 702333 | 965 | 980 | 61439 | 61454 | CAGATTTAGCATTTGG | kk-d10-keke | 51 | 462 |
| 702334 | 1074 | 1089 | 68329 | 68344 | CGCTTATAAGTGTTGG | kk-d10-keke | 23 | 252 |
| 702337 | 2580 | 2595 | 80528 | 80543 | AACACTTTGCAGCTGG | kk-d10-keke | 62 | 493 |
| 702344 | 964 | 979 | 61438 | 61453 | AGATTTAGCATTTGGT | kk-d10-keke | 20 | 102 |
| 702345 | 1073 | 1088 | 68328 | 68343 | GCTTATAAGTGTTGGG | kk-d10-keke | 50 | 652 |
| 702348 | 2579 | 2594 | 80527 | 80542 | ACACTTTGCAGCTGGT | kk-d10-keke | 63 | 1029 |
| 702355 | 965 | 980 | 61439 | 61454 | CAGATTTAGCATTTGG | kk-d9-kekek | 71 | 462 |
| 702356 | 1074 | 1089 | 68329 | 68344 | CGCTTATAAGTGTTGG | kk-d9-kekek | 50 | 252 |
| 702359 | 2580 | 2595 | 80528 | 80543 | AACACTTTGCAGCTGG | kk-d9-kekek | 76 | 493 |
| 702366 | 964 | 979 | 61438 | 61453 | AGATTTAGCATTTGGT | kk-d9-kekek | 15 | 102 |
| 702367 | 1073 | 1088 | 68328 | 68343 | GCTTATAAGTGTTGGG | kk-d9-kekek | 50 | 652 |
| 702370 | 2579 | 2594 | 80527 | 80542 | ACACTTTGCAGCTGGT | kk-d9-kekek | 74 | 1029 |
| 702377 | 965 | 980 | 61439 | 61454 | CAGATTTAGCATTTGG | kkk-d9-kkke | 56 | 462 |
| 702378 | 1074 | 1089 | 68329 | 68344 | CGCTTATAAGTGTTGG | kkk-d9-kkke | 24 | 252 |
| 702381 | 2580 | 2595 | 80528 | 80543 | AACACTTTGCAGCTGG | kkk-d9-kkke | 54 | 493 |
| 702388 | 964 | 979 | 61438 | 61453 | AGATTTAGCATTTGGT | kkk-d9-kkke | 20 | 102 |
| 702389 | 1073 | 1088 | 68328 | 68343 | GCTTATAAGTGTTGGG | kkk-d9-kkke | 50 | 652 |

TABLE 18-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702392 | 2579 | 2594 | 80527 | 80542 | ACACTTTGCAGCTGGT | kkk-d9-kkke | 47 | 1029 |
| 702399 | 965 | 980 | 61439 | 61454 | CAGATTTAGCATTTGG | kkk-d8-kekek | 64 | 462 |
| 702400 | 1074 | 1089 | 68329 | 68344 | CGCTTATAAGTGTTGG | kkk-d8-kekek | 57 | 252 |
| 702403 | 2580 | 2595 | 80528 | 80543 | AACACTTTGCAGCTGG | kkk-d8-kekek | 62 | 493 |
| 702410 | 965 | 980 | 61439 | 61454 | CAGATTTAGCATTTGG | kkk-d9-keke | 70 | 462 |
| 702411 | 1074 | 1089 | 68329 | 68344 | CGCTTATAAGTGTTGG | kkk-d9-keke | 29 | 252 |
| 702414 | 2580 | 2595 | 80528 | 80543 | AACACTTTGCAGCTGG | kkk-d9-keke | 47 | 493 |
| 702436 | 965 | 980 | 61439 | 61454 | CAGATTTAGCATTTGG | kkk-d8-kdkdk | 86 | 462 |
| 702437 | 1074 | 1089 | 68329 | 68344 | CGCTTATAAGTGTTGG | kkk-d8-kdkdk | 37 | 252 |
| 702462 | 964 | 979 | 61438 | 61453 | AGATTTAGCATTTGGT | kk-d9-kdkdk | 21 | 102 |
| 702463 | 1073 | 1088 | 68328 | 68343 | GCTTATAAGTGTTGGG | kk-d9-kdkdk | 54 | 652 |
| 702862 | 964 | 979 | 61438 | 61453 | AGATTTAGCATTTGGT | k-d10-kekek | 23 | 102 |
| 702863 | 1092 | 1107 | 68347 | 68362 | GCTGTTTCTGTGTTCT | k-d10-kekek | 42 | 662 |
| 702867 | 962 | 977 | 61436 | 61451 | ATTTAGCATTTGGTCC | k-d10-kekek | 81 | 460 |
| 702868 | 1090 | 1105 | 68345 | 68360 | TGTTTCTGTGTTCTTC | k-d10-kekek | 66 | 1055 |
| 702872 | 964 | 979 | 61438 | 61453 | AGATTTAGCATTTGGT | k-d9-kekeke | 42 | 102 |
| 702873 | 1092 | 1107 | 68347 | 68362 | GCTGTTTCTGTGTTCT | k-d9-kekeke | 61 | 662 |
| 702877 | 962 | 977 | 61436 | 61451 | ATTTAGCATTTGGTCC | k-d9-kekeke | 75 | 460 |
| 702878 | 1090 | 1105 | 68345 | 68360 | TGTTTCTGTGTTCTTC | k-d9-kekeke | 52 | 1055 |
| 702882 | 1092 | 1107 | 68347 | 68362 | GCTGTTTCTGTGTTCT | kk-d10-keke | 36 | 662 |
| 702886 | 963 | 978 | 61437 | 61452 | GATTTAGCATTTGGTC | kk-d10-keke | 44 | 461 |
| 702887 | 1091 | 1106 | 68346 | 68361 | CTGTTTCTGTGTTCTT | kk-d10-keke | 32 | 1056 |
| 702891 | 1092 | 1107 | 68347 | 68362 | GCTGTTTCTGTGTTCT | kk-d9-kekek | 39 | 662 |
| 702895 | 963 | 978 | 61437 | 61452 | GATTTAGCATTTGGTC | kk-d9-kekek | 30 | 461 |
| 702896 | 1091 | 1106 | 68346 | 68361 | CTGTTTCTGTGTTCTT | kk-d9-kekek | 29 | 1056 |
| 702900 | 1092 | 1107 | 68347 | 68362 | GCTGTTTCTGTGTTCT | kkk-d9-kkke | 40 | 662 |
| 702904 | 963 | 978 | 61437 | 61452 | GATTTAGCATTTGGTC | kkk-d9-kkke | 41 | 461 |
| 702905 | 1091 | 1106 | 68346 | 68361 | CTGTTTCTGTGTTCTT | kkk-d9-kkke | 28 | 1056 |
| 702909 | 964 | 979 | 61438 | 61453 | AGATTTAGCATTTGGT | kkk-d8-kekek | 20 | 102 |
| 702910 | 1092 | 1107 | 68347 | 68362 | GCTGTTTCTGTGTTCT | kkk-d8-kekek | 51 | 662 |
| 702916 | 963 | 978 | 61437 | 61452 | GATTTAGCATTTGGTC | kkk-d8-kekek | 49 | 461 |
| 702917 | 1073 | 1088 | 68328 | 68343 | GCTTATAAGTGTTGGG | kkk-d8-kekek | 62 | 652 |
| 702918 | 1091 | 1106 | 68346 | 68361 | CTGTTTCTGTGTTCTT | kkk-d8-kekek | 31 | 1056 |
| 702927 | 964 | 979 | 61438 | 61453 | AGATTTAGCATTTGGT | kk-d8-kekekk | 55 | 102 |
| 702928 | 1092 | 1107 | 68347 | 68362 | GCTGTTTCTGTGTTCT | kk-d8-kekekk | 62 | 662 |
| 702934 | 1073 | 1088 | 68328 | 68343 | GCTTATAAGTGTTGGG | kk-d8-kekekk | 65 | 652 |

TABLE 18-continued

Percent control of human EZH2 mRNA with gapmers
with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702935 | 1091 | 1106 | 68346 | 68361 | CTGTTTCTGTGTTCTT | kk-d8-kekekk | 45 | 1056 |
| 702949 | 963 | 978 | 61437 | 61452 | GATTTAGCATTTGGTC | kk-d9-kdkdk | 27 | 461 |
| 702950 | 1091 | 1106 | 68346 | 68361 | CTGTTTCTGTGTTCTT | kk-d9-kdkdk | 53 | 1056 |
| 702954 | 964 | 979 | 61438 | 61453 | AGATTTAGCATTTGGT | kkk-d8-kdkdk | 18 | 102 |
| 702955 | 1092 | 1107 | 68347 | 68362 | GCTGTTTCTGTGTTCT | kkk-d8-kdkdk | 38 | 662 |
| 702959 | 964 | 979 | 61438 | 61453 | AGATTTAGCATTTGGT | kkk-d9-keke | 18 | 102 |
| 702960 | 1092 | 1107 | 68347 | 68362 | GCTGTTTCTGTGTTCT | kkk-d9-keke | 37 | 662 |

TABLE 19

Percent control of human EZH2 mRNA with gapmers with phosphorothioate
internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633335 | 654 | 669 | 59124 | 59139 | TCATTTATAAACCCAC | kkk-d10-kkk | 40 | 97 |
| 633365 | 1074 | 1089 | 68329 | 68344 | CGCTTATAAGTGTTGG | kkk-d10-kkk | 40 | 252 |
| 633398 | 1492 | 1507 | 70710 | 70725 | GTAAGTGCCAATGAGG | kkk-d10-kkk | 40 | 39 |
| 633473 | 2390 | 2405 | 80338 | 80353 | AAGGGATTTCCATTTC | kkk-d10-kkk | 61 | 279 |
| 662648 | 1541 | 1556 | 70759 | 70774 | TACATGTTTTGGTCCC | kkk-d10-kkk | 44 | 829 |
| 662710 | 1728 | 1743 | 72992 | 73007 | GGATGATCACAGGGTT | kkk-d10-kkk | 34 | 900 |
| 662950 | 2509 | 2524 | 80457 | 80472 | GTACTTTGCAAATTCA | kkk-d10-kkk | 55 | 998 |
| 702264 | 1728 | 1743 | 72992 | 73007 | GGATGATCACAGGGTT | k-d10-kekek | 55 | 900 |
| 702265 | 2509 | 2524 | 80457 | 80472 | GTACTTTGCAAATTCA | k-d10-kekek | 60 | 998 |
| 702266 | 2580 | 2595 | 80528 | 80543 | AACACTTTGCAGCTGG | k-d10-kekek | 86 | 493 |
| 702275 | 1726 | 1741 | 72990 | 73005 | ATGATCACAGGGTTGA | k-d10-kekek | 80 | 898 |
| 702276 | 2507 | 2522 | 80455 | 80470 | ACTTTGCAAATTCAGA | k-d10-kekek | 51 | 1022 |
| 702277 | 2578 | 2593 | 80526 | 80541 | CACTTTGCAGCTGGTG | k-d10-kekek | 88 | 492 |
| 702286 | 1728 | 1743 | 72992 | 73007 | GGATGATCACAGGGTT | k-d9-kekeke | 81 | 900 |
| 702287 | 2509 | 2524 | 80457 | 80472 | GTACTTTGCAAATTCA | k-d9-kekeke | 58 | 998 |
| 702288 | 2580 | 2595 | 80528 | 80543 | AACACTTTGCAGCTGG | k-d9-kekeke | 103 | 493 |
| 702297 | 1726 | 1741 | 72990 | 73005 | ATGATCACAGGGTTGA | k-d9-kekeke | 70 | 898 |
| 702298 | 2507 | 2522 | 80455 | 80470 | ACTTTGCAAATTCAGA | k-d9-kekeke | 40 | 1022 |
| 702299 | 2578 | 2593 | 80526 | 80541 | CACTTTGCAGCTGGTG | k-d9-kekeke | 110 | 492 |
| 702308 | 1728 | 1743 | 72992 | 73007 | GGATGATCACAGGGTT | kk-d8-kekekk | 62 | 900 |
| 702309 | 2509 | 2524 | 80457 | 80472 | GTACTTTGCAAATTCA | kk-d8-kekekk | 77 | 998 |
| 702335 | 1728 | 1743 | 72992 | 73007 | GGATGATCACAGGGTT | kk-d10-keke | 33 | 900 |
| 702336 | 2509 | 2524 | 80457 | 80472 | GTACTTTGCAAATTCA | kk-d10-keke | 63 | 998 |

TABLE 19-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702346 | 1727 | 1742 | 72991 | 73006 | GATGATCACAGGGTTG | kk-d10-keke | 54 | 899 |
| 702347 | 2508 | 2523 | 80456 | 80471 | TACTTTGCAAATTCAG | kk-d10-keke | 46 | 1023 |
| 702357 | 1728 | 1743 | 72992 | 73007 | GGATGATCACAGGGTT | kk-d9-kekek | 50 | 900 |
| 702358 | 2509 | 2524 | 80457 | 80472 | GTACTTTGCAAATTCA | kk-d9-kekek | 64 | 998 |
| 702368 | 1727 | 1742 | 72991 | 73006 | GATGATCACAGGGTTG | kk-d9-kekek | 46 | 899 |
| 702369 | 2508 | 2523 | 80456 | 80471 | TACTTTGCAAATTCAG | kk-d9-kekek | 31 | 1023 |
| 702379 | 1728 | 1743 | 72992 | 73007 | GGATGATCACAGGGTT | kkk-d9-kkke | 36 | 900 |
| 702380 | 2509 | 2524 | 80457 | 80472 | GTACTTTGCAAATTCA | kkk-d9-kkke | 50 | 998 |
| 702390 | 1727 | 1742 | 72991 | 73006 | GATGATCACAGGGTTG | kkk-d9-kkke | 42 | 899 |
| 702391 | 2508 | 2523 | 80456 | 80471 | TACTTTGCAAATTCAG | kkk-d9-kkke | 34 | 1023 |
| 702401 | 1728 | 1743 | 72992 | 73007 | GGATGATCACAGGGTT | kkk-d8-kekek | 50 | 900 |
| 702402 | 2509 | 2524 | 80457 | 80472 | GTACTTTGCAAATTCA | kkk-d8-kekek | 75 | 998 |
| 702412 | 1728 | 1743 | 72992 | 73007 | GGATGATCACAGGGTT | kkk-d9-keke | 27 | 900 |
| 702413 | 2509 | 2524 | 80457 | 80472 | GTACTTTGCAAATTCA | kkk-d9-keke | 54 | 998 |
| 702438 | 1728 | 1743 | 72992 | 73007 | GGATGATCACAGGGTT | kkk-d8-kdkdk | 34 | 900 |
| 702439 | 2509 | 2524 | 80457 | 80472 | GTACTTTGCAAATTCA | kkk-d8-kdkdk | 67 | 998 |
| 702464 | 1727 | 1742 | 72991 | 73006 | GATGATCACAGGGTTG | kk-d9-kdkdk | 62 | 899 |
| 702465 | 2508 | 2523 | 80456 | 80471 | TACTTTGCAAATTCAG | kk-d9-kdkdk | 55 | 1023 |
| 702864 | 1492 | 1507 | 70710 | 70725 | GTAAGTGCCAATGAGG | k-d10-kekek | 58 | 39 |
| 702865 | 1541 | 1556 | 70759 | 70774 | TACATGTTTTGGTCCC | k-d10-kekek | 79 | 829 |
| 702869 | 1490 | 1505 | 70708 | 70723 | AAGTGCCAATGAGGAC | k-d10-kekek | 82 | 804 |
| 702870 | 1539 | 1554 | 70757 | 70772 | CATGTTTTGGTCCCAA | k-d10-kekek | 78 | 828 |
| 702874 | 1492 | 1507 | 70710 | 70725 | GTAAGTGCCAATGAGG | k-d9-kekeke | 59 | 39 |
| 702875 | 1541 | 1556 | 70759 | 70774 | TACATGTTTTGGTCCC | k-d9-kekeke | 102 | 829 |
| 702879 | 1490 | 1505 | 70708 | 70723 | AAGTGCCAATGAGGAC | k-d9-kekeke | 66 | 804 |
| 702880 | 1539 | 1554 | 70757 | 70772 | CATGTTTTGGTCCCAA | k-d9-kekeke | 76 | 828 |
| 702883 | 1492 | 1507 | 70710 | 70725 | GTAAGTGCCAATGAGG | kk-d10-keke | 70 | 39 |
| 702884 | 1541 | 1556 | 70759 | 70774 | TACATGTTTTGGTCCC | kk-d10-keke | 62 | 829 |
| 702888 | 1491 | 1506 | 70709 | 70724 | TAAGTGCCAATGAGGA | kk-d10-keke | 57 | 805 |
| 702889 | 1540 | 1555 | 70758 | 70773 | ACATGTTTTGGTCCCA | kk-d10-keke | 64 | 1061 |
| 702892 | 1492 | 1507 | 70710 | 70725 | GTAAGTGCCAATGAGG | kk-d9-kekek | 48 | 39 |
| 702893 | 1541 | 1556 | 70759 | 70774 | TACATGTTTTGGTCCC | kk-d9-kekek | 101 | 829 |
| 702897 | 1491 | 1506 | 70709 | 70724 | TAAGTGCCAATGAGGA | kk-d9-kekek | 53 | 805 |
| 702898 | 1540 | 1555 | 70758 | 70773 | ACATGTTTTGGTCCCA | kk-d9-kekek | 77 | 1061 |
| 702901 | 1492 | 1507 | 70710 | 70725 | GTAAGTGCCAATGAGG | kkk-d9-kkke | 30 | 39 |
| 702902 | 1541 | 1556 | 70759 | 70774 | TACATGTTTTGGTCCC | kkk-d9-kkke | 71 | 829 |

TABLE 19-continued

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 702906 | 1491 | 1506 | 70709 | 70724 | TAAGTGCCAATGAGGA | kkk-d9-kkke | 71 | 805 |
| 702907 | 1540 | 1555 | 70758 | 70773 | ACATGTTTTGGTCCCA | kkk-d9-kkke | 79 | 1061 |
| 702911 | 1492 | 1507 | 70710 | 70725 | GTAAGTGCCAATGAGG | kkk-d8-kekek | 32 | 39 |
| 702912 | 1541 | 1556 | 70759 | 70774 | TACATGTTTTGGTCCC | kkk-d8-kekek | 118 | 829 |
| 702919 | 1491 | 1506 | 70709 | 70724 | TAAGTGCCAATGAGGA | kkk-d8-kekek | 66 | 805 |
| 702920 | 1540 | 1555 | 70758 | 70773 | ACATGTTTTGGTCCCA | kkk-d8-kekek | 86 | 1061 |
| 702921 | 1727 | 1742 | 72991 | 73006 | GATGATCACAGGGTTG | kkk-d8-kekek | 84 | 899 |
| 702922 | 2508 | 2523 | 80456 | 80471 | TACTTTGCAAATTCAG | kkk-d8-kekek | 40 | 1023 |
| 702929 | 1492 | 1507 | 70710 | 70725 | GTAAGTGCCAATGAGG | kk-d8-kekekk | 60 | 39 |
| 702930 | 1541 | 1556 | 70759 | 70774 | TACATGTTTTGGTCCC | kk-d8-kekekk | 76 | 829 |
| 702936 | 1491 | 1506 | 70709 | 70724 | TAAGTGCCAATGAGGA | kk-d8-kekekk | 66 | 805 |
| 702937 | 1540 | 1555 | 70758 | 70773 | ACATGTTTTGGTCCCA | kk-d8-kekekk | 105 | 1061 |
| 702938 | 1727 | 1742 | 72991 | 73006 | GATGATCACAGGGTTG | kk-d8-kekekk | 92 | 899 |
| 702939 | 2508 | 2523 | 80456 | 80471 | TACTTTGCAAATTCAG | kk-d8-kekekk | 57 | 1023 |
| 702951 | 1491 | 1506 | 70709 | 70724 | TAAGTGCCAATGAGGA | kk-d9-kdkdk | 54 | 805 |
| 702952 | 1540 | 1555 | 70758 | 70773 | ACATGTTTTGGTCCCA | kk-d9-kdkdk | 64 | 1061 |
| 702956 | 1492 | 1507 | 70710 | 70725 | GTAAGTGCCAATGAGG | kkk-d8-kdkdk | 43 | 39 |
| 702957 | 1541 | 1556 | 70759 | 70774 | TACATGTTTTGGTCCC | kkk-d8-kdkdk | 82 | 829 |
| 702961 | 1492 | 1507 | 70710 | 70725 | GTAAGTGCCAATGAGG | kkk-d9-keke | 44 | 39 |
| 702962 | 1541 | 1556 | 70759 | 70774 | TACATGTTTTGGTCCC | kkk-d9-keke | 67 | 829 |

Example 6: Effect of 3-10-3 cEt Gapmers and Mixed MOE and cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured A431 cells at a density of 5,000 cells per well were transfected via free uptake with 1,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (described hereinabove in Example 1) was used to measure mRNA levels. EZH2 mRNA levels were adjusted according to total RNA content, as measured by RiboGreen®. Results are presented in the table below as percent control of the amount of EZH2 mRNA, relative to untreated control cells (UTC).

The modified oligonucleotides in the table below are cEt and/or MOE containing gapmers. The gapmers have a central gap segment comprises 2'-deoxynucleosides which is flanked by wing segments on both the 5' end and on the 3' end. At least one nucleoside in the 5' wing segment and/or one nucleoside in the 3' wing segment has a MOE and/or cEt sugar modification. The "Chemistry" column describes the sugar modifications of each oligonucleotide. "k" indicates a cEt sugar modification; "d" indicates deoxyribose; and "e" indicates a MOE modification. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 20

Percent control of human EZH2 mRNA with gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | Chemistry | EZH2 (% UTC) | SEQ ID NO |
|---|---|---|---|---|---|---|---|---|
| 633301 | 256 | 271 | 40765 | 40780 | CAGTCGCATGTACTCT | kkk-d10-kkk | 63 | 236 |
| 633335 | 654 | 669 | 59124 | 59139 | TCATTTATAAACCCAC | kkk-d10-kkk | 48 | 97 |
| 633355 | 964 | 979 | 61438 | 61453 | AGATTTAGCATTTGGT | kkk-d10-kkk | 28 | 102 |
| 633365 | 1074 | 1089 | 68329 | 68344 | CGCTTATAAGTGTTGG | kkk-d10-kkk | 30 | 252 |
| 633473 | 2390 | 2405 | 80338 | 80353 | AAGGGATTTCCATTTC | kkk-d10-kkk | 59 | 279 |
| 633473 | 2390 | 2405 | 80338 | 80353 | AAGGGATTTCCATTTC | kkk-d10-kkk | 54 | 279 |
| 662423 | 919 | 934 | 61393 | 61408 | AAGTGCGCCTGGGAGC | kkk-d10-kkk | 42 | 443 |
| 662493 | 1092 | 1107 | 68347 | 68362 | GCTGTTTCTGTGTTCT | kkk-d10-kkk | 40 | 662 |
| 662964 | 2580 | 2595 | 80528 | 80543 | AACACTTTGCAGCTGG | kkk-d10-kkk | 41 | 493 |
| 703722 | 256 | 271 | 40765 | 40780 | CAGTCGCATGTACTCT | kkk-d8-kkkkk | 70 | 236 |
| 703723 | 700 | 715 | 59170 | 59185 | ATCATTATATTGACCA | kkk-d8-kkkkk | 59 | 387 |
| 703724 | 919 | 934 | 61393 | 61408 | AAGTGCGCCTGGGAGC | kkk-d8-kkkkk | 66 | 443 |
| 703725 | 964 | 979 | 61438 | 61453 | AGATTTAGCATTTGGT | kkk-d8-kkkkk | 26 | 102 |
| 703726 | 965 | 980 | 61439 | 61454 | CAGATTTAGCATTTGG | kkk-d8-kkkkk | 90 | 462 |
| 703727 | 1074 | 1089 | 68329 | 68344 | CGCTTATAAGTGTTGG | kkk-d8-kkkkk | 62 | 252 |
| 703728 | 1092 | 1107 | 68347 | 68362 | GCTGTTTCTGTGTTCT | kkk-d8-kkkkk | 66 | 662 |
| 703729 | 1492 | 1507 | 70710 | 70725 | GTAAGTGCCAATGAGG | kkk-d8-kkkkk | 30 | 39 |
| 703730 | 1541 | 1556 | 70759 | 70774 | TACATGTTTTGGTCCC | kkk-d8-kkkkk | 76 | 829 |
| 703731 | 1728 | 1743 | 72992 | 73007 | GGATGATCACAGGGTT | kkk-d8-kkkkk | 45 | 900 |
| 703732 | 2509 | 2524 | 80457 | 80472 | GTACTTTGCAAATTCA | kkk-d8-kkkkk | 81 | 998 |
| 703733 | 2580 | 2595 | 80528 | 80543 | AACACTTTGCAGCTGG | kkk-d8-kkkkk | 102 | 493 |
| 703734 | N/A | N/A | 6590 | 6605 | ATGTATTTGTGCAAGG | kkk-d8-kkkkk | 61 | 535 |
| 703735 | N/A | N/A | 18224 | 18239 | CACAAGTTGTTCCATT | kkk-d8-kkkkk | 46 | 1065 |

Example 7: Effect of 3-10-3 cEt Gapmers with Phosphorothioate Internucleoside Linkages on Human EZH2 In Vitro, Single Dose Modified oligonucleotides complementary to a human EZH2 nucleic acid were designed and tested for their effect on EZH2 mRNA in vitro.

Cultured A431 cells at a density of 5,000 cells per well were transfected via free uptake with 1,000 nM concentration of modified oligonucleotide or no modified oligonucleotide for untreated controls. After approximately 24 hours, RNA was isolated from the cells and EZH2 mRNA levels were measured by quantitative real-time PCR. Human primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC).

The modified oligonucleotides in the tables below are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human EZH2 nucleic acid sequences SEQ ID NO: 1 or SEQ ID NO: 2 as indicated. 'N/A' indicates that the modified oligonucleotide is not complementary to that particular nucleic acid sequence with 100% complementarity. As shown below, modified oligonucleotides complementary to human EZH2 reduced the amount of human EZH2 mRNA.

TABLE 21

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 19 | 252 |
| 663097 | N/A | N/A | 6590 | 6605 | ATGTATTTGTGCAAGG | 6 | 535 |
| 663144 | N/A | N/A | 18224 | 18239 | CACAAGTTGTTCCATT | 33 | 1065 |
| 702233 | N/A | N/A | 6589 | 6604 | TGTATTTGTGCAAGGC | 0 | 1038 |
| 755828 | N/A | N/A | 5090 | 5105 | AAACATTTCTCCATGC | 103 | 1068 |
| 755830 | N/A | N/A | 5125 | 5140 | ACTGTGGACAGCACAC | 88 | 1069 |
| 755832 | N/A | N/A | 5135 | 5150 | AGGAAGTTTAACTGTG | 69 | 1070 |
| 755834 | N/A | N/A | 5147 | 5162 | CCTGTGTGATAAAGGA | 94 | 1071 |
| 755836 | N/A | N/A | 5157 | 5172 | TGTTACAGATCCTGTG | 80 | 1072 |
| 755838 | N/A | N/A | 5194 | 5209 | TAGCAAAGACACATTT | 91 | 1073 |
| 755840 | N/A | N/A | 5204 | 5219 | TTTAAGTAAATAGCAA | 96 | 1074 |
| 755842 | N/A | N/A | 5214 | 5229 | AAAGCAAGCCTTTAAG | 90 | 1075 |
| 755844 | N/A | N/A | 5225 | 5240 | TTGAACCCTAAAAAGC | 91 | 1076 |
| 755846 | N/A | N/A | 5235 | 5250 | AATAACTTGCTTGAAC | 100 | 1077 |
| 755848 | N/A | N/A | 5253 | 5268 | CCACAAAATTAAACTA | 89 | 1078 |
| 755849 | N/A | N/A | 5274 | 5289 | TTTTATGATGACATCA | 51 | 1079 |
| 755851 | N/A | N/A | 5289 | 5304 | GTTTATTAAATGCTGT | 54 | 1080 |
| 755853 | N/A | N/A | 5300 | 5315 | GTTTTTCAAAGGTTTA | 25 | 1081 |
| 755855 | N/A | N/A | 5317 | 5332 | ATTGTGACAGCATTCG | 71 | 1082 |
| 755857 | N/A | N/A | 5327 | 5342 | ACTACATTCAATTGTG | 66 | 1083 |
| 755859 | N/A | N/A | 5340 | 5355 | CCTAAAAGTATAAACT | 77 | 1084 |
| 755861 | N/A | N/A | 5350 | 5365 | CTCCAAAACCCCTAAA | 77 | 1085 |
| 755863 | N/A | N/A | 5371 | 5386 | TGAAGAGTAATAGAAA | 93 | 1086 |
| 755865 | N/A | N/A | 5381 | 5396 | CTAATGCTTATGAAGA | 86 | 1087 |
| 755867 | N/A | N/A | 5391 | 5406 | GAATTAGTTGCTAATG | 95 | 1088 |
| 755869 | N/A | N/A | 5401 | 5416 | TCCTAAACATGAATTA | 70 | 1089 |
| 755871 | N/A | N/A | 5412 | 5427 | TTGTACAGTATTCCTA | 89 | 1090 |
| 755873 | N/A | N/A | 5424 | 5439 | AGGATTACACACTTGT | 31 | 1091 |
| 755875 | N/A | N/A | 5434 | 5449 | TAAACAAGTTAGGATT | 83 | 1092 |
| 755877 | N/A | N/A | 5453 | 5468 | CTGCAAATAAAATTAC | 115 | 1093 |
| 755879 | N/A | N/A | 5465 | 5480 | ATACTTGTTTTCCTGC | 46 | 1094 |
| 755881 | N/A | N/A | 5495 | 5510 | CCATGAATAGAAAATT | 96 | 1095 |
| 755883 | N/A | N/A | 5505 | 5520 | ACTTTAGAGACCATGA | 60 | 1096 |
| 755884 | N/A | N/A | 5515 | 5530 | CCTATTCCTAACTTTA | 102 | 1097 |
| 755886 | N/A | N/A | 5525 | 5540 | TAGAATCCTACCTATT | 99 | 1098 |
| 755888 | N/A | N/A | 5535 | 5550 | TATCTATGACTAGAAT | 120 | 1099 |

TABLE 21-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 755891 | N/A | N/A | 5555 | 5570 | AGAGAGAACAAGACGC | 89 | 1100 |
| 755893 | N/A | N/A | 5565 | 5580 | ACCTCCGAAAAGAGAG | 74 | 1101 |
| 755895 | N/A | N/A | 5575 | 5590 | CACCCAACACACCTCC | 64 | 1102 |
| 755897 | N/A | N/A | 5585 | 5600 | AATATTACATCACCCA | 72 | 1103 |
| 755899 | N/A | N/A | 5595 | 5610 | GGAAACCTTAAATATT | 108 | 1104 |
| 755901 | N/A | N/A | 5605 | 5620 | CCTGTTTCCGGGAAAC | 86 | 1105 |
| 755903 | N/A | N/A | 5615 | 5630 | ATGCAGTGTTCCTGTT | 99 | 1106 |
| 755905 | N/A | N/A | 5625 | 5640 | AGAATTAAGATGCAG | 53 | 1107 |
| 755907 | N/A | N/A | 5635 | 5650 | CACAAAAACGAGAATT | 116 | 1108 |
| 755909 | N/A | N/A | 5645 | 5660 | ATTCACTTTCCACAAA | 119 | 1109 |
| 755911 | N/A | N/A | 5655 | 5670 | CTTGGAATATATTCAC | 46 | 1110 |
| 755913 | N/A | N/A | 5665 | 5680 | AACTTGTTTTCTTGGA | 56 | 1111 |
| 755915 | N/A | N/A | 5675 | 5690 | ATGTTTTTCTAACTTG | 74 | 1112 |
| 755917 | N/A | N/A | 5693 | 5708 | GCAACCAGAAGAACGC | 84 | 1113 |
| 755919 | N/A | N/A | 5703 | 5718 | ATAGGACAGTGCAACC | 81 | 1114 |
| 755921 | N/A | N/A | 5724 | 5739 | TGCACATTAGATCTTT | 68 | 1115 |
| 755923 | N/A | N/A | 5734 | 5749 | AGTTAGCAGATGCACA | 81 | 1116 |
| 755924 | N/A | N/A | 5744 | 5759 | TGAAACCTTAAGTTAG | 70 | 1117 |
| 755927 | N/A | N/A | 5765 | 5780 | ATTTATTTGTCTCCAT | 34 | 1118 |
| 755929 | N/A | N/A | 5798 | 5813 | CTCTCCAAAATATATG | 84 | 1119 |
| 755930 | N/A | N/A | 5813 | 5828 | ACAGTGGTGTCAACAC | 89 | 1120 |
| 755932 | N/A | N/A | 5823 | 5838 | GAATGCCCGTACAGTG | 58 | 1121 |
| 755934 | N/A | N/A | 5833 | 5848 | CCAGCACCTGGAATGC | 98 | 1122 |
| 755936 | N/A | N/A | 5843 | 5858 | AACACTTAGACCAGCA | 82 | 1123 |
| 755938 | N/A | N/A | 5853 | 5868 | ATAATGTCTCAACACT | 68 | 1124 |
| 755940 | N/A | N/A | 5882 | 5897 | GTAACTAATATAAACG | 98 | 1125 |
| 755942 | N/A | N/A | 5917 | 5932 | ATTATTAATAGGATTT | 67 | 1126 |
| 755944 | N/A | N/A | 5927 | 5942 | AATGGACAAGATTATT | 99 | 1127 |
| 755946 | N/A | N/A | 5937 | 5952 | CTTATCTCATAATGGA | 86 | 1128 |
| 755948 | N/A | N/A | 5947 | 5962 | GCATAACTACCTTATC | 44 | 1129 |
| 755950 | N/A | N/A | 5957 | 5972 | CCAAAAATCTGCATAA | 94 | 1130 |
| 755952 | N/A | N/A | 5967 | 5982 | CGAATTCTGCCAAAA | 58 | 1131 |
| 755954 | N/A | N/A | 5977 | 5992 | CTAAATATCCGAATT | 105 | 1132 |
| 755956 | N/A | N/A | 5988 | 6003 | ACATATGTATCCTAAA | 118 | 1133 |
| 755958 | N/A | N/A | 6279 | 6294 | GTACATCACTTCAGGT | 98 | 1134 |
| 755960 | N/A | N/A | 6289 | 6304 | GCGGAGGCGGGTACAT | 80 | 1135 |

TABLE 21-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 755962 | N/A | N/A | 6306 | 6321 | GATCAGCATTTTGGGA | 54 | 1136 |
| 755964 | N/A | N/A | 6340 | 6355 | TTTATCCTAGGCTGGG | 65 | 1137 |
| 755966 | N/A | N/A | 6350 | 6365 | GTTAGAAATTTTTATC | 54 | 1138 |
| 755968 | N/A | N/A | 6360 | 6375 | CAAGGGCAAAGTTAGA | 65 | 1139 |
| 755970 | N/A | N/A | 6370 | 6385 | AGAGAACACTCAAGGG | 79 | 1140 |
| 755972 | N/A | N/A | 6380 | 6395 | TATCAAATACAGAGAA | 83 | 1141 |
| 755974 | N/A | N/A | 6390 | 6405 | GAATAGTAATTATCAA | 75 | 1142 |

TABLE 22

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 44 | 252 |
| 663097 | N/A | N/A | 6590 | 6605 | ATGTATTTGTGCAAGG | 19 | 535 |
| 663144 | N/A | N/A | 18224 | 18239 | CACAAGTTGTTCCATT | 50 | 1065 |
| 702233 | N/A | N/A | 6589 | 6604 | TGTATTTGTGCAAGGC | 7 | 1038 |
| 755976 | N/A | N/A | 6400 | 6415 | CAAGTACAAAGAATAG | 86 | 1143 |
| 755978 | N/A | N/A | 6410 | 6425 | TATCTCATGGCAAGTA | 56 | 1144 |
| 755980 | N/A | N/A | 6439 | 6454 | CCAATTCCCCAAAGAG | 72 | 1145 |
| 755982 | N/A | N/A | 6472 | 6487 | GTACCAGAAAATAATT | 88 | 1146 |
| 755984 | N/A | N/A | 6482 | 6497 | ATTCTCAATTGTACCA | 54 | 1147 |
| 755986 | N/A | N/A | 6492 | 6507 | GACTAAATACATTCTC | 68 | 1148 |
| 755988 | N/A | N/A | 6502 | 6517 | TACTTAAACTGACTAA | 86 | 1149 |
| 755990 | N/A | N/A | 6512 | 6527 | AAGTCACTGCTACTTA | 78 | 1150 |
| 755992 | N/A | N/A | 6524 | 6539 | CAAGTGTGTTTTAAGT | 59 | 1151 |
| 755993 | N/A | N/A | 6534 | 6549 | ACTAGATCAACAAGTG | 88 | 1152 |
| 755995 | N/A | N/A | 6544 | 6559 | TTCTAACTACACTAGA | 93 | 1153 |
| 755997 | N/A | N/A | 6554 | 6569 | TCAGAACTTTTTCTAA | 88 | 1154 |
| 755999 | N/A | N/A | 6564 | 6579 | TATCAAAGTATCAGAA | 88 | 1155 |
| 756001 | N/A | N/A | 6574 | 6589 | CAAAGCTAGGTATCAA | 72 | 1156 |
| 756003 | N/A | N/A | 6580 | 6595 | GCAAGGCAAAGCTAGG | 47 | 1157 |
| 756005 | N/A | N/A | 6601 | 6616 | TATTCACTTAAATGTA | 86 | 1158 |
| 756007 | N/A | N/A | 6612 | 6627 | CAACATAAAGATATTC | 93 | 1159 |
| 756009 | N/A | N/A | 6622 | 6637 | TTTAAATGGCCAACAT | 91 | 1160 |
| 756011 | N/A | N/A | 6639 | 6654 | GAAATTTGCCTAAAAT | 98 | 1161 |

TABLE 22-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756014 | N/A | N/A | 6649 | 6664 | ATGACTTGGAGAAATT | 71 | 1162 |
| 756015 | N/A | N/A | 6659 | 6674 | AAATTCCAGTATGACT | 74 | 1163 |
| 756018 | N/A | N/A | 6669 | 6684 | TATCCTGGGAAAATTC | 91 | 1164 |
| 756019 | N/A | N/A | 6679 | 6694 | AGAAGGAAGGTATCCT | 52 | 1165 |
| 756022 | N/A | N/A | 6689 | 6704 | CTACCTCAAAAGAAGG | 99 | 1166 |
| 756024 | N/A | N/A | 6699 | 6714 | CTTGAGCACACTACCT | 93 | 1167 |
| 756026 | N/A | N/A | 6709 | 6724 | ATTCAGAATCCTTGAG | 78 | 1168 |
| 756028 | N/A | N/A | 6725 | 6740 | GGTAATACTGAAATAA | 102 | 1169 |
| 756030 | N/A | N/A | 6735 | 6750 | TCATGTAAAGGGTAAT | 91 | 1170 |
| 756032 | N/A | N/A | 6747 | 6762 | CTCAATCACTGCTCAT | 63 | 1171 |
| 756033 | N/A | N/A | 6757 | 6772 | GATCAACTTTCTCAAT | 74 | 1172 |
| 756035 | N/A | N/A | 6781 | 6796 | GTCCTTGTTGGTTTTT | 41 | 1173 |
| 756038 | N/A | N/A | 6793 | 6808 | ATTGGAGGATTTGTCC | 68 | 1174 |
| 756040 | N/A | N/A | 6803 | 6818 | AATACATTATATTGGA | 90 | 1175 |
| 756041 | N/A | N/A | 6813 | 6828 | TTAACCACAGAATACA | 73 | 1176 |
| 756043 | N/A | N/A | 6824 | 6839 | ATCATTGCTAATTAAC | 72 | 1177 |
| 756045 | N/A | N/A | 6834 | 6849 | TAATCCATAAATCATT | 106 | 1178 |
| 756047 | N/A | N/A | 6844 | 6859 | ACTTCAAGGCTAATCC | 71 | 1179 |
| 756049 | N/A | N/A | 6854 | 6869 | TGATATAAAGACTTCA | 89 | 1180 |
| 756051 | N/A | N/A | 6866 | 6881 | TGTCATCTATACTGAT | 64 | 1181 |
| 756053 | N/A | N/A | 6876 | 6891 | ACAGAAAATTTGTCAT | 91 | 1182 |
| 756055 | N/A | N/A | 6897 | 6912 | ATATAGAATCTATCAT | 108 | 1183 |
| 756057 | N/A | N/A | 6907 | 6922 | TCACCTACTCATATAG | 68 | 1184 |
| 756059 | N/A | N/A | 6917 | 6932 | CCCGAAGATTTCACCT | 96 | 1185 |
| 756061 | N/A | N/A | 6930 | 6945 | ACTTATGCTCTCCCCC | 55 | 1186 |
| 756063 | N/A | N/A | 6943 | 6958 | ATTGCTGCTGTTCACT | 60 | 1187 |
| 756065 | N/A | N/A | 6953 | 6968 | AATTTAATGAATTGCT | 87 | 1188 |
| 756067 | N/A | N/A | 6963 | 6978 | CCTTTCTCTGAATTTA | 57 | 1189 |
| 756069 | N/A | N/A | 6973 | 6988 | TGACCATGAACCTTTC | 57 | 1190 |
| 756071 | N/A | N/A | 6983 | 6998 | ATGTATCATCTGACCA | 60 | 1191 |
| 756073 | N/A | N/A | 6993 | 7008 | AAGGTAAAGTATGTAT | 77 | 1192 |
| 756075 | N/A | N/A | 7003 | 7018 | AGACCTCCAGAAGGTA | 85 | 1193 |
| 756077 | N/A | N/A | 7013 | 7028 | AATTCAGGGAAGACCT | 89 | 1194 |
| 756079 | N/A | N/A | 7023 | 7038 | CAAGAGTGGGAATTCA | 67 | 1195 |
| 756081 | N/A | N/A | 7036 | 7051 | CCCTGTGGGAACACAA | 79 | 1196 |
| 756082 | N/A | N/A | 7049 | 7064 | AAATATGATAAAACCC | 101 | 1197 |

TABLE 22-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756084 | N/A | N/A | 7061 | 7076 | CATGCTACAATAAAAT | 86 | 1198 |
| 756087 | N/A | N/A | 7071 | 7086 | ACAATTGAGTCATGCT | 67 | 1199 |
| 756089 | N/A | N/A | 7081 | 7096 | TGATTACAATACAATT | 95 | 1200 |
| 756090 | N/A | N/A | 7091 | 7106 | CATAAACAAGTGATTA | 89 | 1201 |
| 756092 | N/A | N/A | 7102 | 7117 | AGAGAGGGATGCATAA | 58 | 1202 |
| 756094 | N/A | N/A | 7112 | 7127 | ACTGTAGGGAAGAGAG | 81 | 1203 |
| 756096 | N/A | N/A | 7122 | 7137 | AGGCACTTTGACTGTA | 65 | 1204 |
| 756098 | N/A | N/A | 7132 | 7147 | CTCTACCAGGAGGCAC | 91 | 1205 |
| 756100 | N/A | N/A | 7143 | 7158 | TAAGACAGAGCCTCTA | 72 | 1206 |
| 756102 | N/A | N/A | 7164 | 7179 | CTAGGTATACAAAGAA | 191 | 1207 |
| 756104 | N/A | N/A | 7186 | 7201 | CTAGCAAATACCAACG | 91 | 1208 |
| 756106 | N/A | N/A | 7199 | 7214 | AAACCCCTATTCTCTA | 86 | 1209 |
| 756108 | N/A | N/A | 7209 | 7224 | ACTATATTTAAAACCC | 97 | 1210 |
| 756110 | N/A | N/A | 7219 | 7234 | AATTCATTCAACTATA | 96 | 1211 |
| 756112 | N/A | N/A | 7230 | 7245 | CATATTTCCTTAATTC | 79 | 1212 |
| 756114 | N/A | N/A | 7242 | 7257 | CCCTACATTTTTCATA | 90 | 1213 |
| 756116 | N/A | N/A | 7252 | 7267 | CAAATTATTTCCCTAC | 92 | 1214 |
| 756118 | N/A | N/A | 7262 | 7277 | GTTCCTTTGTCAAATT | 75 | 1215 |
| 756120 | N/A | N/A | 7272 | 7287 | CACTTTGCAAGTTCCT | 58 | 1216 |
| 756122 | N/A | N/A | 7283 | 7298 | CATATCCTGTTCACTT | 70 | 1217 |

TABLE 23

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 33 | 252 |
| 663097 | N/A | N/A | 6590 | 6605 | ATGTATTTGTGCAAGG | 14 | 535 |
| 663144 | N/A | N/A | 18224 | 18239 | CACAAGTTGTTCCATT | 36 | 1065 |
| 702233 | N/A | N/A | 6589 | 6604 | TGTATTTGTGCAAGGC | 9 | 1038 |
| 756124 | N/A | N/A | 7293 | 7308 | TGAATACTAACATATC | 104 | 1518 |
| 756126 | N/A | N/A | 7304 | 7319 | AGTTCCTCACATGAAT | 82 | 1519 |
| 756128 | N/A | N/A | 7314 | 7329 | CACATTTCAAAGTTCC | 45 | 1520 |
| 756130 | N/A | N/A | 7333 | 7348 | TATTAAAGAGGGAGAA | 94 | 1521 |
| 756132 | N/A | N/A | 7343 | 7358 | AATCATTCCCTATTAA | 84 | 1522 |

TABLE 23-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756134 | N/A | N/A | 7362 | 7377 | GACAACTATTTTTCTT | 64 | 1523 |
| 756136 | N/A | N/A | 7375 | 7390 | ACTTGTTCACCTTGAC | 46 | 1524 |
| 756138 | N/A | N/A | 7385 | 7400 | AAAACTTGGAACTTGT | 79 | 1525 |
| 756140 | N/A | N/A | 7395 | 7410 | ATAACTAGGAAAAACT | 109 | 1526 |
| 756142 | N/A | N/A | 7405 | 7420 | ACTACAGATTATAACT | 94 | 1527 |
| 756144 | N/A | N/A | 7415 | 7430 | AATGTTTAGTACTACA | 87 | 1528 |
| 756146 | N/A | N/A | 7425 | 7440 | AAGGATATCTAATGTT | 62 | 1529 |
| 756148 | N/A | N/A | 7435 | 7450 | GTTGCATCTAAAGGAT | 84 | 1530 |
| 756150 | N/A | N/A | 7448 | 7463 | TCCGAGTGTAATAGTT | 45 | 1531 |
| 756152 | N/A | N/A | 7458 | 7473 | TCTCCAGTTGTCCGAG | 91 | 1532 |
| 756154 | N/A | N/A | 7468 | 7483 | CATCAAGTTCTCTCCA | 77 | 1533 |
| 756156 | N/A | N/A | 7478 | 7493 | CCAGATGATTCATCAA | 104 | 1534 |
| 756158 | N/A | N/A | 7488 | 7503 | TACTAAATATCCAGAT | 93 | 1535 |
| 756160 | N/A | N/A | 7498 | 7513 | CAAATACTATTACTAA | 95 | 1536 |
| 756162 | N/A | N/A | 7512 | 7527 | TAAATCAAATTAAGCA | 83 | 1537 |
| 756164 | N/A | N/A | 7522 | 7537 | ATATCAACATTAAATC | 89 | 1538 |
| 756166 | N/A | N/A | 7536 | 7551 | CAAAGAGATCATCAAT | 79 | 1539 |
| 756168 | N/A | N/A | 7549 | 7564 | CCTTATATTTTGCAA | 92 | 1540 |
| 756170 | N/A | N/A | 7571 | 7586 | ACCCTCTCTCGCCCTT | 70 | 1541 |
| 756172 | N/A | N/A | 7581 | 7596 | AAGATCTACTACCCTC | 80 | 1542 |
| 756174 | N/A | N/A | 7591 | 7606 | TTTCAGTTAAAAGATC | 110 | 1543 |
| 756176 | N/A | N/A | 7601 | 7616 | CAAAACAGCTTTTCAG | 83 | 1544 |
| 756178 | N/A | N/A | 7611 | 7626 | TGAATTATAACAAAAC | 111 | 1545 |
| 756180 | N/A | N/A | 7621 | 7636 | AAAGAACTCATGAATT | 106 | 1546 |
| 756182 | N/A | N/A | 7631 | 7646 | TTACTCCAATAAAGAA | 87 | 1547 |
| 756184 | N/A | N/A | 7641 | 7656 | CTACCTCAATTTACTC | 101 | 1548 |
| 756186 | N/A | N/A | 7651 | 7666 | GCTCCAAAACCTACCT | 88 | 1549 |
| 756188 | N/A | N/A | 7661 | 7676 | TTCAGTTTTAGCTCCA | 18 | 1550 |
| 756190 | N/A | N/A | 7671 | 7686 | CGCTACATCCTTCAGT | 106 | 1551 |
| 756192 | N/A | N/A | 7686 | 7701 | ATCCAATTACACTGTC | 69 | 1552 |
| 756194 | N/A | N/A | 7696 | 7711 | CCAATAAATGATCCAA | 67 | 1553 |
| 756196 | N/A | N/A | 7706 | 7721 | GAAAAGCATCCCAATA | 87 | 1554 |
| 756198 | N/A | N/A | 7735 | 7750 | CTGTATTTAAATCATT | 95 | 1555 |
| 756200 | N/A | N/A | 7745 | 7760 | ATTTGCTAATCTGTAT | 87 | 1556 |
| 756201 | N/A | N/A | 7755 | 7770 | GTATCACTAAATTTGC | 95 | 1557 |
| 756203 | N/A | N/A | 7765 | 7780 | AACTTTTGAGGTATCA | 49 | 1558 |

TABLE 23-continued

Percent control of human EZH2 mRNA with 3-10-3 cEt gapmers
with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756205 | N/A | N/A | 7775 | 7790 | TACCAGCTGTAACTTT | 79 | 1559 |
| 756207 | N/A | N/A | 7785 | 7800 | CTTAGAAATTTACCAG | 94 | 1560 |
| 756210 | N/A | N/A | 7795 | 7810 | GTGCAACTATCTTAGA | 76 | 1561 |
| 756212 | N/A | N/A | 7805 | 7820 | ATATGGAATGGTGCAA | 47 | 1562 |
| 756214 | N/A | N/A | 7815 | 7830 | CAGTGGCAAGATATGG | 52 | 1563 |
| 756216 | N/A | N/A | 7836 | 7851 | TTTTTATACCAAGTAG | 81 | 1564 |
| 756218 | N/A | N/A | 7850 | 7865 | ACAAATTTGTCATATT | 81 | 1565 |
| 756220 | N/A | N/A | 7860 | 7875 | TAATCTAAACACAAAT | 79 | 1566 |
| 756222 | N/A | N/A | 7871 | 7886 | TGCTAACCACATAATC | 90 | 1567 |
| 756224 | N/A | N/A | 7886 | 7901 | CAATTATTAAGAAACT | 99 | 1568 |
| 756226 | N/A | N/A | 7897 | 7912 | GAAAACAAGACCAATT | 91 | 1569 |
| 756228 | N/A | N/A | 7907 | 7922 | ATTGTTAATGGAAAAC | 96 | 1570 |
| 756230 | N/A | N/A | 7920 | 7935 | GTTCTGTCTTGCTATT | 79 | 1571 |
| 756232 | N/A | N/A | 7930 | 7945 | CTATGATCTTGTTCTG | 90 | 1572 |
| 756234 | N/A | N/A | 8014 | 8029 | AATGGTGTGCACTGGT | 78 | 1573 |
| 756236 | N/A | N/A | 8024 | 8039 | AAGTCACCACAATGGT | 94 | 1574 |
| 756238 | N/A | N/A | 8064 | 8079 | AAGCAGGATCCCATCT | 112 | 1575 |
| 756240 | N/A | N/A | 8136 | 8151 | ATCCCTGTACTTTAAG | 102 | 1576 |
| 756242 | N/A | N/A | 8174 | 8189 | AAAAAGTATCTGGGTC | 83 | 1577 |
| 756244 | N/A | N/A | 8271 | 8286 | TAAATAAATTAGCCGA | 65 | 1578 |
| 756246 | N/A | N/A | 8407 | 8422 | TACTTGAGAGGTGAGG | 79 | 1579 |
| 756248 | N/A | N/A | 8592 | 8607 | ATAAAAATTATCGGAG | 84 | 1580 |
| 756250 | N/A | N/A | 8672 | 8687 | GACGAGGCAGGTCAAT | 88 | 1581 |
| 756252 | N/A | N/A | 8721 | 8736 | ACACAGCAGGGTGTGG | 88 | 1582 |
| 756254 | N/A | N/A | 9056 | 9071 | AAGTATCCAGGCCAGG | 90 | 1583 |
| 756256 | N/A | N/A | 9109 | 9124 | TGACAACAAGACCCTG | 89 | 1584 |
| 756258 | N/A | N/A | 9373 | 9388 | CAAAAGCTGGGTGCAG | 86 | 1585 |
| 756260 | N/A | N/A | 9413 | 9428 | CTGTTGGCAGACACAA | 92 | 1586 |
| 756261 | N/A | N/A | 9461 | 9476 | CTCCTTTTATGTTTTC | 47 | 1587 |
| 756264 | N/A | N/A | 9532 | 9547 | TTATGTCTGAATTATT | 81 | 1588 |
| 756266 | N/A | N/A | 9572 | 9587 | TATTCTCCAGCTCCAT | 85 | 1589 |
| 756268 | N/A | N/A | 9610 | 9625 | TACAAAAGGTTGTATC | 86 | 1590 |
| 756270 | N/A | N/A | 9648 | 9663 | ACCTCATATAAATGAG | 97 | 1591 |
| 756272 | N/A | N/A | 9721 | 9736 | ATTCACCTCTCCCCTC | 94 | 1592 |

TABLE 24

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 49 | 252 |
| 663097 | N/A | N/A | 6590 | 6605 | ATGTATTTGTGCAAGG | 17 | 535 |
| 663144 | N/A | N/A | 18224 | 18239 | CACAAGTTGTTCCATT | 42 | 1065 |
| 702233 | N/A | N/A | 6589 | 6604 | TGTATTTGTGCAAGGC | 6 | 1038 |
| 756274 | N/A | N/A | 9760 | 9775 | ACCATTCCAAACAGAA | 93 | 1218 |
| 756276 | N/A | N/A | 9798 | 9813 | GTTCAACCATCACTAT | 90 | 1219 |
| 756278 | N/A | N/A | 9867 | 9882 | GTGTAAAATTTACCAT | 78 | 1220 |
| 756280 | N/A | N/A | 9917 | 9932 | GTAAGATATATAGATA | 88 | 1221 |
| 756282 | N/A | N/A | 9955 | 9970 | AAAGGTTTTCGGAGTG | 47 | 1222 |
| 756284 | N/A | N/A | 10001 | 10016 | CTTAACTCCTCCCCTG | 80 | 1223 |
| 756286 | N/A | N/A | 10040 | 10055 | CCGAATGCAAATTCCC | 105 | 1224 |
| 756288 | N/A | N/A | 10078 | 10093 | GTAGATAATATGTAGT | 47 | 1225 |
| 756290 | N/A | N/A | 10116 | 10131 | CAGAAAGCCAGCAGAT | 94 | 1226 |
| 756292 | N/A | N/A | 10154 | 10169 | AACTCATTCTTCTCGG | 61 | 1227 |
| 756294 | N/A | N/A | 10192 | 10207 | ACCTACTTTTAAATGT | 97 | 1228 |
| 756296 | N/A | N/A | 10241 | 10256 | CTTTAGTCTGTCTAGG | 86 | 1229 |
| 756298 | N/A | N/A | 10282 | 10297 | CTATTACCACTCTGGC | 85 | 1230 |
| 756300 | N/A | N/A | 10321 | 10336 | ATCCTTAGAACTCTAC | 87 | 1231 |
| 756302 | N/A | N/A | 10359 | 10374 | CAGGGACTGGAACCCA | 96 | 1232 |
| 756303 | N/A | N/A | 10397 | 10412 | CATCAAGAGGATAACA | 91 | 1233 |
| 756306 | N/A | N/A | 10435 | 10450 | TCATTATCCTCACCAA | 90 | 1234 |
| 756308 | N/A | N/A | 10476 | 10491 | ATCAATTCCTTTAATC | 76 | 1235 |
| 756310 | N/A | N/A | 10514 | 10529 | CACTTTTTGCCAGGTA | 69 | 1236 |
| 756312 | N/A | N/A | 10552 | 10567 | AATAATATTGGCACAA | 73 | 1237 |
| 756314 | N/A | N/A | 10593 | 10608 | AAGTGTTTGGTTCCAT | 27 | 1238 |
| 756315 | N/A | N/A | 10634 | 10649 | TTTGTAACTTACCAGT | 73 | 1239 |
| 756318 | N/A | N/A | 10675 | 10690 | GACATTTCTAAATTGA | 68 | 1240 |
| 756320 | N/A | N/A | 10714 | 10729 | ATTGTTTCAGTAGTTT | 38 | 1241 |
| 756322 | N/A | N/A | 10752 | 10767 | AACAGGGATCAATACG | 85 | 1242 |
| 756324 | N/A | N/A | 10790 | 10805 | AGAATATACACCAAAC | 75 | 1243 |
| 756325 | N/A | N/A | 10864 | 10879 | TAACTTGGTCCCATTT | 77 | 1244 |
| 756328 | N/A | N/A | 10902 | 10917 | TTGTATTGACCTTAAA | 80 | 1245 |
| 756330 | N/A | N/A | 10940 | 10955 | CTAAAGGAATATCAAT | 91 | 1246 |
| 756332 | N/A | N/A | 10978 | 10993 | AATAATGACTTAGAAG | 82 | 1247 |
| 756334 | N/A | N/A | 11030 | 11045 | AACTAGTTGTTACTTA | 113 | 1248 |
| 756336 | N/A | N/A | 11076 | 11091 | GACTTTGAAGCTAACG | 58 | 1249 |

TABLE 24-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756338 | N/A | N/A | 11121 | 11136 | CAGCTCACAGGCCTTA | 73 | 1250 |
| 756340 | N/A | N/A | 11186 | 11201 | TTATATGTTCTTCAGG | 76 | 1251 |
| 756342 | N/A | N/A | 11227 | 11242 | TGGTAAGTATTTTAGG | 67 | 1252 |
| 756344 | N/A | N/A | 11273 | 11288 | ATGGCTTAGAGCAAGG | 78 | 1253 |
| 756346 | N/A | N/A | 11311 | 11326 | TACTATGCACCCCCCT | 88 | 1254 |
| 756348 | N/A | N/A | 11352 | 11367 | ACAGATTGGTTTGCTG | 89 | 1255 |
| 756350 | N/A | N/A | 11391 | 11406 | GTTCACTTCTTTTCAG | 82 | 1256 |
| 756352 | N/A | N/A | 11429 | 11444 | GAAAATTGTCACACAA | 92 | 1257 |
| 756354 | N/A | N/A | 11467 | 11482 | CTAGAAATGTTCATAA | 83 | 1258 |
| 756356 | N/A | N/A | 11513 | 11528 | GTTGTTTTAACTAAAA | 86 | 1259 |
| 756358 | N/A | N/A | 11560 | 11575 | TCAAATGTGTGCTTTT | 47 | 1260 |
| 756360 | N/A | N/A | 11603 | 11618 | GTGCAGGTGCATACAT | 86 | 1261 |
| 756362 | N/A | N/A | 11641 | 11656 | GATGATGGCAACCATT | 87 | 1262 |
| 756364 | N/A | N/A | 11681 | 11696 | GTTGAGAGAATGACTG | 69 | 1263 |
| 756366 | N/A | N/A | 11921 | 11936 | GAGGTGAGAGGTTCGA | 62 | 1264 |
| 756368 | N/A | N/A | 12030 | 12045 | AACCATCCTGGGCGAC | 91 | 1265 |
| 756370 | N/A | N/A | 12110 | 12125 | AAGTCAGGTGCCGCGG | 77 | 1266 |
| 756371 | N/A | N/A | 12148 | 12163 | ATGCCTACAATGGAAT | 96 | 1267 |
| 756374 | N/A | N/A | 12195 | 12210 | GTCCTATGTGTCCATC | 50 | 1268 |
| 756376 | N/A | N/A | 12233 | 12248 | ACAAATGGTGATAGCA | 76 | 1269 |
| 756378 | N/A | N/A | 12271 | 12286 | ATCAATATTTACCACT | 88 | 1270 |
| 756380 | N/A | N/A | 12311 | 12326 | CTATTTTGGAAAAGAG | 82 | 1271 |
| 756382 | N/A | N/A | 12349 | 12364 | ACAGTTACAACTGTAA | 89 | 1272 |
| 756384 | N/A | N/A | 12387 | 12402 | AAGTGTCAATGAAAAT | 78 | 1273 |
| 756386 | N/A | N/A | 12425 | 12440 | CTCATTTGATGGCCAA | 51 | 1274 |
| 756388 | N/A | N/A | 12465 | 12480 | ATCATCTGAGAAACAC | 76 | 1275 |
| 756390 | N/A | N/A | 12515 | 12530 | AAGTACACAAATGGCC | 95 | 1276 |
| 756392 | N/A | N/A | 12564 | 12579 | CAGACAAACAATCCAA | 74 | 1277 |
| 756394 | N/A | N/A | 12602 | 12617 | ATGTACCCAGAACATA | 84 | 1278 |
| 756396 | N/A | N/A | 12693 | 12708 | TAACTTGATCTTTATA | 92 | 1279 |
| 756398 | N/A | N/A | 12731 | 12746 | ACATAATTTATCTGAT | 103 | 1280 |
| 756399 | N/A | N/A | 12769 | 12784 | CTAATTAAATGACTCG | 48 | 1281 |
| 756401 | N/A | N/A | 12808 | 12823 | AGTTTACAAGTTTCTG | 56 | 1282 |
| 756403 | N/A | N/A | 12846 | 12861 | CATCCATACACCTAAC | 81 | 1283 |
| 756405 | N/A | N/A | 12897 | 12912 | GAATTACTAAATACAA | 100 | 1284 |
| 756407 | N/A | N/A | 12940 | 12955 | ACTCACTAATAAATGA | 93 | 1285 |

TABLE 24-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756409 | N/A | N/A | 13010 | 13025 | TTCTAAGATCAAGGTC | 70 | 1286 |
| 756411 | N/A | N/A | 13050 | 13065 | GGGAAACTAAGTTTGG | 72 | 1287 |
| 756413 | N/A | N/A | 13208 | 13223 | AAAAAAATTTACGGGA | 94 | 1288 |
| 756415 | N/A | N/A | 13246 | 13261 | AAGTATATATAATCTG | 90 | 1289 |
| 756417 | N/A | N/A | 13285 | 13300 | AACTGCTACTTTACAA | 67 | 1290 |
| 756419 | N/A | N/A | 13325 | 13340 | AAAAATTTATTGTGGG | 92 | 1291 |
| 756421 | N/A | N/A | 13363 | 13378 | GGAAAAGTTATGTATT | 72 | 1292 |

TABLE 25

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 39 | 252 |
| 663097 | N/A | N/A | 6590 | 6605 | ATGTATTTGTGCAAGG | 11 | 535 |
| 663144 | N/A | N/A | 18224 | 18239 | CACAAGTTGTTCCATT | 41 | 1065 |
| 702233 | N/A | N/A | 6589 | 6604 | TGTATTTGTGCAAGGC | 7 | 1038 |
| 756424 | N/A | N/A | 13404 | 13419 | CAGCTTGCTTTATATA | 74 | 1293 |
| 756426 | N/A | N/A | 13443 | 13458 | ACCTACAGTGGTGGTA | 111 | 1294 |
| 756428 | N/A | N/A | 13483 | 13498 | CCACAGCCATGAGAAG | 77 | 1295 |
| 756430 | N/A | N/A | 13524 | 13539 | ACTACCTGGAATGCTA | 109 | 1296 |
| 756432 | N/A | N/A | 13562 | 13577 | AGATAATACTAATTCA | 97 | 1297 |
| 756434 | N/A | N/A | 13815 | 13830 | AGCTCAGGAATCTTGA | 81 | 1298 |
| 756436 | N/A | N/A | 13888 | 13903 | TACCAGGGCCAGGCAC | 92 | 1299 |
| 756438 | N/A | N/A | 13926 | 13941 | CAAGTGAGATCAACAG | 76 | 1300 |
| 756439 | N/A | N/A | 13973 | 13988 | AGGCACAGAATCTCCA | 104 | 1301 |
| 756442 | N/A | N/A | 14011 | 14026 | GAGATGCTAAAATAAG | 91 | 1302 |
| 756444 | N/A | N/A | 14066 | 14081 | AACTTGGTTGGGATGG | 80 | 1303 |
| 756445 | N/A | N/A | 14113 | 14128 | GATTAATACACATGTT | 95 | 1304 |
| 756447 | N/A | N/A | 14151 | 14166 | GAGCTTAAAATGAAGG | 94 | 1305 |
| 756450 | N/A | N/A | 14190 | 14205 | AACCTTTTTCTAAGCT | 87 | 1306 |
| 756452 | N/A | N/A | 14232 | 14247 | ATCAACTTCACAAATA | 114 | 1307 |
| 756454 | N/A | N/A | 14271 | 14286 | ATTGAGTTGCTTACAG | 81 | 1308 |
| 756456 | N/A | N/A | 14309 | 14324 | CAGTACACTGGGTGAG | 72 | 1309 |
| 756458 | N/A | N/A | 14360 | 14375 | CAAGGATATACTTTAA | 91 | 1310 |
| 756459 | N/A | N/A | 14399 | 14414 | AGAGTTTCTCAAGCTT | 121 | 1311 |

TABLE 25-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756461 | N/A | N/A | 14442 | 14457 | TTTCATGCTCTTCATT | 75 | 1312 |
| 756463 | N/A | N/A | 14812 | 14827 | CTGTGTACAAAAAGA | 113 | 1313 |
| 756465 | N/A | N/A | 14874 | 14889 | GTCTGAGGATGTAGTG | 75 | 1314 |
| 756467 | N/A | N/A | 15034 | 15049 | CAGCTTTGGGAGGACA | 93 | 1315 |
| 756470 | N/A | N/A | 15072 | 15087 | GATAAAGATCACTGGG | 88 | 1316 |
| 756472 | N/A | N/A | 15110 | 15125 | ACTATGTATGAATTTA | 74 | 1317 |
| 756474 | N/A | N/A | 15160 | 15175 | GTCTITTTGATACCIT | 41 | 1318 |
| 756476 | N/A | N/A | 15200 | 15215 | AACTAAGAGACTAAAA | 105 | 1319 |
| 756478 | N/A | N/A | 15238 | 15253 | TGTTAAAGCATTTCTC | 51 | 1320 |
| 756480 | N/A | N/A | 15276 | 15291 | AAATAATTAACTGTCT | 105 | 1321 |
| 756481 | N/A | N/A | 15334 | 15349 | TGACATCAAAAAATAC | 106 | 1322 |
| 756483 | N/A | N/A | 15372 | 15387 | ATCTACAAACAGAATA | 95 | 1323 |
| 756485 | N/A | N/A | 15414 | 15429 | AATTAGTTCTATTATG | 86 | 1324 |
| 756487 | N/A | N/A | 15452 | 15467 | ATGTATATTAGGTACA | 96 | 1325 |
| 756489 | N/A | N/A | 15515 | 15530 | ATTAATTTACTATGGG | 77 | 1326 |
| 756492 | N/A | N/A | 15582 | 15597 | ATCTGTTGTGCAACAA | 82 | 1327 |
| 756494 | N/A | N/A | 15630 | 15645 | CTCAATGGGTACAGAA | 76 | 1328 |
| 756496 | N/A | N/A | 15670 | 15685 | CTGCCAAGAATTTGGG | 106 | 1329 |
| 756498 | N/A | N/A | 15708 | 15723 | ACAGTCAAAAATCATG | 85 | 1330 |
| 756499 | N/A | N/A | 15746 | 15761 | GCAAATACTGTTTAAT | 88 | 1331 |
| 756501 | N/A | N/A | 15784 | 15799 | TGACATTATGCTAAGC | 68 | 1332 |
| 756503 | N/A | N/A | 15840 | 15855 | GCCTTTACAGAAAAGA | 95 | 1333 |
| 756505 | N/A | N/A | 15898 | 15913 | CACCAATAGATAAATG | 99 | 1334 |
| 756507 | N/A | N/A | 15936 | 15951 | AATAGTGAATCACCAA | 75 | 1335 |
| 756509 | N/A | N/A | 15974 | 15989 | TACCAACATTTACTGC | 79 | 1336 |
| 756511 | N/A | N/A | 16022 | 16037 | CCATATATCCAAAGA | 103 | 1337 |
| 756514 | N/A | N/A | 16060 | 16075 | GATCCACATAGTTCAA | 95 | 1338 |
| 756516 | N/A | N/A | 16100 | 16115 | TTCTATCTATGGCTGG | 70 | 1339 |
| 756517 | N/A | N/A | 16356 | 16371 | ATGGCATGAATAACAG | 111 | 1340 |
| 756520 | N/A | N/A | 16397 | 16412 | TTTTGAGCAGGGTCTT | 88 | 1341 |
| 756522 | N/A | N/A | 16435 | 16450 | TTCACATCCCACAAAT | 85 | 1342 |
| 756524 | N/A | N/A | 16473 | 16488 | CTGCATATACAAAAAG | 109 | 1343 |
| 756526 | N/A | N/A | 16513 | 16528 | ATTCACTCATACTCAA | 94 | 1344 |
| 756527 | N/A | N/A | 16551 | 16566 | GAATAAGACTGGTTCC | 103 | 1345 |
| 756529 | N/A | N/A | 16593 | 16608 | GACGAATAATTAAAAA | 105 | 1346 |
| 756531 | N/A | N/A | 16631 | 16646 | CCACAGCATATGCAGA | 91 | 1347 |

TABLE 25-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756533 | N/A | N/A | 16688 | 16703 | CATTAAAATAGAACTA | 104 | 1348 |
| 756535 | N/A | N/A | 16744 | 16759 | TAGGACTGTAAAAATC | 94 | 1349 |
| 756537 | N/A | N/A | 16756 | 16771 | GTGCACTGTGGGTAGG | 85 | 1350 |
| 756539 | N/A | N/A | 16766 | 16781 | CGAAACCTTTGTGCAC | 86 | 1351 |
| 756541 | N/A | N/A | 16776 | 16791 | GCAGAGACATCGAAAC | 90 | 1352 |
| 756543 | N/A | N/A | 16816 | 16831 | CTACCAAAAGAAACAG | 82 | 1353 |
| 756545 | N/A | N/A | 16829 | 16844 | ATTATGTTGGCCACTA | 86 | 1354 |
| 756547 | N/A | N/A | 16873 | 16888 | TGTTAATGCAAATCAA | 99 | 1355 |
| 756549 | N/A | N/A | 16885 | 16900 | GATACTCAACATTGTT | 55 | 1356 |
| 756551 | N/A | N/A | 16895 | 16910 | AAACATGAAGGATACT | 86 | 1357 |
| 756553 | N/A | N/A | 16935 | 16950 | GATTTTCAATAAATTC | 102 | 1358 |
| 756555 | N/A | N/A | 16960 | 16975 | TGAGTTTTACATAATT | 98 | 1359 |
| 756557 | N/A | N/A | 16977 | 16992 | CAAATGATGCATGGTA | 43 | 1360 |
| 756560 | N/A | N/A | 16991 | 17006 | CTTTTCCCATTTAACA | 108 | 1361 |
| 756562 | N/A | N/A | 17002 | 17017 | GACAAATTCTCCTTTT | 84 | 1362 |
| 756564 | N/A | N/A | 17012 | 17027 | TAGTCATAAGGACAAA | 86 | 1363 |
| 756566 | N/A | N/A | 17033 | 17048 | CCTTATTAGAATATTT | 90 | 1364 |
| 756568 | N/A | N/A | 17043 | 17058 | AAAAGGTTCACCTTAT | 108 | 1365 |
| 756569 | N/A | N/A | 17227 | 17242 | GACTCTATAAAAATGC | 106 | 1366 |
| 756571 | N/A | N/A | 17257 | 17272 | TTACCAGCCAGGCCAA | 88 | 1367 |

TABLE 26

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 38 | 252 |
| 663097 | N/A | N/A | 6590 | 6605 | ATGTATTTGTGCAAGG | 12 | 535 |
| 663144 | N/A | N/A | 18224 | 18239 | CACAAGTTGTTCCATT | 33 | 1065 |
| 702233 | N/A | N/A | 6589 | 6604 | TGTATTTGTGCAAGGC | 7 | 1038 |
| 756573 | N/A | N/A | 17267 | 17282 | GTTCATCTTATTACCA | 68 | 1368 |
| 756575 | N/A | N/A | 17277 | 17292 | AAAGTATAAAGTTCAT | 105 | 1369 |
| 756577 | N/A | N/A | 17321 | 17336 | GCACCTAGGTGACAGA | 92 | 1370 |
| 756579 | N/A | N/A | 17403 | 17418 | ATCCCAGATACCTGAG | 90 | 1371 |
| 756581 | N/A | N/A | 17498 | 17513 | TCCTAGGAGTTCTAGA | 99 | 1372 |

TABLE 26-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756583 | N/A | N/A | 17510 | 17525 | GAGATCACTTGATCCT | 112 | 1373 |
| 756585 | N/A | N/A | 17520 | 17535 | TCCAAGGTGGGAGATC | 95 | 1374 |
| 756587 | N/A | N/A | 17572 | 17587 | AAGTTCTGGCCCAATG | 79 | 1375 |
| 756589 | N/A | N/A | 17582 | 17597 | AATAAGTATAAAGTTC | 102 | 1376 |
| 756591 | N/A | N/A | 17592 | 17607 | CATACTGTTTAATAAG | 92 | 1377 |
| 756593 | N/A | N/A | 17602 | 17617 | CTATCATCAGCATACT | 70 | 1378 |
| 756595 | N/A | N/A | 17613 | 17628 | ACAGTTTTTCCTATC | 62 | 1379 |
| 756597 | N/A | N/A | 17623 | 17638 | TAAGGATTGCACAGTT | 32 | 1380 |
| 756599 | N/A | N/A | 17634 | 17649 | AATTTTATGAATAAGG | 98 | 1381 |
| 756601 | N/A | N/A | 17644 | 17659 | TTTAGATCAGAATTTT | 92 | 1382 |
| 756603 | N/A | N/A | 17661 | 17676 | ATTTAATATAACACG | 98 | 1383 |
| 756605 | N/A | N/A | 17674 | 17689 | GCATTATTAATTAATT | 100 | 1384 |
| 756607 | N/A | N/A | 17684 | 17699 | AATTTTGCTTGCATTA | 83 | 1385 |
| 756609 | N/A | N/A | 17698 | 17713 | CAAATAAATTTGCCAA | 98 | 1386 |
| 756611 | N/A | N/A | 17719 | 17734 | AGTAGCCCAAAATGGG | 73 | 1387 |
| 756613 | N/A | N/A | 17729 | 17744 | TAATTTTCGAAGTAGC | 75 | 1388 |
| 756615 | N/A | N/A | 17739 | 17754 | GATCCATAAATAATTT | 113 | 1389 |
| 756618 | N/A | N/A | 17749 | 17764 | AACCTTTTCTGATCCA | 31 | 1390 |
| 756620 | N/A | N/A | 17760 | 17775 | AAGTATTTCCCAACCT | 69 | 1391 |
| 756622 | N/A | N/A | 17770 | 17785 | TACTCTAGAAAAGTAT | 133 | 1392 |
| 756624 | N/A | N/A | 17787 | 17802 | TACAGGGCCTGCTCAA | 68 | 1393 |
| 756626 | N/A | N/A | 17798 | 17813 | CTTCTGCCATCTACAG | 110 | 1394 |
| 756628 | N/A | N/A | 17809 | 17824 | TTCAAGCAACACTTCT | 66 | 1395 |
| 756630 | N/A | N/A | 17820 | 17835 | CTCTACGCCAGTTCAA | 84 | 1396 |
| 756631 | N/A | N/A | 17831 | 17846 | ACACTTTCTTCCTCTA | 52 | 1397 |
| 756633 | N/A | N/A | 17841 | 17856 | GGGCAATTCAACACTT | 96 | 1398 |
| 756636 | N/A | N/A | 17855 | 17870 | TAAGGAATTAAGTGGG | 46 | 1399 |
| 756638 | N/A | N/A | 17865 | 17880 | CAAAATTACTTAAGGA | 87 | 1400 |
| 756640 | N/A | N/A | 17876 | 17891 | CTCCAAAGAGGCAAAA | 86 | 1401 |
| 756641 | N/A | N/A | 17886 | 17901 | GGCAAATATTCTCCAA | 63 | 1402 |
| 756643 | N/A | N/A | 17896 | 17911 | CTCTATTTCAGGCAAA | 44 | 1403 |
| 756645 | N/A | N/A | 17906 | 17921 | AACTTGAGTTCTCTAT | 73 | 1404 |
| 756647 | N/A | N/A | 17916 | 17931 | TTCATAGCATAACTTG | 50 | 1405 |
| 756649 | N/A | N/A | 17927 | 17942 | CAAAAGAATCTTCAT | 111 | 1406 |
| 756651 | N/A | N/A | 17954 | 17969 | GCAATGTGAGACCCTG | 78 | 1407 |
| 756653 | N/A | N/A | 17999 | 18014 | AAGGTGAAAGGGTCAC | 101 | 1408 |

TABLE 26-continued

Percent control of human EZH2 mRNA with 3-10-3 cEt gapmers
with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756655 | N/A | N/A | 18062 | 18077 | CCAAAATATCTTCTTG | 84 | 1409 |
| 756657 | N/A | N/A | 18072 | 18087 | ATGTAGCCCTCCAAAA | 110 | 1410 |
| 756659 | N/A | N/A | 18082 | 18097 | TACTGGTGGGATGTAG | 93 | 1411 |
| 756662 | N/A | N/A | 18092 | 18107 | AACATCAAGCTACTGG | 71 | 1412 |
| 756664 | N/A | N/A | 18102 | 18117 | CTCTTTGTACAACATC | 31 | 1413 |
| 756666 | N/A | N/A | 18115 | 18130 | CCAGAGCCTACCACTC | 71 | 1414 |
| 756668 | N/A | N/A | 18127 | 18142 | GCAGAGCCTCGCCCAG | 81 | 1415 |
| 756670 | N/A | N/A | 18137 | 18152 | TAGTATAATGGCAGAG | 68 | 1416 |
| 756672 | N/A | N/A | 18147 | 18162 | GAAATACAACTAGTAT | 88 | 1417 |
| 756673 | N/A | N/A | 18170 | 18185 | ATCCACAAAAGCTACG | 82 | 1418 |
| 756675 | N/A | N/A | 18180 | 18195 | AAGAGGAGAGATCCAC | 81 | 1419 |
| 756677 | N/A | N/A | 18190 | 18205 | TGTCACCATGAAGAGG | 100 | 1420 |
| 756680 | N/A | N/A | 18200 | 18215 | ATCTCATTCATGTCAC | 77 | 1421 |
| 756682 | N/A | N/A | 18213 | 18228 | CCATTATTTATTCATC | 103 | 1422 |
| 756684 | N/A | N/A | 18235 | 18250 | TACTCAGTAAACACAA | 66 | 1423 |
| 756686 | N/A | N/A | 18246 | 18261 | TACATGGTAGATACTC | 43 | 1424 |
| 756688 | N/A | N/A | 18257 | 18272 | CTGCAGGCACATACAT | 95 | 1425 |
| 756690 | N/A | N/A | 18268 | 18283 | AGACATCCTCTCTGCA | 71 | 1426 |
| 756691 | N/A | N/A | 18289 | 18304 | ATTACTTCATCTGCAA | 85 | 1427 |
| 756693 | N/A | N/A | 18301 | 18316 | AGTTATTTACTAATTA | 96 | 1428 |
| 756695 | N/A | N/A | 18311 | 18326 | AACCTAGGCAAGTTAT | 101 | 1429 |
| 756697 | N/A | N/A | 18321 | 18336 | TACCTGAGGGAACCTA | 94 | 1430 |
| 756699 | N/A | N/A | 18331 | 18346 | AAGGGCCCACTACCTG | 96 | 1431 |
| 756701 | N/A | N/A | 18342 | 18357 | GCCCATTCTTCAAGGG | 92 | 1432 |
| 756703 | N/A | N/A | 18352 | 18367 | GGCCATAAAAGCCCAT | 107 | 1433 |
| 756705 | N/A | N/A | 18362 | 18377 | CAATGCACTTGGCCAT | 111 | 1434 |
| 756707 | N/A | N/A | 18494 | 18509 | AATGCCACCACATGTG | 111 | 1435 |
| 756709 | N/A | N/A | 18523 | 18538 | ACTCTCCCATGCAGCT | 99 | 1436 |
| 756711 | N/A | N/A | 18536 | 18551 | ACCCTCTCACCTCACT | 105 | 1437 |
| 756713 | N/A | N/A | 18562 | 18577 | CAGTCTCTACCTTCTG | 103 | 1438 |
| 756715 | N/A | N/A | 18667 | 18682 | CCCTATAGGCAGCAAT | 96 | 1439 |
| 756717 | N/A | N/A | 18677 | 18692 | CTAAAAGGACCCTAT | 116 | 1440 |
| 756718 | N/A | N/A | 18687 | 18702 | AGTATTTGCACTAAAA | 99 | 1441 |
| 756720 | N/A | N/A | 18697 | 18712 | TTAGAATCCTAGTATT | 95 | 1442 |

TABLE 27

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 633365 | 1074 | 1089 | 68329 | 68344 | CGCTTATAAGTGTTGG | 39 | 252 |
| 663097 | N/A | N/A | 6590 | 6605 | ATGTATTTGTGCAAGG | 15 | 535 |
| 663144 | N/A | N/A | 18224 | 18239 | CACAAGTTGTTCCATT | 57 | 1065 |
| 702233 | N/A | N/A | 6589 | 6604 | TGTATTTGTGCAAGGC | 8 | 1038 |
| 756722 | N/A | N/A | 18707 | 18722 | AACCAAGTGCTTAGAA | 72 | 1443 |
| 756724 | N/A | N/A | 18717 | 18732 | GGGTAACAGAAACCAA | 99 | 1444 |
| 756726 | N/A | N/A | 18729 | 18744 | ATAGTTTGACCTGGGT | 70 | 1445 |
| 756728 | N/A | N/A | 18739 | 18754 | CTCCAAAGAAATAGTT | 77 | 1446 |
| 756730 | N/A | N/A | 18749 | 18764 | TAATCAAACTCTCCAA | 102 | 1447 |
| 756732 | N/A | N/A | 18760 | 18775 | ACCTGTGATGGTAATC | 94 | 1448 |
| 756734 | N/A | N/A | 18771 | 18786 | ATCTTACCATCACCTG | 100 | 1449 |
| 756736 | N/A | N/A | 18782 | 18797 | AGCTAGGGAGAATCTT | 86 | 1450 |
| 756738 | N/A | N/A | 18792 | 18807 | ATTAAATGCCAGCTAG | 81 | 1451 |
| 756740 | N/A | N/A | 18802 | 18817 | TAACCACTGGATTAAA | 93 | 1452 |
| 756742 | N/A | N/A | 18820 | 18835 | ATTTGGGAAAGATGCA | 69 | 1453 |
| 756744 | N/A | N/A | 18830 | 18845 | TTGATAAAGAATTTGG | 76 | 1454 |
| 756746 | N/A | N/A | 18840 | 18855 | ATTGACCAACTTGATA | 96 | 1455 |
| 756748 | N/A | N/A | 18851 | 18866 | ATGTTCTATGAATTGA | 74 | 1456 |
| 756749 | N/A | N/A | 18861 | 18876 | TCAGCATTAGATGTTC | 51 | 1457 |
| 756750 | N/A | N/A | 18871 | 18886 | AGGCTTATAATCAGCA | 86 | 1458 |
| 756751 | N/A | N/A | 18881 | 18896 | GCAAGATAATAGGCTT | 83 | 1459 |
| 756752 | N/A | N/A | 18892 | 18907 | CAGAGACACAAGCAAG | 72 | 1460 |
| 756753 | N/A | N/A | 18902 | 18917 | GCCCATAGTGCAGAGA | 92 | 1461 |
| 756754 | N/A | N/A | 18912 | 18927 | GTGCTATTATGCCCAT | 81 | 1462 |
| 756755 | N/A | N/A | 18922 | 18937 | AAGCTTTTAGGTGCTA | 89 | 1463 |
| 756756 | N/A | N/A | 18932 | 18947 | ATTATAGCAAAAGCTT | 88 | 1464 |
| 756757 | N/A | N/A | 18942 | 18957 | ATCATAGTCCATTATA | 80 | 1465 |
| 756758 | N/A | N/A | 18952 | 18967 | ATTCAGATACATCATA | 87 | 1466 |
| 756759 | N/A | N/A | 18962 | 18977 | AAGGTAATTTATTCAG | 60 | 1467 |
| 756760 | N/A | N/A | 18979 | 18994 | AGATTTGATTGTTTAT | 78 | 1468 |
| 756761 | N/A | N/A | 18989 | 19004 | TTGCCAATTTAGATTT | 90 | 1469 |
| 756762 | N/A | N/A | 18999 | 19014 | AAATTTGAACTTGCCA | 80 | 1470 |
| 756763 | N/A | N/A | 19014 | 19029 | TAAGAAAAATTGGGTA | 107 | 1471 |
| 756764 | N/A | N/A | 19024 | 19039 | GTAAATTCTATAAGAA | 95 | 1472 |
| 756765 | N/A | N/A | 19034 | 19049 | AACTGCAAAGGTAAAT | 72 | 1473 |
| 756766 | N/A | N/A | 19047 | 19062 | CAATTATTTCTTTAAC | 79 | 1474 |

TABLE 27-continued

Percent control of human EZH2 mRNA with 3-10-3 cEt gapmers with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756767 | N/A | N/A | 19062 | 19077 | ACAAATGGTAAAAAAC | 116 | 1475 |
| 756768 | N/A | N/A | 19072 | 19087 | GTCATACTAGACAAAT | 91 | 1476 |
| 756769 | N/A | N/A | 19082 | 19097 | TAAATAACAAGTCATA | 110 | 1477 |
| 756770 | N/A | N/A | 19093 | 19108 | CATGCTATTTGTAAAT | 92 | 1478 |
| 756771 | N/A | N/A | 19106 | 19121 | AGCTGGCCAGTTACAT | 85 | 1479 |
| 756772 | N/A | N/A | 19116 | 19131 | TGTATAGTACAGCTGG | 50 | 1480 |
| 756773 | N/A | N/A | 19126 | 19141 | CTAGAAAATGTGTATA | 98 | 1481 |
| 756774 | N/A | N/A | 19162 | 19177 | AGGCACCCAATAAGAA | 98 | 1482 |
| 756775 | N/A | N/A | 19172 | 19187 | TAAAAGACTAAGGCAC | 74 | 1483 |
| 756776 | N/A | N/A | 19182 | 19197 | CCCTAATGGGTAAAAG | 81 | 1484 |
| 756777 | N/A | N/A | 19192 | 19207 | ATTTGAATAGCCCTAA | 80 | 1485 |
| 756778 | N/A | N/A | 19202 | 19217 | CTCATTCTTTATTTGA | 85 | 1486 |
| 756779 | N/A | N/A | 19213 | 19228 | TAAGAGAATATCTCAT | 91 | 1487 |
| 756780 | N/A | N/A | 19223 | 19238 | TTCTAGAGAATAAGAG | 97 | 1488 |
| 756781 | N/A | N/A | 19237 | 19252 | TATAGAATGTCTCTTT | 77 | 1489 |
| 756782 | N/A | N/A | 19247 | 19262 | TTTCCATTAGTATAGA | 73 | 1490 |
| 756783 | N/A | N/A | 19258 | 19273 | AAAAGTTGGTATTTCC | 47 | 1491 |
| 756784 | N/A | N/A | 19268 | 19283 | GTCTAGATTTAAAAGT | 97 | 1492 |
| 756785 | N/A | N/A | 19278 | 19293 | TTTTTTGGTAGTCTAG | 55 | 1493 |
| 756786 | N/A | N/A | 19296 | 19311 | GTAGAAAAACATGACT | 93 | 1494 |
| 756787 | N/A | N/A | 19312 | 19327 | ATCTATAGCCTCTAGG | 88 | 1495 |
| 756788 | N/A | N/A | 19322 | 19337 | GACATTAAGAATCTAT | 90 | 1496 |
| 756789 | N/A | N/A | 19332 | 19347 | ATGAGTGGCTGACATT | 90 | 1497 |
| 756790 | N/A | N/A | 19343 | 19358 | AGAGGGCCAGGATGAG | 68 | 1498 |
| 756791 | N/A | N/A | 19365 | 19380 | CATATGGGAAAAGAAG | 94 | 1499 |
| 756792 | N/A | N/A | 19375 | 19390 | CTAGAACTTCCATATG | 100 | 1500 |
| 756793 | N/A | N/A | 19385 | 19400 | CTATATCACCCTAGAA | 93 | 1501 |
| 756794 | N/A | N/A | 19398 | 19413 | CCACAGAGCCAAACTA | 102 | 1502 |
| 756795 | N/A | N/A | 19428 | 19443 | ATTACAATTTGACGCG | 92 | 1503 |
| 756796 | N/A | N/A | 19445 | 19460 | CTCCTCCAACTTTGGG | 96 | 1504 |
| 756797 | N/A | N/A | 19459 | 19474 | TTCCCACCAGACCCCT | 86 | 1505 |
| 756798 | N/A | N/A | 19492 | 19507 | CAAGGGAAAGTCTGC | 98 | 1506 |
| 756799 | N/A | N/A | 19505 | 19520 | GTCAGGAGAACAGCAA | 85 | 1507 |
| 756800 | N/A | N/A | 19515 | 19530 | AGAACTCACTGTCAGG | 76 | 1508 |
| 756801 | N/A | N/A | 19525 | 19540 | CACTGTCACGAGAACT | 90 | 1509 |
| 756802 | N/A | N/A | 19564 | 19579 | GTGCTACATAATTTTA | 83 | 1510 |

TABLE 27-continued

Percent control of human EZH2 mRNA with 3-10-3 cEt gapmers
with phosphorothioate internucleoside linkages

| ION Number | SEQ ID NO: 1 Start Site | SEQ ID NO: 1 Stop Site | SEQ ID NO: 2 Start Site | SEQ ID NO: 2 Stop Site | Sequence (5' to 3') | EZH2 (% UTC) | SEQ ID NO |
|---|---|---|---|---|---|---|---|
| 756803 | N/A | N/A | 19574 | 19589 | AAAGTGGCAGGTGCTA | 88 | 1511 |
| 756804 | N/A | N/A | 19585 | 19600 | GAAGAGAGAGCAAAGT | 94 | 1512 |
| 756805 | N/A | N/A | 19617 | 19632 | AGCCAGCACATTATAC | 104 | 1513 |
| 756806 | N/A | N/A | 19647 | 19662 | ACTTATCATCACAGTG | 94 | 1514 |
| 756807 | N/A | N/A | 19689 | 19704 | CAGCAGGCTATACAGG | 73 | 1515 |
| 756808 | N/A | N/A | 19699 | 19714 | GCTTACAGTTCAGCAG | 89 | 1516 |
| 756809 | N/A | N/A | 19709 | 19724 | GGTTTAATTTGCTTAC | 80 | 1517 |

Example 8: Effect of 3-10-3 cEt Gapmers with Phosphorothioate Internucleoside Linkages on Human EZH2 In Vitro, Multiple Doses Modified oligonucleotides selected from the examples above were tested at various doses in HepG2 cells. Cells were plated at a density of 20,000 cells per well and transfected using electroporation with 222.2 nM, 666.6 nM, 2,000 nM, and 6,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 28

Dose-dependent percent reduction of human EZH2 mRNA by modified oligonucleotides

| ION Number | EZH2 expression (% UTC) | | | | $IC_{50}$ ($\mu M$) |
|---|---|---|---|---|---|
| | 0.222 $\mu M$ | 0.666 $\mu M$ | 2.0 $\mu M$ | 6.0 $\mu M$ | |
| 633299 | 35 | 15 | 14 | 7 | <0.2 |
| 633302 | 69 | 46 | 21 | 13 | 0.6 |
| 633322 | 59 | 27 | 16 | 10 | 0.3 |
| 633323 | 54 | 34 | 17 | 13 | 0.2 |
| 633331 | 61 | 34 | 21 | 15 | 0.3 |
| 633335 | 46 | 25 | 21 | 8 | <0.2 |
| 633355 | 33 | 22 | 11 | 9 | <0.2 |
| 633358 | 37 | 20 | 8 | 8 | <0.2 |
| 633398 | 53 | 30 | 12 | 10 | 0.2 |
| 633414 | 63 | 34 | 18 | 10 | 0.3 |
| 633418 | 43 | 22 | 14 | 11 | <0.2 |
| 633455 | 56 | 37 | 15 | 9 | 0.3 |
| 633462 | 63 | 37 | 20 | 15 | 0.4 |
| 633483 | 48 | 37 | 15 | 12 | 0.2 |
| 633486 | 65 | 39 | 21 | 10 | 0.4 |
| 633530 | 61 | 38 | 19 | 9 | 0.4 |
| 633538 | 75 | 43 | 19 | 12 | 0.6 |
| 633562 | 64 | 40 | 18 | 7 | 0.4 |
| 633570 | 64 | 44 | 17 | 10 | 0.5 |

TABLE 29

Dose-dependent percent reduction of human EZH2 mRNA by modified oligonucleotides

| ION Number | EZH2 expression (% UTC) | | | | $IC_{50}$ ($\mu M$) |
|---|---|---|---|---|---|
| | 0.222 $\mu M$ | 0.666 $\mu M$ | 2.0 $\mu M$ | 6.0 $\mu M$ | |
| 633301 | 53 | 36 | 24 | 14 | 0.3 |
| 633329 | 65 | 41 | 25 | 21 | 0.5 |
| 633343 | 86 | 66 | 38 | 19 | 1.3 |
| 633344 | 69 | 43 | 23 | 21 | 0.5 |
| 633352 | 46 | 34 | 16 | 8 | 0.2 |
| 633355 | 57 | 32 | 15 | 8 | 0.3 |
| 633356 | 65 | 38 | 20 | 16 | 0.4 |
| 633357 | 28 | 15 | 16 | 12 | <0.2 |
| 633365 | 50 | 30 | 15 | 10 | 0.2 |
| 633371 | 72 | 41 | 26 | 19 | 0.6 |
| 633389 | 55 | 30 | 19 | 14 | 0.2 |
| 633416 | 56 | 38 | 19 | 11 | 0.3 |
| 633420 | 72 | 37 | 31 | 12 | 0.6 |
| 633456 | 59 | 34 | 34 | 14 | 0.4 |
| 633473 | 49 | 26 | 23 | 11 | <0.2 |
| 633481 | 54 | 43 | 17 | 19 | 0.3 |
| 633497 | 73 | 43 | 23 | 14 | 0.6 |
| 633521 | 59 | 39 | 23 | 12 | 0.4 |
| 633537 | 71 | 43 | 34 | 11 | 0.6 |

Example 9: Effect of 3-10-3 cEt Gapmers with Phosphorothioate Internucleoside Linkages on Human EZH2 In Vitro, Multiple Doses Modified oligonucleotides selected from the examples above were tested at various doses in HepG2 cells. Cells were plated at a density of 20,000 cells per well and transfected using electroporation with 62.5 nM, 250 nM, 1,000 nM, and 4,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 30

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 75 | 49 | 18 | 6 |
| 633358 | 56 | 23 | 8 | 4 |
| 633473 | 72 | 40 | 28 | 13 |
| 662423 | 56 | 38 | 20 | 9 |
| 662433 | 69 | 44 | 16 | 8 |
| 662438 | 63 | 42 | 18 | 5 |
| 662441 | 64 | 57 | 24 | 11 |
| 662442 | 39 | 29 | 17 | 4 |
| 662453 | 42 | 23 | 10 | 9 |
| 662454 | 53 | 22 | 20 | 4 |
| 662455 | 59 | 22 | 10 | 2 |
| 662456 | 62 | 37 | 14 | 5 |
| 662458 | 64 | 48 | 18 | 7 |
| 662463 | 69 | 48 | 15 | 4 |
| 662466 | 75 | 33 | 17 | 3 |
| 662964 | 71 | 38 | 14 | 5 |
| 663097 | 57 | 25 | 11 | 6 |
| 663116 | 72 | 53 | 30 | 11 |

TABLE 31

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 83 | 43 | 19 | 8 |
| 640672 | 79 | 56 | 28 | 13 |
| 640677 | 66 | 49 | 26 | 11 |
| 640678 | 58 | 45 | 18 | 10 |
| 640679 | 51 | 31 | 13 | 3 |
| 640684 | 91 | 73 | 28 | 12 |
| 662546 | 78 | 59 | 24 | 6 |
| 662560 | 74 | 66 | 37 | 15 |
| 662565 | 91 | 62 | 26 | 11 |
| 662571 | 81 | 69 | 30 | 12 |
| 662578 | 60 | 34 | 11 | 7 |
| 662579 | 58 | 51 | 16 | 8 |
| 662595 | 68 | 61 | 23 | 15 |
| 662602 | 75 | 55 | 30 | 14 |
| 662610 | 58 | 31 | 18 | 5 |
| 662616 | 72 | 52 | 16 | 7 |
| 662647 | 79 | 57 | 24 | 10 |
| 662648 | 74 | 47 | 25 | 5 |
| 662649 | 89 | 59 | 24 | 10 |

TABLE 32

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 79 | 43 | 26 | 13 |
| 633398 | 69 | 47 | 16 | 11 |
| 633414 | 64 | 56 | 26 | 13 |
| 633418 | 80 | 52 | 22 | 11 |
| 640714 | 76 | 50 | 20 | 9 |
| 640717 | 78 | 74 | 38 | 19 |
| 662658 | 76 | 65 | 34 | 10 |
| 662695 | 72 | 55 | 38 | 13 |
| 662698 | 73 | 60 | 25 | 12 |
| 662701 | 81 | 62 | 45 | 15 |
| 662703 | 102 | 69 | 25 | 13 |
| 662704 | 76 | 49 | 20 | 9 |
| 662708 | 86 | 75 | 39 | 22 |
| 662710 | 61 | 47 | 23 | 9 |
| 662723 | 73 | 52 | 40 | 19 |
| 662724 | 80 | 60 | 17 | 10 |
| 662725 | 72 | 45 | 20 | 6 |
| 662726 | 86 | 57 | 42 | 20 |
| 662731 | 78 | 70 | 31 | 15 |

TABLE 33

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 70 | 67 | 17 | 8 |
| 633365 | 36 | 47 | 13 | 7 |
| 633483 | 53 | 48 | 18 | 9 |
| 662478 | 69 | 46 | 35 | 13 |
| 662483 | 64 | 72 | 33 | 8 |
| 662489 | 81 | 54 | 25 | 8 |
| 662493 | 59 | 66 | 32 | 22 |
| 662499 | 78 | 36 | 10 | 10 |
| 662501 | 56 | 36 | 16 | 12 |
| 662577 | 42 | 58 | 16 | 9 |
| 662962 | 64 | 60 | 23 | 6 |
| 662992 | 68 | 33 | 24 | 12 |
| 663092 | 43 | 34 | 20 | 18 |
| 663102 | 87 | 33 | 27 | 11 |
| 663110 | 75 | 101 | 22 | 19 |
| 663117 | 50 | 67 | 11 | 10 |
| 663202 | 107 | 43 | 17 | 11 |
| 663217 | 110 | 70 | 37 | 15 |
| 663242 | 125 | 101 | 30 | 12 |

TABLE 34

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 83 | 43 | 19 | 8 |
| 640672 | 79 | 56 | 28 | 13 |
| 640677 | 66 | 49 | 26 | 11 |
| 640678 | 58 | 45 | 18 | 10 |
| 640679 | 51 | 31 | 13 | 3 |
| 640684 | 91 | 73 | 28 | 12 |
| 662546 | 78 | 59 | 24 | 6 |

TABLE 34-continued

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 662560 | 74 | 66 | 37 | 15 |
| 662565 | 91 | 62 | 26 | 11 |
| 662571 | 81 | 69 | 30 | 12 |
| 662578 | 60 | 34 | 11 | 7 |
| 662579 | 58 | 51 | 16 | 8 |
| 662595 | 68 | 61 | 23 | 15 |
| 662602 | 75 | 55 | 30 | 14 |
| 662610 | 58 | 31 | 18 | 5 |
| 662616 | 72 | 52 | 16 | 7 |
| 662647 | 79 | 57 | 24 | 10 |
| 662648 | 74 | 47 | 25 | 5 |
| 662649 | 89 | 59 | 24 | 10 |

TABLE 35

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 79 | 43 | 26 | 13 |
| 633398 | 69 | 47 | 16 | 11 |
| 633414 | 64 | 56 | 26 | 13 |
| 633418 | 80 | 52 | 22 | 11 |
| 640714 | 76 | 50 | 20 | 9 |
| 640717 | 78 | 74 | 38 | 19 |
| 662658 | 76 | 65 | 34 | 10 |
| 662695 | 72 | 55 | 38 | 13 |
| 662698 | 73 | 60 | 25 | 12 |
| 662701 | 81 | 62 | 45 | 15 |
| 662703 | 102 | 69 | 25 | 13 |
| 662704 | 76 | 49 | 20 | 9 |
| 662708 | 86 | 75 | 39 | 22 |
| 662710 | 61 | 47 | 23 | 9 |
| 662723 | 73 | 52 | 40 | 19 |
| 662724 | 80 | 60 | 17 | 10 |
| 662725 | 72 | 45 | 20 | 6 |
| 662726 | 86 | 57 | 42 | 20 |
| 662731 | 78 | 70 | 31 | 15 |

TABLE 36

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633323 | 86 | 54 | 23 | 11 |
| 633335 | 70 | 44 | 22 | 7 |
| 662053 | 84 | 47 | 18 | 6 |
| 662056 | 86 | 61 | 38 | 13 |
| 662132 | 76 | 50 | 22 | 9 |
| 662146 | 71 | 43 | 18 | 14 |
| 662212 | 65 | 38 | 14 | 5 |
| 662219 | 78 | 55 | 25 | 9 |
| 662285 | 72 | 39 | 17 | 8 |
| 662301 | 68 | 43 | 21 | 8 |
| 662302 | 81 | 44 | 20 | 12 |
| 662322 | 83 | 65 | 31 | 16 |
| 662696 | 75 | 53 | 25 | 9 |
| 662699 | 83 | 71 | 36 | 11 |

TABLE 36-continued

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 662702 | 75 | 54 | 28 | 10 |
| 662705 | 80 | 60 | 32 | 17 |
| 662713 | 81 | 62 | 34 | 12 |
| 662714 | 78 | 55 | 28 | 17 |
| 662732 | 88 | 71 | 44 | 11 |

TABLE 37

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 72 | 47 | 21 | 8 |
| 662249 | 81 | 66 | 36 | 23 |
| 662252 | 72 | 54 | 33 | 18 |
| 662255 | 81 | 48 | 29 | 12 |
| 662256 | 77 | 58 | 33 | 12 |
| 662290 | 83 | 62 | 42 | 22 |
| 662292 | 88 | 64 | 37 | 12 |
| 662295 | 94 | 78 | 34 | 15 |
| 662296 | 73 | 46 | 19 | 9 |
| 662305 | 77 | 60 | 32 | 10 |
| 662306 | 68 | 51 | 34 | 19 |
| 662308 | 82 | 52 | 41 | 14 |
| 662309 | 84 | 59 | 32 | 16 |
| 662312 | 68 | 37 | 19 | 9 |
| 662314 | 77 | 58 | 33 | 20 |
| 662315 | 74 | 56 | 32 | 11 |
| 662318 | 74 | 58 | 30 | 10 |
| 662320 | 63 | 47 | 20 | 7 |
| 662884 | 83 | 55 | 26 | 13 |

TABLE 38

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 90 | 51 | 21 | 6 |
| 633455 | 63 | 40 | 17 | 11 |
| 633456 | 73 | 39 | 16 | 7 |
| 662843 | 71 | 47 | 24 | 12 |
| 662867 | 73 | 35 | 22 | 10 |
| 662868 | 62 | 37 | 17 | 6 |
| 662875 | 73 | 40 | 20 | 4 |
| 662879 | 65 | 44 | 24 | 12 |
| 662882 | 74 | 41 | 19 | 8 |
| 663132 | 85 | 47 | 22 | 9 |
| 663138 | 69 | 50 | 26 | 11 |
| 663142 | 63 | 46 | 24 | 14 |
| 663144 | 53 | 36 | 17 | 7 |
| 663185 | 98 | 65 | 29 | 13 |
| 663278 | 67 | 41 | 22 | 9 |
| 663343 | 73 | 35 | 13 | 5 |
| 663354 | 66 | 41 | 14 | 6 |
| 663384 | 70 | 45 | 28 | 11 |
| 663386 | 76 | 54 | 21 | 11 |

TABLE 39

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 64 | 37 | 17 | 9 |
| 633481 | 64 | 41 | 19 | 10 |
| 662358 | 60 | 47 | 24 | 9 |
| 662366 | 68 | 55 | 35 | 11 |
| 662368 | 53 | 27 | 14 | 6 |
| 662380 | 65 | 41 | 26 | 13 |
| 662896 | 75 | 53 | 25 | 8 |
| 662940 | 18 | 11 | 6 | 4 |
| 662941 | 54 | 29 | 9 | 3 |
| 662944 | 16 | 16 | 7 | 4 |
| 662950 | 54 | 42 | 12 | 4 |
| 662951 | 75 | 44 | 26 | 8 |
| 662957 | 61 | 44 | 18 | 7 |
| 662959 | 64 | 43 | 22 | 8 |
| 663143 | 68 | 48 | 28 | 9 |
| 663147 | 70 | 50 | 29 | 12 |
| 663157 | 66 | 51 | 28 | 12 |
| 663176 | 73 | 50 | 32 | 13 |
| 663180 | 60 | 41 | 19 | 6 |

Example 10: Effect of 3-10-3 cEt Gapmers with Phosphorothioate Internucleoside Linkages on Human EZH2 In Vitro, Multiple Doses Modified oligonucleotides selected from the examples above were tested at various doses in HepG2 cells. Cells were plated at a density of 20,000 cells per well and transfected using electroporation with 62.5 nM, 250 nM, 1,000 nM, and 4,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1985 (described hereinabove in Example 4) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 40

Dose-dependent percent reduction of human EZH2 mRNA by modified oligonucleotides

| ION Number | EZH2 expression (% UTC) | | | |
|---|---|---|---|---|
| | 62.5 nM | 250 nM | 1,000 nM | 4,000 nM |
| 633335 | 65 | 37 | 12 | 6 |
| 633481 | 63 | 52 | 20 | 14 |
| 662358 | 67 | 39 | 18 | 6 |
| 662366 | 75 | 62 | 30 | 10 |
| 662368 | 52 | 25 | 9 | 4 |
| 662380 | 65 | 36 | 21 | 12 |
| 662896 | 77 | 53 | 26 | 12 |
| 662940 | 60 | 42 | 16 | 8 |
| 662941 | 59 | 33 | 13 | 5 |
| 662944 | 66 | 55 | 23 | 10 |
| 662950 | 59 | 36 | 13 | 5 |
| 662951 | 70 | 48 | 23 | 9 |
| 662957 | 69 | 42 | 20 | 7 |
| 662959 | 68 | 43 | 22 | 8 |
| 663143 | 73 | 54 | 24 | 6 |
| 663147 | 77 | 49 | 29 | 12 |
| 663157 | 74 | 49 | 30 | 11 |
| 663176 | 90 | 57 | 23 | 11 |
| 663180 | 69 | 34 | 16 | 5 |

Example 11: Effect of 3-10-3 cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 5,000 cells per well and transfected via free uptake with 40 nM, 200 nM, 1,000 nM, and 5,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 41

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 91 | 28 | 7 | 6 |
| 633483 | 95 | 76 | 66 | 43 |
| 640679 | 94 | 32 | 10 | 5 |
| 662478 | 103 | 57 | 24 | 11 |
| 662483 | 101 | 59 | 31 | 17 |
| 662489 | 79 | 40 | 17 | 9 |
| 662493 | 80 | 32 | 14 | 7 |
| 662499 | 77 | 38 | 11 | 5 |
| 662501 | 79 | 42 | 17 | 9 |
| 662577 | 79 | 29 | 11 | 5 |
| 662962 | 85 | 61 | 33 | 15 |
| 662992 | 91 | 66 | 27 | 12 |
| 663092 | 102 | 85 | 45 | 20 |
| 663102 | 85 | 85 | 52 | 29 |
| 663110 | 92 | 70 | 33 | 9 |
| 663117 | 96 | 64 | 24 | 6 |
| 663202 | 89 | 56 | 16 | 8 |
| 663217 | 86 | 78 | 32 | 12 |
| 663242 | 94 | 77 | 45 | 20 |

TABLE 42

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 80 | 27 | 8 | 6 |
| 633398 | 108 | 39 | 10 | 8 |
| 640672 | 84 | 76 | 49 | 28 |
| 640677 | 83 | 53 | 23 | 13 |
| 640678 | 99 | 43 | 21 | 11 |
| 640684 | 95 | 75 | 60 | 32 |
| 662546 | 87 | 60 | 43 | 18 |
| 662560 | 79 | 62 | 32 | 20 |
| 662565 | 80 | 66 | 18 | 9 |
| 662571 | 85 | 55 | 18 | 10 |
| 662578 | 66 | 18 | 7 | 5 |
| 662579 | 85 | 28 | 10 | 9 |
| 662595 | 87 | 69 | 30 | 14 |
| 662602 | 102 | 58 | 45 | 21 |
| 662610 | 82 | 38 | 19 | 10 |
| 662616 | 70 | 42 | 14 | 7 |
| 662647 | 97 | 41 | 35 | 20 |
| 662648 | 84 | 37 | 15 | 12 |
| 662649 | 76 | 60 | 30 | 20 |

TABLE 43

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633355 | 87 | 58 | 21 | 10 |
| 633365 | 80 | 26 | 12 | 5 |
| 633414 | 104 | 78 | 34 | 17 |
| 633418 | 89 | 57 | 25 | 11 |
| 640714 | 116 | 61 | 24 | 11 |
| 640717 | 72 | 57 | 31 | 16 |
| 662658 | 97 | 68 | 43 | 20 |
| 662695 | 105 | 80 | 47 | 26 |
| 662698 | 103 | 102 | 63 | 41 |
| 662701 | 109 | 76 | 35 | 16 |
| 662703 | 86 | 65 | 32 | 12 |
| 662704 | 83 | 56 | 18 | 7 |
| 662708 | 100 | 74 | 34 | 17 |
| 662710 | 84 | 41 | 11 | 6 |
| 662723 | 97 | 68 | 40 | 19 |
| 662724 | 94 | 67 | 33 | 15 |
| 662725 | 87 | 69 | 29 | 13 |
| 662726 | 94 | 77 | 40 | 21 |
| 662731 | 110 | 67 | 46 | 22 |

TABLE 44

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 107 | 36 | 8 | 6 |
| 662249 | 69 | 70 | 51 | 30 |
| 662252 | 74 | 60 | 29 | 21 |
| 662255 | 104 | 80 | 69 | 52 |
| 662256 | 77 | 57 | 20 | 11 |
| 662290 | 89 | 86 | 80 | 73 |
| 662292 | 82 | 77 | 48 | 29 |

TABLE 44-continued

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 662295 | 105 | 86 | 40 | 24 |
| 662296 | 102 | 57 | 18 | 14 |
| 662305 | 79 | 52 | 24 | 18 |
| 662306 | 91 | 71 | 39 | 20 |
| 662308 | 120 | 70 | 31 | 21 |
| 662309 | 112 | 86 | 56 | 27 |
| 662312 | 100 | 82 | 47 | 46 |
| 662314 | 105 | 74 | 29 | 10 |
| 662315 | 94 | 75 | 28 | 15 |
| 662318 | 78 | 45 | 18 | 16 |
| 662320 | 89 | 44 | 19 | 8 |
| 662884 | 94 | 44 | 14 | 6 |

TABLE 45

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 97 | 30 | 10 | 5 |
| 633455 | 95 | 76 | 40 | 20 |
| 633456 | 91 | 64 | 35 | 17 |
| 662843 | 108 | 59 | 22 | 11 |
| 662867 | 111 | 92 | 55 | 28 |
| 662868 | 75 | 67 | 37 | 25 |
| 662875 | 101 | 64 | 26 | 11 |
| 662879 | 113 | 102 | 75 | 64 |
| 662882 | 113 | 50 | 18 | 10 |
| 663132 | 98 | 76 | 34 | 17 |
| 663138 | 108 | 105 | 64 | 28 |
| 663142 | 104 | 73 | 39 | 32 |
| 663144 | 86 | 36 | 9 | 6 |
| 663185 | 99 | 51 | 24 | 13 |
| 663278 | 99 | 49 | 18 | 10 |
| 663343 | 103 | 76 | 51 | 38 |
| 663354 | 100 | 44 | 21 | 14 |
| 663384 | 101 | 76 | 49 | 19 |
| 663386 | 90 | 73 | 47 | 21 |

TABLE 46

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 82 | 32 | 7 | 7 |
| 633481 | 91 | 53 | 17 | 7 |
| 662358 | 88 | 60 | 17 | 8 |
| 662366 | 109 | 72 | 42 | 20 |
| 662368 | 71 | 37 | 12 | 7 |
| 662380 | 100 | 73 | 50 | 26 |
| 662896 | 68 | 82 | 38 | 16 |
| 662940 | 31 | 22 | 17 | 12 |
| 662941 | 51 | 28 | 8 | 5 |
| 662944 | 15 | 12 | 6 | 3 |
| 662950 | 76 | 37 | 14 | 8 |
| 662951 | 88 | 37 | 12 | 5 |
| 662957 | 100 | 69 | 19 | 8 |
| 662959 | 98 | 79 | 52 | 32 |

TABLE 46-continued

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 663143 | 92 | 35 | 10 | 7 |
| 663147 | 83 | 45 | 12 | 5 |
| 663157 | 87 | 71 | 33 | 17 |
| 663176 | 78 | 83 | 53 | 36 |
| 663180 | 101 | 80 | 30 | 18 |

TABLE 47

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633358 | 80 | 74 | 54 | 26 |
| 633365 | 89 | 44 | 22 | 15 |
| 633473 | 84 | 78 | 52 | 45 |
| 662423 | 97 | 90 | 48 | 29 |
| 662433 | 88 | 80 | 51 | 42 |
| 662438 | 96 | 69 | 34 | 20 |
| 662441 | 95 | 60 | 43 | 25 |
| 662442 | 89 | 64 | 39 | 19 |
| 662453 | 92 | 65 | 33 | 18 |
| 662454 | 90 | 58 | 44 | 28 |
| 662455 | 86 | 59 | 28 | 19 |
| 662456 | 97 | 80 | 60 | 30 |
| 662458 | 88 | 83 | 70 | 56 |
| 662463 | 89 | 76 | 50 | 30 |
| 662466 | 77 | 64 | 30 | 14 |
| 662964 | 92 | 74 | 48 | 29 |
| 663097 | 88 | 32 | 8 | 6 |
| 663116 | 103 | 93 | 84 | 65 |

TABLE 48

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633323 | 127 | 56 | 16 | 8 |
| 633365 | 109 | 37 | 9 | 5 |
| 662053 | 98 | 64 | 28 | 14 |
| 662056 | 100 | 92 | 54 | 34 |
| 662132 | 80 | 76 | 46 | 27 |
| 662146 | 117 | 47 | 18 | 10 |
| 662212 | 92 | 69 | 31 | 18 |
| 662219 | 92 | 67 | 30 | 13 |
| 662285 | 94 | 63 | 31 | 16 |
| 662301 | 85 | 59 | 25 | 15 |
| 662302 | 106 | 56 | 16 | 10 |
| 662322 | 100 | 57 | 28 | 16 |
| 662696 | 118 | 118 | 86 | 54 |
| 662699 | 92 | 95 | 50 | 26 |
| 662702 | 90 | 79 | 29 | 13 |
| 662705 | 94 | 91 | 45 | 21 |
| 662713 | 102 | 104 | 70 | 56 |
| 662714 | 92 | 96 | 59 | 37 |
| 662732 | 99 | 97 | 47 | 26 |

Example 12: Effect of 3-10-3 cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 20,000 cells per well and transfected using electroporation with 40 nM, 200 nM, 1,000 nM, and 5,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 49

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633358 | 82 | 42 | 10 | 3 |
| 633365 | 78 | 23 | 7 | 3 |
| 633473 | 99 | 49 | 29 | 18 |
| 662423 | 124 | 49 | 16 | 4 |
| 662433 | 101 | 43 | 22 | 6 |
| 662438 | 86 | 54 | 11 | 3 |
| 662441 | 91 | 66 | 15 | 3 |
| 662442 | 111 | 45 | 12 | 3 |
| 662453 | 69 | 29 | 6 | 2 |
| 662454 | 80 | 35 | 11 | 4 |
| 662455 | 72 | 31 | 6 | 3 |
| 662456 | 93 | 50 | 17 | 3 |
| 662458 | 124 | 54 | 31 | 14 |
| 662463 | 118 | 69 | 21 | 6 |
| 662466 | 124 | 29 | 8 | 3 |
| 662964 | 89 | 88 | 63 | 55 |
| 663097 | 60 | 7 | 3 | 3 |
| 663116 | 105 | 112 | 59 | 17 |

TABLE 50

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 72 | 24 | 7 | 4 |
| 633483 | 80 | 59 | 27 | 15 |
| 640679 | 62 | 20 | 6 | 4 |
| 662478 | 85 | 44 | 14 | 4 |
| 662483 | 89 | 46 | 19 | 10 |
| 662489 | 81 | 40 | 18 | 8 |
| 662493 | 66 | 46 | 17 | 7 |
| 662499 | 68 | 25 | 12 | 4 |
| 662501 | 67 | 25 | 14 | 7 |
| 662577 | 56 | 29 | 9 | 4 |
| 662962 | 89 | 45 | 16 | 6 |
| 662992 | 92 | 41 | 11 | 4 |
| 663092 | 86 | 77 | 32 | 10 |

TABLE 50-continued

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 663102 | 88 | 66 | 32 | 12 |
| 663110 | 93 | 61 | 25 | 5 |
| 663117 | 74 | 44 | 12 | 3 |
| 663202 | 99 | 37 | 12 | 5 |
| 663217 | 109 | 47 | 23 | 8 |
| 663242 | 97 | 60 | 29 | 8 |

TABLE 51

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 80 | 21 | 6 | 4 |
| 633398 | 86 | 31 | 8 | 5 |
| 640672 | 104 | 94 | 35 | 11 |
| 640677 | 46 | 34 | 16 | 8 |
| 640678 | 51 | 41 | 13 | 6 |
| 640684 | 66 | 140 | 48 | 14 |
| 662546 | 65 | 43 | 24 | 9 |
| 662560 | 82 | 40 | 35 | 13 |
| 662565 | 86 | 54 | 16 | 8 |
| 662571 | 81 | 51 | 25 | 10 |
| 662578 | 67 | 23 | 8 | 4 |
| 662579 | 69 | 15 | 7 | 4 |
| 662595 | 69 | 89 | 20 | 14 |
| 662602 | 156 | 96 | 29 | 11 |
| 662610 | 90 | 22 | 8 | 4 |
| 662616 | 105 | 26 | 18 | 8 |
| 662647 | 132 | 82 | 42 | 13 |
| 662648 | 94 | 29 | 16 | 5 |
| 662649 | 53 | 75 | 32 | 13 |

TABLE 52

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633355 | 113 | 58 | 12 | 2 |
| 633365 | 74 | 20 | 5 | 2 |
| 633414 | 100 | 75 | 59 | 7 |
| 633418 | 90 | 53 | 14 | 5 |
| 640714 | 44 | 34 | 11 | 4 |
| 640717 | 67 | 48 | 16 | 8 |
| 662658 | 98 | 102 | 44 | 55 |
| 662695 | 125 | 88 | 32 | 11 |
| 662698 | 114 | 84 | 31 | 11 |
| 662701 | 87 | 60 | 19 | 4 |
| 662703 | 95 | 59 | 14 | 6 |
| 662704 | 81 | 39 | 7 | 3 |
| 662708 | 126 | 175 | 28 | 15 |
| 662710 | 85 | 27 | 6 | 5 |
| 662723 | 137 | 89 | 26 | 8 |
| 662724 | 71 | 61 | 16 | 6 |
| 662725 | 92 | 53 | 17 | 6 |
| 662726 | 79 | 77 | 28 | 8 |
| 662731 | 108 | 86 | 23 | 7 |

TABLE 53

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633323 | 61 | 50 | 12 | 4 |
| 633365 | 56 | 22 | 6 | 3 |
| 662053 | 136 | 87 | 20 | 10 |
| 662056 | 116 | 71 | 44 | 15 |
| 662132 | 111 | 54 | 24 | 12 |
| 662146 | 92 | 44 | 11 | 7 |
| 662212 | 197 | 68 | 14 | 6 |
| 662219 | 114 | 43 | 21 | 6 |
| 662285 | 78 | 93 | 29 | 7 |
| 662301 | 191 | 53 | 27 | 18 |
| 662302 | 97 | 42 | 21 | 7 |
| 662322 | 122 | 93 | 40 | 20 |
| 662696 | 108 | 84 | 74 | 33 |
| 662699 | 63 | 63 | 43 | 27 |
| 662702 | 75 | 70 | 27 | 10 |
| 662705 | 86 | 91 | 24 | 15 |
| 662713 | 85 | 97 | 57 | 36 |
| 662714 | 79 | 78 | 40 | 20 |
| 662732 | 100 | 69 | 80 | 15 |

TABLE 54

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 304 | 10 | 54 | 9 |
| 662249 | 108 | 113 | 34 | 14 |
| 662252 | 59 | 52 | 22 | 9 |
| 662255 | 106 | 458 | 443 | 14 |
| 662256 | 49 | 239 | 26 | 7 |
| 662290 | 81 | 81 | 34 | 120 |
| 662292 | 167 | 231 | 24 | 10 |
| 662295 | 492 | 359 | 22 | 5 |
| 662296 | 118 | 55 | 15 | 37 |
| 662305 | 180 | 63 | 40 | 6 |
| 662306 | 1607 | 125 | 36 | 71 |
| 662308 | 129 | 46 | 297 | 114 |
| 662309 | 487 | 120 | 146 | 32 |
| 662312 | 48 | 133 | 33 | 10 |
| 662314 | 484 | 39 | 81 | 28 |
| 662315 | 229 | 74 | 12 | 5 |
| 662318 | 52 | 524 | 59 | 17 |
| 662320 | 50 | 30 | 14 | 3 |
| 662884 | 148 | 481 | 52 | 5 |

TABLE 55

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 70 | 24 | 8 | 4 |
| 633455 | 80 | 73 | 21 | 7 |
| 633456 | 97 | 59 | 18 | 8 |
| 662843 | 88 | 52 | 15 | 6 |
| 662867 | 92 | 71 | 35 | 16 |
| 662868 | 83 | 66 | 22 | 11 |
| 662875 | 100 | 52 | 14 | 6 |

TABLE 55-continued

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 662879 | 123 | 96 | 37 | 16 |
| 662882 | 85 | 42 | 14 | 6 |
| 663132 | 96 | 67 | 25 | 13 |
| 663138 | 90 | 73 | 31 | 23 |
| 663142 | 91 | 54 | 31 | 20 |
| 663144 | 83 | 27 | 9 | 5 |
| 663185 | 101 | 51 | 19 | 9 |
| 663278 | 66 | 37 | 17 | 4 |
| 663343 | 81 | 55 | 24 | 15 |
| 663354 | 81 | 38 | 13 | 7 |
| 663384 | 80 | 67 | 34 | 7 |
| 663386 | 103 | 63 | 27 | 10 |

TABLE 56

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 70 | 25 | 8 | 5 |
| 633481 | 57 | 53 | 17 | 8 |
| 662358 | 74 | 56 | 17 | 5 |
| 662366 | 92 | 84 | 39 | 14 |
| 662368 | 64 | 26 | 9 | 5 |
| 662380 | 87 | 58 | 33 | 18 |
| 662896 | 78 | 71 | 43 | 20 |
| 662940 | 35 | 14 | 7 | 3 |
| 662941 | 56 | 18 | 8 | 4 |
| 662944 | 21 | 13 | 5 | 3 |
| 662950 | 66 | 31 | 12 | 4 |
| 662951 | 73 | 37 | 15 | 6 |
| 662957 | 88 | 51 | 21 | 6 |
| 662959 | 100 | 80 | 43 | 14 |
| 663143 | 70 | 34 | 12 | 5 |
| 663147 | 78 | 41 | 14 | 4 |
| 663157 | 97 | 63 | 26 | 9 |
| 663176 | 94 | 77 | 43 | 11 |
| 663180 | 97 | 70 | 27 | 8 |

Example 13: Effect of 3-10-3 cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 5,000 cells per well and transfected via free uptake with 40 nM, 200 nM, 1,000 nM, and 5,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1985 (described hereinabove in Example 4) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 57

Dose-dependent percent reduction of human EZH2 mRNA by modified oligonucleotides

| ION Number | EZH2 expression (% UTC) | | | |
|---|---|---|---|---|
| | 40 nM | 200 nM | 1,000 nM | 5,000 nM |
| 633365 | 92 | 27 | 7 | 4 |
| 633481 | 82 | 53 | 19 | 12 |
| 662358 | 89 | 50 | 17 | 7 |
| 662366 | 117 | 74 | 36 | 19 |
| 662368 | 74 | 41 | 8 | 6 |
| 662380 | 105 | 74 | 43 | 27 |
| 662896 | 82 | 84 | 64 | 45 |
| 662940 | 85 | 70 | 45 | 32 |
| 662941 | 83 | 41 | 15 | 7 |
| 662944 | 89 | 55 | 23 | 12 |
| 662950 | 69 | 42 | 16 | 14 |
| 662951 | 90 | 37 | 16 | 8 |
| 662957 | 92 | 61 | 27 | 14 |
| 662959 | 95 | 82 | 56 | 41 |
| 663143 | 92 | 39 | 11 | 5 |
| 663147 | 98 | 47 | 13 | 5 |
| 663157 | 97 | 80 | 28 | 17 |
| 663176 | 78 | 87 | 53 | 38 |
| 663180 | 96 | 82 | 30 | 15 |

Example 14: Effect of 3-10-3 cEt Gapmers and Mixed MOE and cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 5,000 cells per well and transfected via free uptake with 24 nM, 120 nM, 600 nM, and 3,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 58

Dose-dependent percent reduction of human EZH2 mRNA by modified oligonucleotides

| ION Number | EZH2 expression (% UTC) | | | | |
|---|---|---|---|---|---|
| | 0.024 μM | 0.12 μM | 0.60 μM | 3.0 μM | $IC_{50}$ (μM) |
| 633365 | 107 | 80 | 39 | 20 | 0.5 |
| 663097 | 98 | 68 | 21 | 6 | 0.2 |
| 702217 | 103 | 79 | 44 | 18 | 0.5 |
| 702232 | 103 | 76 | 25 | 10 | 0.3 |
| 702233 | 105 | 63 | 13 | 4 | 0.2 |
| 702249 | 109 | 84 | 41 | 16 | 0.5 |
| 702250 | 100 | 70 | 22 | 9 | 0.3 |
| 702252 | 111 | 102 | 50 | 23 | 0.8 |
| 702253 | 106 | 89 | 43 | 22 | 0.6 |
| 702267 | 109 | 95 | 48 | 27 | 0.8 |
| 702278 | 100 | 86 | 37 | 18 | 0.5 |

TABLE 58-continued

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.024 μM | 0.12 μM | 0.60 μM | 3.0 μM | |
| 702338 | 109 | 86 | 20 | 8 | 0.3 |
| 702349 | 97 | 80 | 20 | 8 | 0.3 |
| 702371 | 88 | 81 | 29 | 17 | 0.3 |
| 702382 | 88 | 91 | 37 | 15 | 0.4 |
| 702415 | 125 | 86 | 23 | 8 | 0.4 |
| 702467 | 110 | 94 | 37 | 15 | 0.5 |
| 702830 | 95 | 86 | 44 | 26 | 0.6 |
| 702925 | 117 | 67 | 26 | 13 | 0.4 |

TABLE 59

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.024 μM | 0.12 μM | 0.60 μM | 3.0 μM | |
| 633365 | 109 | 83 | 32 | 15 | 0.4 |
| 662368 | 89 | 73 | 36 | 15 | 0.3 |
| 702273 | 109 | 91 | 43 | 18 | 0.6 |
| 702334 | 94 | 75 | 24 | 11 | 0.3 |
| 702344 | 100 | 74 | 22 | 8 | 0.3 |
| 702366 | 89 | 67 | 20 | 8 | 0.2 |
| 702373 | 85 | 71 | 21 | 10 | 0.2 |
| 702378 | 92 | 84 | 34 | 16 | 0.4 |
| 702384 | 86 | 58 | 30 | 17 | 0.2 |
| 702388 | 96 | 65 | 19 | 8 | 0.2 |
| 702395 | 105 | 71 | 31 | 14 | 0.4 |
| 702417 | 92 | 65 | 30 | 15 | 0.3 |
| 702462 | 96 | 69 | 24 | 11 | 0.3 |
| 702469 | 94 | 77 | 28 | 13 | 0.3 |
| 702862 | 88 | 72 | 28 | 10 | 0.3 |
| 702909 | 88 | 70 | 23 | 8 | 0.2 |
| 702949 | 109 | 92 | 36 | 16 | 0.5 |
| 702954 | 90 | 72 | 24 | 10 | 0.3 |
| 702959 | 96 | 59 | 19 | 7 | 0.2 |

TABLE 60

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.024 μM | 0.12 μM | 0.60 μM | 3.0 μM | |
| 633365 | 94 | 101 | 27 | 14 | 0.4 |
| 662710 | 71 | 109 | 37 | 15 | 0.5 |
| 662964 | 96 | 92 | 56 | 36 | 1.2 |
| 702263 | 99 | 88 | 53 | 24 | 0.7 |
| 702295 | 93 | 84 | 64 | 38 | 1.5 |
| 702335 | 94 | 94 | 37 | 19 | 0.5 |
| 702369 | 92 | 93 | 36 | 12 | 0.4 |
| 702391 | 98 | 82 | 22 | 9 | 0.3 |
| 702411 | 97 | 77 | 34 | 14 | 0.4 |
| 702437 | 104 | 83 | 45 | 22 | 0.6 |
| 702863 | 71 | 75 | 51 | 28 | 0.5 |
| 702882 | 102 | 67 | 37 | 21 | 0.4 |
| 702887 | 107 | 87 | 38 | 22 | 0.5 |
| 702895 | 78 | 69 | 42 | 24 | 0.4 |
| 702896 | 99 | 68 | 42 | 18 | 0.4 |
| 702901 | 103 | 81 | 33 | 9 | 0.4 |

TABLE 60-continued

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.024 μM | 0.12 μM | 0.60 μM | 3.0 μM | |
| 702904 | 93 | 112 | 43 | 23 | 0.8 |
| 702911 | 105 | 85 | 36 | 14 | 0.4 |
| 702918 | 91 | 65 | 39 | 17 | 0.3 |

TABLE 61

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.024 μM | 0.12 μM | 0.60 μM | 3.0 μM | |
| 633365 | 75 | 66 | 23 | 7 | 0.2 |
| 633398 | 100 | 71 | 37 | 24 | 0.4 |
| 662423 | 101 | 78 | 55 | 28 | 0.8 |
| 662648 | 86 | 43 | 30 | 29 | 0.2 |
| 662964 | 78 | 80 | 51 | 25 | 0.6 |
| 702298 | 103 | 75 | 32 | 11 | 0.3 |
| 702922 | 109 | 81 | 43 | 16 | 0.5 |
| 702956 | 78 | 68 | 35 | 26 | 0.3 |
| 702961 | 80 | 77 | 30 | 14 | 0.3 |
| 703725 | 99 | 69 | 34 | 13 | 0.3 |

Example 15: Effect of 3-10-3 cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 5,000 cells per well and transfected via free uptake with 111.1 nM, 333.3 nM, 1,000 nM, and 3,000 nM concentrations of modified oligonucleotide, as specified in the tables below. After a treatment period of approximately 24 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 62

Dose-dependent percent reduction of human EZH2 mRNA by modified oligonucleotides

| ION Number | EZH2 expression (% UTC) | | | | IC$_{50}$ (μM) |
|---|---|---|---|---|---|
| | 0.111 μM | 0.333 μM | 1.0 μM | 3.0 μM | |
| 633365 | 76 | 39 | 21 | 11 | 0.3 |
| 663097 | 49 | 23 | 8 | 3 | 0.1 |
| 663144 | 80 | 43 | 24 | 12 | 0.3 |
| 702233 | 45 | 11 | 4 | 3 | <0.1 |
| 755853 | 73 | 51 | 36 | 21 | 0.4 |

TABLE 62-continued

Dose-dependent percent reduction of human EZH2 mRNA by modified oligonucleotides

| ION Number | EZH2 expression (% UTC) | | | | IC$_{50}$ (µM) |
|---|---|---|---|---|---|
| | 0.111 µM | 0.333 µM | 1.0 µM | 3.0 µM | |
| 755873 | 80 | 46 | 26 | 12 | 0.4 |
| 755905 | 74 | 54 | 28 | 21 | 0.4 |
| 755927 | 79 | 57 | 34 | 24 | 0.5 |
| 755948 | 74 | 85 | 89 | 66 | >3 |
| 755984 | 101 | 78 | 44 | 28 | 1.0 |
| 756003 | 84 | 54 | 30 | 19 | 0.5 |
| 756019 | 95 | 77 | 66 | 49 | 2.8 |
| 756035 | 77 | 52 | 26 | 19 | 0.4 |
| 756188 | 52 | 23 | 9 | 4 | 0.1 |
| 756282 | 77 | 42 | 34 | 18 | 0.4 |
| 756288 | 89 | 53 | 33 | 18 | 0.5 |
| 756314 | 65 | 39 | 14 | 8 | 0.2 |
| 756320 | 65 | 43 | 22 | 10 | 0.2 |
| 756358 | 76 | 66 | 38 | 29 | 0.7 |

TABLE 63

Dose-dependent percent reduction of human EZH2 mRNA by modified oligonucleotides

| ION Number | EZH2 expression (% UTC) | | | | IC$_{50}$ (µM) |
|---|---|---|---|---|---|
| | 0.111 µM | 0.333 µM | 1.0 µM | 3.0 µM | |
| 633365 | 79 | 51 | 21 | 12 | 0.4 |
| 663097 | 61 | 24 | 8 | 5 | 0.1 |
| 663144 | 71 | 49 | 27 | 14 | 0.3 |
| 702233 | 54 | 15 | 5 | 3 | 0.1 |
| 756336 | 113 | 59 | 50 | 33 | 1.0 |
| 756374 | 100 | 64 | 61 | 29 | 1.2 |
| 756386 | 73 | 67 | 48 | 36 | 1.0 |
| 756399 | 89 | 61 | 46 | 19 | 0.7 |
| 756401 | 95 | 66 | 48 | 32 | 1.0 |
| 756474 | 78 | 50 | 26 | 12 | 0.4 |
| 756557 | 76 | 44 | 24 | 13 | 0.3 |
| 756597 | 81 | 43 | 25 | 11 | 0.4 |
| 756618 | 74 | 50 | 26 | 12 | 0.3 |
| 756664 | 78 | 57 | 26 | 11 | 0.4 |
| 756749 | 72 | 69 | 41 | 21 | 0.6 |
| 756759 | 90 | 73 | 45 | 36 | 1.1 |
| 756772 | 79 | 56 | 32 | 23 | 0.5 |
| 756783 | 77 | 64 | 24 | 12 | 0.4 |
| 756785 | 72 | 55 | 33 | 22 | 0.4 |

Example 16: Effect of 3-10-3 cEt Gapmers and Mixed MOE and cEt Gapmers with Phosphorothioate Internucleoside Linkages on Human EZH2 In Vitro, Multiple Doses Modified oligonucleotides selected from the examples above were tested at various doses in A431 cells. Cells were plated at a density of 12,000 cells per well and transfected via free uptake with 19.5 nM, 78.1 nM, 312.5 nM, 1,250 nM, and 5,000 nM concentrations of modified oligonucleotide, as specified in the tables below. After a treatment period of approximately 48 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells. ION 754175 is a cEt and MOE containing gapmer having the motif k-d10-kekek and the nucleobase sequence TGTATTTGTGCAAGGC (SEQ ID NO: 1038), wherein "k" indicates a cEt sugar modification; "d" indicates deoxyribose; and "e" indicates a MOE modification. Each internucleoside linkage of ION 754175 is a phosphorothioate internucleoside linkage and each cytosine residue is a 5-methyl cytosine.

TABLE 64

Dose-dependent percent reduction of human EZH2 mRNA by modified oligonucleotides

| ION Number | EZH2 expression (% UTC) | | | | | IC$_{50}$ (µM) |
|---|---|---|---|---|---|---|
| | 0.0195 µM | 0.078 µM | 0.312 µM | 1.25 µM | 5.0 µM | |
| 633365 | 75 | 31 | 10 | 5 | 2 | 0.043 |
| 662368 | 78 | 45 | 16 | 6 | 1 | 0.064 |
| 662950 | 72 | 38 | 15 | 8 | 4 | 0.050 |
| 702334 | 70 | 36 | 11 | 4 | 2 | 0.043 |
| 702366 | 53 | 21 | 5 | 2 | 1 | 0.021 |
| 754175 | 66 | 26 | 8 | 3 | 2 | 0.033 |

Example 17: Effect of 3-10-3 cEt Gapmers and Mixed MOE and cEt Gapmers with Phosphorothioate Internucleoside Linkages on Human EZH2 In Vitro, Multiple Doses Modified oligonucleotides selected from the examples above were tested at various doses in SH-SY5Y cells. Cells were plated at a density of 35,000 cells per well and transfected using electroporation with 19.5 nM, 78.1 nM, 312.5 nM, 1,250 nM, and 5,000 nM concentrations of modified oligonucleotide, as specified in the tables below. After a treatment period of approximately 20 hours, total RNA was isolated from the cells and EZH2 mRNA levels were measured by quantitative real-time PCR. Human EZH2 primer probe set RTS1986 (described hereinabove in Example 1) was used to measure mRNA levels. EZH2 mRNA levels were adjusted according to total RNA content, as measured by RiboGreen®. Results are presented in the tables below as percent control of the amount of EZH2 mRNA, relative to untreated control cells (UTC). As illustrated in the tables below, EZH2 mRNA levels were reduced in a dose-dependent manner in modified oligonucleotide-treated cells.

TABLE 65

Dose-dependent percent reduction of human EZH2 mRNA by modified oligonucleotides

| ION Number | EZH2 expression (% UTC) | | | | | IC$_{50}$ (µM) |
|---|---|---|---|---|---|---|
| | 0.0195 µM | 0.078 µM | 0.312 µM | 1.25 µM | 5.0 µM | |
| 633365 | 96 | 76 | 50 | 30 | 14 | 0.365 |
| 662368 | 93 | 68 | 44 | 17 | 7 | 0.216 |
| 662950 | 94 | 81 | 48 | 27 | 18 | 0.351 |
| 702334 | 97 | 84 | 60 | 37 | 13 | 0.560 |
| 702366 | 90 | 72 | 44 | 20 | 7 | 0.242 |
| 754175 | 88 | 84 | 51 | 24 | 10 | 0.350 |

Example 18: Activity of Modified Oligonucleotides Targeting hEZH2 in Cancer Cell Lines Modified oligonucleotides described above were tested at various doses in epidermoid carcinoma A431, neuroblastoma SHSY, and neuroblastoma Kelly cell lines. Compounds were incubated with cells at various concentrations to determine a dose-response curve. A431 and Kelly cells were transfected by free uptake, while SHSY cells were transfected by electroporation. Cells were isolated after addition of modified oligonucleotide, and RNA was extracted and analyzed by RT-qPCR. Primer probe set RTS1985 (described hereinabove in Example 4) was used to detect hEZH2.

TABLE 66

Activity of hEZH2 modified oligonucleotides in cancer cell lines

| ION Number | A431 IC$_{50}$ (µM) | SHSY IC$_{50}$ (µM) | Kelly IC$_{50}$ (µM) |
|---|---|---|---|
| 633365 | 0.043 | 0.365 | 0.056 |
| 662368 | 0.064 | 0.216 | 0.068 |
| 662950 | 0.050 | 0.351 | 0.080 |
| 702334 | 0.043 | 0.560 | 0.033 |
| 702366 | 0.021 | 0.242 | 0.033 |
| 754175 | 0.033 | 0.350 | 0.052 |

Example 19: Activity of Modified Oligonucleotides Targeting hEZH2 in KARPAS422 (Y641N) Cells Experimental Conditions Modified oligonucleotide 633365 described above was tested at various doses in human non-Hodgkin's B-cell lymphoma KARPAS422 harboring Y641N mutation on EZH2. A control oligonucleotide 549148 was also tested. 549148 is a 3-10-3 cEt gapmer with a full phosphorothioate backbone with the sequence GGCTACTACGCCGTCA (SEQ ID NO:X) that is not complementary to any known human genes. Cells were plated at 0.5×10$^6$ cells/well and treated with compounds at the indicated concentrations by free uptake. Cells were split every 3 days and replated at the original cell density of 0.5×10$^6$ cells/well.

Cell Viability

Cell viability was counted using a BD Vi-cell counter at the indicated day after addition of the modified oligonucleotide.

Protein Levels

At day 2, 4, 7, and 11 after the addition of modified oligonucleotide, a western blot was run to evaluate the protein levels of EZH2 and H3K27me3, an indicator of EZH2 activity. Equal amounts of protein were added to each lane as determined by a BCA assay. Treatment with 633365 decreased protein levels of EZH2 and H3K27me in a dose-dependent manner.

Example 20: Activity of Modified Oligonucleotides Targeting hEZH2 in Diffuse Large B-Cell Lymphoma (DLBCL) SU-DHL-6 Cells Experimental Conditions Modified oligonucleotides described above were tested at various doses in human B-cell lymphoma SU-DHL-6 cells. Cells were plated at 0.5×10$^6$ cells/well and treated with compounds at the indicated concentrations by free uptake. Cells were split every 3 days and replated at the original cell density of 0.5×10$^6$ cells/well. Modified oligonucleotides were maintained at the given concentrations in the media for the duration of the experiment.

Cell Viability

Cell viability was counted using a BD Vi-cell counter at the indicated day after addition of the modified oligonucleotide.

TABLE 68

Total Viable Cell Number

| ION Number | Dose (µM) | Day 0 | Day 4 | Day 7 | Day 12 | Day 15 | Day 18 |
|---|---|---|---|---|---|---|---|
| | | \multicolumn{6}{c}{Viable Cell number (×10$^6$)} | | | | | |
| Untreated* | | 0.50 | 2.1 | 7.3 | 57.6 | 103.0 | 363.5 |
| 549148 | 0.01 | 0.50 | 2.2 | 8.0 | 66.6 | 120.7 | 410.5 |
| | 0.05 | 0.50 | 2.2 | 7.3 | 58.1 | 108.3 | 398.0 |
| | 0.10 | 0.50 | 2.1 | 7.4 | 61.6 | 101.3 | 310.2 |
| | 0.25 | 0.50 | 2.0 | 7.2 | 58.7 | 101.7 | 340.3 |
| | 0.50 | 0.50 | 2.0 | 6.5 | 48.3 | 75.7 | 279.4 |
| 633323 | 0.01 | 0.50 | 0.5 | 2.0 | 7.1 | 55.2 | 94.5 |
| | 0.05 | 0.50 | 0.5 | 1.9 | 7.0 | 54.0 | 98.1 |
| | 0.10 | 0.50 | 0.5 | 2.0 | 7.4 | 52.8 | 110.2 |
| | 0.25 | 0.50 | 0.5 | 1.9 | 6.7 | 52.9 | 95.0 |
| | 0.50 | 0.50 | 0.5 | 1.9 | 6.3 | 47.6 | 88.8 |
| 633335 | 0.01 | 0.50 | 0.5 | 2.0 | 7.3 | 54.5 | 102.2 |
| | 0.05 | 0.50 | 0.5 | 1.9 | 6.5 | 51.6 | 89.2 |
| | 0.10 | 0.50 | 0.5 | 1.9 | 6.7 | 51.0 | 93.1 |
| | 0.25 | 0.50 | 0.5 | 2.1 | 7.3 | 53.4 | 99.6 |
| | 0.50 | 0.50 | 0.5 | 1.9 | 6.7 | 49.5 | 76.7 |
| 633365 | 0.01 | 0.50 | 2.1 | 6.8 | 53.0 | 96.6 | 308.9 |
| | 0.05 | 0.50 | 2.1 | 7.0 | 58.5 | 102.1 | 315.1 |
| | 0.10 | 0.50 | 2.1 | 6.7 | 55.4 | 92.5 | 286.6 |
| | 0.25 | 0.50 | 2.1 | 7.2 | 53.7 | 86.0 | 241.6 |
| | 0.50 | 0.50 | 2.0 | 5.8 | 26.5 | 34.9 | 64.9 |

*Untreated control value represents the average of four independent experiments

TABLE 67

Total Viable Cell Number

| ION Number | Dose (µM) | Day 0 | Day 3 | Day 6 | Day 9 | Day 13 | Day 16 | Day 21 | Day 26 |
|---|---|---|---|---|---|---|---|---|---|
| | | \multicolumn{8}{c}{Viable Cell number (×10$^6$)} | | | | | | | |
| untreated | N/A | 0.50 | 1.12 | 5.46 | 29.5 | 114.4 | 355 | 1,465 | 12,644 |
| 549148 | 0.25 | 0.50 | 0.51 | 2.68 | 17.1 | 72.4 | 264 | 1,107 | 8,413 |
| | 0.75 | 0.50 | 0.44 | 2.14 | 14.9 | 63.8 | 177 | 672 | 4,390 |
| | 2.25 | 0.50 | 0.54 | 2.82 | 18.3 | 80.7 | 273 | 1,247 | 7,456 |
| 633365 | 0.25 | 0.50 | 0.75 | 4.23 | 7.33 | 5.88 | 1.98 | 1.22 | 0.70 |
| | 0.75 | 0.50 | 0.54 | 2.79 | 5.91 | 3.23 | 2.38 | 0.82 | 0.27 |
| | 2.25 | 0.50 | 0.82 | 4.35 | 6.99 | 2.98 | 0.92 | 0.19 | 0.038 |

633365 inhibited cell proliferation and survival in a dose-dependent manner.

TABLE 69

Apoptotic Cells on Day 18

| Ion Number | 0 | 10 nM | 50 nM | 100 nM | 250 nM | 500 nM | $IC_{50}$ (μM) for EZH2 mRNA inhibition |
|---|---|---|---|---|---|---|---|
| | | | % Annexin V+/PI cells by FACS | | | | |
| 549148 | 1.0 | 0.67 | 1.50 | 3.17 | 1.83 | 2.00 | n/a |
| 633323 | | 1.63 | 0 | 0 | 0.93 | 7.67 | 3.60 |
| 633335 | | 0 | 2.1 | 1.8 | 2.7 | 10.2 | n/a |
| 633365 | | 0 | 0.6 | 4.2 | 20.8 | 69.7 | 0.87 |

633365 induced apoptosis in a dose dependent manner.

Example 21: Activity of Modified Oligonucleotides Targeting hEZH2 in SU-DHL-6 Cells in Combination with E7438

Experimental Conditions

Modified oligonucleotides described above were tested at various doses in SU-DHL-6 cells in combination with the EZH2 inhibitor E7438. Cells were plated at $0.5 \times 10^6$ cells/well and treated with modified oligonucleotide at the indicated concentrations by free uptake. On day 3, E7438 was added at the indicated concentration for combination conditions. Cells were split on day 4 and every 3 days and replated at the original cell density of $0.5 \times 10^6$ cells/well. Modified oligonucleotides and E7438 were maintained at the given concentrations in the media for the duration of the experiment.

Cell Viability

Cell viability was counted using a BD Vi-cell counter at the indicated day after addition of the modified oligonucleotide. The combination index was calculated using the CalcuSyn software, where combination between the two compounds is synergistic if the value is below 1.0.

TABLE 70

Total Viable Cell Number

| Condition | Dose 633365 (μM) | Dose E7438 (μM) | 0 | 4 | 7 | 11 | 14 | 17 | 21 | 24 |
|---|---|---|---|---|---|---|---|---|---|---|
| | | | | | Viable Cell number (×10⁶) | | | | | |
| Untreated control | 0 | 0 | 0.5 | 2.1 | 14.8 | 31.1 | 288 | 805 | 6609 | 21478 |
| 633365 | 0.05 | 0 | 0.5 | 2.4 | 17.1 | 38.4 | 343 | 1038 | 8563 | 27397 |
| 633365 | 0.20 | 0 | 0.5 | 2.3 | 17.0 | 30.6 | 233 | 585 | 3597 | 9037 |
| 633365 + E7438 | 0.05 | 0.01 | 0.5 | 2.3 | 16.0 | 34.5 | 260 | 663 | 4656 | 12082 |
| 633365 + E7438 | 0.05 | 0.05 | 0.5 | 2.3 | 16.8 | 27.9 | 102 | 186 | 324 | 612 |
| 633365 + E7438 | 0.05 | 0.20 | 0.5 | 1.9 | 11.6 | 13.2 | 12.5 | 6.1 | 3.7 | 4.0 |
| 633365 + E7438 | 0.20 | 0.1 | 0.5 | 2.5 | 15.2 | 26.7 | 144 | 315 | 1342 | 2899 |
| 633365 + E7438 | 0.20 | 0.05 | 0.5 | 2.0 | 11.4 | 13.4 | 15.8 | 13.2 | 10.6 | 6.6 |
| 633365 + E7438 | 0.20 | 0.20 | 0.5 | 1.9 | 9.5 | 7.8 | 5.1 | 2.3 | 2.6 | 2.1 |
| E7438 | 0 | 0.01 | 0.5 | 2.1 | 16.2 | 31.4 | 261 | 658 | 4655 | 11337 |
| E7438 | 0 | 0.05 | 0.5 | 2.2 | 13.4 | 26.3 | 87.5 | 125 | 162 | 132 |
| E7438 | 0 | 0.20 | 0.5 | 2.2 | 11.6 | 9.8 | 4.8 | 6.2 | 4.4 | 3.4 |

TABLE 71

Combination Index

| Condition | Dose 633365 (μM) | Dose E7438 (μM) | Combo. Index Day 14 | Combo. Index Day 17 |
|---|---|---|---|---|
| 633365 + E7438 | 0.05 | 0.01 | 1.26 | 1.30 |
| 633365 + E7438 | 0.05 | 0.05 | 1.27 | 1.41 |
| 633365 + E7438 | 0.05 | 0.20 | 1.39 | 1.02 |
| 633365 + E7438 | 0.20 | 0.01 | 0.84 | 0.95 |
| 633365 + E7438 | 0.20 | 0.05 | 0.53 | 0.50 |
| 633365 + E7438 | 0.20 | 0.20 | 1.06 | 1.11 |

Example 22: Activity of Modified Oligonucleotides Targeting hEZH2 in Liver Carcinoma HepG2 Cells

Experimental Conditions

Modified oligonucleotides described above were tested at the indicated doses in liver carcinoma Hep2G cells. Cells were plated at 100,000 cells/well in 6 well plates and transfected with modified oligonucleotide 24 hours later using RNAi MAX.

Cell Proliferation

Cell proliferation was measured by a clonogenic assay on day 6. Results are presented relative to untreated control cells (UTC) in the table below.

TABLE 72

Total Viable Cell Number

| ION Number | 0.5 nM | 2.5 nM | 10 nM | 20 nM |
|---|---|---|---|---|
| 549148 | 85.4 | 100.5 | 98.4 | 88.5 |
| 633365 | 76.4 | 84.4 | 49.5 | 18.0 |
| 702366 | 76.1 | 93.0 | 57.2 | 34.4 |

Protein Levels

At days 3 after the addition of modified oligonucleotides, a western blot was run to evaluate the protein levels of EZH2, H3, H3K27me3, and SUZ12. Tubulin was included as a control for protein loading. Equal amounts of protein were added to each lane as determined by a BCA assay. 633365 decreased EZH2, SUZ12, and H3K27me3 in a dose-dependent manner.

mRNA Analysis

RT-qPCR analysis was performed on cells at three days after the addition of modified oligonucleotide or small molecule inhibitor. Primer probe set RTS1985 (described hereinabove in Example 4) was used to detect hEZH2, and the levels of EZH2 mRNA relative to untreated control are represented in the table below.

TABLE 73

EZH2 mRNA

| ION Number | 0.5 nM | 2.5 nM | 10 nM | 20 nM |
|---|---|---|---|---|
| 549148 | 107 | 104 | 102 | 81 |
| 633365 | 73 | 30 | 3.6 | n.d* |
| 702366 | 83 | 67 | 18 | 3.3 |
| 680122 | 83 | 63 | 55 | 50 |

*not determined

Example 23: Activity of Modified Oligonucleotides Targeting hEZH2 in a Human B-Cell Lymphoma TMD8 Xenograft Tumor Model A xenograft tumor model was used to evaluate activity of modified oligonucleotides targeted to human EZH2. $4.5 \times 10^6$ ABC-DLBCL TMD8 cells were implanted into the flanks of NOD/SCID mice. When tumors reached an average volume of 100 mm$^3$, approximately two weeks post-implantation, groups of eight mice were administered at 50 mg/kg/day with modified oligonucleotides for two weeks. ION 792169 was administered as a control. ION 792169 is a 3-10-3 cEt gapmer with a full phosphorothioate backbone and the sequence CGCCGATAAGGTACAC (SEQ ID NO: X), and is not complementary to any known human gene. Tumor volume was measured at the indicated days in the table below. Mice were sacrificed when tumors from PBS-treated mice reached 2,000 mm$^3$. Tumor samples were collected for measurement of EZH2 mRNA levels by RT-qPCR and presented relative to PBS-treated animals.

TABLE 74

Tumor volume (mm$^3$)

| Days post-implantation ION Number | 15 | 19 | 22 | 25 | 27 | 29 | 32 |
|---|---|---|---|---|---|---|---|
| | | | Tumor Volume (mm$^3$) | | | | |
| PBS | 100 | 276 | 602 | 872 | 1162 | 1365 | 2012 |
| 792169 | 100 | 232 | 488 | 797 | 1044 | 1359 | 1850 |
| 633365 | 100 | 256 | 541 | 687 | 832 | 915 | 979 |

TABLE 75 hEZH2 mRNA levels in tumors

| | hEZH2 mRNA Level |
|---|---|
| PBS | 100 |
| 792169 | 156 |
| 633365 | 46 |

Example 24: Tolerability of Modified Oligonucleotides Targeting hEZH2 in CD1 Mice CD1® mice (Charles River, Mass.) are frequently utilized for safety and efficacy testing. The mice were treated with antisense oligonucleotides selected from studies described above and evaluated for changes in the levels of various plasma chemistry markers.

Treatment

Groups of male CD1 mice were injected subcutaneously twice a week for four weeks with 50 mg/kg of modified oligonucleotides (100 mg/kg/week dose). One group of CD1 mice was injected subcutaneously twice a week for 4 weeks with PBS. Mice were euthanized 48 hours after the last dose, and organs and plasma were collected for further analysis.

Plasma Chemistry Markers

To evaluate the effect of modified oligonucleotides on liver and kidney function, plasma levels of transaminases, bilirubin, and BUN were measured using an automated clinical chemistry analyzer (Hitachi Olympus AU400e, Melville, N.Y.). The results are presented in the tables below. Modified oligonucleotides that caused changes in the levels of any of the liver or kidney function markers outside the expected range for modified oligonucleotides were excluded in further studies.

TABLE 76

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 34 | 81 | 25.7 | 2.72 | 0.24 |
| 662285 | 1326 | 1338 | 22.9 | 4.00 | 0.37 |
| 662454 | 1409 | 759 | 22.7 | 3.21 | 0.19 |
| 662455 | 903 | 823 | 21.4 | 2.50 | 0.26 |
| 662456 | 216 | 158 | 22.1 | 2.61 | 0.21 |
| 662578 | 3168 | 3766 | 21.0 | 2.65 | 1.55 |
| 662579 | 1439* | 1393* | 21.1* | 2.09* | 0.24* |
| 662610 | 3737* | 2129* | 33.4* | 4.30* | 5.84* |
| 662962 | 1887* | 2764* | 68.4* | 3.69* | 6.14* |

*values represent the average of 2-3 mice

TABLE 77

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 27 | 44 | 26.6 | 2.33 | 0.25 |
| 633365 | 32 | 59 | 24.6 | 2.31 | 0.30 |
| 633358 | 1693 | 1030 | 24.8 | 1.65 | 0.34 |
| 633483 | 1296 | 837 | 24.6 | 2.41 | 0.27 |
| 662312 | 961 | 458 | 29.0 | 2.01 | 0.28 |
| 662358 | 45 | 67 | 24.0 | 1.97 | 0.19 |
| 662368 | 50 | 79 | 24.7 | 2.05 | 0.25 |
| 662423 | 1910 | 4281 | 22.4 | 1.69 | 0.52 |
| 662442 | 54 | 86 | 22.2 | 1.41 | 0.14 |
| 662868 | 584 | 445 | 25.1 | 2.54 | 0.30 |
| 662940 | 29 | 49 | 25.6 | 2.28 | 0.20 |
| 662941 | 465* | 233* | 25.2* | 2.09* | 0.17* |

*Values represent the average of 3 mice

TABLE 78

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 35 | 66 | 27.4 | 2.73 | 0.23 |
| 662212 | 94 | 93 | 27.8 | 2.75 | 0.17 |
| 662438 | 2635* | 2308* | 22.4* | 2.70* | 0.33* |
| 662453 | 3626 | 2411 | 21.9 | 2.88 | 0.46 |
| 662950 | 745 | 337 | 25.0 | 2.51 | 0.76 |

TABLE 78-continued

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| 662964 | 2078 | 1674 | 21.3 | 2.86 | 3.38 |
| 662992 | 49 | 67 | 25.8 | 2.57 | 0.17 |
| 663092 | 84 | 322 | 21.8 | 2.47 | 0.20 |
| 663097 | 5256 | 4254 | 19.7 | 1.81 | 3.45 |
| 663116 | 573 | 322 | 23.8 | 2.50 | 0.20 |
| 663117 | 1451* | 1556* | 22.9* | 2.07* | 0.81* |
| 663144 | 4398 | 1997 | 28.3 | 2.55 | 0.55 |
| 663180 | 45 | 54 | 27.8 | 2.65 | 0.25 |
| 663343 | 118 | 92 | 23.4 | 2.79 | 0.23 |

*Values represent the average of 3 mice

TABLE 79

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 35 | 66 | 27.4 | 2.73 | 0.23 |
| 633398 | 32 | 65 | 21.0 | 2.61 | 0.23 |
| 662301 | 362 | 181 | 24.8 | 2.32 | 0.15 |
| 662320 | 1376 | 1120 | 23.4 | 2.33 | 0.18 |
| 662380 | 170 | 217 | 24.8 | 2.31 | 0.14 |
| 662466 | 261 | 226 | 24.6 | 2.31 | 0.28 |
| 662489 | 54 | 77 | 24.2 | 2.38 | 0.21 |
| 662616 | 1194 | 836 | 19.4 | 2.55 | 0.37 |
| 662648 | 1914 | 1440 | 25.5 | 2.53 | 0.85 |
| 662649 | 2031* | 2535* | 17.0* | 1.86* | 0.31* |
| 662704 | 2088 | 1372 | 23.8 | 2.23 | 0.34 |
| 662843 | 80 | 104 | 21.5 | 2.00 | 0.14 |
| 662875 | 478 | 275 | 22.0 | 2.50 | 0.19 |
| 662882 | 146* | 103* | 24.7* | 2.10* | 0.17* |
| 662944 | 1560 | 3223 | 31.6 | 1.84 | 3.88 |
| 662951 | 1197 | 1209 | 19.3 | 2.17 | 11.57 |
| 663143 | 549* | 363* | 20.9* | 1.17* | 0.16* |
| 663202 | 1931 | 1137 | 19.2 | 1.89 | 0.29 |
| 663278 | 975 | 590 | 23.6 | 3.23 | 0.35 |

*Values represent the average of 2-3 mice

TABLE 80

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 27 | 91 | 23.6 | 2.83 | 0.31 |
| 633323 | 326 | 291 | 20.6 | 2.52 | 0.23 |
| 640677 | 2328 | 1676 | 21.7 | 2.55 | 0.46 |
| 640714 | 635 | 340 | 20.0 | 2.94 | 0.21 |
| 640717 | 82 | 114 | 23.2 | 2.59 | 0.24 |
| 662219 | 1784 | 2603 | 25.8 | 3.06 | 0.45 |
| 662256 | 952 | 846 | 19.5 | 2.98 | 9.37 |
| 662296 | 3878* | 5188* | 25.1* | 3.25* | 4.23* |
| 662302 | 945 | 824 | 20.8 | 2.70 | 0.53 |
| 662305 | 44 | 67 | 20.8 | 2.55 | 0.18 |
| 662478 | 1637* | 3882* | 43.6* | 1.98* | 0.48* |
| 662571 | 365 | 194 | 23.2 | 2.97 | 0.18 |
| 662595 | 126 | 160 | 25.0 | 3.19 | 0.21 |
| 662647 | 488 | 1178 | 23.3 | 2.84 | 0.33 |
| 662724 | 2858 | 2079 | 24.5 | 3.39 | 0.55 |
| 662725 | 3366 | 1937 | 29.3 | 3.64 | 1.11 |
| 662884 | 3318* | 1908* | 25.9* | 3.45* | 6.86* |
| 662957 | 339 | 278 | 21.6 | 2.46 | 0.17 |
| 663147 | 110 | 127 | 23.3 | 2.66 | 0.18 |
| 663185 | 1664 | 837 | 25.2 | 3.01 | 0.24 |
| 680122 | 41 | 88 | 21.5 | 2.62 | 0.15 |

*Values represent the average of 2-3 mice

TABLE 81

Plasma chemistry markers in CD1 mouse plasma at week 4

| ION Number | ALT (U/L) | AST (U/L) | BUN (mg/dL) | Albumin (g/dL) | T. Bil (mg/dL) |
|---|---|---|---|---|---|
| PBS | 49 | 51 | 27.9 | 3.84 | 0.19 |
| 633365 | 50 | 59 | 27.5 | 2.87 | 0.19 |
| 702366 | 473* | 454* | 28.8* | 1.62* | 0.13* |
| 702954 | 265 | 230 | 23.9 | 2.57 | 0.17 |
| 702909 | 72 | 135 | 27.1 | 1.69 | 0.18 |

*Values represent the average of 2 mice

TABLE 82

Plasma chemistry markers in CD1 mouse plasma at week 4

| ION Number | ALT (U/L) | AST (U/L) | BUN (mg/dL) | T. Bil (mg/dL) |
|---|---|---|---|---|
| PBS | 26.5 | 55 | 23.2 | 0.31 |
| 702366 | 40.5 | 84.8 | 21.1 | 0.27 |

TABLE 83

Plasma chemistry markers in CD1 mouse plasma at week 4

| ION Number | ALT (U/L) | AST (U/L) | BUN (mg/dL) | T. Bil (mg/dL) |
|---|---|---|---|---|
| PBS | 24.5 | 37 | 25.5 | 0.27 |
| 702334 | 48.8 | 49.3 | 25.0 | 0.27 |

TABLE 84

Plasma chemistry markers in CD1 mouse plasma at week 4

| ION Number | ALT (U/L) | AST (U/L) | BUN (mg/dL) | T. Bil (mg/dL) |
|---|---|---|---|---|
| PBS | 24 | 26 | 11.5 | 0.11 |
| 754175 | 41 | 40 | 11.4 | 0.10 |
| 754179 | 4668* | 3785* | 13.9* | 0.39* |
| 754181 | 4130 | 3346 | 13.0 | 0.25 |
| 754182 | 1143 | 769 | 10.3 | 0.11 |
| 754205 | 1690 | 789 | 10.9 | 0.08 |
| 754206 | 2420 | 1338 | 12.6 | 0.25 |
| 754207 | 1480 | 832 | 12.1 | 0.13 |
| 754208 | 1108* | 1096* | 27.5* | 0.13* |

*Values represent the average of 2-3 mice

TABLE 85

Plasma chemistry markers in CD1 mouse plasma at week 4

| ION Number | ALT (U/L) | AST (U/L) | BUN (mg/dL) | T. Bil (mg/dL) |
|---|---|---|---|---|
| PBS | 24 | 38 | 25 | 0.30 |
| 756188 | 3175 | 2830 | 23 | 0.87 |

Organ Weights

Liver, kidney, and spleen weights were measured at the end of the study, and are presented in the table below. Modified oligonucleotides that caused any changes in organ weights outside the expected range for modified oligonucleotides were excluded from further studies.

TABLE 86

Organ Weights (g)

| ION Number | Liver | Kidney | Spleen |
|---|---|---|---|
| PBS | 2.00 | 0.60 | 0.11 |
| 662285 | 3.20 | 0.54 | 0.17 |
| 662454 | 2.06 | 0.49 | 0.14 |
| 662455 | 2.34 | 0.46 | 0.14 |
| 662456 | 2.20 | 0.52 | 0.13 |
| 662578 | 1.95 | 0.44 | 0.10 |
| 662579 | 2.29 | 0.55 | 0.24 |
| 662610 | 3.18 | 0.36 | 0.05 |
| 662962 | 2.33 | 0.56 | 0.19 |

TABLE 87

Organ Weights (g)

| ION Number | Liver | Kidney | Spleen |
|---|---|---|---|
| PBS | 1.96 | 0.56 | 0.12 |
| 633365 | 2.01 | 0.58 | 0.12 |
| 633358 | 2.95 | 0.57 | 0.16 |
| 633483 | 2.52 | 0.50 | 0.13 |
| 662312 | 2.23 | 0.49 | 0.12 |
| 662358 | 1.96 | 0.56 | 0.15 |
| 662368 | 1.86 | 0.51 | 0.13 |
| 662423 | 2.49 | 0.63 | 0.31 |
| 662442 | 2.27 | 0.56 | 0.17 |
| 662868 | 2.46 | 0.55 | 0.16 |
| 662940 | 2.06 | 0.54 | 0.13 |
| 662941 | 2.59* | 0.58* | 0.16* |

*Values represent the average of 3 mice

TABLE 88

Organ Weights (g)

| ION Number | Liver | Kidney | Spleen |
|---|---|---|---|
| PBS | 1.94 | 0.57 | 0.16 |
| 662212 | 2.29 | 0.56 | 0.16 |
| 662438 | 2.94* | 0.62* | 0.35* |
| 662453 | 2.34 | 0.39 | 0.14 |
| 662950 | 2.38 | 0.54 | 0.18 |
| 662964 | 3.53 | 0.65 | 0.50 |
| 662992 | 2.10 | 0.58 | 0.15 |
| 663092 | 2.24 | 0.66 | 0.13 |
| 663097 | 1.72 | 0.43 | 0.08 |
| 663116 | 2.76 | 0.60 | 0.24 |
| 663117 | 1.85* | 0.42* | 0.08* |
| 663144 | 2.69 | 0.58 | 0.23 |
| 663180 | 2.33 | 0.60 | 0.15 |
| 663343 | 2.32 | 0.68 | 0.17 |

*Values represent the average of 3 mice

TABLE 89

Organ Weights (g)

| ION Number | Liver | Kidney | Spleen |
|---|---|---|---|
| PBS | 1.87 | 0.60 | 0.13 |
| 662252 | 1.95 | 0.51 | 0.19 |
| 662301 | 2.22 | 0.52 | 0.13 |
| 662320 | 2.68 | 0.70 | 0.28 |
| 662380 | 1.97 | 0.56 | 0.10 |
| 662466 | 1.91 | 0.59 | 0.19 |
| 662565 | 2.32 | 0.55 | 0.13 |

TABLE 89-continued

Organ Weights (g)

| ION Number | Liver | Kidney | Spleen |
|---|---|---|---|
| 662616 | 3.05 | 0.59 | 0.08 |
| 662648 | 2.89 | 0.69 | 0.40 |
| 662649 | 2.37* | 0.64* | 0.23* |
| 662704 | 2.08 | 0.65 | 0.20 |
| 662843 | 2.07 | 0.57 | 0.17 |
| 662875 | 1.86 | 0.54 | 0.15 |
| 662882 | 1.82* | 0.45* | 0.05* |
| 662944 | 1.51 | 0.41 | 0.06 |
| 662951 | 2.20 | 0.51 | 0.40 |
| 663143 | 1.84* | 0.47* | 0.17* |
| 663202 | 3.30 | 0.66 | 0.25 |
| 663354 | 3.56 | 0.51 | 0.17 |

*Values represent the average of 2-3 mice

TABLE 90

Organ Weights (g)

| ION Number | Liver | Kidney | Spleen |
|---|---|---|---|
| PBS | 1.88 | 0.57 | 0.16 |
| 633323 | 2.10 | 0.50 | 0.20 |
| 640677 | 1.85 | 0.51 | 0.17 |
| 640714 | 2.41 | 0.52 | 0.38 |
| 640717 | 2.03 | 0.59 | 0.15 |
| 662219 | 2.55 | 0.53 | 0.19 |
| 662256 | 1.40 | 0.48 | 0.09 |
| 662296 | 2.48* | 0.48* | 0.37* |
| 662302 | 2.73 | 0.53 | 0.21 |
| 662305 | 1.65 | 0.56 | 0.16 |
| 662478 | 2.53* | 0.42* | 0.16* |
| 662571 | 2.54 | 0.63 | 0.17 |
| 662595 | 1.97 | 0.52 | 0.21 |
| 662647 | 2.09 | 0.59 | 0.18 |
| 662724 | 1.82 | 0.49 | 0.12 |
| 662725 | 1.65 | 0.41 | 0.11 |
| 662884 | 2.05* | 0.27* | 0.05* |
| 662957 | 2.39 | 0.59 | 0.21 |
| 663147 | 1.73 | 0.55 | 0.12 |
| 663185 | 3.42 | 0.45 | 0.22 |
| 680122 | 1.46 | 0.55 | 0.23 |

*Values represent the average of 2-3 mice

TABLE 91

Organ Weights (g)

| ION Number | Liver | Kidney | Spleen |
|---|---|---|---|
| PBS | 1.80 | 0.55 | 0.13 |
| 633365 | 1.92 | 0.53 | 0.14 |
| 702366 | 2.14* | 0.51* | 0.19* |
| 702954 | 2.22 | 0.55 | 0.20 |
| 702909 | 1.91 | 0.45 | 0.16 |

*Values represent the average of 2 mice

TABLE 92

Organ Weights (g)

| ION Number | Liver | Kidney | Spleen |
|---|---|---|---|
| PBS | 1.74 | 0.54 | 0.12 |
| 702366 | 2.14 | 0.57 | 0.20 |

TABLE 93

Organ Weights (g)

| ION Number | Liver | Kidney | Spleen |
|---|---|---|---|
| PBS | 1.91 | 0.62 | 0.13 |
| 702334 | 2.01 | 0.58 | 0.15 |

TABLE 94

Organ Weights (g)

| ION Number | Liver | Kidney | Spleen |
|---|---|---|---|
| PBS | 1.75 | 0.55 | 0.14 |
| 754175 | 1.74 | 0.53 | 0.12 |
| 754179 | 2.67* | 0.56* | 0.16* |
| 754181 | 2.11 | 0.42 | 0.13 |
| 754182 | 2.31 | 0.53 | 0.17 |
| 754205 | 2.64 | 0.52 | 0.23 |
| 754206 | 1.80 | 0.40 | 0.11 |
| 754207 | 1.40 | 0.37 | 0.10 |
| 754208 | 1.48* | 0.39* | 0.06* |

*Values represent the average of 2-3 mice

TABLE 95

Organ Weights (g)

| ION Number | Liver | Kidney | Spleen |
|---|---|---|---|
| PBS | 1.84 | 0.56 | 0.14 |
| 756188 | 2.45 | 0.52 | 0.17 |

The data above demonstrated that 633365 was tolerable in CD1 mice.

Example 25: Tolerability of Modified Oligonucleotides Targeting hEZH2 in Sprague-Dawley Rats Sprague-Dawley rats are a multipurpose model used for safety and efficacy evaluations. The rats were treated with modified antisense oligonucleotides from the studies described in the Examples above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with 50 mg/kg of modified oligonucleotides (50 mg/kg weekly dose). Forty eight hours after the last dose, rats were euthanized and organs and plasma were harvested for further analysis.

Liver and Kidney Function

To evaluate the effect of modified oligonucleotides on hepatic function, plasma levels of transaminases were measured using an automated clinical chemistry analyzer (Hitachi Olympus AU400e, Melville, N.Y.). Plasma levels of ALT (alanine transaminase), AST (aspartate transaminase), blood urea nitrogen (BUN), and T. bilirubin were measured and the results are presented in the table below. Plasma levels of bilirubin were also measured using the same clinical chemistry analyzer and the results are also presented in the table below. Values represent the % change normalized to PBS-treated animals. Modified oligonucleotides that caused changes in the levels of any markers of liver function outside the expected range for antisense oligonucleotides were excluded in further studies.

TABLE 96

Liver function markers in Sprague-Dawley rats

| ION Number | Alt (IU/L) | AST (IU/L) | T. Bil (mg/dL) | BUN (mg/dL) | Albumin (g/dL) |
|---|---|---|---|---|---|
| PBS | 54 | 84 | 0.17 | 16.35 | 3.20 |
| 633365 | 65 | 86 | 0.12 | 19.63 | 3.02 |
| 662368 | 60 | 79 | 0.14 | 19.63 | 2.74 |
| 662442 | 105 | 138 | 0.14 | 23.08 | 2.63 |
| 662950 | 59 | 88 | 0.13 | 22.55 | 2.82 |

TABLE 97

Liver function markers in Sprague-Dawley rats

| ION Number | Alt (IU/L) | AST (IU/L) | T. Bil (mg/dL) | BUN (mg/dL) | Albumin (g/dL) |
|---|---|---|---|---|---|
| PBS | 58 | 106 | 0.16 | 19.75 | 3.51 |
| 702334 | 59 | 74 | 0.12 | 22.15 | 3.30 |
| 702366 | 88 | 133 | 0.12 | 43.93 | 2.46 |
| 702909 | 148 | 187 | 0.18 | 40.65 | 2.02 |
| 702954 | 72 | 91 | 0.13 | 29.30 | 2.09 |

TABLE 98

Liver function markers in Sprague-Dawley rats

| ION Number | Alt (IU/L) | AST (IU/L) | T. Bil (mg/dL) | BUN (mg/dL) | Albumin (g/dL) |
|---|---|---|---|---|---|
| PBS | 56 | 77 | 0.12 | 18.48 | 3.34 |
| 754175 | 47 | 85 | 0.11 | 24.85 | 3.10 |

Hematology Assays

Blood obtained from all rat groups was measured for hematocrit (HCT), blood cells, such as WBC, RBC, and total hemoglobin content. The results are presented in the table below. Modified oligonucleotides that caused changes in the levels of any of the hematology markers outside the expected range for antisense oligonucleotides were excluded in further studies.

TABLE 99

Hematology markers in Sprague-Dawley rats

| ION Number | WBC (K/µL) | RBC (M/µL) | HGB (g/dL) | HCT (%) | LYM (K/µL) | MON (K/µL) | EOS (K/µL) | BAS (K/µL) | PLT (K/µL) |
|---|---|---|---|---|---|---|---|---|---|
| PBS | 10.4 | 7.5 | 13.9 | 46.6 | 8642.5 | 398.5 | 165.8 | 48.5 | 580.5 |
| 633365 | 14.0 | 8.2 | 15.5 | 50.8 | 12262.8 | 622.5 | 42.3 | 111.8 | 728.5 |
| 662368 | 16.8 | 7.6 | 14.1 | 47.0 | 15969.3 | 320.5 | 11.3 | 56.8 | 534.8 |
| 662442 | 14.7 | 8.0 | 14.7 | 49.0 | 12793.5 | 483.8 | 19.8 | 33.0 | 798.8 |
| 662950 | 16.9 | 9.0 | 15.1 | 53.0 | 15491.5 | 375.0 | 78.0 | 162.3 | 580.8 |

TABLE 100

Hematology markers in Sprague-Dawley rats

| ION Number | WBC (K/µL) | RBC (M/µL) | HGB (g/dL) | HCT (%) | LYM (K/µL) | MON (K/µL) | EOS (K/µL) | BAS (K/µL) | PLT (K/µL) |
|---|---|---|---|---|---|---|---|---|---|
| PBS | 11.0 | 8.96 | 16.4 | 52.2 | 9474.5 | 588.0 | 78.8 | 20.8 | 1047.3 |
| 702334 | 12.1 | 8.15 | 15.0 | 47.6 | 9717.3 | 874.8 | 56.0 | 20.8 | 863.3 |
| 702366 | 21.0 | 8.46 | 14.9 | 46.1 | 17113.3 | 2695.8 | 25.8 | 153.5 | 725.5 |
| 702909 | 21.9 | 7.56 | 13.3 | 41.7 | 17163.8 | 1908.8 | 38.3 | 171.5 | 991.5 |
| 702954 | 24.8 | 7.09 | 12.8 | 41.0 | 20272.0 | 2503.0 | 45.0 | 176.5 | 738.3 |

TABLE 101

Hematology markers in Sprague-Dawley rats

| ION Number | WBC (K/µL) | RBC (M/µL) | HGB (g/dL) | HCT (%) | LYM (K/µL) | MON (K/µL) | EOS (K/µL) | BAS (K/µL) | PLT (K/µL) |
|---|---|---|---|---|---|---|---|---|---|
| PBS | 11.6 | 8.68 | 16.1 | 50.1 | 10042 | 512 | 160.0 | 15.8 | 779 |
| 754175 | 16.28 | 9.62 | 17.2 | 51.7 | 14598 | 928 | 21.0 | 39.8 | 656 |

Organ Weights

Liver, heart, spleen and kidney weights were measured at the end of the study, and are presented in the table below. Modified oligonucleotides that caused any changes in organ weights outside the expected range for antisense oligonucleotides were excluded from further studies.

TABLE 102

Organ weights (g)

| ION Number | Liver (g) | Kidney (g) | Spleen (g) |
|---|---|---|---|
| PBS | 14.33 | 3.37 | 0.82 |
| 633365 | 14.31 | 3.33 | 1.61 |
| 662368 | 14.69 | 3.80 | 2.40 |
| 662442 | 12.33 | 3.63 | 1.29 |
| 662950 | 13.28 | 2.89 | 1.27 |

TABLE 103

Organ weights (g)

| ION Number | Liver (g) | Kidney (g) | Spleen (g) |
|---|---|---|---|
| PBS | 14.78 | 3.52 | 0.83 |
| 702334 | 15.22 | 3.26 | 1.84 |
| 702366 | 12.68 | 3.30 | 1.70 |
| 702909 | 11.03 | 3.47 | 1.51 |
| 702954 | 12.03 | 3.46 | 1.87 |

TABLE 104

Organ weights (g)

| ION Number | Liver (g) | Kidney (g) | Spleen (g) |
|---|---|---|---|
| PBS | 16.14 | 3.22 | 0.75 |
| 754175 | 16.28 | 3.43 | 1.66 |

The data above demonstrated that 633365 was tolerable in Sprague Dawley rats.

Example 26: Tolerability of Modified Oligonucleotides in Non-Human Primates (NHP)

Modified oligonucleotides described above were further evaluated for potency in non-human primates.

Treatment

Male cynomolgus monkeys were divided into groups of 4 animals each. Groups received a dose of 40 mg/kg of modified oligonucleotide by subcutaneous injection on day 1, 3, 5, and 7, and then once/week for six weeks. One group of NHP received doses of PBS. The PBS-injected group served as the control group to which oligonucleotide-treated groups were compared. After six weeks, NHP were sacrificed and tissues were collected for analysis.

Tolerability

To evaluate the effect of these antisense oligonucleotides on liver and kidney function, samples of blood, plasma, serum and urine were collected from all study groups on day 44. The blood samples were collected via femoral venipuncture, 48 hrs post-dosing. The monkeys were fasted overnight prior to blood collection. Approximately 1.5 mL of blood was collected from each animal into tubes without anticoagulant for serum separation. Levels of the various markers were measured using an automated clinical chemistry analyzer (Hitachi Olympus AU400e, Melville, N.Y.). Total urine protein and urine creatinine levels were measured, and the ratio of total urine protein to creatinine (P/C Ratio) was determined.

To evaluate the effect of the antisense oligonucleotides on hepatic function, plasma concentrations of transaminases (ALT, AST), Albumin (Alb) and total bilirubin ("T. Bil") were measured. To evaluate the effect of the antisense oligonucleotides on kidney function, plasma concentrations of blood urea nitrogen (BUN) and creatinine (Cre) were measured. Urine levels of albumin (Alb), creatinine (Cre) and total urine protein (Micro Total Protein (MTP)) were measured, and the ratio of total urine protein to creatinine (P/C ratio) was determined.

To evaluate any inflammatory effect of the antisense oligonucleotides in cynomolgus monkeys, C-reactive protein (CRP), which is synthesized in the liver and serves as a marker of inflammation, was measured on day 44. For this, blood samples were taken from fasted monkeys, the tubes were kept at room temperature for a minimum of 90 min., and centrifuged at 3,000 rpm for 10 min at room temperature to obtain serum. The results are presented in the Tables below and indicate that most of the antisense oligonucleotides targeting human EZH2 were well tolerated in cynomolgus monkeys.

TABLE 105

Serum and urine clinical chemistry

| ISIS No. | Serum (day 44) | | | | | | | | | Urine (day 44) P/C ratio |
|---|---|---|---|---|---|---|---|---|---|---|
| | ALT U/L | AST U/L | Alb g/dL | BUN mg/dL | CRP mg/L | Cre mg/dL | T.bil mg/dL | Alb mg/dL | Cre mg/dL | |
| PBS | 45.9 | 76.8 | 4.11 | 22.2 | 2.84 | 0.79 | 0.30 | 0.33 | 75.1 | 0.015 |
| 633365 | 47.8 | 59.3 | 3.80 | 22.3 | 4.24 | 0.67 | 0.21 | 0.16 | 58.4 | 0.215 |
| 662368 | 60.6 | 68.5 | 4.06 | 23.0 | 4.30 | 0.79 | 0.24 | 0.87 | 63.1 | 0.060 |
| 662950 | 63.7 | 95.2 | 4.03 | 24.3 | 21.50 | 0.70 | 0.22 | 0.11 | 51.8 | 0.036 |
| 702334 | 67.1 | 80.7 | 4.03 | 22.6 | 2.16 | 0.80 | 0.27 | 0.46 | 39.9 | 0.050 |
| 702366 | 50.6 | 68.6 | 3.93 | 24.6 | 3.92 | 0.80 | 0.24 | 0.02 | 38.1 | 0.030 |
| 754175 | 39.1 | 100.8 | 4.08 | 24.3 | 6.94 | 0.86 | 0.22 | 0.37 | 64.0 | 0.073 |

TABLE 106

Body Weight

| ION Number | Body Weight (g) day −8 | Body weight (g) day 42 |
|---|---|---|
| PBS | 2479 | 2492 |
| 633365 | 2479 | 2743 |
| 662368 | 2461 | 2573 |
| 662950 | 2451 | 2459 |
| 702334 | 2425 | 2416 |
| 702366 | 2494 | 2645 |
| 754175 | 2502 | 2653 |

RNA Analysis

RNA was extracted from various tissues for real-time PCR analysis of mRNA expression of EZH2 as in previous examples. Results are presented as mRNA levels relative to PBS control, normalized with NHP Cyclophylin A. As shown in the table below, treatment with modified oligonucleotides resulted in reduction of EZH2 mRNA in liver compared to the PBS control with some of the treatment groups. 633365 strongly reduced expression of EZH2 mRNA.

TABLE 107

Cynomolgus EZH2 mRNA levels in liver

| ION Number | EZH2 mRNA (% PBS) |
|---|---|
| 633365 | 12 |
| 662368 | 34 |
| 662950 | 58 |
| 702334 | 26 |
| 702366* | 50 |
| 754175** | 100 |

*Compound has one mismatch to cynomolgus monkey EZH2
**Compound has two mismatches to cynomolgus monkey EZH2

The data above demonstrated that 633365 was tolerable and active against monkey EZH2 in non-human primates.

What is claimed:

1. A modified oligonucleotide according to the following chemical structure:

(SEQ ID NO: 252)

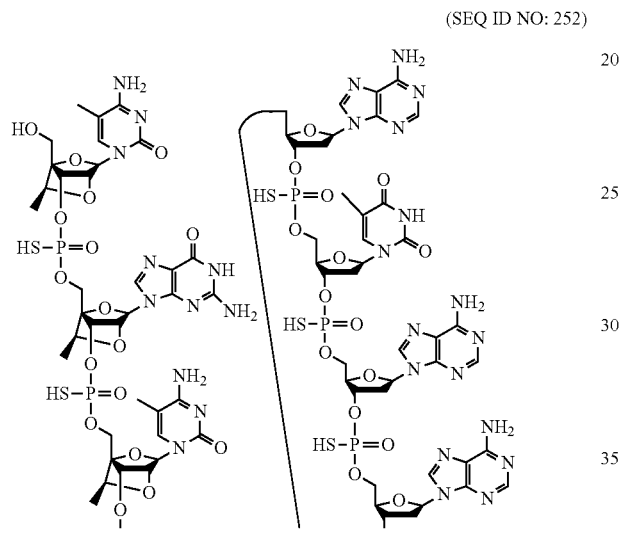
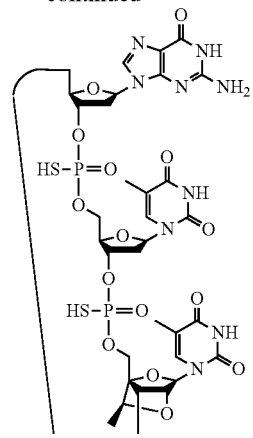
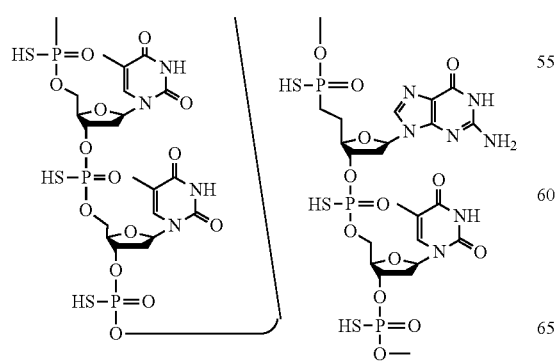
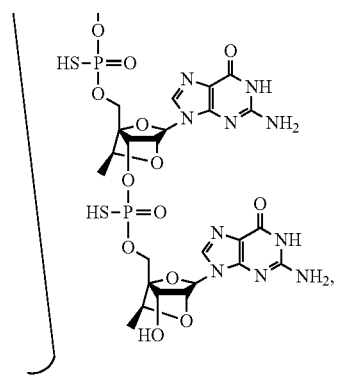

or a salt thereof.

2. The modified oligonucleotide of claim 1, which is the sodium salt or the potassium salt.

3. A modified oligonucleotide according to the following chemical structure:

(SEQ ID NO: 252)

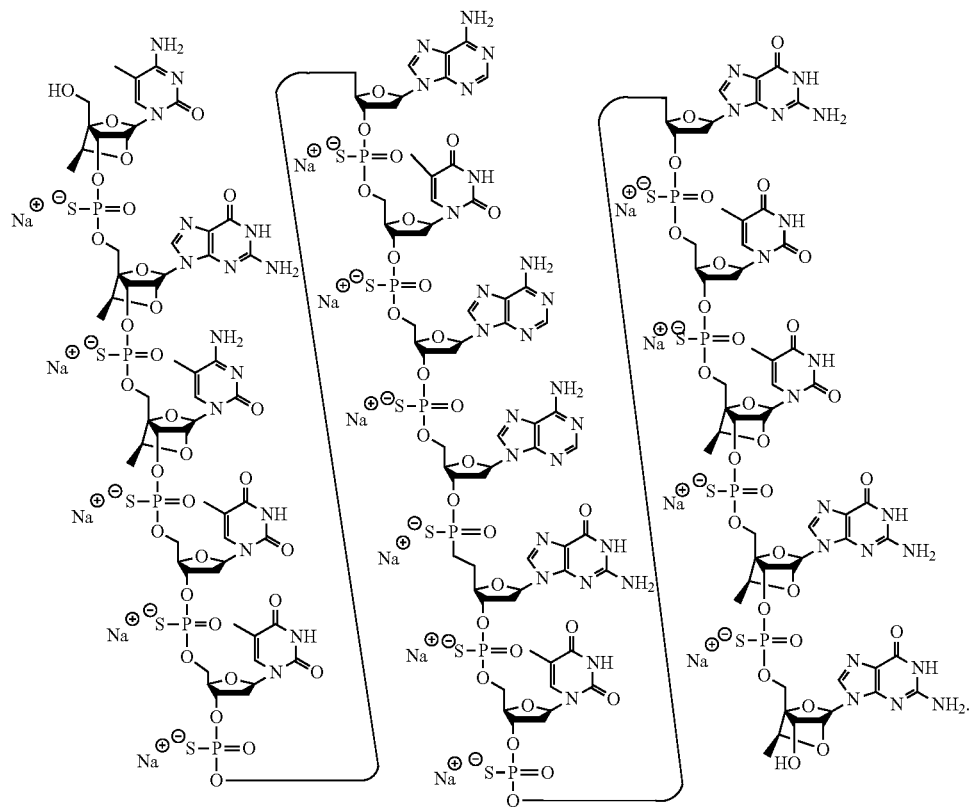

4. An oligomeric compound comprising a modified oligonucleotide consisting of 16 linked nucleobases and having a nucleobase sequence consisting of the nucleobase sequence of SEQ ID NO: 252, wherein the modified oligonucleotide has:
 a gap segment consisting of ten linked 2'-deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine.

5. A population of modified oligonucleotides of any of claims 1-3 or a population of oligomeric compounds of claim 4, wherein all of the phosphorothioate internucleoside linkages of the modified oligonucleotide are stereorandom.

6. A pharmaceutical composition comprising a modified oligonucleotide of any of claims 1-3, or an oligomeric compound of claim 4 and a pharmaceutically acceptable diluent.

7. The pharmaceutical composition of claim 6, wherein the pharmaceutically acceptable diluent is water or PBS.

8. The pharmaceutical composition of claim 7, wherein the pharmaceutical composition consists essentially of the modified oligonucleotide or oligomeric compound and water or PBS.

9. A method comprising administering to a subject a modified oligonucleotide of any of claims 1-3, or an oligomeric compound of claim 4.

10. A method of treating a disease associated with EZH2 comprising administering to a subject having a disease associated with EZH2 a therapeutically effective amount of a modified oligonucleotide of any of claims 1-3, or an oligomeric compound of 4 thereby treating the disease associated with EZH2.

11. The method of claim 10, wherein the disease associated with EZH2 is cancer.

12. The method of claim 11, wherein the cancer is a blood cancer, myeloma, multiple myeloma (MM), B cell malignancy, lymphoma, B cell lymphoma, DLBCL, GC-DLBCL, T cell lymphoma, or leukemia.

13. The method of claim 9, wherein the administering reduces cancer cell proliferation, tumor growth, or metastasis in the subject.

14. A method of reducing expression of EZH2 in a cell comprising contacting the cell with a modified oligonucleotide of any of claims 1-3, or an oligomeric compound of claim 4.

15. The method of claim 14, wherein the cell is a cancer cell.

16. The method of claim 10, wherein the subject is human.

17. The method of claim 14, wherein the cell is a human cell.

18. A method comprising administering to a subject a population of modified oligonucleoties or a population of oligomeric compounds of claim 5.

* * * * *

UNITED STATES PATENT AND TRADEMARK OFFICE
CERTIFICATE OF CORRECTION

PATENT NO. : 11,365,416 B2  
APPLICATION NO. : 17/045426  
DATED : June 21, 2022  
INVENTOR(S) : Minji Jo et al.

Page 1 of 9

It is certified that error appears in the above-identified patent and that said Letters Patent is hereby corrected as shown below:

In the Specification

At Column 15, Line 3, please delete:

"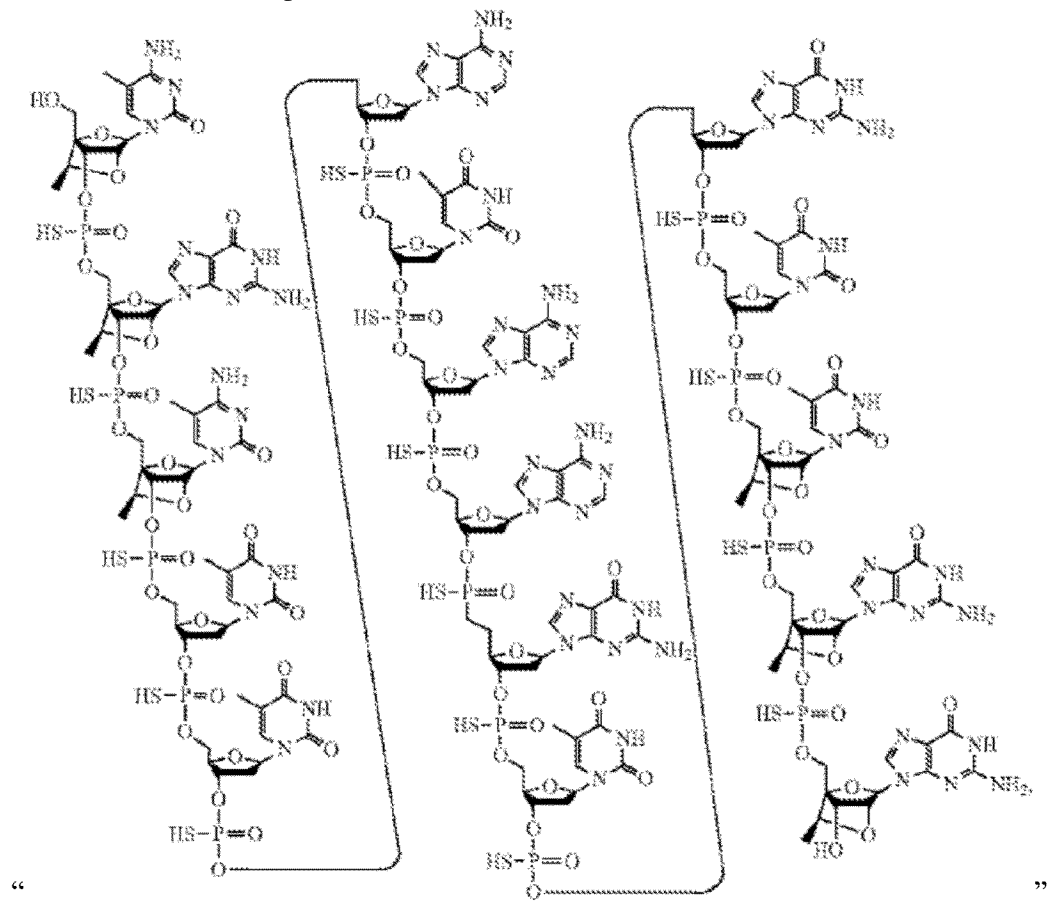"

Signed and Sealed this  
Eighteenth Day of October, 2022

Katherine Kelly Vidal  
*Director of the United States Patent and Trademark Office*

And insert therefore:
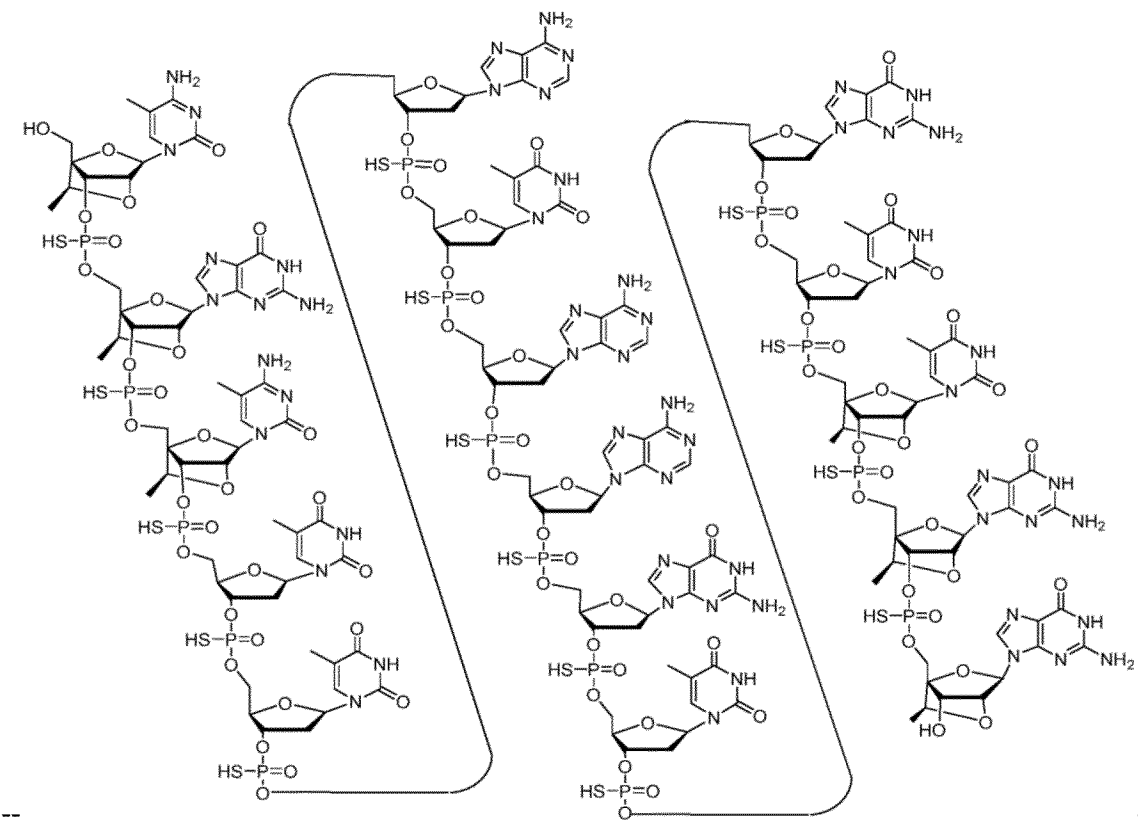
--.
At Column 15, Line 38, please delete:
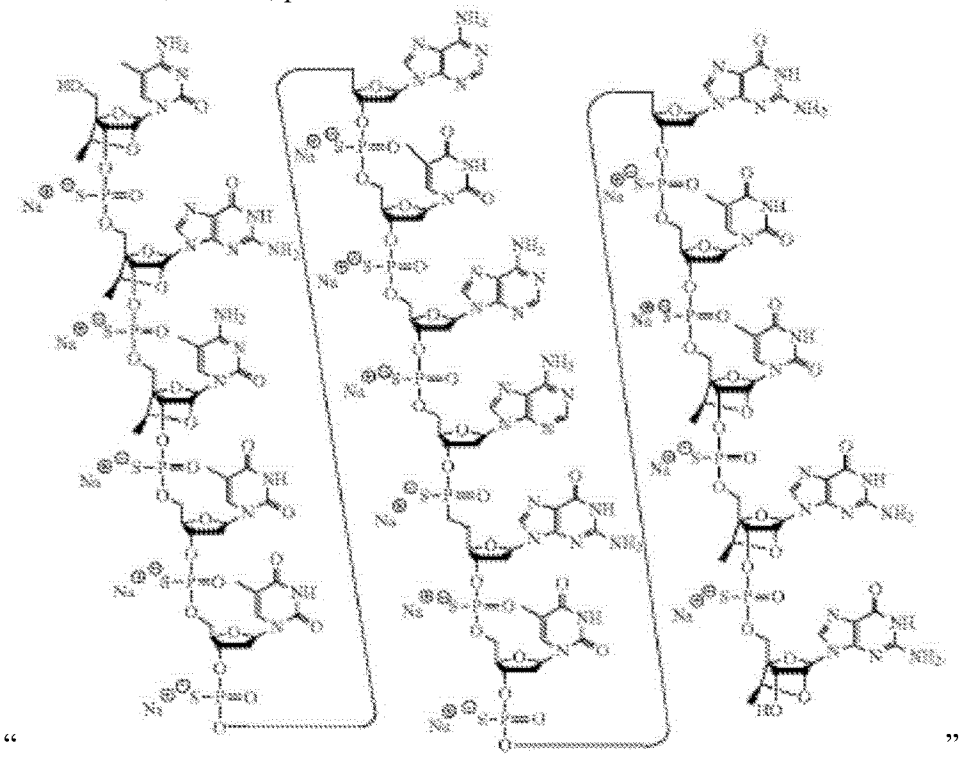
" "

And insert therefore:
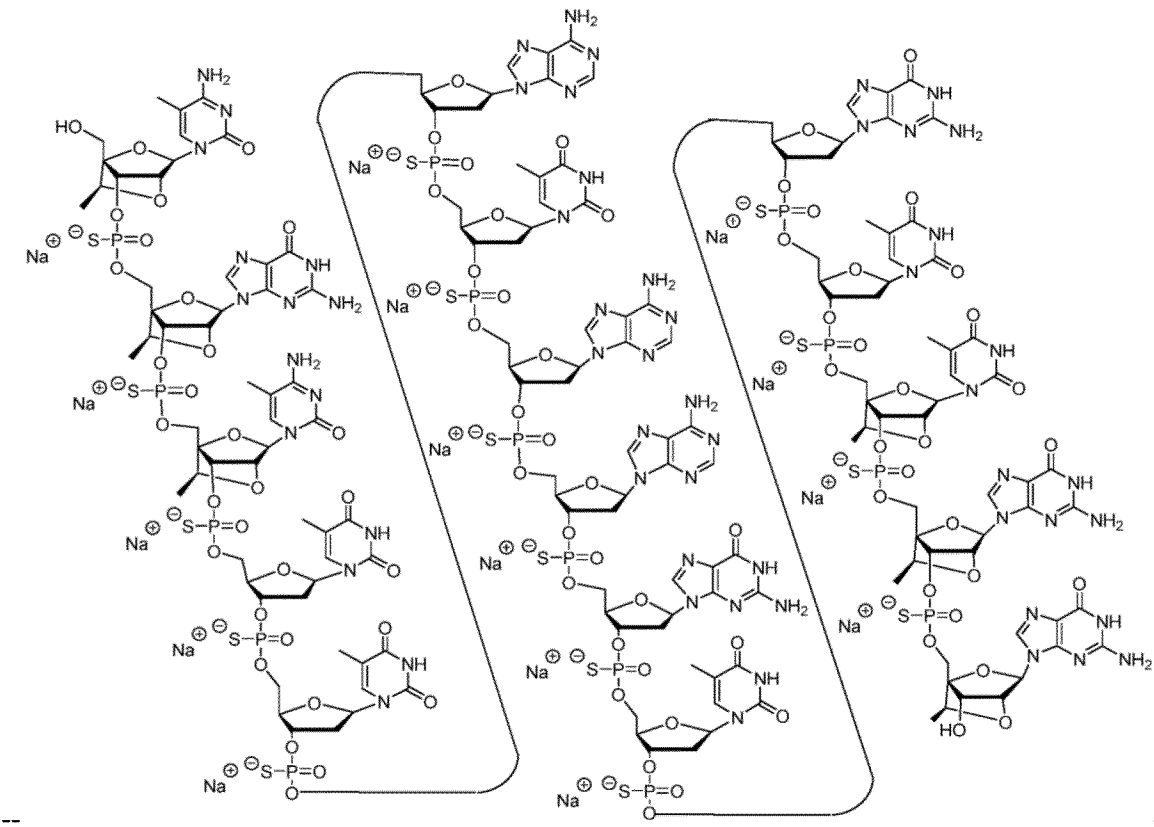
--                                                                                                    --.
At Column 21, Line 3, please delete:
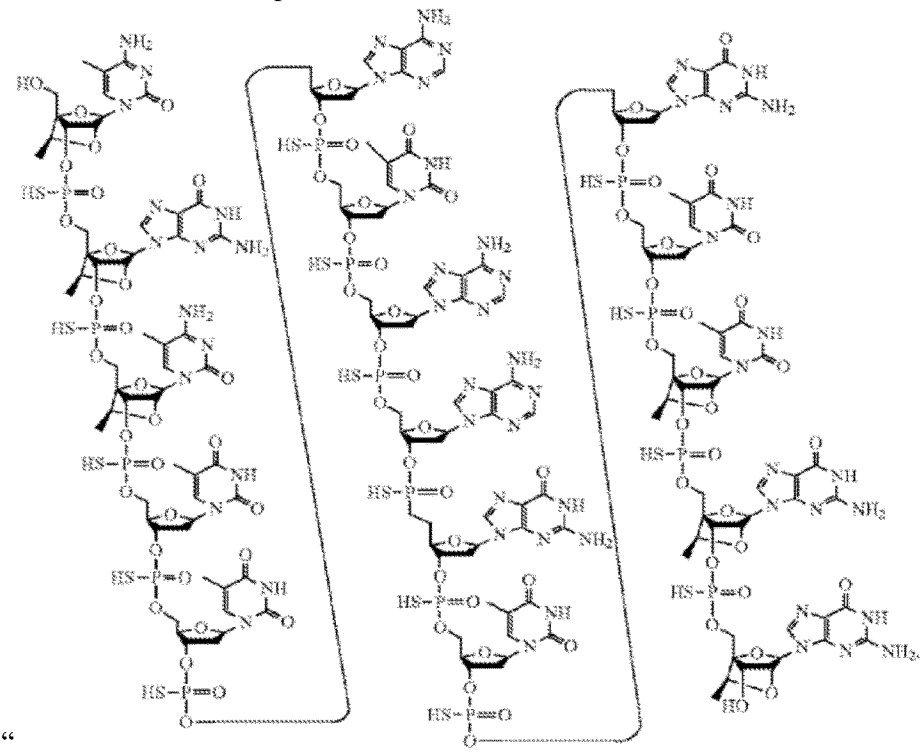
"                                                                                                    "

CERTIFICATE OF CORRECTION (continued)
U.S. Pat. No. 11,365,416 B2

And insert therefore:

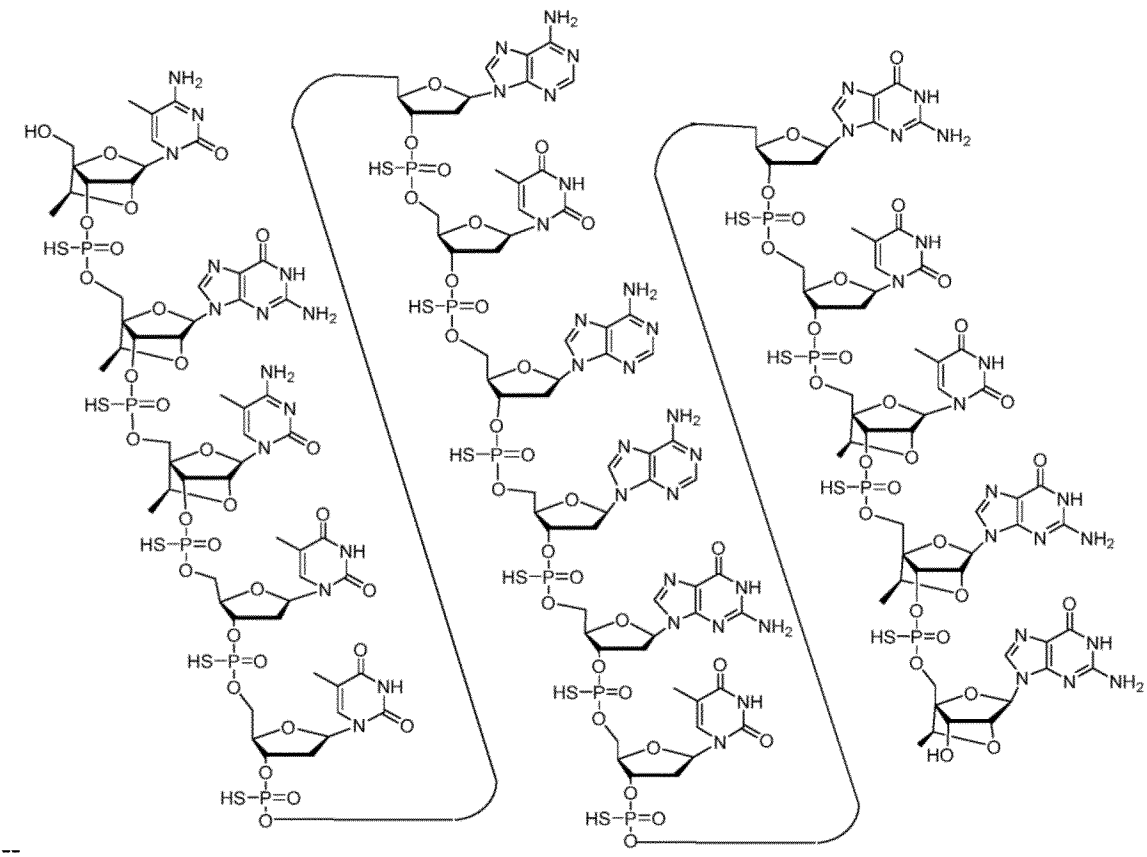

--

At Column 21, Line 38, please delete:

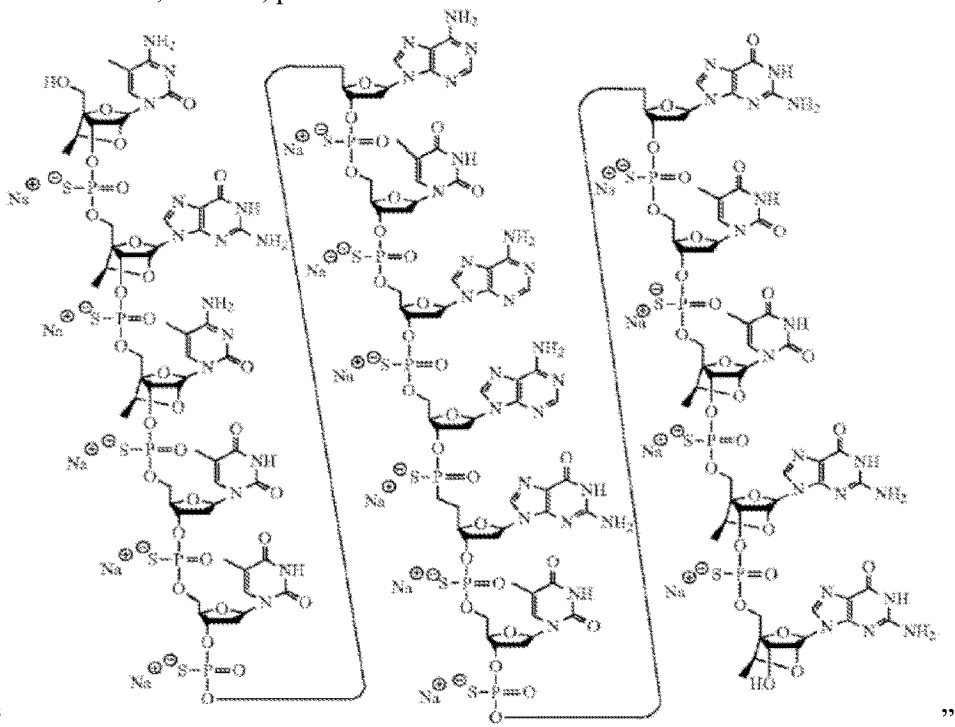

" "

And insert therefore:
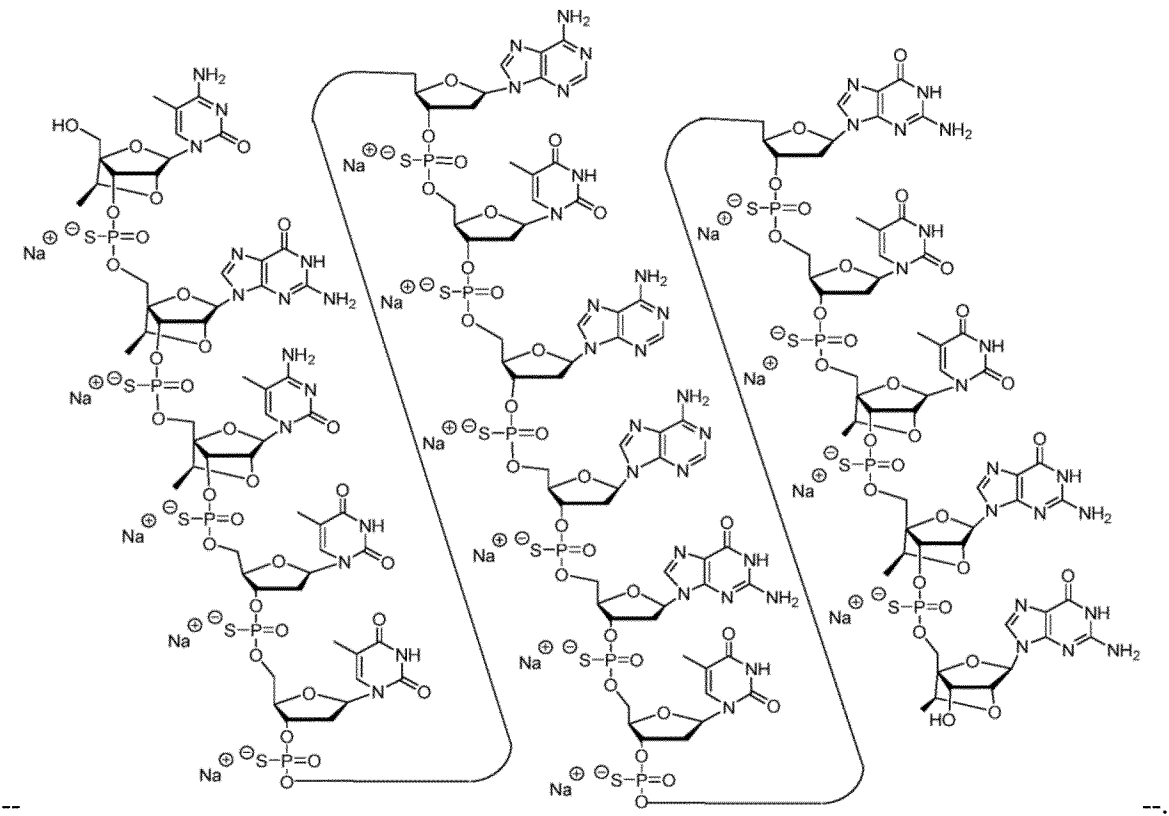
--
At Column 35, Line 35, please delete:
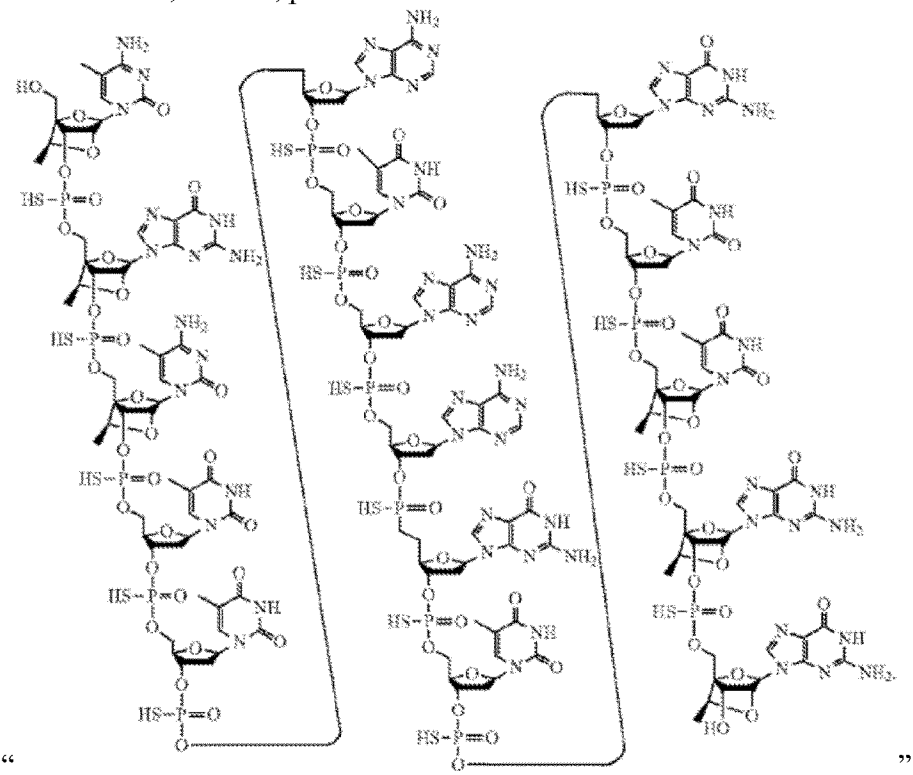
" "

CERTIFICATE OF CORRECTION (continued)
U.S. Pat. No. 11,365,416 B2

And insert therefore:

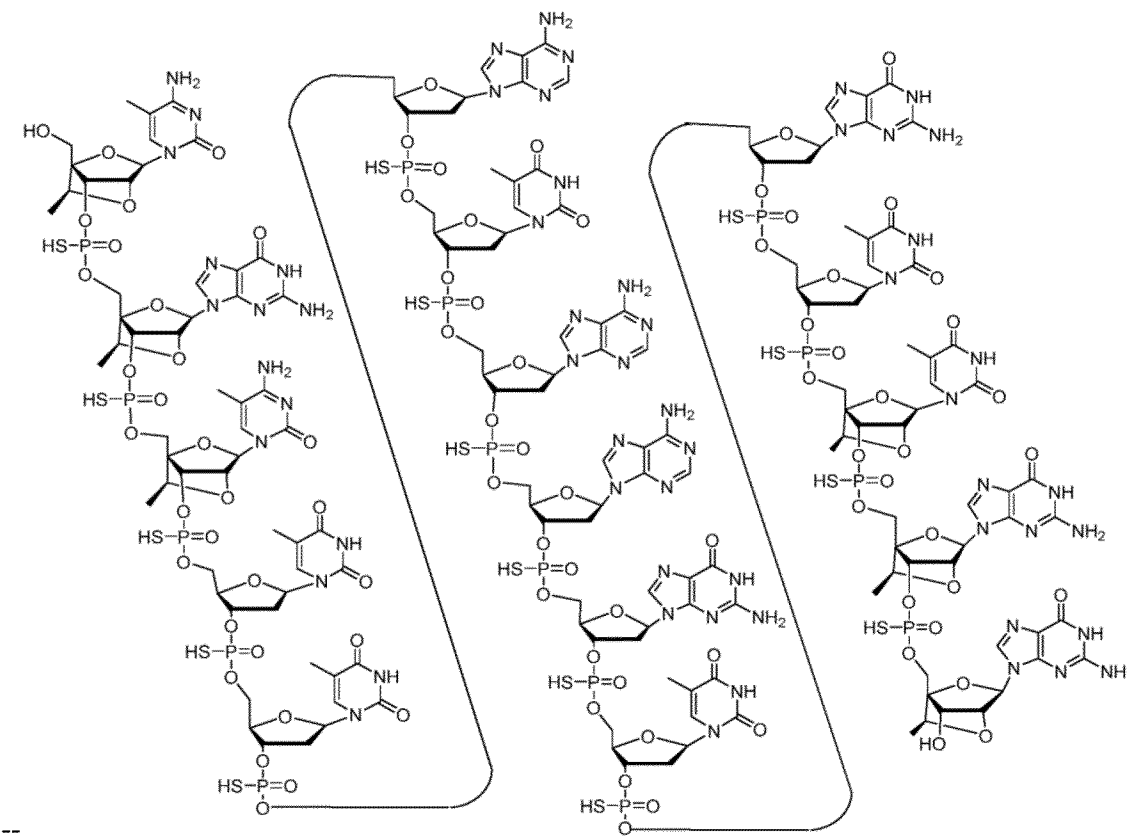

--

At Column 37, Line 5, please delete:

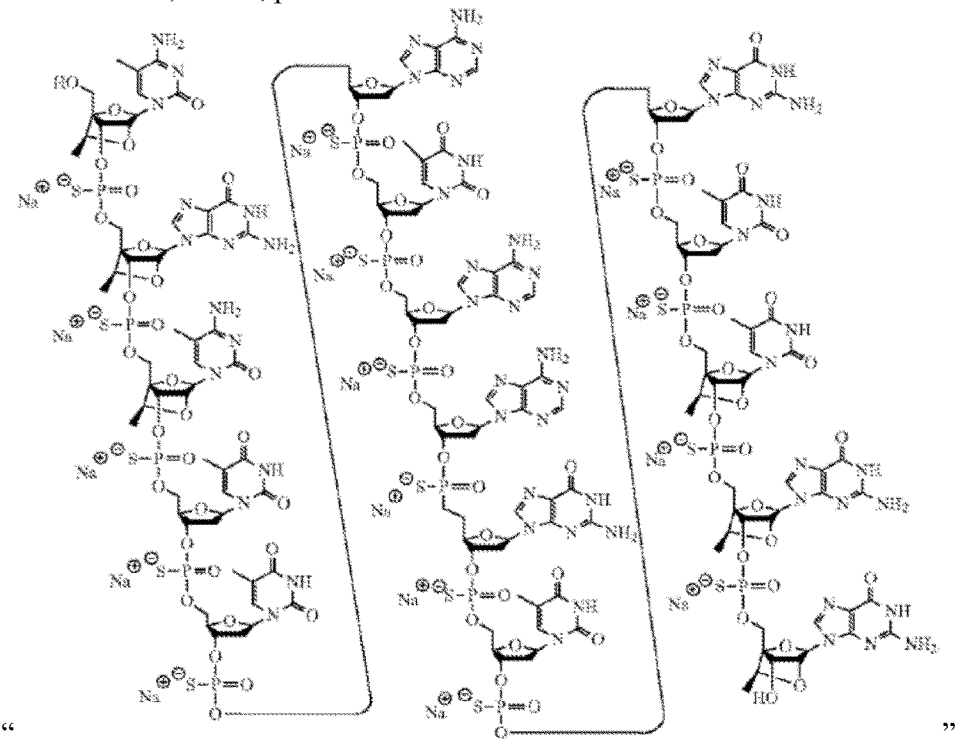

"         "

And insert therefore:
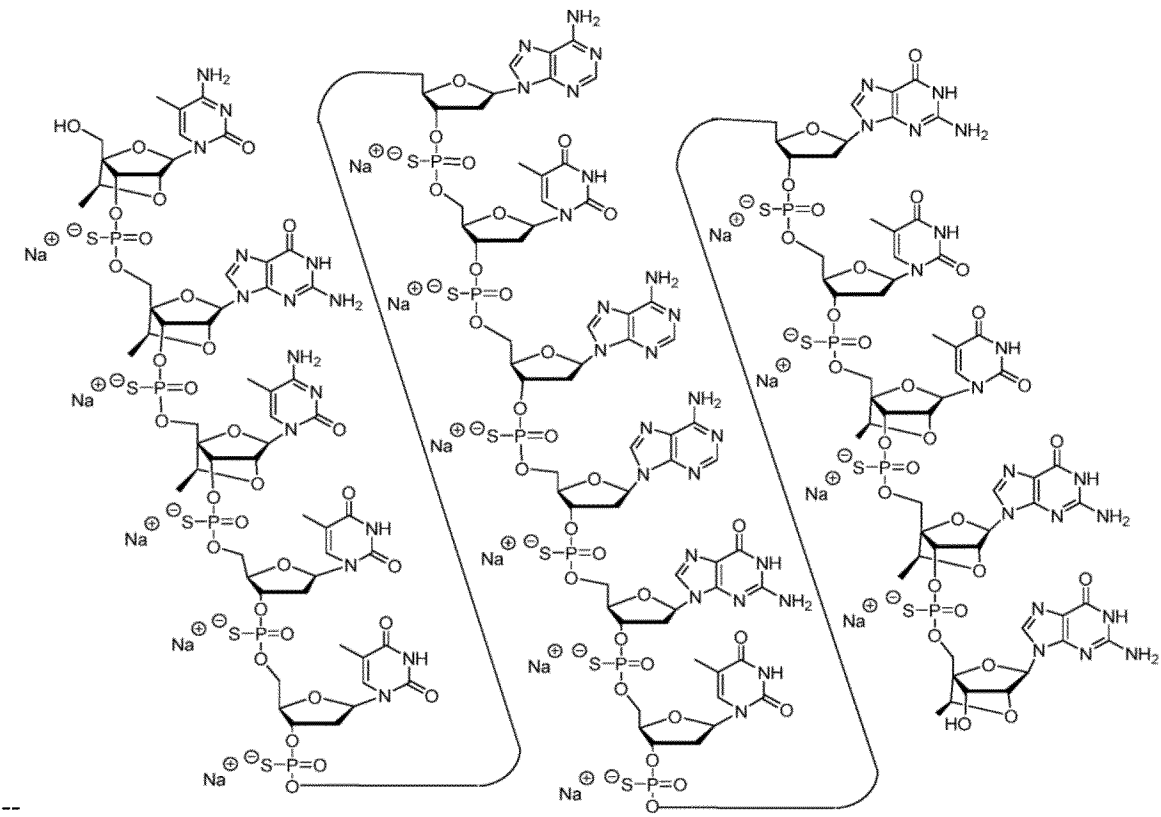
--                                    --.
In the Claims
At Column 783, Line 20, please delete:
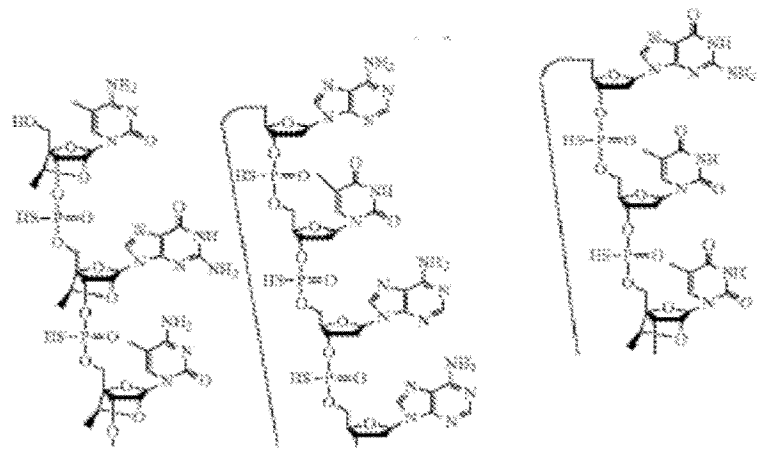
"

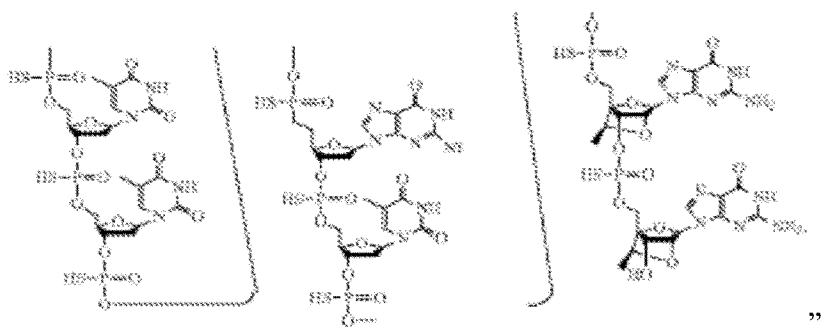
",
And insert therefore:
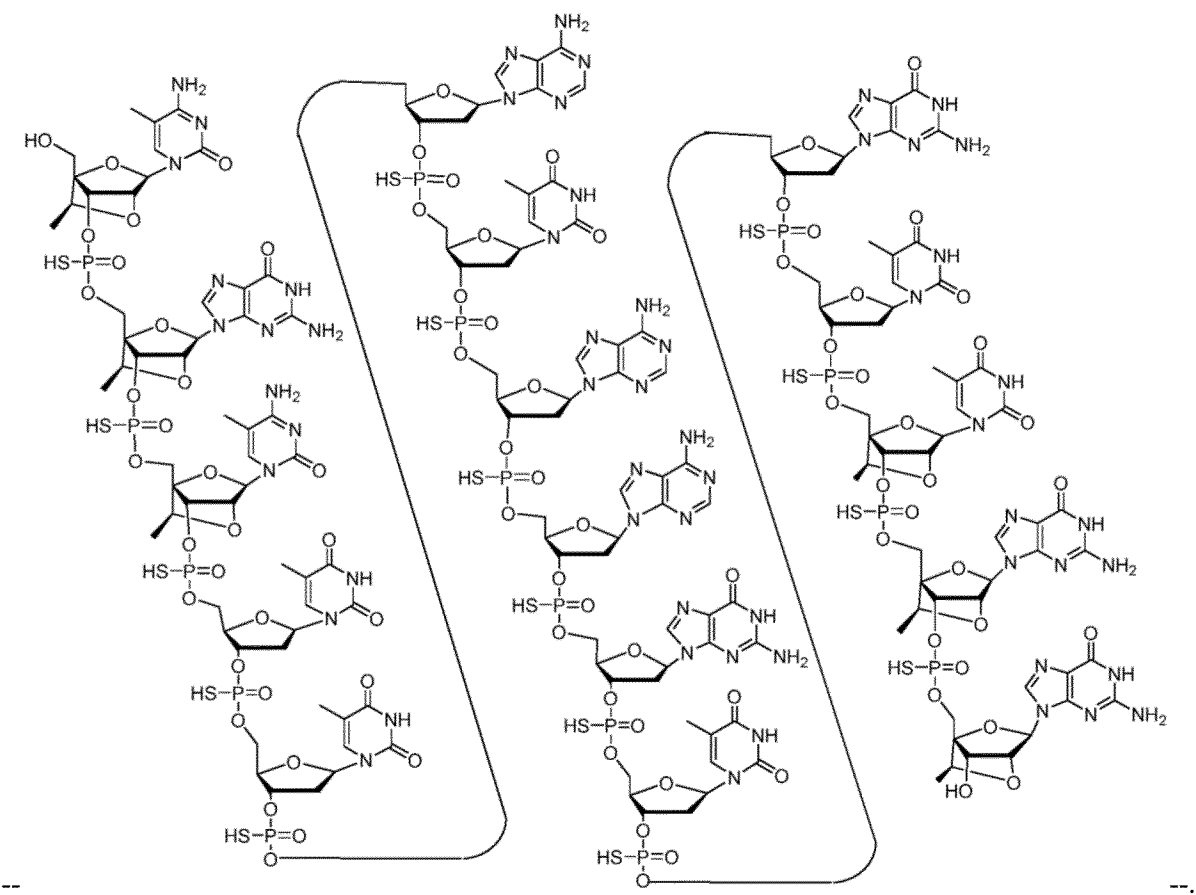
--                                                                                            --.

CERTIFICATE OF CORRECTION (continued)
U.S. Pat. No. 11,365,416 B2

At Column 785, Line 6, please delete:

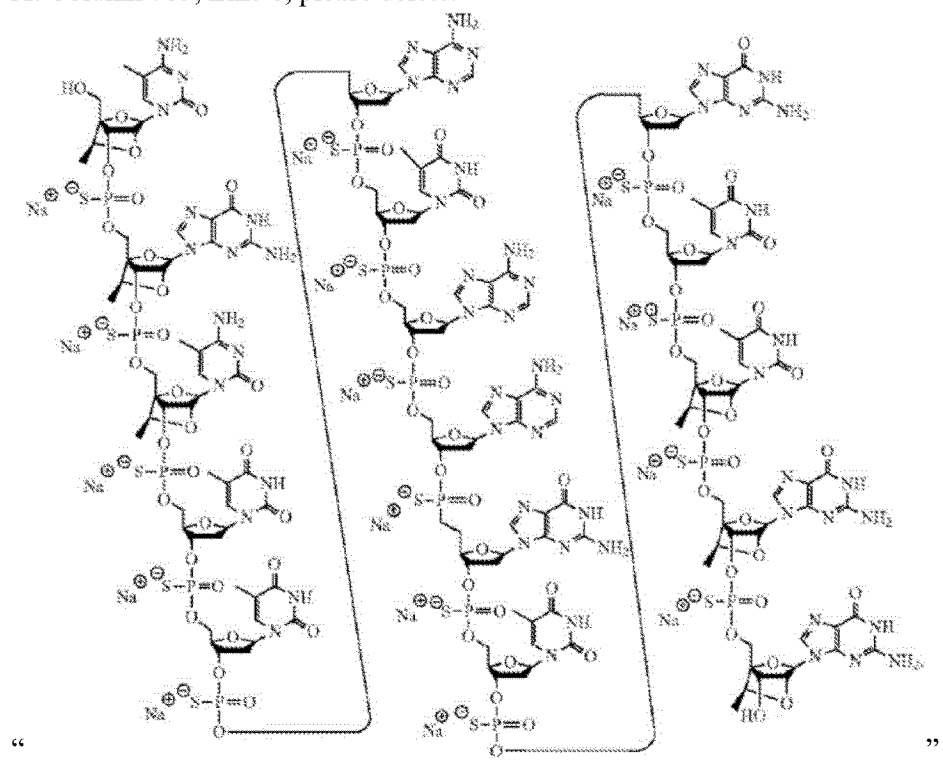

"

"

And insert therefore:

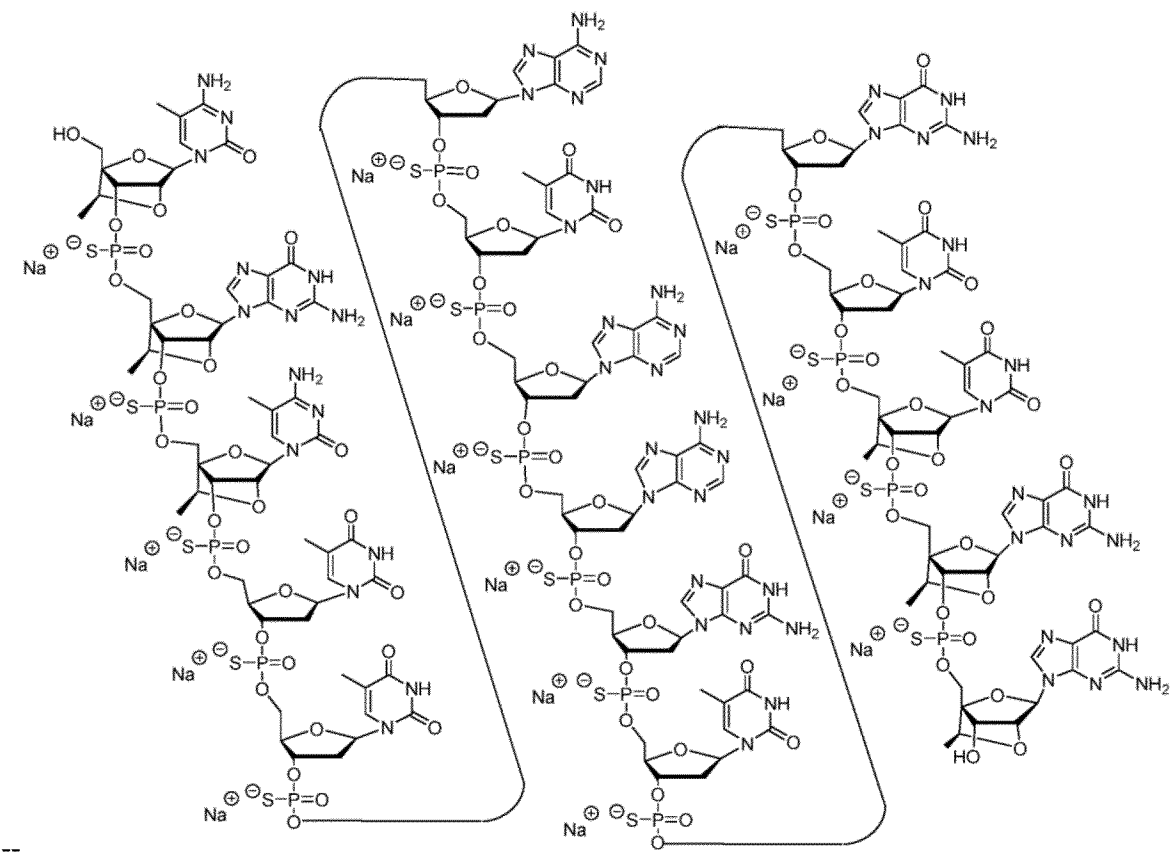

--                                                                          --.